US009593156B2

(12) United States Patent
Dimarchi et al.

(10) Patent No.: US 9,593,156 B2
(45) Date of Patent: Mar. 14, 2017

(54) INSULIN ANALOG DIMERS

(71) Applicant: INDIANA UNIVERSITY RESEARCH AND TECHNOLOGY CORPORATION, Indianapolis, IN (US)

(72) Inventors: Richard D. Dimarchi, Carmel, IN (US); Yan Zhao, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/431,040

(22) PCT Filed: Sep. 25, 2013

(86) PCT No.: PCT/US2013/061676
§ 371 (c)(1),
(2) Date: Mar. 25, 2015

(87) PCT Pub. No.: WO2014/052451
PCT Pub. Date: Apr. 3, 2014

(65) Prior Publication Data
US 2015/0274802 A1    Oct. 1, 2015

Related U.S. Application Data

(60) Provisional application No. 61/705,834, filed on Sep. 26, 2012.

(51) Int. Cl.
| C07K 14/62 | (2006.01) |
| A61K 47/48 | (2006.01) |
| A61K 38/00 | (2006.01) |

(52) U.S. Cl.
CPC ........... *C07K 14/62* (2013.01); *A61K 47/481* (2013.01); *A61K 47/48023* (2013.01); *A61K 47/48215* (2013.01); *A61K 47/48338* (2013.01); *A61K 38/00* (2013.01)

(58) Field of Classification Search
None
See application file for complete search history.

(56) References Cited

U.S. PATENT DOCUMENTS

| 3,740,385 A | 6/1973 | Ondetti |
| 4,275,152 A | 6/1981 | Esders et al. |
| 4,741,897 A | 5/1988 | Andrews et al. |
| 4,876,242 A | 10/1989 | Applebaum et al. |
| 4,985,407 A | 1/1991 | Foxton et al. |
| 5,028,586 A | 7/1991 | Balschmidt et al. |
| 5,359,030 A | 10/1994 | Ekwuribe |
| 5,514,646 A | 5/1996 | Chance et al. |
| 5,759,818 A | 6/1998 | Boime |
| 5,843,634 A | 12/1998 | Brate et al. |
| 6,180,767 B1 | 1/2001 | Wickstrom et al. |
| 6,197,926 B1 | 3/2001 | Gaur et al. |
| 6,476,290 B1 | 11/2002 | Wright et al. |
| 6,630,348 B1 | 10/2003 | Lee et al. |
| 6,746,853 B1 | 6/2004 | Dahiyat et al. |
| 7,045,337 B2 | 5/2006 | Schultz et al. |
| 7,326,688 B2 | 2/2008 | O'Harte |
| 7,521,422 B2 | 4/2009 | Bernard |
| 8,481,485 B2 | 7/2013 | DiMarchi et al. |
| 2002/0038026 A1 | 3/2002 | Rao et al. |
| 2002/0160938 A1 | 10/2002 | Brandenburg et al. |
| 2003/0195147 A1 | 10/2003 | Pillutla et al. |
| 2003/0204063 A1 | 10/2003 | Gravel et al. |
| 2004/0054130 A1 | 3/2004 | Ng et al. |
| 2004/0121940 A1 | 6/2004 | DeGroot et al. |
| 2005/0014679 A1 | 1/2005 | Beals et al. |
| 2005/0187147 A1 | 8/2005 | Newman et al. |
| 2006/0171920 A1 | 8/2006 | Schechter et al. |
| 2006/0210534 A1 | 9/2006 | Lee et al. |
| 2006/0223753 A1 | 10/2006 | Glass |
| 2007/0129284 A1 | 6/2007 | Kjeldsen et al. |
| 2007/0173452 A1 | 7/2007 | DiMarchi et al. |
| 2007/0203058 A1 | 8/2007 | Lau et al. |
| 2007/0224119 A1 | 9/2007 | McTavish |
| 2008/0113411 A1 | 5/2008 | Sheffer |
| 2008/0113905 A1 | 5/2008 | DiMarchi et al. |

(Continued)

FOREIGN PATENT DOCUMENTS

| CN | 101157725 | 4/2008 |
| EP | 0220958 | 5/1987 |

(Continued)

OTHER PUBLICATIONS

PCT Search Report and Written Opinion completed on Apr. 1, 2014 and issued in connection with PCT/US2013/061676.
Cloutier, et al. "Low-Entergy (3-24 eV) Electron Damage to the Peptide Backbone" J. Phys Chem B. 2007, 111(7): 1620-4; p. 1621, Fig. 1.
"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.
De et al., Synthesis and characterization of ester-based prodrugs of glucagon-like peptide 1, *Biopolymers*, 94(4): 448-56 (2010).
Harris, J. Milton, Final Word: PEGylation—A "Sunset" Technology? <http://licence.icopyright.net/user/view/FreeUse.act?fuid=OTU1NjY3OA%3D%3D>, BioPharm International, Jun. 1, 2004.
M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

(Continued)

*Primary Examiner* — Marcela M Cordero Garcia
*Assistant Examiner* — Catherine Mader
(74) *Attorney, Agent, or Firm* — Barnes & Thornburg LLP

(57) ABSTRACT

Disclosed herein are insulin analog dimers having unique insulin receptor agonist activity based on insulin polypeptide sequences, the site of dimerization and the length of the dimerization linker that connects the two insulin polypeptides. In accordance with one embodiment the first and second insulin polypeptide are independently a two chain insulin analog or a single chain analog and the first and second insulin polypeptides are linked to one another via a B29-B29', B1-C8, B1-B1 or C8-C8 linkage.

20 Claims, 71 Drawing Sheets

(56) References Cited

U.S. PATENT DOCUMENTS

| | | | |
|---|---|---|---|
| 2008/0125574 A1 | 5/2008 | Sheffer et al. | |
| 2009/0054305 A1 | 2/2009 | Schlein et al. | |
| 2009/0176964 A1 | 7/2009 | Walensky et al. | |
| 2009/0192072 A1 | 7/2009 | Pillutla et al. | |
| 2009/0209453 A1 | 8/2009 | Moyle | |
| 2009/0221037 A1 | 9/2009 | Lee et al. | |
| 2010/0081614 A1 | 4/2010 | Fares et al. | |
| 2011/0065633 A1 | 3/2011 | DiMarchi et al. | |
| 2011/0257091 A1 | 10/2011 | DiMarchi | |
| 2011/0288003 A1 | 11/2011 | DiMarchi et al. | |
| 2012/0010134 A1 | 1/2012 | Zion et al. | |
| 2012/0184489 A1 | 7/2012 | Rau et al. | |

FOREIGN PATENT DOCUMENTS

| | | | |
|---|---|---|---|
| EP | 0605983 | 7/1994 | |
| EP | 741188 | 11/1996 | |
| EP | 1161452 | 2/2000 | |
| EP | WO 00/50456 * | 8/2000 | ............ C07K 14/62 |
| EP | 2036539 A1 | 3/2009 | |
| EP | 2036923 A1 | 3/2009 | |
| EP | 2479193 | 9/2013 | |
| WO | 90/12814 | 11/1990 | |
| WO | 93/03174 | 2/1993 | |
| WO | 96/34882 | 11/1996 | |
| WO | 98/11126 | 3/1998 | |
| WO | 99/46283 | 9/1999 | |
| WO | 00/50456 | 8/2000 | |
| WO | 02/10195 | 2/2002 | |
| WO | 2004/067548 | 8/2004 | |
| WO | 2004/078777 | 9/2004 | |
| WO | 2005/054291 | 6/2005 | |
| WO | 2006/047214 | 5/2006 | |
| WO | 2006/097521 | 9/2006 | |
| WO | 2007/096332 | 8/2007 | |
| WO | 2008/019368 | 2/2008 | |
| WO | 2008/021560 | 2/2008 | |
| WO | 2008/025528 | 3/2008 | |
| WO | 2008/081418 | 7/2008 | |
| WO | 2008081418 A1 | 7/2008 | |
| WO | WO2009034118 A1 | 3/2009 | |
| WO | WO2009034119 A1 | 3/2009 | |
| WO | 2009/067636 | 5/2009 | |
| WO | 2009/095479 | 8/2009 | |
| WO | 2009/099763 | 8/2009 | |
| WO | 2010/011313 | 1/2010 | |
| WO | 2010/071807 | 6/2010 | |
| WO | 2010/080605 | 7/2010 | |
| WO | 2010/080609 | 7/2010 | |
| WO | 2011/159895 | 12/2011 | |
| WO | 2011/163012 | 12/2011 | |
| WO | 2011/163460 | 12/2011 | |
| WO | 2011/163462 | 12/2011 | |
| WO | 2011159895 A2 | 12/2011 | |
| WO | WO2011159895 | 12/2011 | |

OTHER PUBLICATIONS

De, A. and DiMarchi, R. Synthesis & Analysis of Peptide Hormone-based prodrugs, (2009) Proceedings of the 21st American Peptide Society 160-161.
Battersby et al., "Diketopiperazine Formation and N-Terminal Degradation in Recombinant Human Growth Hormone", *International Journal of Peptide & Protein Research* 44: 215-222, (1994).
Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).
Garcia-Aparicio et al., "Design and Discovery of a Novel Dipeptidyl-peptidase IV (CD26)-Based Prodrug Approach", *J. Med. Chem.* 49: 5339-5351 (2006).
Goolcharran et al., "Comparison of the Rates of Deamidation, Diketopiperazine Formation, and Oxidation in Recombinant Human Vascular Endothelial Growth Factor and Model Peptides", *AAPS Pharmsci* 2000 2(1) article 5: 1-6 (Mar. 17, 2000).

Santos et al., Cyclization-Activated Prodrugs. Synthesis, Reactivity and Toxicity of Dipeptide Esters of Paracetamol, *Bioorganic & Medicinal Chemistry Letters* 15: 1595-1598 (2005).
Sato, H., "Enzymatic procedure for site-specific pegylation of proteins," Advanced Drug Delivery Reviews 54, pp. 487-504 (2002).
Ward, "Fatty Acid Acylation of Peptides: Developing strategies to enhance medicines for treating metabolic disorders," Jan. 14, 2009.
DiMarchi, "Peptides—Development of Prodrug Chemistry," RBF Symposium Feb. 1-4, 2011 India.
Yang et al., "A Novel Approach to Resin-Based Cysteine Alkylation," American Peptide Society, 2005.
PCT International Search Report for PCT/US2009/068745 completed by the US Searching Authority on Feb. 1, 2010.
PCT International Search Report for PCT/US2009/031593 completed by the US Searching Authority on Jul. 16, 2009.
Schuttler, A. and D. Brandenburg, Preparation and Properties of Covalently Linked Insulin Dimers. Hoppe-Seylers Zeitschrift Fur Physiologische Chemie, 1982. 363(3): p. 317-330.
Tatnell, M.A., et al., Evidence Concerning the Mechanism of Insulin-Receptor Interaction and the Structure of the Insulin-Receptor from Biological Properties of Covalently Linked Insulin Dimers. Biochemical Journal, 1983. 216(3): p. 687-694.
Roth, R.A., et al., Effects of Covalently Linked Insulin Dimers on Receptor Kinase-Activity and Receptor down Regulation. Febs Letters, 1984. 170(2): p. 360-364.
Tatnell, M.A., R.H. Jones, and P.H. Sonksen, Covalently-Linked Insulin Dimers—Their Metabolism and Biological Effects Invivo as Partial Competitive Antagonists of Insulin-Clearance. Diabetologia, 1984. 27(1): p. 27-31.
Joost, H.G., et al., Quantitative Dissociation of Glucose-Transport Stimulation and Insulin-Receptor Tyrosine Kinase Activation in Isolated Adipocytes with a Covalent Insulin Dimer (B29,B29'-Sunberoyl-Insulin). Biochemical Pharmacology, 1989. 38(14): p. 2269-2277.
Breiner, M., et al., Heterogeneity of Insulin-Receptors in Rat-Tissues as Detected with the Partial Agonist B29,B29'-Suberoyl-Insulin. Molecular Pharmacology, 1993. 44(2): p. 271-276.
Deppe, C., et al., Structure-Activity Relationship of Covalently Dimerized Insulin Derivatives—Correlation of Partial Agonist Efficacy with Cross-Linkage at Lysine B29. Naunyn-Schmiedebergs Archives of Pharmacology, 1994. 350(2): p. 213-217.
Shojaee-Moradie, F., et al., Demonstration of a Relatively Hepatoselective Effect of Covalent Insulin Dimers on Glucose-Metabolism in Dogs. Diabetologia, 1995. 38(9): p. 1007-1013.
Du X et al, Hydroxyl group of insulin A19Tyris essential for receptor binding: studies on (A9Phe) insulin, BioChem and Mol Biology International, Academic Press, Lindon, GB vol. 45, No. 2, Jun. 1, 1998, pp. 255-260. found in extended EP search report 09837982.9 (08055; 216442).
PCT International Search Report for PCT/US2009/068716 completed by the US Searching Authority on May 3, 2010.
European supplemental search report for EP 09837983.7 completed by the EPO on Mar. 15, 2012.
Cheng et al., "The Development of an Insulin-based Prodrug," APS poster presentation, 2011.
Coffman et al., "Insulin-metal ion interactions: the binding of divalent cations to insulin hexamers and tetramers and the assembly of insulin-hexamers," Biochemistry, Aug. 9, 1988, vol. 27, No. 16, pp. 6179-6187.
De, Design of peptide-based prodrug chemistry and its application to glucagon-like peptide 1. Masters Thesis Aug. 2007. [Retrieved from the Internet on Jun. 16, 2009: <https://scholarworks iu.edu/dspace/browse?value=De%2C+ArnabBtype=author>]; p. 8, para 2; p. 16, para 3; p. 40, para 1; p. 66, para 2; p. 77, para 1-2; p. 79, para 1.
De, et al., "Investigation of the feasibily of an amide-based prodrug under physiological conditions," Int. J. Pept. Res. Ther., 14, pp. 255-262 (2008).
Du et al., "Biochemistry and Molecular Biology International," vol. 45, No. 2, Jun. 1, 1998, pp. 255-260 XP008147747.
GenBank entry AAH05278, Jul. 15, 2006 [http:www/ncbi.nim.nih.gov/protein/13528972>].

(56) References Cited

OTHER PUBLICATIONS

Han et al., "IGF-based Insulin Analogs with an A-Chain Lactam," APS poster presentation, 2011.
Kaur et al., "Novel Single Chain Insulin Analogs Consisting of a Non-Peptide Based Connection," APS poster presentation, May 12, 2011.
Han et al., "Structure-Activity Relationship of Insulin at Position $A^9$," APS poster presentation.
Han et al., "Insulin Chemical Synthesis Using a Two-Step Orthogonal Formation of the Disulfides," APS poster presentation.
Kaur et al., "Chemical Synthesis of Insulin and Related Analogs," APS poster presentation.
Kristensen et al., "Alanine Scanning Mutagenesis of Insulin," The Journal of Biological Chemistry, 1997, 272(20):12978-12983.
Madsen et al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.
Mayer et al., Insulin Structure and Function, Peptide Science 2007, 88(5):687-713.
Mroz, Piotr et al., "Bioactivity of Insulin Analogs with Altered B-Chain Secondary Structure," APS poster presentation.
O'Brien, Assay for DPPIV Activity using a Homogenous, Luminescent Method, Cell Notes, 2005, 11:8-11 (http://www.promega.com/resources/articles/pubhub/cellnotes/assay-for-dppiv-activity-using-a-homogeneous-luminescent-method/).
PCT International Search Report for PCT/US2009/068711 completed by the US Searching Authority on Feb. 4, 2010.
PCT International Search Report for PCT/US2009/068712 completed by the US Searching Authority on Mar. 24, 2010.
PCT International Search Report for PCT/US2009/068713.
PCT International Search Report for PCT/US2011/041601 completed by the US Searching Authority on Nov. 10, 2011.
Phillips et al., "Supramolecular protein engineering: design of zinc-stapled insulin hexamers as a long acting depot," J. Biol. Chem., Apr. 16, 2010, vol. 285, No. 16, pp. 11755-11759.
Schilling et al., "Degradation of Insulin by Trypsin and Alphachymotrypsin," Pharmaceutical Research 1991, 8(6):721-727 (abstract).
Quan et al., "Coordinated Interaction of the Insulin B-chain Helical Domain with the aromatic Active Site," APS poster presentation.
Wang et al., "Identification of Site(s) of Insulin Nitration by Peroxynitrite and Characterization of its Structural Change," Protein & Peptide Letters 2008, 15:1063-1067.
Zhao et al., "Improved Pharmacokinetics through Site-Specific PEGylation of Insulin Analogs," APS poster presentation, 2011.
Gershonov et al, A Novel Approach for a Water-Soluble long Acting Insulin Prodrug . . . , J. Med. Chem (2000) vol. 43, pp. 2530-2537.
Evans et al., "Effect of Ī-Endorphin C-Terminal Peptides on Glucose Uptake in Isolated Skeletal Muscles of the Mouse", Peptides, vol. 18, No. 1, pp. 165-167, (1997).
Kurapkat et al "Inactive conformation of an insulin despite its wild-type sequence", Protein Science, vol. 6, No. 3, pp. 580-587 (Mar. 1997).
Hamel et al "Cyclosporin a prodrugs: Design, systhesis and biophysical properties", J. Peptide Research, vol. 63 No. 2 pp. 147-154 (Feb. 2004).
Coy et al, J of Medicinal Chemistry, 1973, vol. 16, No. 7, 827-829.
Yang et al, "Relationship between insulin a chain regions and insulin biological activities," World J. of Gastroentero, 2000: 6(3): 371-373 (Jun. 2000).
Hinds et al, Advanced Drug Delivery Reviews 2002, (54) 505-530 (Jun. 17, 2002).
Hua et al, J of Biological Chemistry, Mar. 2008, vol. 283, No. 21, 14703-14716 (May 23, 2008).
Weiland et al, "Antagonistic effects of a covalenly dimerized insulin derivatized insulin derivative on insulin receptors in 3T3-L1 adipocytes", PNAS, vol. 87, pp. 1154-1158, Feb. 1990.
G. Rajpal et al, "Single Chain Insulins as Receptor Agonists", Molecular Endocrinology, vol. 23, No. 5, Feb. 19, 2009 p. 679-688.
Suaifan et al, "Effects of steric bulk and stereochemistry on the rates of diketopiperazine formation from N-aminoacyl-2,2-dimethylthiazolidine-4-carboxamides (Dmt dipeptide amides)—a model for a new prodrug linker system," Tetrahedron 62, pp. 11245-11266, (Nov. 2006).
Shechter et al , "Reversible pegylation of insulin facilitates its prolonged action in vitro", Eur. J. Pharm. and Biopharm. 70 (Apr. 7, 2008) p. 19-28.
Hiroshi Ogawa et al "N-Methylation of sleeted peptide bonds on the biological activity of insulin", International J of Peptide and Protein Research, vol. 30, No. 4, p. 460-473 (Oct. 1987).
Shechter et al , "Albumin-insulin conjugate releasing insulin slowly under physiogiacal conditions: a new concept for long-acting insulin", Bioconjugate Chemistry vol. 16, No. 4, p. 913-920 (Jul.-Aug. 2005).
Worrall et al "Synthesis of an organoinsulin molecule tha tcan be activated by antibody catalysis", PNAS vol. 98, No. 24, p. 13514-13518 (Nov. 20, 2001).
PCT International Search Report and Written Opinion, International Application No. PCT/US2013/061676, Apr. 25, 2014, 13 pages.

\* cited by examiner

Synthetic "A⁷-B⁷"-derived Insulin Receptor Binding

Fig. 4

A-Chain

```
                1                    21
Insulin     GIVEQCCTSICSLYQLENYCN
IGF I       ---DE---FRS-D-RR--M--A
IGF II      ----E---FRS-D-AL--T--A
```

B-Chain

```
            1                              30
Insulin    FVNQHLCGSHLVEALYLVCGERGFFYTPKT
IGF I      *GPET---AE---QF---D----YFNKP-
IGF II     AYRPSET---GE---DT-QF---D----YFSRPA
```

C-Chain

```
              1                                    35
Proinsulin  RREAEDLQVGQVELGGGPGAGSLQPLALEGSLQKR
IGF I       GYGSSSRRAPQT
IGF II      SRVSRRSR
```

D-Chain

```
         1      8
IGF I   ********
IGF II  PLKPAKSA
        *T*PAKSE
```

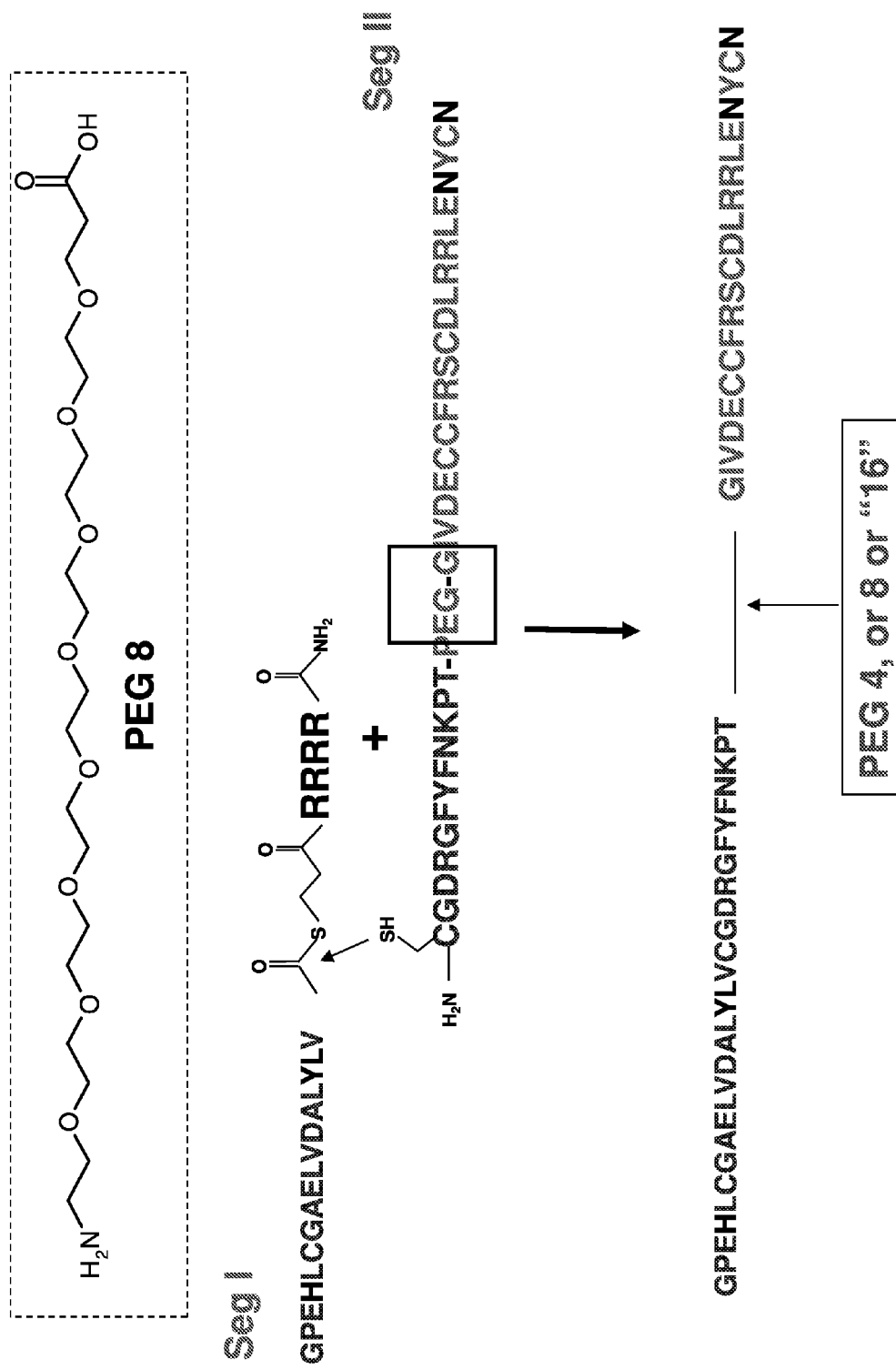

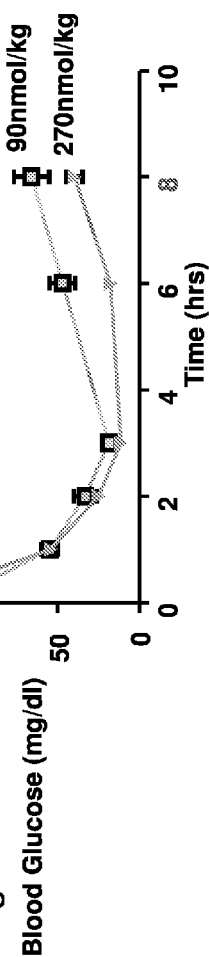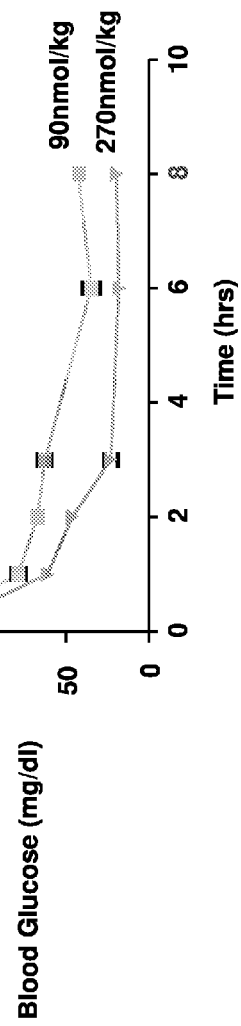
Fig. 9C
Fig. 9D

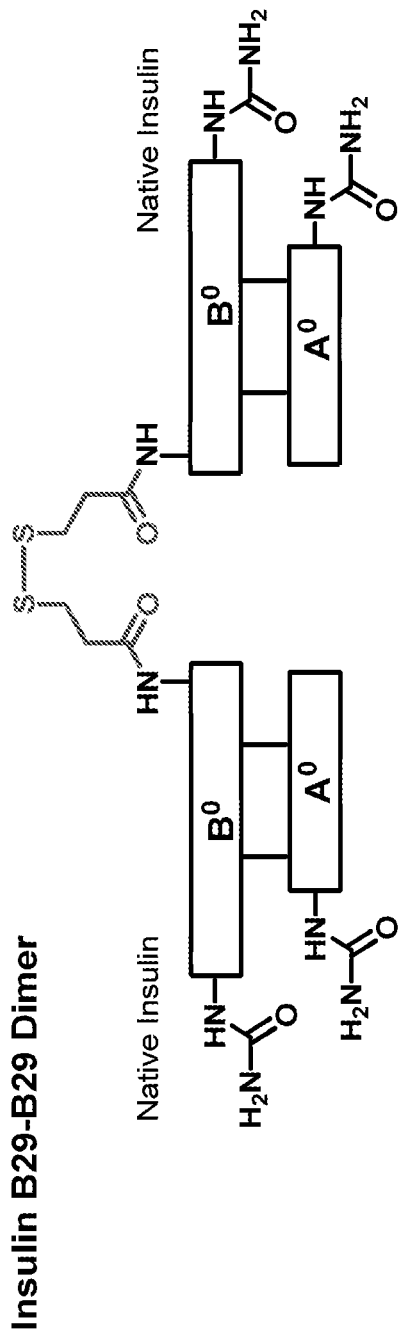
Fig. 11E: Insulin B29-B29' Dimer

*MIU-90 in C57BL/6 mice study*

MIU-1: human insulin
MIU-90: human insulin B29-B29' dimer

MIU-90 in C57BL/6 mice study

MIU-1: human insulin
MIU-90: human insulin B29-B29' dimer

Fig. 13A Synthesis of Full Agonist (DP55, H²² B1-B1' dimer)
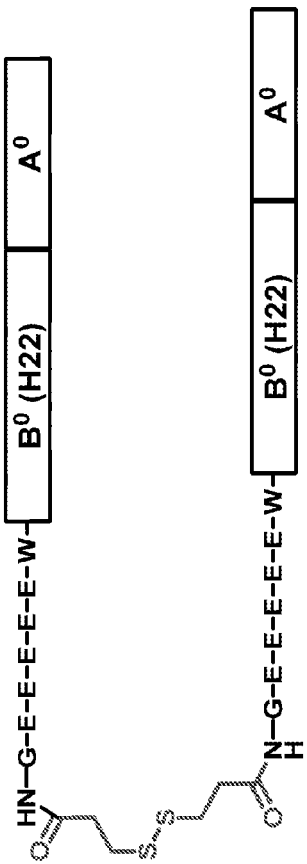
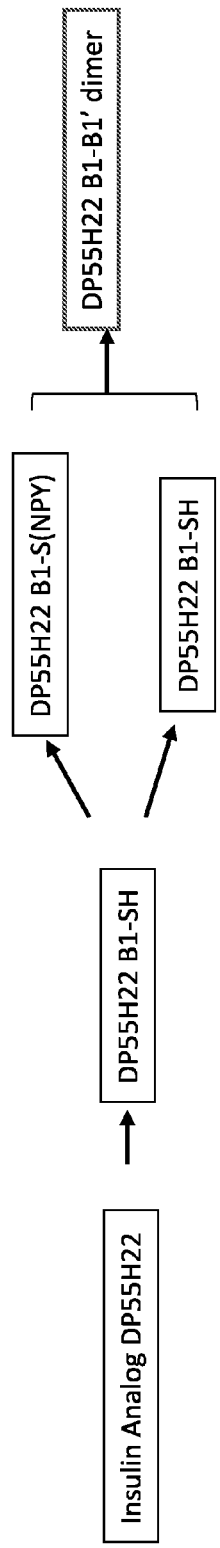
DP55, H²²
GEEEEEWFVNQHLCGSHLVEALYLVCGEHGFFYTPRGIVEQCCTSICSLYQLENYCN

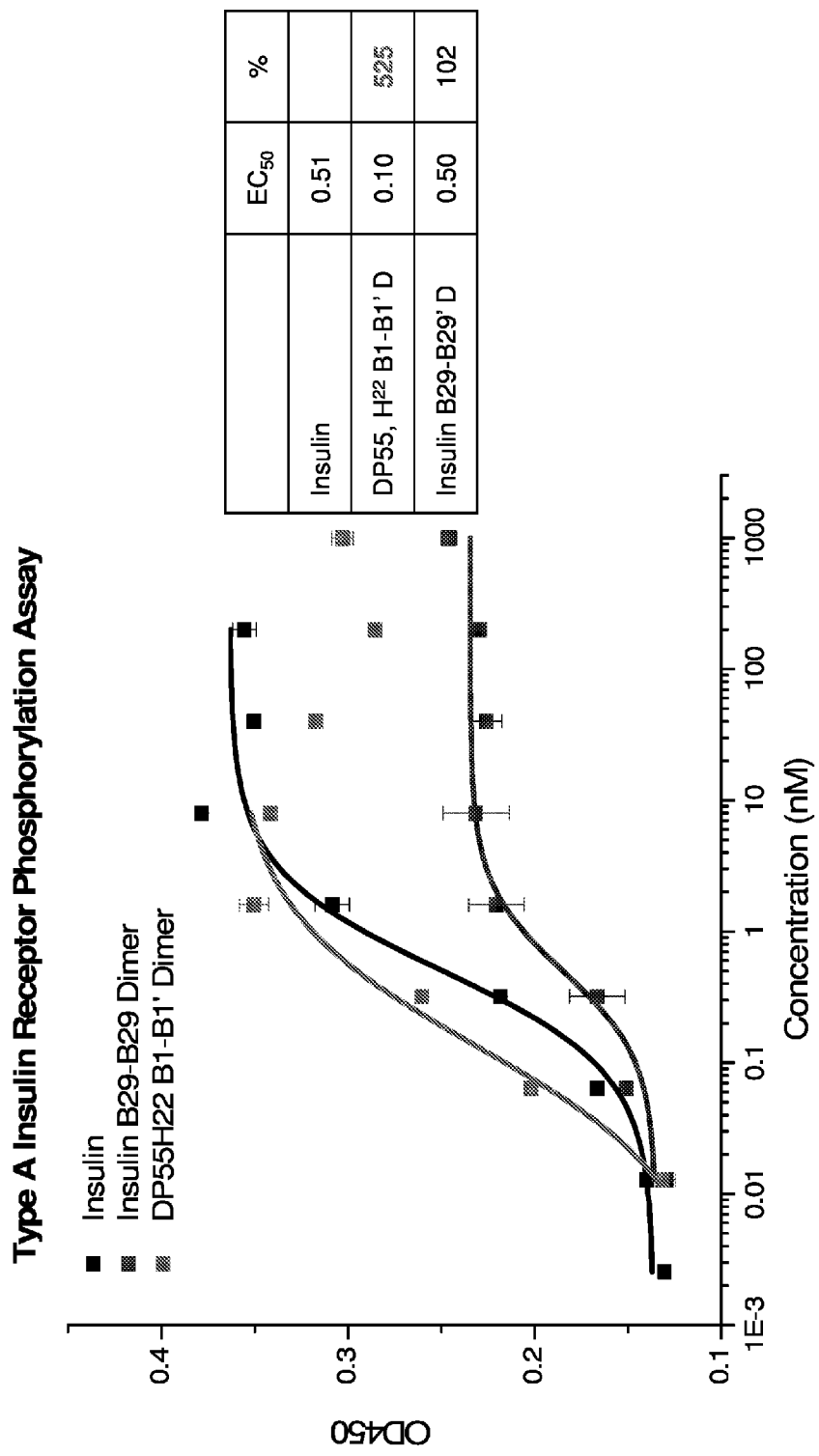
Fig. 13B: B1-B1' vs B29-B29' Activity

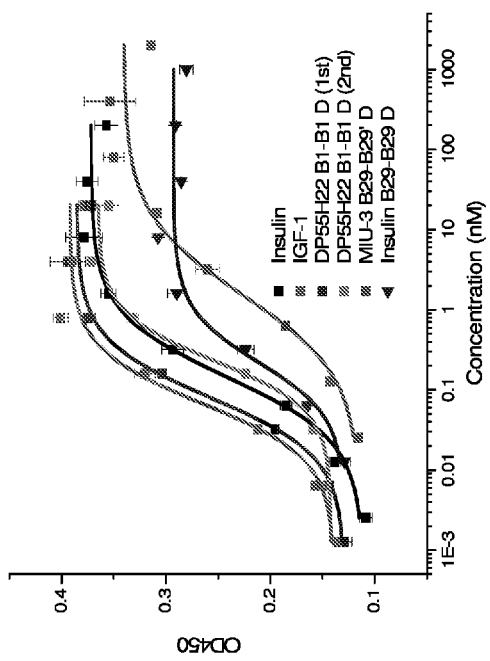
Fig. 13C: B1-B1' dimer

Effect of Insulin on blood glucose in C57BL/6 Mice

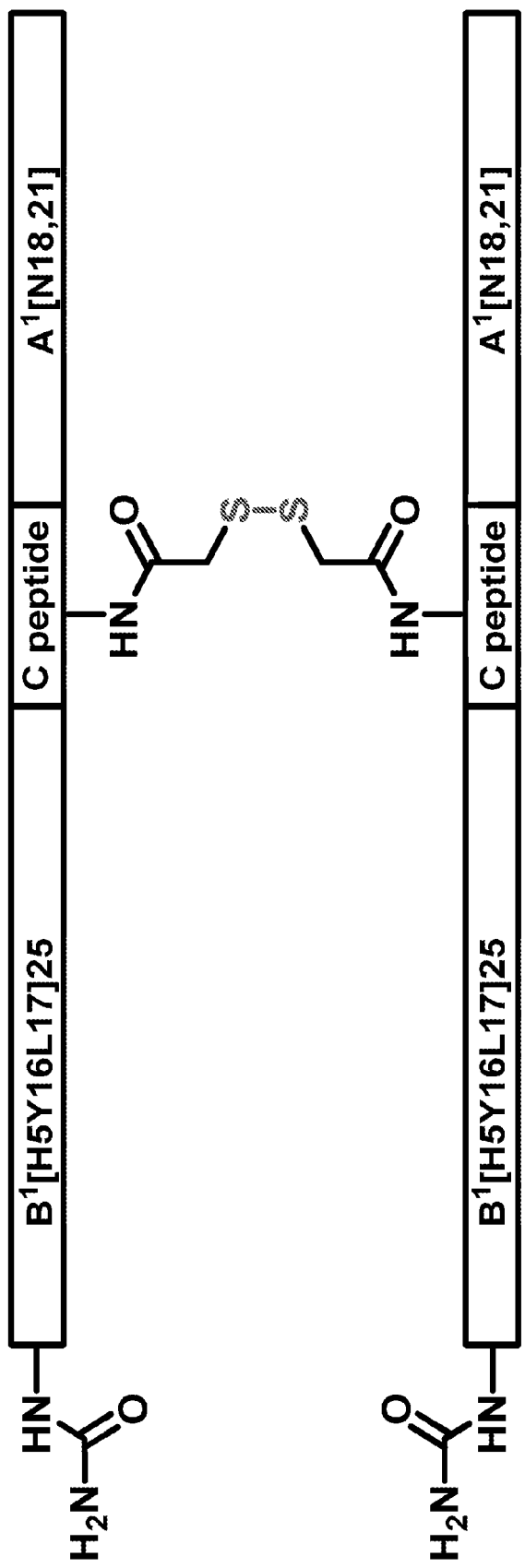
Fig. 16A: C8-C8 Disulfide Dimer

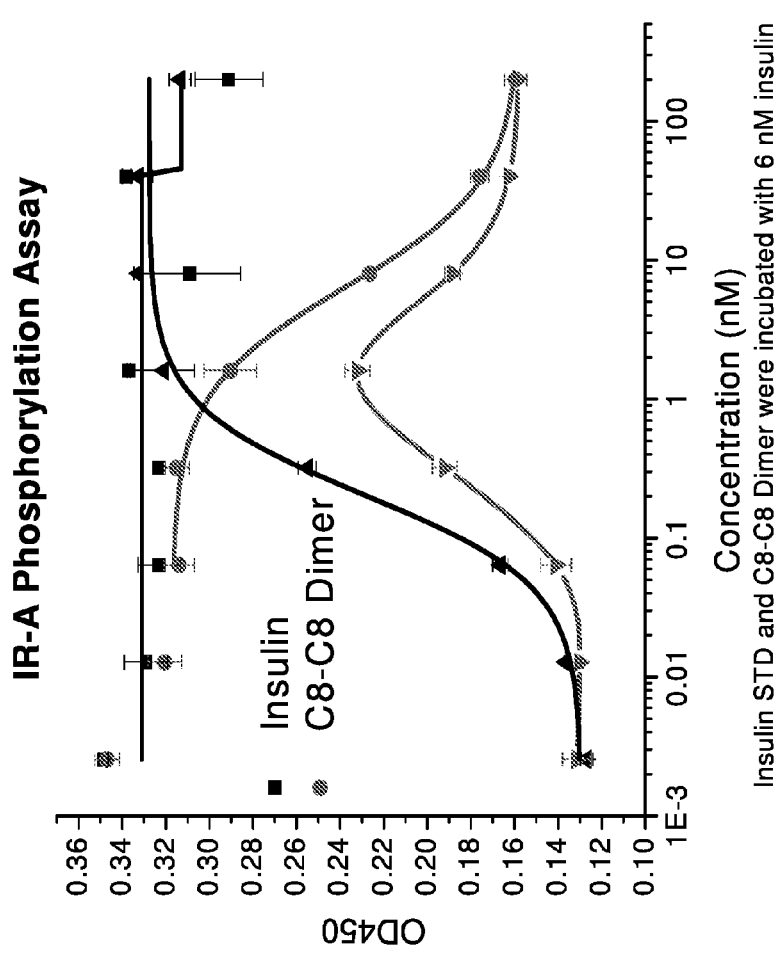

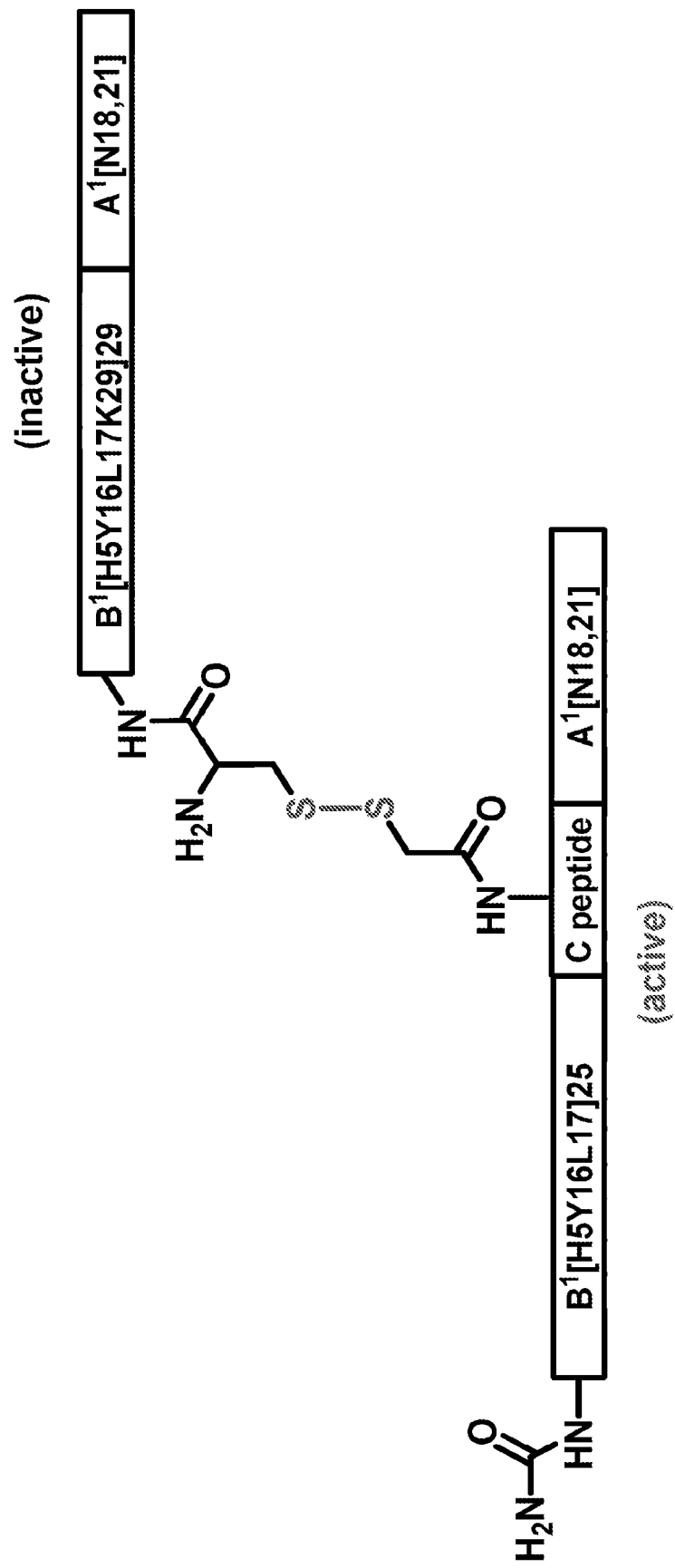
Fig. 19A: B0-C8 Disulfide Dimer (SCI-SCI Dimer)

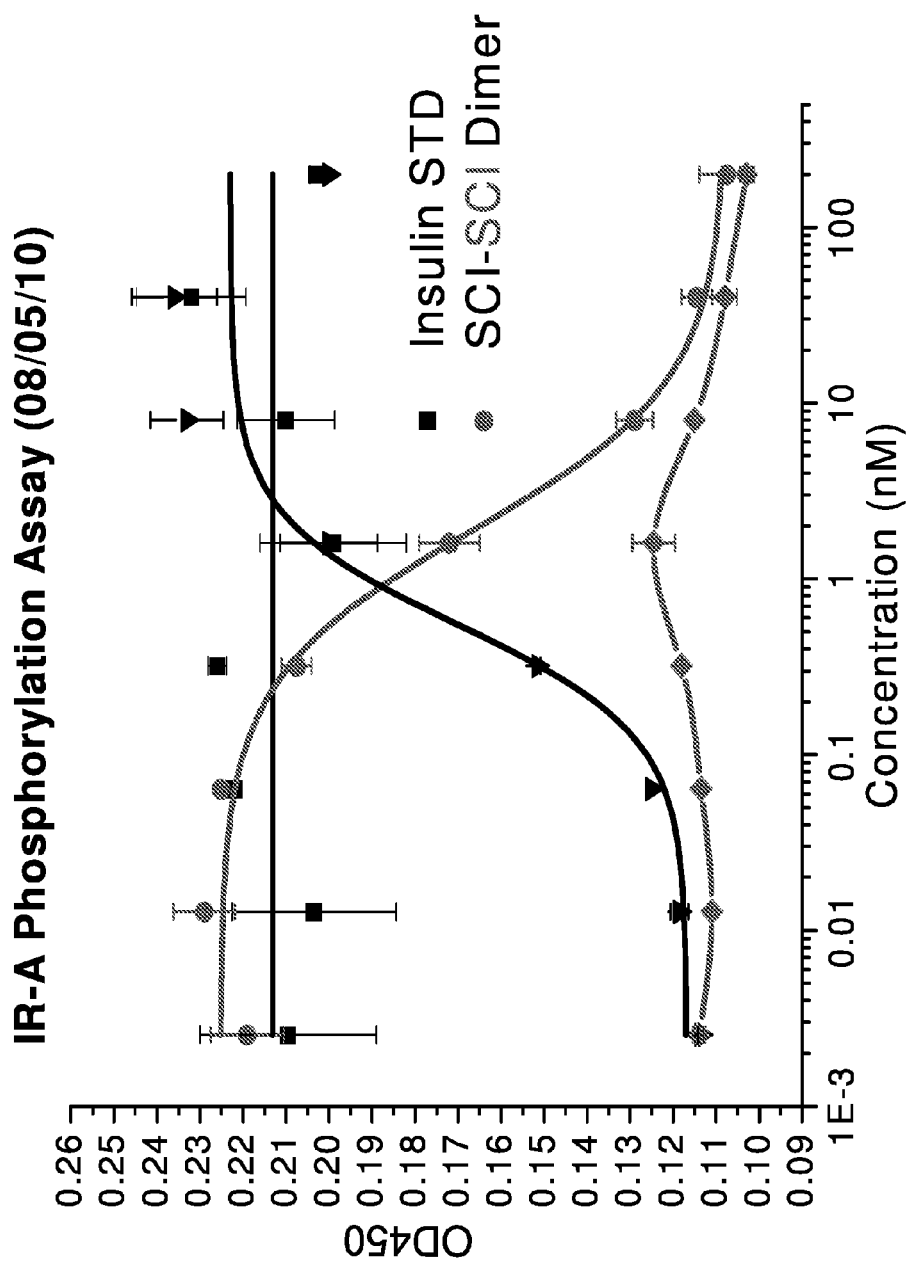

B0-B8 Disulfide Dimer (TCI-SCI Dimer)

Fig. 19C

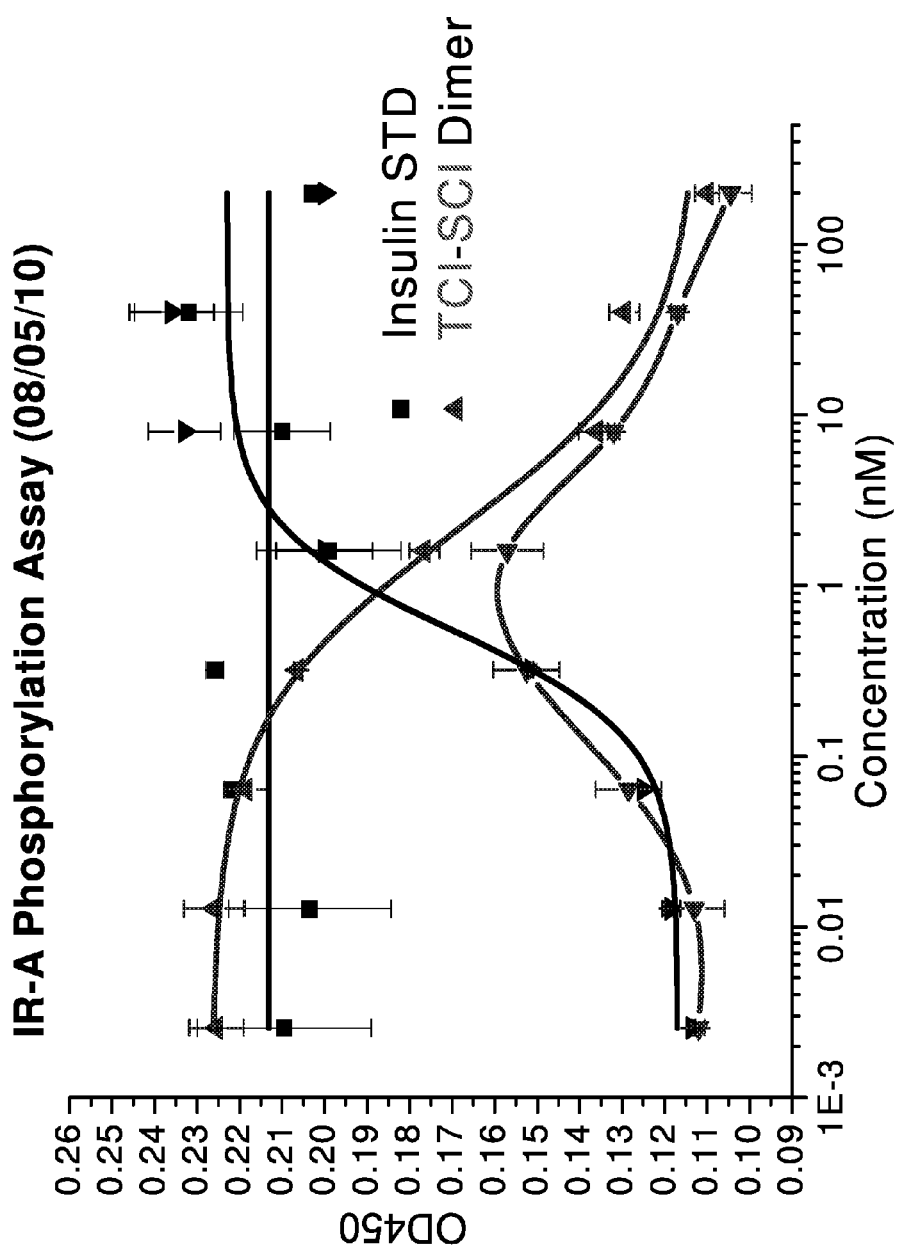
Fig. 19D: B0-C8 Disulfide Dimer: partial agonist & antagonist

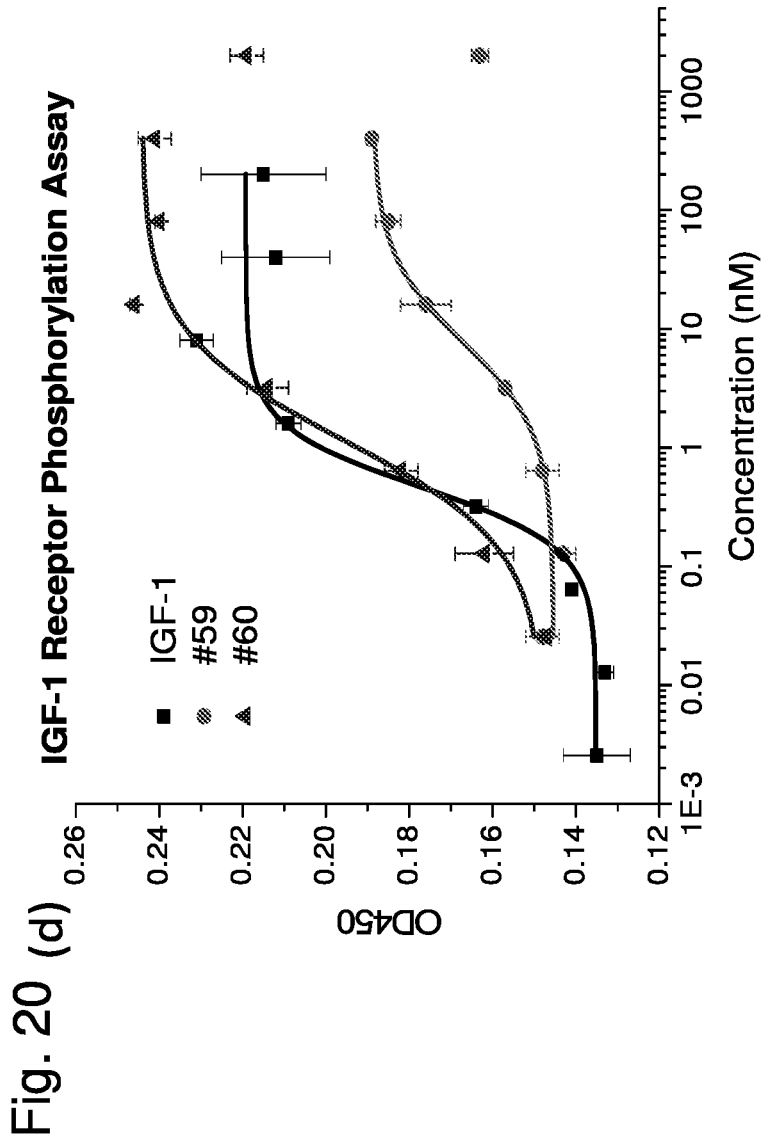

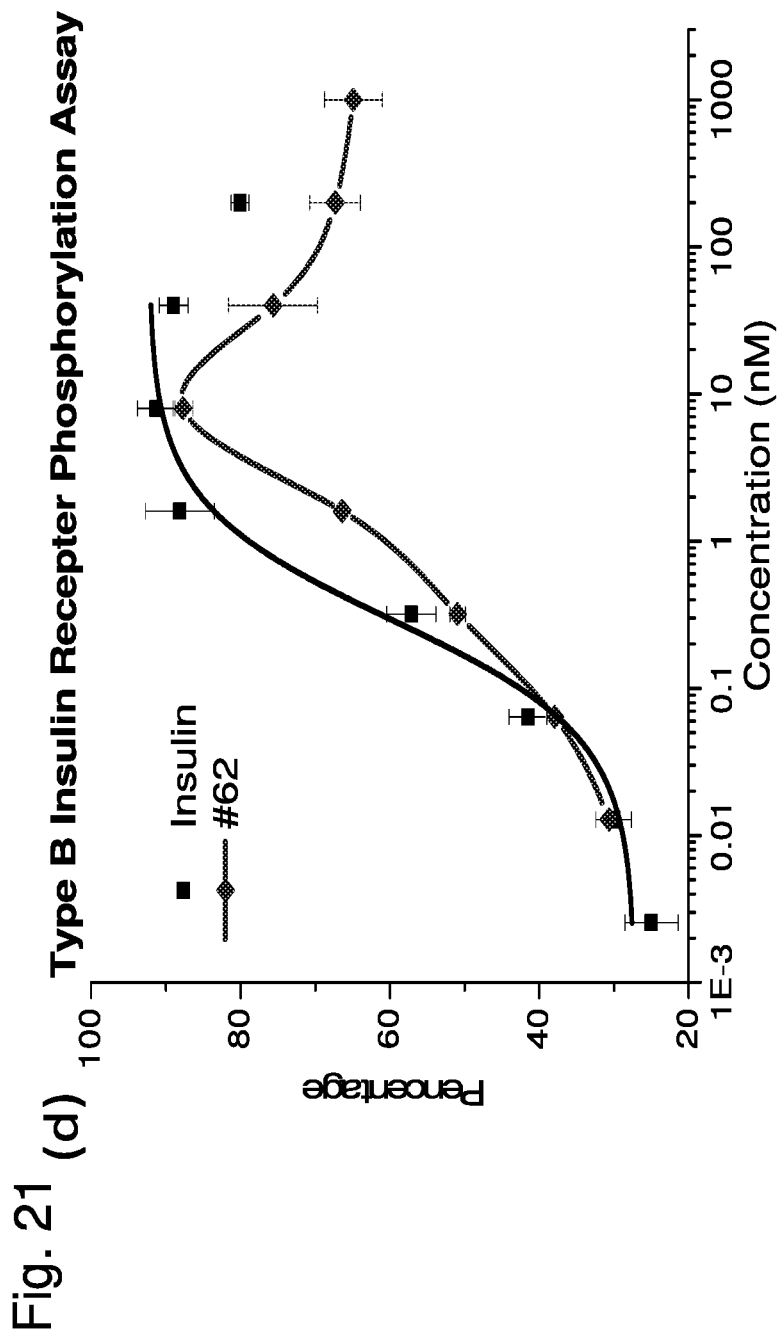

Fig. 22A
Step I: Native Chemical Ligation
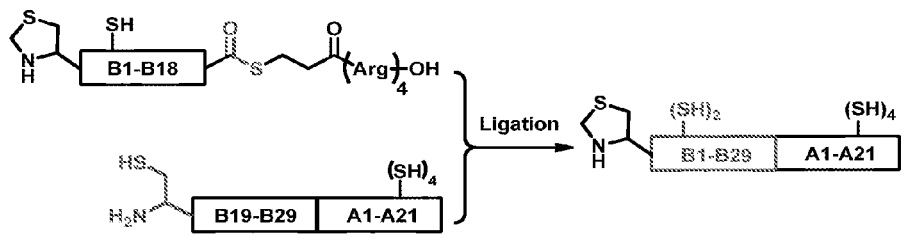
Step II: Peptide Folding and Disulfide Formation
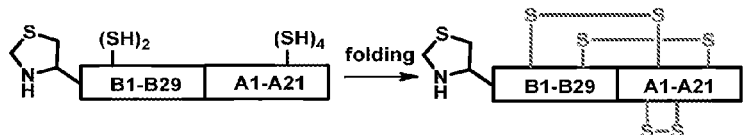
Step III: Converting Thz to Cys
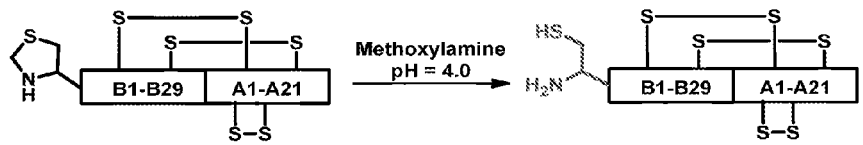
Step IV: Activating Cys$^{B1}$
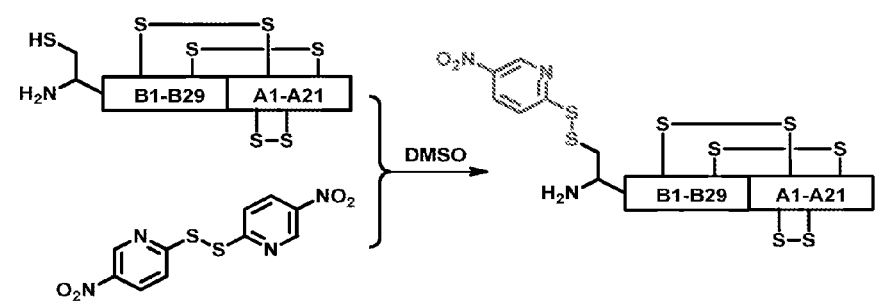
2,2'-DITHIO-bis-(5-NITROPYRIDINE)
Step V: Dimerization
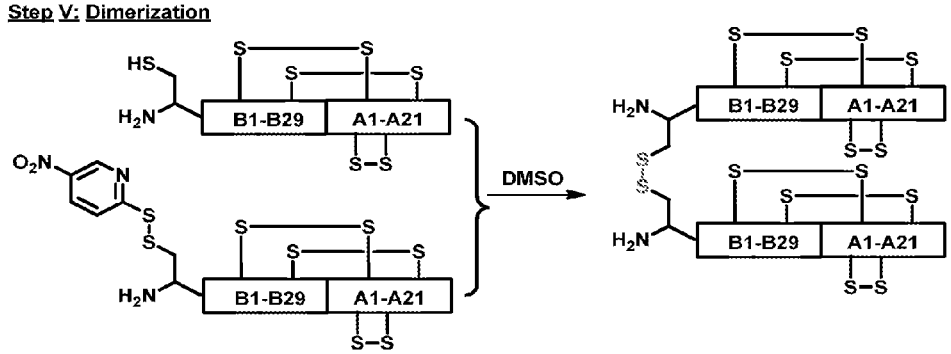

Fig. 25A
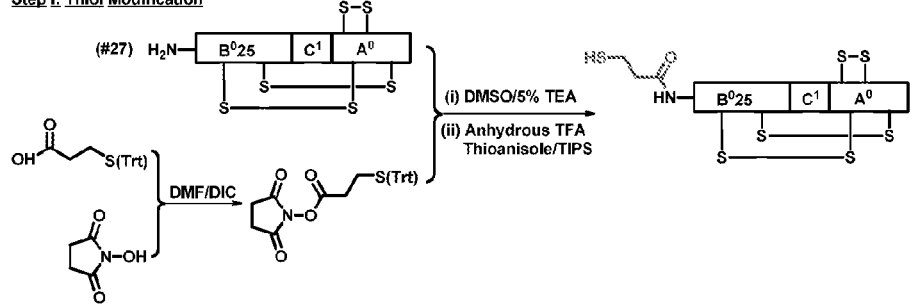
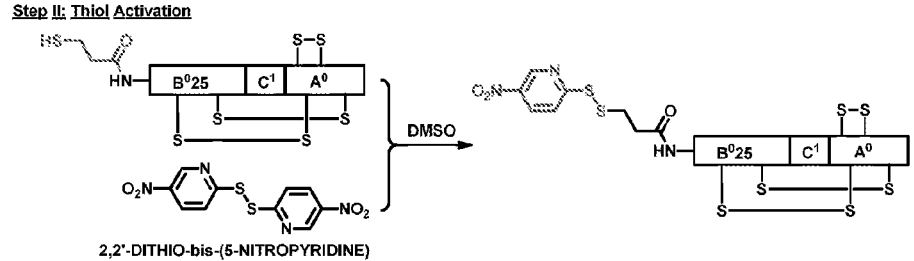

Fig. 26B
(b) IGF-2
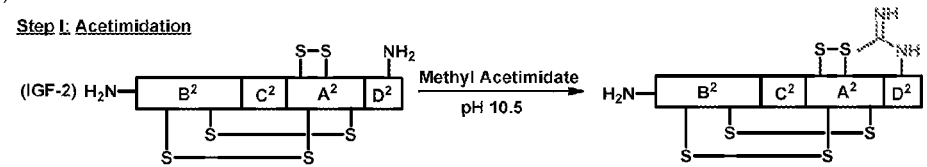
Step I: Acetimidation
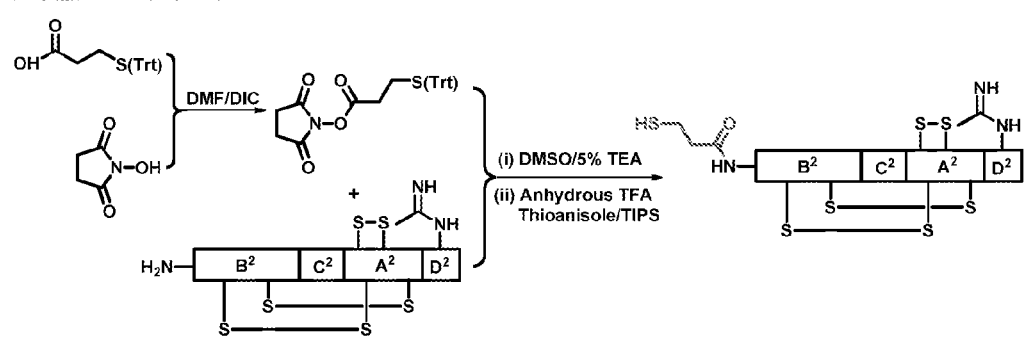
Step II: Thiol Modification

INSULIN ANALOG DIMERS

This application is a U.S. national counterpart application of international application Ser. No. PCT/US2013/061676 filed Sep. 25, 2013, which claims priority to U.S. Provisional Patent Application No. 61/705,834 filed on Sep. 26, 2012, the disclosures of which are expressly incorporated by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 45 kilobytes ACII (text) file named "216463SEQLIST_ST25.txt," created on Sep. 25, 2013.

BACKGROUND

Insulin is a peptide hormone comprised of a two chain heterodimer that is biosynthetically derived from a low potency single chain proinsulin precursor through enzymatic processing. Human insulin is comprised of two peptide chains (an "A chain" (SEQ ID NO: 1) and "B chain" (SEQ ID NO: 2)) bound together by disulfide bonds and having a total of 51 amino acids. The C-terminal region of the B-chain and the two terminal regions of the A-chain associate in a three-dimensional structure to assemble a site for high affinity binding to the insulin receptor.

Insulin demonstrates unparalleled ability to lower glucose in virtually all forms of diabetes. Unfortunately, its pharmacology is not glucose sensitive and as such it is capable of excessive action that can lead to life-threatening hypoglycemia. Inconsistent pharmacology is a hallmark of insulin therapy such that it is extremely difficult to normalize blood glucose without occurrence of hypoglycemia. Furthermore, native insulin is of short duration of action and requires modification to render it suitable for use in control of basal glucose. Established approaches to delay the onset of insulin action include reduction in solubility, and albumin binding.

The insulin-like growth factors 1 and 2 are single chain liner peptide hormones that are highly homologous in their A and B chain sequences, sharing approximately fifty percent homology with native insulin. The IGF A and B chains are linked by a "C-peptide", wherein the C-peptides of the two IGFs differ in size and amino acid sequence, the first being twelve and the second being eight amino acids in length. Human IGF-1 is a 70 aa basic peptide having the protein sequence shown in SEQ ID NO: 3, and has a 43% homology with proinsulin (Rinderknecht et al. (1978) J. Biol. Chem. 253:2769-2776). Human IGF-2 is a 67 amino acid basic peptide having the protein sequence shown in SEQ ID NO: 4. The IGFs demonstrate considerably less activity at the insulin B receptor isoform than the A-receptor isoform.

Applicants have previously identified IGF-1 based insulin peptides analogs, (wherein the native Gln-Phe dipeptide of the B-chain is replaced by Tyr-Leu) that display high activity at the insulin receptor (see PCT/US2009/068713, the disclosure of which is incorporated herein). Such analogs (referred to herein as IGF YL analog peptides) are more readily synthesized than insulin and enable the development of co-agonist analogs for insulin and IGF-1 receptors, and selective insulin receptor specific analogs. Furthermore, these insulin analogs can also be formulated as single chain insulin agonists for use in accordance with the present disclosure (see PCT/US2001/040699, the disclosure of which is incorporated herein).

Multimers of insulin and insulin analogs can be formed and used to treat diabetes in a similar fashion as native human insulin. As disclosed herein, applicants have discovered that the activity of insulin analog dimers is highly dependent on the size and position where the dimerzing linker joins the two insulin polypeptides. As disclosed herein, applicants have discovered insulin dimers that maintain full inherent potency but only partial maximal responsivity as well as dimers that are selective for the subtype B insulin receptor. Such dimers may offer a more precisely controlled onset and duration of insulin action after clearance from the site of administration and equilibration in the plasma.

SUMMARY

Disclosed herein are insulin analog dimers having insulin receptor agonist activity, wherein the level of insulin activity of the dimers is a function of the insulin polypeptide sequences, the site of dimerization and the length of the dimerization linker that connects the two insulin polypeptides. The insulin dimers are formed between a first and second insulin polypeptide wherein each insulin polypeptide comprises an A chain and a B chain. The first and second insulin polypeptides of the dimers disclosed herein can be independently selected from two chain insulin analogs or single chain insulin analogs wherein the first and second insulin polypeptides are covalently linked to one another by a covalent bond or bifunctional linker.

The first and second insulin polypeptides can be covalently bound to one another by formation of a covalent bond between two functional groups using standard techniques known to those skilled in the art. For example the two insulin polypeptides may comprise, or be modified to include, the necessary functional groups to allow the formation of a dimerizing linkage comprising a disulfide linkage, an amide linkage, a thio-ether linkage or an ester linkage. In certain embodiments, a bifunctional linker is provided to link the first and second insulin polypeptide, wherein the bifunctional linker comprises a hydroxyl group and a carboxylate, or an amine group and a carboxylate or a thiol group and a carboxylate or a thiol group and a thiol group. In one embodiment the first and second insulin polypeptides are linked via a disulfide bond and in an alternative embodiment the first and second insulin polypeptides are linked via a thio-ether bond.

In one embodiment the insulin dimer is an insulin super agonist (i.e., have greater activity at the insulin receptor than native insulin) comprising a first and second insulin polypeptide wherein the first and second insulin polypeptide are each two chain insulins. More particularly, the first insulin polypeptide is linked to the second insulin polypeptide via the N-terminal alpha amine of each B chain or via the side chains of the B1 amino acids of the first and second insulin polypeptides. In one embodiment the first and second insulin polypeptides are linked to one another via a disulfide bond located at the N-terminal alpha amine of each B chain of the respective first and second insulin single chain polypeptides. In one embodiment the A and B chains of the first and second insulin polypeptides are native human insulin A and B chains. In one embodiment an improved method of treating diabetes is provided wherein a patient is administered an insulin super agonist. Advantageously, use of a super agonist allows for the administration of the insulin dimer in a reduced concentration, including at a concentration 33%, 30%, 25% 20%, or less than 20% of standard dose concentration of native insulin. In addition, conjugates can be formed using the super agonist insulin dimer wherein the size of the non-insulin component is reduced in half (relative to what would be used with an insulin monomer) since the non-insulin component would be linked to both the first and second insulin polypeptides comprising the dimer. For example the first and second insulin polypeptides can be pegylated, wherein the individual PEG chains are 5-10 or 5-20 Kd in size. Administration of reduced concentrations of the insulin super agonist with reduced molecular weight conjugate moieties linked to the first and second insulin polypeptides are anticipated to provide beneficial results from a commercial and therapeutic perspective.

In one embodiment the insulin dimer exhibits insulin partial agonist activity. Applicants do not wish to be bound to any one theory, but the partial agonist activity of the insulin dimers disclosed herein is believed to derive from the fact that the dimers exhibit mixed agonist/antagonist activity. In one embodiment an insulin partial agonist dimer is provided comprising a first and second insulin polypeptide wherein the first and second insulin polypeptide are each two chain insulin polypeptides and the first insulin polypeptide is linked to the second insulin polypeptide via the carboxy terminus of each of the B chain, including for example, through an amino acid side chain of an amino acid position independently selected from B26, B27, B28, B29 and B30. In one embodiment the insulin partial agonist has less than 66%, 50%, 40%, 33% or 20% maximal activity at the insulin receptor relative to native insulin. In one embodiment the first and second insulin polypeptides are linked to one another via a disulfide bond between the amino acid side chains of a B Chain C-terminal amino acid (e.g. cysteine) optionally through a linker added to the side chain of a C-terminal amino acid (e.g. B27-B30). In one embodiment the first and second insulin polypeptide are linked via a disulfide bond formed between the amino acid side chains of the respective B29 amino acids of the first and second insulin polypeptides. In one embodiment the B29 amino acid is a modified lysine with a side chain of Structure I:

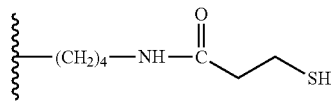

and the first and second insulin polypeptides are linked via a disulfide bond. In one embodiment the A and B chains of the first and second insulin polypeptides are native human insulin A and B chains.

In an alternative embodiment an insulin dimer is provided that exhibits insulin partial agonist activity wherein at least one of the first and second insulin polypeptides is a single chain insulin and the first and second insulin polypeptides are linked to one another via an amino acid side chain of the linking moiety of the single chain insulin polypeptide and the N-terminal alpha amine, or the side chain of an N-terminal amino acid, of the B chain of the second insulin polypeptide. Optionally, the first and second insulin polypeptides are joined via a linker (e.g. cysteine) added to the side chain of an amino acid of the single chain insulin analog, added to the N-terminal alpha amine, or to the side chain of an N-terminal amino acid (e.g., B1-B4) of the respective B chains of the first and second insulin polypeptides. In one embodiment the first and second insulin polypeptides each comprise a modified lysine having a side chain of Structure I:

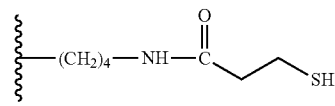

and the first and second insulin polypeptides are linked via a disulfide bond. In one embodiment both the first and the second insulin polypeptides are single chain insulin polypeptides with the B chain linked to the A chain via a linking moiety and insulin dimer formed by linking an amino acid side chain of each of the respective linking moieties of the first and second insulin polypeptides to one another. In accordance with one embodiment the first and second insulin polypeptides comprise a B chain and A chain of human insulin, or analogs or derivatives thereof. In one embodiment, the side chain of the amino acid at position 8 of the linking moiety of the single chain insulin polypeptide is linked to N-terminal amino acid of the B chain of the second insulin polypeptide (i.e., a B1-C8 linkage). In one embodiment the dimer comprises a human insulin polypeptide linked to an IGF1 or IGF II, or analog thereof, via a B1 to C8 linkage.

In one embodiment, one or both of the insulin polypeptides of the insulin dimers disclosed herein further comprises a self-cleaving dipeptide element (U-B) covalently linked to an N-terminal alpha amine or side chain amine of an amino acid of the first or second insulin polypeptide of the dimer via an amide or ester linkage (see International applications WO 2009/099763 and PCT/US2009/068713 the disclosures of which are incorporated by reference herein). Subsequent removal of the dipeptide will occur under physiological conditions and in the absence of enzymatic activity. In one embodiment the prodrug element comprises a dipeptide of the structure U-B, wherein U is an amino acid or a hydroxy acid, B is an N-alkylated amino acid linked to said single chain insulin agonist through an amide bond between a carboxyl moiety of B and an amine of an insulin polypeptide, wherein U, B, or the amino acid of the single chain insulin agonist to which U-B is linked is a non-coded amino acid.

Additional derivatives of the insulin agonist dimers are encompassed by the present disclosure including modifications that improve the solubility of the underlying insulin polypeptides. In one embodiment the solubility of the insulin polypeptides is enhanced by the covalent linkage of a hydrophilic moiety to the N-terminus of the A or B chain or to a side chain of an amino acid of one or both of the first and second insulin polypeptides, including the linkage to a side chain of an amino acid of the linking peptide of single chain insulin polypeptides. In one embodiment the hydrophilic moiety is linked to the side chain of an amino acid at a position selected from the group consisting of A9, A14 and A15 of the A chain or positions B1, B2, B10, B22, B28 or B29 of the B chain. In one embodiment the hydrophilic moiety is a polyethylene glycol chain, an acyl group or an alkyl group. In one embodiment the hydrophilic moiety is albumin, including for example, albumins such as human serum albumin (HSA) and recombinant human albumin (rHA). In one embodiment the hydrophilic moiety is a polyethylene glycol (PEG) chain, having a molecular weight selected from the range of about 500 to about 40,000

Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons.

Acylation or alkylation can increase the half-life of the insulin polypeptides in circulation. Acylation or alkylation can advantageously delay the onset of action and/or extend the duration of action at the insulin receptors. The insulin analogs may be acylated or alkylated at the same amino acid position where a hydrophilic moiety is linked, including for example, at position 8 of the linking moiety or on the side chain of an amino acid comprising a self-cleaving dipeptide element.

Also encompassed by the present disclosure are pharmaceutical compositions comprising the insulin dimers disclosed herein, and a pharmaceutically acceptable carrier. In accordance with one embodiment a pharmaceutical composition is provided comprising any of the insulin dimers disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an insulin dimer as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment an improved method of regulating blood glucose levels in insulin dependent patients is provided, and more particularly, a method of treating diabetes with a reduced risk of hypoglycemia is provided. The method comprises the steps of administering to a patient a partial insulin agonist dimer in an amount therapeutically effective for the control of diabetes. In one embodiment the partial agonist insulin dimer comprises a first and second insulin polypeptide that are linked to one another through a dimerization linker, wherein the first and second insulin polypeptides each independently comprise an insulin polypeptide selected from the group consisting of
i) a two chain insulin analog comprising an A chain and a B chain linked via interchain disulfide bonds; and ii) a single chain insulin analog comprising an A chain, a B chain and a linking moiety, wherein a first end of said linking moiety is covalently bound to the carboxy terminus of the B chain and a second end of said linking moiety is covalently bound to the amino terminus of the A chain. In one embodiment the A chain comprises a sequence of GIVX$_4$X$_5$CCX$_8$X$_9$X$_{10}$CX$_{12}$LX$_{14}$X$_{15}$LEX$_{18}$X$_{19}$CX$_{21}$-R$_{13}$ (SEQ ID NO: 70), the B chain comprises a sequence of X$_{25}$LCGX$_{29}$X$_{30}$LVX$_{33}$X$_{34}$LYLVCGX$_{41}$X$_{42}$GFX$_{45}$ (SEQ ID NO: 44); and
a) the first and second insulin polypeptides are linked to one another via the side chain of the amino acids at position B29 of the respective first and second insulin polypeptides;

b) at least one of said first and second insulin polypeptides is a single chain insulin polypeptide and the first and second insulin polypeptides are linked to one another via the side chain of the amino acid at position B1 of one of said first and second insulin polypeptides and the side chain of an amino acid of said linking moiety; or
c) both the first and second insulin polypeptides are single chain insulin polypeptides and the first and second insulin polypeptides are linked to one another via the side chain of amino acids of the linking moieties moiety of the respective first and second insulin polypeptides. Advantageously, the partial agonist dimers exhibit a decreased maximal dose response, thus applicants anticipate they will decrease the risk of hypoglycemia upon administration to a patient.

In a further embodiment insulin dimers are provided that are selective for the subtype B insulin receptor (IR-B). Applicants have discovered that a dimer formed between an insulin based polypeptide and a polypeptide (e.g., IGF I or IGF II) that exhibits a higher IR-A/IR-B ratio (i.e., higher affinity for IR-A relative to IR-B) relative to native insulin showed a preference for IR-B activation as indicated by the higher level of maximal receptor response at IR-B relative to IR-A. In one embodiment insulin dimers are provided that are selective for the subtype B insulin receptor. In one embodiment the dimer comprises a first and second insulin polypeptide, each of which are single chain insulin polypeptides comprising an A chain, a B chain and a linking moiety, wherein a first end of said linking moiety is covalently bound to the carboxy terminus of the B chain and a second end of said linking moiety is covalently bound to the amino terminus of the A chain, wherein
the first insulin polypeptide comprises
an A chain sequence of GIVEQCCTSICSLYQLENYCN (SEQ ID NO: 1);
a B chain sequence of FVNQHLCGSHLVEALYLVCGERGFF (SEQ ID NO: 2); and
a first linking moiety comprising a sequence selected from the group consisting of PEG8-K-PEG4 and GYGSSSRX$_{68}$APQT (SEQ ID NO: 9), and the second polypeptide comprises
an A chain sequence of TPAX$_{75}$SEGIVEECCFRSCDLALLETYCA (SEQ ID NO: 88) or GIVDECCFRSCDLRRLEMYCA (SEQ ID NO: 5);
a B chain sequence of AYRPSETLCGGELVDTLQFVCGDRGFYFSRPA (SEQ ID NO: 87) or GPETLCGAELVDALQFVCGDRGFYFNKPT (SEQ ID NO: 10); and
a second linking moiety comprising a sequence selected from the group consisting of PEG8-K-PEG4 and GYGSSSRX$_{68}$APQT (SEQ ID NO: 9), wherein
X$_{68}$ is arginine, ornithine, lysine or an amino acid comprising a side chain of Structure I:

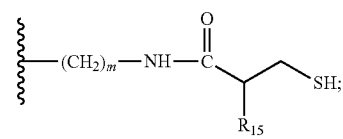

X$_{75}$ is lysine or arginine; and m is an integer selected from 1-4, and R$_{15}$ is H or NH$_2$, further wherein
the first and second insulin polypeptides are linked to one another via (i) the N terminal amine or side chain of the N-terminal amino acid of one of said first or second insulin polypeptide and the side chain of the linking moiety of the other insulin polypeptide or (ii) the side chain of an amino acid of each respective the linking moiety of the first and second insulin polypeptide.

BRIEF DESCRIPTION OF THE DRAWINGS

FIG. 4 is an alignment of the human proinsulin (A chain, SEQ ID NO: 1; B chain, SEQ ID NO: 2 and the C chain, SEQ ID NO: 92) and insulin-like growth factors I and II (IGF I; SEQ ID NO: 3 and IGF II; SEQ ID NO: 4) amino acid sequences. The alignment demonstrates that these three peptides share a high level of sequence identity (* indicates a space with no corresponding amino acid and a dash (-) indicates the identical amino acid as present in insulin).

FIG. 5A is a graph comparing relative insulin receptor binding of native insulin and the A19 IGF prodrug derivative (IGF1YL: dK,(N-isobutylG) over time (0 hours, 5 hours and 52 hours) incubated in PBS. FIG. 5B is a graph comparing relative insulin receptor binding of native insulin and the A19 IGF prodrug derivative (IGF1YL: dK,(N-isobutylG) over time (0 hours, 3.6 hours and 24.8 hours) incubated in 20% plasma/PBS at 37° C. As indicated by the data presented in the graph, increased activity is recovered from the A19 IGF prodrug derivative sample as the prodrug form is converted to the active IGF1YL peptide.

FIGS. 8A-8C relate to single chain insulin analogs that use a PEG polymer as the linking moiety. FIG. 8A is a schematic drawing showing the preparation of an IGF-1 YL single chain insulin analog that uses a PEG polymer as the linking moiety. FIGS. 8B & 8C are graphs depicting the relative in vitro binding activity (FIG. 8B) and phosphorylation activity (FIG. 8C) of single chain insulin analogs linked via a 4, 8 or 16 monomeric PEG linking moiety relative to the native insulin heteroduplex.

FIGS. 9A-9D are graphs showing the results of comparative insulin tolerance tests conducted on mice comparing the ability of human insulin to reduce and sustain low blood glucose concentration relative to three different acylated insulin analogs. The polypeptides were tested at two different concentrations (27 nmol/kg and 90 nmol/kg). The acylated insulins included MIU-41, MIU-36 and MIU-37. MIU-41[$B^1$(H5,H10,Y16,L17)26A: $A^1$(H8,rEC16-K14,N18,N21)], is a two chain insulin analog having a C16 acylation via a gamma glutamic acid linker attached to a lysine residue located at position A14. MIU-36 [$B^1$(C16-K0,H5,H10,Y16,L17)26A: $A^1$(N18,N21)], is a two chain insulin analog having a C16 acylation linked to the N-terminus of the B chain). MIU-37 [$B^1$(H5,H10,Y16,L17,C16rE-K22)26A: $A^1$(N18,N21)], is a two chain insulin analog having a C16 acylation via a gamma glutamic acid linker attached to a lysine residue located at position B22.

FIGS. 10A and 10B are graphs showing the results of insulin tolerance tests comparing the ability of the acylated insulin analog Detemir relative to the pegylated single chain insulin analog MIU-56 to reduce and maintain low blood glucose levels. FIGS. 10C and 10D show the blood glucose $AUC_{24\ hrs}$ in mice administered Detemir and MIU-56, respectively.

FIG. 11E shows the structure of the B29-B29' insulin. The dimer has been modified relative to native insulin in that the N-terminus of the A and B chains have been carbamylated as well as the lysine at position B29 to allow the attachment of sulfhydyl linkers for forming the disulfide bond at B29. The two insulin polypeptides each comprising a native human insulin A chain and B chain linked to one another by the native insulin disulfides (A6-A11, A7-B7, A20-B19) that are not shown but are resident in the dimer form.

FIGS. 13A-13C demonstrates the in vitro insulin activity for the B1-B1' insulin dimer. FIG. 13A shows the synthesis of the B1-B1' insulin dimer wherein two single chain insulin analogs are linked via a disulfide bond through the B1 amino acid side chain. The initial dimer is inactive since the A china is directly linked to the carboxy terminus of the B chain. However upon cleavage of the single chain entity with trypsin, thus converting the single chain insulin analogs into two chain insulin analogs and forming an insulin dimer comprising two chain insulin polypeptides, activity is restored, FIG. 13B shows the relative in vitro activity of native insulin, the B1-B1' insulin dimer (after cleavage with trypsin) and the B29-B29' insulin dimer at the type A insulin receptor. The B1-B1' insulin dimer (after cleavage with trypsin) is a full insulin agonist with greater potency than native insulin. As shown in FIG. 13C the B1-B1' insulin dimer has activity at both the type A and Type B insulin receptors and replacement of the histidine with the native arginine at position B22 has no significant impact on activity.

FIG. 16A-16C demonstrates the in vitro insulin activity for an insulin agonist dimer formed between two single chain IGF-1 insulin agonist analogs wherein the first and second insulin agonist analog polypeptides comprising the dimer each have an A chain, a B chain and a C-peptide, wherein the N-terminus of the A chain is linked to the C-terminus of the B chain via the C-peptide and the two single chain IGF-1 insulin agonist analogs are linked to one another via a disulfide bond between the side chain of the two C8 amino acids. FIG. 16A shows the general structure of the C8-C8' IGF-1 analog dimer. FIG. 16B shows results of in vitro activity of the C8-C8' IGF-1 analog dimer at the subtype A insulin receptor. The C8-C8' IGF-1 analog dimer has an appreciably reduced (approximately 75%) maximal dose response relative to native insulin (see FIG. 16B, ▼). Furthermore, at higher concentrations (e.g., greater than 1 nmole/kg) the C8-C8' IGF-1 analog dimer has antagonist properties (see FIG. 16B, ●). FIG. 16C demonstrates that the C8-C8' IGF-1 analog dimer retains selectivity for the insulin receptor relative to the IGF-1 receptor.

Figure 19C:
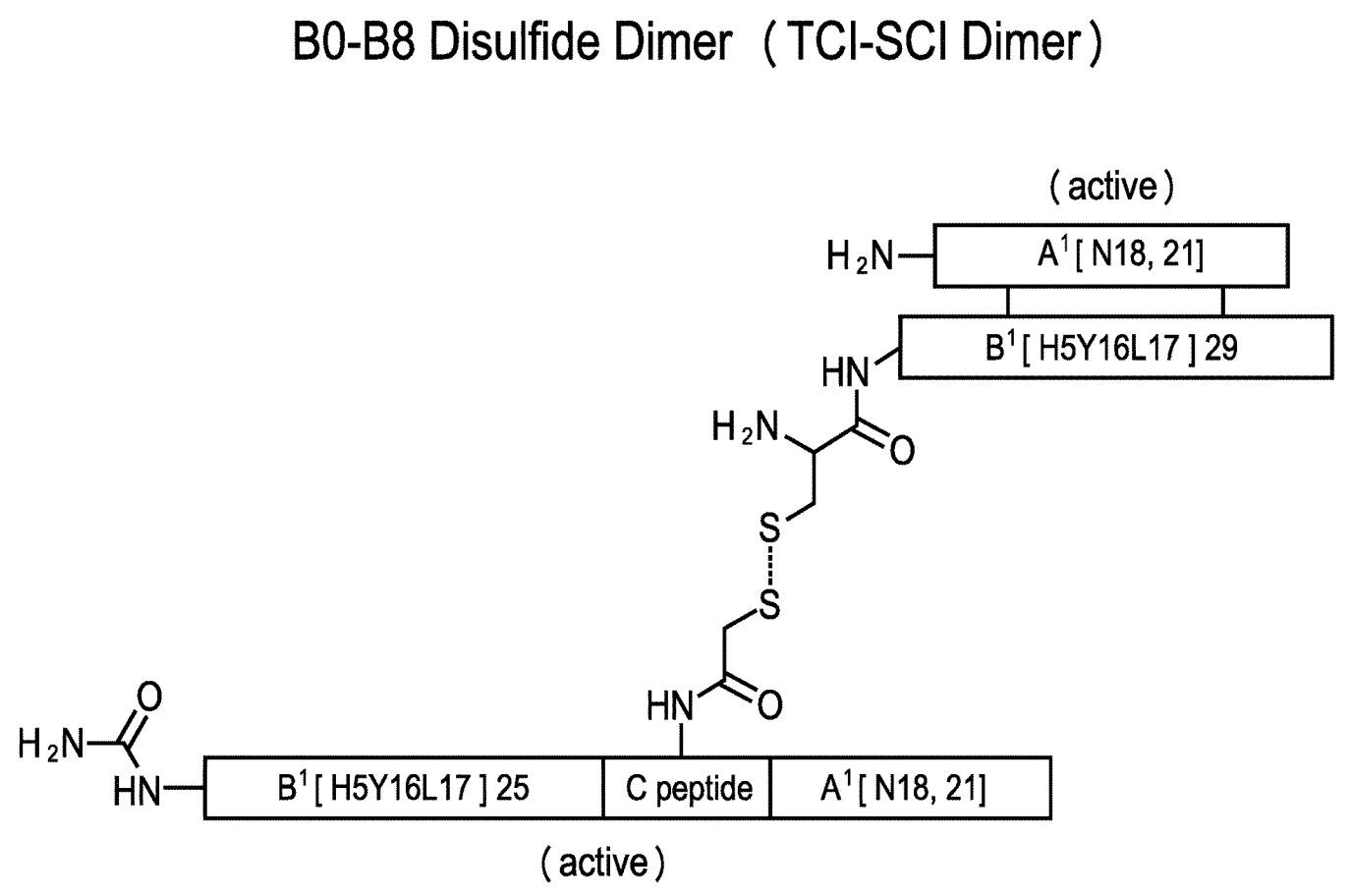

FIGS. 19A-19D demonstrates the activities of an insulin dimer comprising two IGF-1 insulin agonist analogs. FIG. 19A provides the structure of an insulin dimer formed between a first inactive insulin polypeptide and a second insulin polymer via a disulfide bond formed between the side chain of the N-terminal amino acid of the first inactive insulin polymer and the side chain of the C8 amino acid of the second single chain IGF-1 insulin agonist analog. The first insulin polypeptide is inactive since the A chain has been fused directly to the B chain. As indicated by the data presented in FIG. 19B this polypeptide is an insulin antagonist. However, a dimer formed using the same B0-C8 linkage between two active insulin polypeptides has been discovered to exhibit partial agonist and antagonist activity. FIG. 19C shows the structure of a dimer formed between a single chain IGF-1 insulin agonist and a two chain IGF-1 insulin agonist wherein the two insulin polypeptides are linked by a disulfide bond between the side chain of the N-terminal amino acid of the first insulin polypeptide and the side chain of the C8 amino acid of the second insulin polypeptide. As indicated by the data presented in FIG. 19D this polypeptide exhibits insulin partial agonist and antagonist activity.

FIG. 22A: Synthetic Scheme for the preparation of compound #48 (CysB1-CysB1 #2 dimer; see Tables 15-17).

FIG. 25A: Synthetic scheme for the preparation of B1-thiol-activated insulin analog #27.

FIG. 26B: Synthetic scheme for the preparation of B1-thiol-modified IGF-2.

DETAILED DESCRIPTION

Definitions

Figure 1:
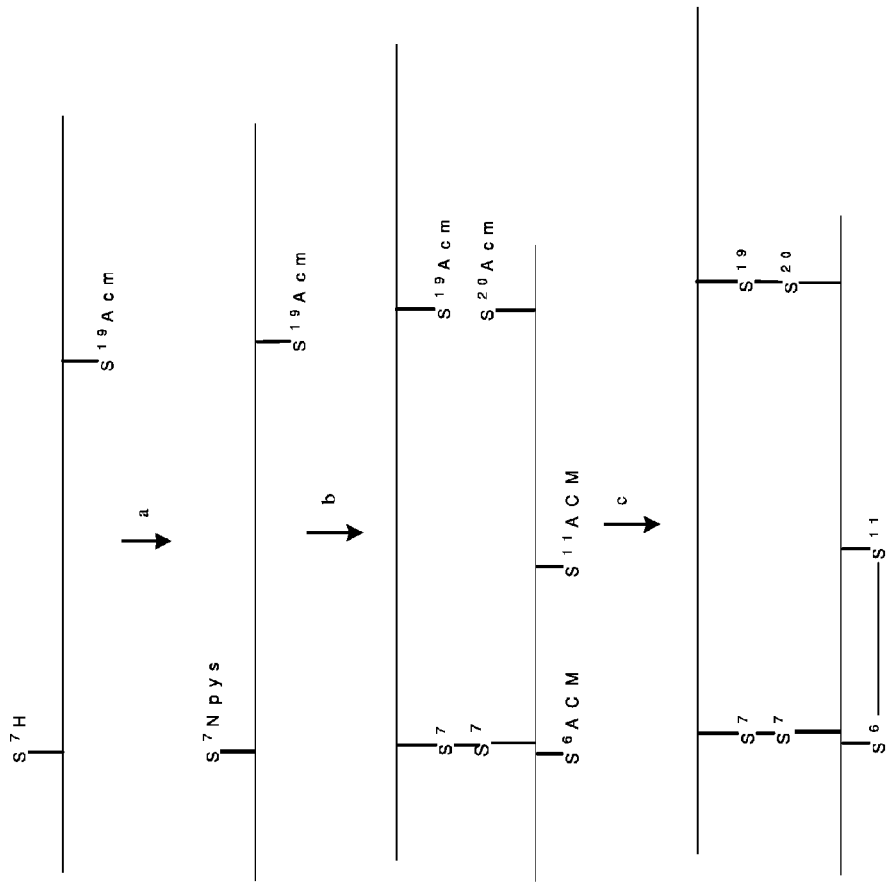
FIG. 1. is a schematic overview of the two step synthetic strategy for preparing human insulin. Details of the procedure are provided in Example 1.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "prodrug" is defined as any compound that undergoes chemical modification before exhibiting its pharmacological effects.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid without specifying its stereochemistry is intended to encompass either the L or D form of the amino acid, or a racemic mixture. However, in the instance where an amino acid is designated by its three letter code and includes a superscript number, the D form of the amino acid is specified by inclusion of a lower case d before the three letter code and superscript number (e.g., dLys⁻¹), wherein the designation lacking the lower case d (e.g., Lys⁻¹) is intended to specify the native L form of the amino acid. In this nomenclature, the inclusion of the superscript number designates the position of the amino acid in the insulin analog sequence, wherein amino acids that are located within the insulin analog sequence are designated by positive superscript numbers numbered consecutively from the N-terminus. Additional amino acids linked to the insulin analog peptide either at the N-terminus or through a side chain are numbered starting with 0 and increasing in negative integer value as they are further removed from the insulin analog sequence. For example, the position of an amino acid within a dipeptide prodrug linked to the N-terminus of an insulin analog is designated aa⁻¹-aa⁰-insulin analog, wherein aa⁰ represents the carboxy terminal amino acid of the dipeptide and aa⁻¹ designates the amino terminal amino acid of the dipeptide.

As used herein the term "hydroxyl acid" encompasses amino acids that have been modified to replace the alpha carbon amino group with a hydroxyl group.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

A "dipeptide" is a compound formed by linkage of an alpha amino acid or an alpha hydroxyl acid to another amino acid, through a peptide bond.

As used herein the term "chemical cleavage" absent any further designation encompasses a non-enzymatic reaction that results in the breakage of a covalent chemical bond.

A "bioactive polypeptide" refers to polypeptides which are capable of exerting a biological effect in vitro and/or in vivo.

As used herein a general reference to a peptide/polypeptide is intended to encompass peptides/polypeptides that have modified amino and carboxy termini. For example, an amino acid sequence designating the standard amino acids is intended to encompass standard amino acids at the N- and C-terminus as well as a corresponding hydroxyl acid at the N-terminus and/or a corresponding C-terminal amino acid modified to comprise an amide group in place of the terminal carboxylic acid.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In some embodiments, the acyl group causes the peptide to have one or more of (i) a prolonged half-life in circulation, (ii) a delayed onset of action, (iii) an extended duration of action, (iv) an improved resistance to proteases, such as DPP-IV, and (v) increased potency at the IGF and/or insulin peptide receptors.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases, such as DPP-IV, and increased potency at the IGF and/or insulin receptors.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" encompasses salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "hydrophilic moiety" encompasses any compound that is readily water-soluble or readily absorbs water, and which are tolerated in vivo by mammalian species without toxic effects (i.e. are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of an insulin analog refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

Throughout the application, all references to a particular amino acid position by letter and number (e.g. position A5) refer to the amino acid at that position of either the A chain (e.g. position A5) or the B chain (e.g. position B5) in the respective native human insulin A chain (SEQ ID NO: 1) or B chain (SEQ ID NO: 2), or the corresponding amino acid position in any analogs thereof. For example, a reference herein to "position B28" absent any further elaboration would mean the corresponding position B27 of the B chain of an insulin analog in which the first amino acid of SEQ ID NO: 2 has been deleted. Similarly, amino acids added to the N-terminus of the native B chain are numbered starting with B0, followed by numbers of increasing negative value (e.g., B-1, B-2 . . . ) as amino acids are added to the N-terminus. Alternatively, any reference to an amino acid position in the linking moiety of a single chain analog, is made in reference to the native C chain of IGF 1 (SEQ ID NO: 17). For example, position 9 of the native C chain (or the "position C9") has an alanine residue.

As used herein the term "native human insulin peptide" is intended to designate the 51 amino acid heteroduplex comprising the A chain of SEQ ID NO: 1 and the B chain of SEQ ID NO: 2, as well as single-chain insulin analogs that comprise SEQ ID NOS: 1 and 2. The term "insulin polypeptide" as used herein, absent further descriptive language is intended to encompass the 51 amino acid heteroduplex comprising the A chain of SEQ ID NO: 1 and the B chain of SEQ ID NO: 2, as well as single-chain insulin analogs thereof (including for example those disclosed in published international application WO96/34882 and U.S. Pat. No. 6,630,348, the disclosures of which are incorporated herein by reference), including heteroduplexes and single-chain analogs that comprise modified analogs of the native A chain and/or B chain and derivatives thereof (e.g. IGF1 and IGF2) that have activity at the insulin receptors. Such modified analogs include modification of the amino acid at position A19, B16 or B25 to a 4-amino phenylalanine or one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. Insulin polypeptides as defined herein can also be analogs derived from a naturally occurring insulin by insertion or substitution of a non-peptide moiety, e.g. a retroinverso fragment, or incorporation of non-peptide bonds such as an azapeptide bond (CO substituted by NH) or pseudo-peptide bond (e.g. NH substituted with CH$_2$) or an ester bond (e.g., a depsipeptide, wherein one or more of the amide (—CONHR—) bonds are replaced by ester (COOR) bonds).

An "A19 insulin analog" is an insulin peptide that has a substitution of 4-amino phenylalanine or 4-methoxy phenylalanine for the native tyrosine residue at position 19 of the A chain of native insulin.

An "IGF1 analog" as used herein is a generic term that encompasses polypeptides that comprise an A and B chain wherein each of the A and B chain sequences share 90% or greater sequence identity with native IGF1 A and B chain sequences, respectively. The term also encompasses IGF YL analogs.

An "IGF2 analog" as used herein is a generic term that encompasses polypeptides that comprise an A and B chain wherein each of the A and B chain sequences share 90% or greater sequence identity with native IGF2 A and B chain sequences, respectively.

An "IGF YL analog" is a peptide comprising an IGF A chain of SEQ ID NO: 19 and an IGF B chain of SEQ ID NO: 51.

As used herein, the term "single-chain insulin analog" encompasses a group of structurally-related proteins wherein insulin or IGF A and B chains, or analogs or derivatives thereof, are covalently linked to one another to form a linear polypeptide chain. As disclosed herein the single-chain insulin analog comprises the covalent linkage of the carboxy terminus of the B chain to the amino terminus of the A chain via a linking moiety.

As used herein the term "insulin A chain", absent further descriptive language is intended to encompass the 21 amino acid sequence of SEQ ID NO: 1 as well as functional analogs and derivatives thereof, including the A chain of A19 insulin analogs and other analogs known to those skilled in the art, including modification of the sequence of SEQ ID NO: 1 by one or more amino acid insertions, deletions or substitutions at positions selected from A4, A5, A8, A9, A10, A12, A14, A15, A17, A18, A21.

As used herein the term "insulin B chain", absent further descriptive language is intended to encompass the 30 amino acid sequence of SEQ ID NO: 2, as well as modified functional analogs of the native B chain, including modification of the amino acid at position B16 or B25 to a 4-amino phenylalanine or one or more amino acid insertions, deletions or substitutions at positions selected from B1, B2, B3, B4, B5, B9, B10, B13, B14, B17, B20, B21, B22, B23, B25, B26, B27, B28, B29 and B30 or deletions of any or all of positions B1-4 and B26-30.

As used herein the term "derivative" is intended to encompass chemical modification to a compound (e.g., an amino acid), including chemical modification in vitro, e.g. by introducing a group in a side chain in one or more positions of a polypeptide, e.g. a nitro group in a tyrosine residue, or iodine in a tyrosine residue, or by conversion of a free carboxylic group to an ester group or to an amide group, or by converting an amino group to an amide by acylation, or by acylating a hydroxy group rendering an ester, or by alkylation of a primary amine rendering a secondary amine or linkage of a hydrophilic moiety to an amino acid side chain. Other derivatives are obtained by oxidation or reduction of the side-chains of the amino acid residues in the polypeptide.

As used herein the term IGF A chain, absent further descriptive language is intended to encompass the 21 amino acid sequence of native IGF 1 or IGF 2 (SEQ ID NOs: 5 and 7 respectively), as well as functional analogs thereof known to those skilled in the art, including modification of the sequence of SEQ ID NO: 5 and 7 by one or more amino acid substitutions at positions selected from A5, A8, A9, A10, A12, A14, A15, A17, A18, A21.

As used herein the term "IGF YL B chain", absent further descriptive language is intended to encompass an amino acid sequence comprising SEQ ID NO: 21, including for example the sequence of SEQ ID NO: 6, as well as analogs of the IGF YL B chain and derivatives thereof, including modification of the amino acid at position B16 or B25 to a 4-amino phenylalanine or one or more amino acid substitutions at positions selected from B1, B2, B3, B4, B5, B9, B10, B13, B14, B17, B20, B21, B22, B23, B26, B27, B28, B29 and B30 or deletions of any or all of positions B1-4 and B26-30.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an $EC_{50}$ of 1 nM at a first receptor and an $EC_{50}$ of 100 nM at a second receptor has 100-fold selectivity for the first receptor relative to the second receptor.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine As used herein the general term "polyethylene glycol chain" or "PEG chain", encompasses mixtures of condensation polymers of ethylene oxide and water, in a branched or straight chain, represented by the general formula H(OCH$_2$CH$_2$)$_n$OH, wherein n is at least 2. "Polyethylene glycol chain" or "PEG chain" is used in combination with a numeric suffix to indicate the approximate average molecular weight thereof. For example, PEG-5,000 refers to polyethylene glycol chain having a total molecular weight average of about 5,000 Daltons.

As used herein the term "pegylated" and like terms includes any compound that has been modified from its native state by linking a polyethylene glycol chain to the compound. A "pegylated polypeptide" is a polypeptide that has a PEG chain covalently bound to the polypeptide.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein an "insulin dimer" is a complex comprising two insulin polypeptides covalently bound to one another via a linker. The term insulin dimer, when used absent any qualifying language, encompasses both insulin homodimers and insulin heterodimers. An insulin homodimer comprises two identical insulin polypeptides, whereas an insulin heterodimer comprises two insulin polypeptides that differ.

The term "C$_1$-C$_n$ alkyl" wherein n can be from 1 through 6, as used herein, represents a branched or linear alkyl group having from one to the specified number of carbon atoms. Typical C$_1$-C$_6$ alkyl groups include, but are not limited to, methyl, ethyl, n-propyl, iso-propyl, butyl, iso-Butyl, sec-butyl, tert-butyl, pentyl, hexyl and the like.

The terms "C$_2$-C$_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—CH$_2$—CH=CH$_2$), 1,3-butadienyl, (—CH=CHCH=CH$_2$), 1-butenyl (—CH=CHCH$_2$CH$_3$), hexenyl, pentenyl, and the like.

The term "C$_2$-C$_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "(C$_1$-C$_3$ alkyl)(C$_6$-C$_{10}$ aryl)" refers to a 5 to 10 membered aryl that is attached to a parent moiety via a one to three membered alkyl chain.

The term "heteroaryl" as used herein refers to a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "(C$_1$-C$_n$ alkyl)(C$_5$-C$_6$ heteroaryl)" refers to a 5 or 6 membered heteroaryl that is attached to a parent moiety via a one to "n" membered alkyl chain.

As used herein, the term "halo" refers to one or more members of the group consisting of fluorine, chlorine, bromine, and iodine.

As used herein the term "patient" without further designation is intended to encompass any warm blooded vertebrate domesticated animal (including for example, but not limited to livestock, horses, cats, dogs and other pets) and humans.

The term "isolated" as used herein means having been removed from its natural environment. In some embodiments, the analog is made through recombinant methods and the analog is isolated from the host cell.

The term "purified," as used herein encompasses the isolation of a molecule or compound in a form that is substantially free of contaminants normally associated with the molecule or compound in a native or natural environment and means having been increased in purity as a result of being separated from other components of the original composition. The term "purified polypeptide" is used herein to describe a polypeptide which has been separated from other compounds including, but not limited to nucleic acid molecules, lipids and carbohydrates.

A "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. For example a peptidomimetic may include a sequence of naturally-occurring amino acids with the insertion or substitution of a non-peptide moiety, e.g. a retroinverso fragment, or incorporation of non-peptide bonds such as an azapeptide bond (CO substituted by NH) or pseudo-peptide bond (e.g. NH substituted with CH$_2$), or an ester bond (e.g., depsipeptides, wherein one or more of the amide (—CONHR—) bonds are replaced by ester (COOR) bonds). Alternatively the peptidomimetic may be devoid of any naturally-occurring amino acids.

As used herein the term "charged amino acid" or "charged residue" refers to an amino acid that comprises a side chain that is negatively charged (i.e., de-protonated) or positively charged (i.e., protonated) in aqueous solution at physiological pH. For example, negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

As used herein the term "acidic amino acid" refers to an amino acid that comprises a second acidic moiety (other than the alpha carboxylic acid of the amino acid), including for example, a side chain carboxylic acid or sulfonic acid group.

As used herein the term "a mini-PEG linker" absent further descriptive language is a linear polymer of ethylene glycol, comprising 4-16 ethylene glycol units, that covalently links a polypeptide to a second polymer, typically a second polypeptide. Optionally the mini-PEG may comprise amino acids.

Abbreviations

Insulin analogs will be abbreviated as follows:

The insulin A and B chains will be designated by a capital A for the A chain and a capital B for the B chain wherein a superscript 0 (e.g., A$^0$ or B$^0$) will designate the base sequence is an insulin sequence (A chain: SEQ ID NO: 1, B chain SEQ ID NO: 2) and a superscript 1 (e.g., $A^1$ or $B^1$) will designate the base sequence is an IGF-1 sequence (A chain: SEQ ID NO: 5, B chain SEQ ID NO: 87). Modifications that deviate from the native insulin and IGF sequence are indicated in parenthesis following the designation of the A or B chain (e.g., $[B^1(H5,H10,Y16,L17): A^1(H8,N18,N21)]$) with the single letter amino acid abbreviation indicating the substitution and the number indicating the position of the substitution in the respective A or B chain, using native insulin numbering. A colon between the A and B chain indicates a two chain insulin whereas a dash will indicate a covalent bond and thus a single chain analog. In single chain analogs a linking moiety will be included between the A and B chains and the designation C1 refers to the native IGF 1 C peptide, SEQ ID NO: 17. The designation "position C8" in reference to the linking moiety designates an amino acid located at the position corresponding to the eighth amino acid of SEQ ID NO: 17.

Embodiments

Disclosed herein are insulin analog dimers that have insulin receptor agonist activity. The level of insulin activity of the dimers is a function of the dimeric structure, and in particular, the sequence of the insulin analog, the length of the dimerization linker and the site of dimerization that connects the two insulin polypeptides. The insulin dimers disclosed herein are formed between a first and second insulin polypeptide wherein each insulin polypeptide comprises an A chain and a B chain. The first and second insulin polypeptides can be independently selected from two chain insulin analogs (i.e., wherein the A and B chains are linked only via interchain disulfide bonds between internal cysteine residues) and single chain insulin analogs (i.e., wherein the A and B chains are covalently linked to one another in a linear chain, and also include interchain disulfide bonds) wherein the first and second insulin polypeptides are linked to one another to form the dimer by a covalent bond or bifunctional linker. In accordance with one embodiment the first and second insulin polypeptides are linked to one another by a disulfide bond or a bifunctional linker joining:

A) the N-terminal alpha amine or N-terminal amino acid side chain of the B chain of the first insulin polypeptide to
  i) the N-terminal alpha amine or N-terminal amino acid side chain of the second insulin polypeptide; or
  ii) the side chain of an amino acid of the linking moiety joining the B chain to the A chain of the second insulin polypeptide, when the second insulin polypeptide is a single chain insulin analog;

B) the side chain of the B29 amino acid of the B chain of the first insulin polypeptide to
  i) the side chain of the B29 amino acid of the B chain of the second insulin polypeptide; or
  ii) the side chain of an amino acid of the linking moiety joining the B chain to the A chain of the second insulin polypeptide; or C) the side chain of an amino acid of a first linking moiety joining the B chain to the A chain of the first insulin polypeptide, when the first insulin polypeptide is a single chain insulin analog, to the side chain of an amino acid of a second linking moiety joining the B chain to the A chain of the second insulin polypeptide. In one embodiment when the dimerizing linker joins the first and second insulin polypeptides through a side chain of an amino acid of the linking moiety, the linkage occurs through the amino acid at position C8 of the linking moiety.

In one embodiment the linking moiety of the single chain analog comprises a mini-PEG linker, a short linear polymer of about 8-16 ethylene glycol units and optionally one or more amino acids. In one embodiment the mini-PEG linker comprises the structure $(PEG)_{6-8}$-K-$PEG_{4-6}$, including for example, PEG8-K-PEG4. Dimers formed between single chain insulin polypeptides comprising a mini-PEG linking moiety, in one embodiment, are linked together by a dimerization bond or bifunctional linker, optionally attached to the side chain of an amino acid (e.g., lysine) of the mini-PEG linker. For example, in one embodiment the side chain of the lysine of the mini-PEG linker PEG8-K-PEG4 can be further modified to provide the structure

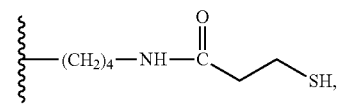

allowing the side chain to participate in a disulfide bond. In another embodiment the linking moiety is a peptide linker, including for example the IGF 1 $C^1$ or IGF 2 $C^2$ peptide. In one embodiment the first and second insulin polypeptides are linked together by a bond or bifunctional linker attached to the side chain of the 8th amino acid of a 12 amino acid peptide linker. In one embodiment the $C^1$ or $C^2$ peptide linking moiety of the single chain insulin analog is modified, optionally by a substitution at position 8, to comprise an amino acid comprising a side chain of the structure

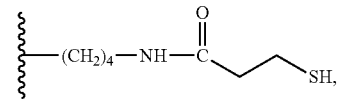

allowing the side chain to participate in a disulfide bond.

The insulin dimers disclosed herein can comprise any of the derivatives of native human insulin that are known to have activity at the insulin receptor. In one embodiment the first and second insulin polypeptides of the dimers comprise an A chain amino acid sequence of $GIVX_4X_5CCX_8X_9X_{10}CX_{12}LX_{14}X_{15}LEX_{18}X_{19}CX_{21}$-$R_{13}$ (SEQ ID NO: 70) and a B chain amino acid sequence of $X_{25}LCGX_{29}X_{30}LVX_{33}X_{34}LYLVCGX_{41}X_{42}GFX_{45}$ (SEQ ID NO: 44), wherein $X_4$ is glutamic acid or aspartic acid; $X_5$ is glutamic acid or glutamine; $X_8$ is threonine, histidine or phenylalanine; $X_9$ is serine, arginine, ornithine or alanine; $X_{10}$ is serine or isoleucine; $X_{12}$ is serine or aspartic acid; $X_{14}$ is arginine, tyrosine, ornithine or alanine; $X_{15}$ is glutamine, arginine, alanine, ornithine or leucine; $X_{18}$ is methionine, asparagine or threonine; $X_{19}$ is tyrosine, 4-methoxy-phenylalanine or 4-amino phenylalanine; $X_{21}$ is alanine, glycine or asparagine; $X_{25}$ is histidine or threonine; $X_{29}$ is alanine, glycine or serine; $X_{30}$ is histidine, aspartic acid, glutamic acid, homocysteic acid or cysteic acid; $X_{33}$ is aspartic acid or glutamic acid; $X_{34}$ is alanine or threonine; $X_{41}$ is aspartic acid or glutamic acid; $X_{42}$ is alanine, ornithine or arginine; $X_{45}$ is tyrosine or phenylalanine; and $R_{13}$ is COOH or $CONH_2$. In one embodiment the two A chains are identical, and the B chains are identical or different. In another embodiment the two B chains are identical, and the two A chains are identical or different; and in another embodiment the first and second insulin polypeptides are identical in sequence. In one embodiment the A chains comprise a sequence independently selected from GIVEQCCTSICSLY-QLENYCN (SEQ ID NO: 1), GIVEECCFRSCDLAL- LENYCN (SEQ ID NO: 12) and GIVDECCFRSCDLR-RLENYCN (SEQ ID NO: 11) and the B chains comprise a sequence independently selected from FVNQHLCG-SHLVEALYLVCGERGFFYTPKT (SEQ ID NO: 2), FVN-QHLCGSHLVEALYLVCGEHGFFYTPR (SEQ ID NO: 13) and GPEHLCGAELVDALYLVCGDRGFY (SEQ ID NO: 14).

In one embodiment one or both of the insulin polypeptides of the dimer are single chain insulin analogs wherein the carboxy terminus of the B chain is linked to the amino terminus of the A chain via a linking peptide. In one embodiment the linking peptide of the insulin polypeptide comprises an 8 to 17 amino acid peptide, and more particularly, in one embodiment the peptide represents the IGF-1 C peptide or analog thereof. In one embodiment the linking peptide of the insulin polypeptides comprises a sequence selected from the group consisting of GYGSSSR$X_{68}$APQT (SEQ ID NO: 9), GAGSSSR$X_{68}$APQT (SEQ ID NO: 15), SRVSR$X_{68}$SR (SEQ ID NO: 98), $X_{51}X_{52}$GSSS$X_{57}X_{68}$APQT (SEQ ID NO: 17, $X_{51}X_{52}$GSSS$X_{57}X_{58}$APQT (SEQ ID NO: 16), (SSSS$X_{59}$APPPSLPSPSRLPGPSDTPILPQ$X_{60})_n$ (SEQ ID NO: 18) and MGSSS$X_{59}$APPPSLPSPSRLPGPSDTPILPQEEEEE$X_{60}$ (SEQ ID NO: 19), wherein n is an integer selected from the group consisting of 1, 2 or 3, $X_{51}$ is selected from the group consisting of glycine, alanine, valine, leucine, isoleucine and proline; $X_{52}$ is alanine, tyrosine, valine, leucine, isoleucine or proline; $X_{57}$ and $X_{58}$ are independently arginine, lysine, cysteine, homocysteine, acetyl-phenylalanine or ornithine; $X_{59}$ and $X_{60}$ are independently arginine, lysine or an amino acid comprising a side chain of Structure I:

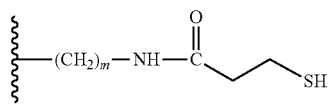

and $X_{68}$ is lysine, ornithine, arginine or an amino acid comprising a side chain of Structure I:

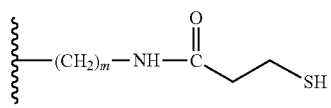

wherein m is 1, 2, 3 or 4, and in on embodiment m is 4. In one embodiment, the A chain is independently selected from GIVEQCCTSICSLYQLENYCN(SEQ ID NO: 1), GIVEECCFRSCDLALLENYCN (SEQ ID NO: 12) and GIVDECCFRSCDLRRLENYCN (SEQ ID NO: 11), the B chain comprises the sequence FVNQHLCGSHLVEALYL-VCGERGFFYTPKT (SEQ ID NO: 2) or GPEHLCGAEL-VDALYLVCGDRGFY (SEQ ID NO: 14) and the linking peptide joining the A and B chains consists of the sequence GYGSSSR$X_{68}$APQT (SEQ ID NO: 9), wherein $X_{68}$ is an amino acid comprising a side chain of the structure:

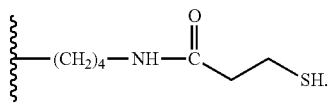

In one embodiment the insulin dimer is an insulin super agonist (i.e., have greater activity at the insulin receptor than native insulin). In one embodiment the first insulin polypeptide is linked to the second insulin polypeptide via the N-terminal alpha amine, or the side chain of N terminal amino acid, of the B chains of the first and second insulin polypeptides (i.e., a head to head fashion), wherein the dimer exhibits 2 fold or 5 fold increased potency relative to native insulin. In one embodiment the super agonist insulin dimer comprises a first and second insulin polypeptide wherein the first and second insulin polypeptide are each two chain insulin analogs. More particularly, the first insulin polypeptide is linked to the second insulin polypeptide via a disulfide linkage, or other linking moiety, between the two N terminal alpha amines of each B chain of the first and second insulin polypeptides (i.e., a head to head fashion). In one embodiment the A chain for both the first and second insulin polypeptide comprises the native human insulin sequence (GIVEQCCTSICSLYQLENYCN; SEQ ID NO: 1) and at least one of the B chains comprises the sequence FVNQHLCGSHLVEALYLVCGEHGFFYTPKT (SEQ ID NO: 20). In one embodiment the first and second insulin polypeptides are each native human insulin, and the two insulin polypeptides are linked to one another via a disulfide bond linking the N-terminal amino groups of each insulin polypeptide.

In one embodiment the insulin dimer is an insulin partial agonist comprising a dimer formed between a first and second insulin polypeptide, wherein the two insulin polypeptides are linked to one another via a linking moiety that joins the amino acid side chains of a C-terminal amino acid of the B chain, independently selected from positions B26, B27, B28, B29 and B30 of the respective first and second insulin polypeptides. In one embodiment the insulin dimer is an insulin partial agonist comprising a dimer formed between a first and second insulin polypeptide, wherein the two insulin polypeptides are linked to one another via a linking moiety that joins the amino acid side chains of a C-terminal amino acid of the B chain, independently selected from positions B28, B29 and B30 of the respective first and second insulin polypeptides. In one embodiment the linkage is selected form the group consisting of B26-B26', B26-B27', B26-B28', B26-B29', B26-B30', B27-B26', B27-B27', B27-B28', B27-B29', B27-B30', B28-B26', B28-B27', B28-B28', B28-B29', B28-B30', B29-B26', B29-B27', B29-B28', B29-B29', B29-B30', B30-B26', B30-B27', B30-B28', B30-B29', and B30-B30'. In one embodiment an amino acid selected from positions B26, B27, B28, B29 and B30 of the first and second insulin polypeptides, comprises a side chain of Structure I:

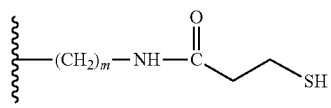

wherein m is an integer selected from 1 to 4 to allow the formation of the dimer by a disulfide bond between the two C-terminal amino acids. In one embodiment the insulin partial agonist dimer comprises a dimer formed between a first and second insulin polypeptide, wherein the two insulin polypeptides are linked to one another via a linking moiety that joins the amino acid side chains of the respective B29 amino acids of the first and second insulin polypeptides. In one embodiment the B29 amino acids of the first and second insulin polypeptides comprises a side chain of Structure I:

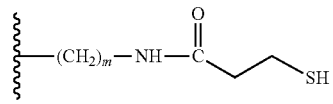

wherein m is an integer selected from 1 to 4, optionally wherein m is 4, and the first and second insulin polypeptides are linked via a disulfide bond between the B29 and B29' amino acid side chains. In one embodiment the insulin partial agonist has less than 66%, 50%, 40%, 33% or 20% activity at the insulin receptor relative to native insulin. In on embodiment the A chain for the first and second insulin polypeptide is independently selected from GIVEQC-CTSICSLYQLENYCN (SEQ ID NO: 1) and GIVDEC-CFRSCDLRRLENYCN (SEQ ID NO: 11) and the B chains comprise a sequence independently selected from FVN-QHLCGSHLVEALYLVCGERGFFYTPKT (SEQ ID NO: 2), FVNQHLCGSHLVEALYLVCGEHGFFYTPR (SEQ ID NO: 13), GPEHLCGAELVDALYLVCGDRGFY (SEQ ID NO: 14) and GPEHLCGAELVDALYLVCGDRGFYF-NKPT (SEQ ID NO: 22). In one embodiment the A chain for both the first and second insulin polypeptide comprises the native human insulin sequence, GIVEQCCTSICSLY-QLENYCN (SEQ ID NO: 1) and at least one of the B chains comprises the sequence FVNQHLCGSHLVEALYLVCGE-HGFFYTPKT (SEQ ID NO: 20). In one embodiment the first and second insulin polypeptide comprises human native insulin A and B chain sequences.

In one embodiment the insulin dimer has insulin receptor agonist activity at a first concentration but insulin receptor antagonist activity at a second higher concentration (i.e., a partial agonist/antagonist insulin analog). In one embodiment a partial agonist/antagonist insulin analog is provided comprising a dimer formed between a first insulin polypeptide and a second insulin polypeptide, wherein the first insulin and second insulin polypeptides are both two chain insulin analogs each comprising an A chain and a B chain linked to one another through interchain disulfide bonds. In this embodiment the first and second insulin polypeptides are linked to one another via a dimerization linker joining the side chain of a carboxy terminal amino acid of the respective two B chains, wherein the A chain of the first and second insulin polypeptide are independently selected from the group consisting of GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7) and the B chain of the first and second insulin comprise a sequence independently selected from the group consisting of FVNQHLCGSHLVEALYLVCGERGFFYTPX$_{68}$T (SEQ ID NO: 2) and GPETLCGAELVDALYLVCGDRGFYFNX$_{68}$PT (SEQ ID NO: 99), wherein X$_{68}$ is an amino acid comprising a side chain of the structure:

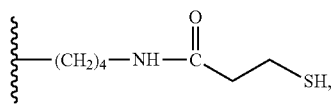

allowing the side chain to participate in a disulfide bond. In one embodiment the first and second insulin polypeptides comprise native insulin sequences wherein the lysine at B29 and B29' have been modified to comprise a side chain of the structure:

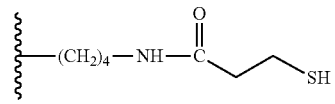

and the dimer is formed by a disulfide linkage between the B29 and B29' side chains.

In one embodiment a partial agonist/antagonist insulin analog is provided comprising two insulin polypeptides wherein at least one of the insulin polypeptides is a single chain insulin and the first and second insulin polypeptides are linked to one another via an amino acid side chain of an amino acid contained within the linking peptide of the single chain insulin polypeptide, and the N-terminal alpha amine, or the side chain of the N-terminal amino acid, of the second insulin polypeptide. In accordance with one embodiment the first and second insulin polypeptides comprise a B chain and A chain of human insulin, or analogs or derivatives thereof.

In one embodiment one or both of the insulin polypeptides of the dimer are insulin single chain analogs wherein the carboxy terminus of the B chain is linked to the amino terminus of the A chain via a peptide comprising a sequence selected from the group consisting of GYGSSSRX$_{68}$APQT (SEQ ID NO: 9), GYGSSSRKAPQT (SEQ ID NO: 21), SRVSRX$_{68}$SR (SEQ ID NO: 98) or X$_{51}$X$_{52}$GSSSX$_{57}$X$_{58}$APQT (SEQ ID NO: 16), wherein X$_{51}$ is selected from the group consisting of glycine, alanine, valine, leucine, isoleucine and proline; X$_{52}$ is alanine, tyrosine, valine, leucine, isoleucine or proline; X$_{57}$ and X$_{58}$ are independently arginine, lysine, cysteine, homocysteine, acetyl-phenylalanine, ornithine or an amino acid comprising a side chain of Structure I:

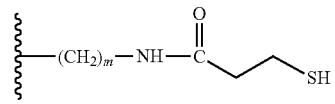

and X$_{68}$ is lysine, arginine or an amino acid comprising a side chain of Structure I:

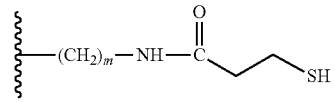

wherein m is an integer selected from 1 to 4. In a further embodiment a partial insulin agonist/antagonist is provided comprising a first insulin polypeptide and a second insulin polypeptide, wherein said first insulin polypeptide is a single chain insulin analog, comprising a first A chain sequence, a first B chain sequence and a first linking peptide, wherein a first end of said first linking peptide is covalently bound to the C-terminus of the first B chain and a second end of said first linking peptide is covalently bound to the amino terminus of the first A chain. The second insulin polypeptide is optionally either a single chain insulin analog or a two chain insulin analog comprising a second A chain sequence and a second B chain sequence with the proviso that when said second insulin polypeptide is a single chain insulin analog, said second insulin polypeptide further comprises a second linking peptide, wherein a first end of said second linking peptide is covalently bound to the carboxy terminus of the B chain and a second end of said second linking peptide is covalently bound to the amino terminus of the A chain. The first and second insulin polypeptides are linked to one another through a bond or a bifunctional linking moiety that covalently links the side chain of an amino acid of said first linking peptide (optionally at position 8) to a) the N-terminal alpha amine or to the side chain of the N-terminal amino acid of the B chain of the second insulin polypeptide; or b) an amino acid side chain of an amino acid of the second linking peptide, and in one embodiment to position 8 of the second linking peptide.

In one embodiment the A chains of the partial agonist dimer comprise the sequence GIVX$_4$X$_5$CCX$_8$X$_9$X$_{10}$CX$_{12}$LX$_{14}$X$_5$LEX$_{18}$X$_{19}$CX$_{21}$-R$_3$ (SEQ ID NO: 70), and the B chains of the dimer comprise the sequence X$_{25}$LCGX$_{29}$X$_{30}$LVX$_{33}$X$_{34}$LYLVCGX$_{41}$X$_{42}$GFX$_{45}$ (SEQ ID NO: 44), wherein X$_4$ is glutamic acid or aspartic acid; X$_5$ is glutamic acid or glutamine; X$_8$ is threonine, histidine or phenylalanine; X$_9$ is serine, arginine, ornithine or alanine; X$_{10}$ is serine or isoleucine; X$_{12}$ is serine or aspartic acid; X$_{14}$ is arginine, tyrosine, ornithine or alanine; X$_{15}$ is glutamine, arginine, alanine, ornithine or leucine; X$_{18}$ is methionine, asparagine or threonine; X$_{19}$ is tyrosine, 4-methoxy-phenylalanine or 4-amino phenylalanine; X$_{21}$ is alanine, glycine or asparagine; X$_{25}$ is histidine or threonine; X$_{29}$ is alanine, glycine or serine; X$_{30}$ is histidine, aspartic acid, glutamic acid, homocysteic acid or cysteic acid; X$_{33}$ is aspartic acid or glutamic acid; X$_{34}$ is alanine or threonine; X$_{41}$ is aspartic acid or glutamic acid; X$_{42}$ is alanine, ornithine or arginine; X$_{45}$ is tyrosine or phenylalanine; and R$_{13}$ is COOH or CONH$_2$. In one embodiment the linking peptide of the single chain insulin analog is selected from the group consisting of GYGSSSRX$_{68}$APQT (SEQ ID NO: 9), SRVSRX$_{68}$SR (SEQ ID NO: 98), GYGSSSRKAPQT (SEQ ID NO: 21), and X$_{51}$X$_{52}$GSSSX$_{57}$X$_{58}$APQT (SEQ ID NO: 16), wherein X$_{51}$ is selected from the group consisting of glycine, alanine, valine, leucine, isoleucine and proline; X$_{52}$ is alanine, tyrosine, valine, leucine, isoleucine or proline; X$_{57}$ and X$_{58}$ are independently arginine, lysine, cysteine, homocysteine, acetyl-phenylalanine or ornithine; and X$_{68}$ is an amino acid comprising a side chain of Structure I:

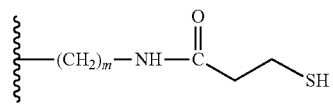

wherein m is an integer selected from 1 to 4. In one embodiment the linking peptide of the single chain insulin analog is selected from the group consisting of GYGSSSRX$_{68}$APQT (SEQ ID NO: 9), SRVSRX$_{68}$SR (SEQ ID NO: 98), and PEG8-X$_{68}$-PEG4, and in one embodiment the linking peptide of the single chain insulin analog is GYGSSSRX$_{68}$APQT (SEQ ID NO: 9) or PEG8-X$_{68}$-PEG4. In one embodiment the linking peptide of the single chain insulin analog is GYGSSSRX$_{68}$APQT (SEQ ID NO: 9).

In one embodiment the first and second insulin polypeptides are identical in sequence. In one embodiment the partial agonist dimer comprises two A chains that are identical wherein the B chains are identical or different, in another embodiment the two B chains are identical and the A chains are identical or different. In one embodiment the A chains comprise a sequence independently selected from GIVEQCCTSICSLYQLENYCN (SEQ ID NO: 1) and GIVDECCFRSCDLRRLENYCN (SEQ ID NO: 11) and the B chains comprise a sequence independently selected from FVNQHLCGSHLVEALYLVCGERGFFYTPKT (SEQ ID NO: 2), FVNQHLCGSHLVEALYLVCGEHGFFYTPR (SEQ ID NO: 13) and GPEHLCGAELVDALYL-VCGDRGFY (SEQ ID NO: 14). In one embodiment the A chains each comprise the sequence GIVDECCFRSCDLR-RLENYCN (SEQ ID NO: 11) and the B chains each comprise the sequence GPEHLCGAELVDALYL-VCGDRGFY (SEQ ID NO: 14). In another embodiment, both the first and the second insulin polypeptide are single chain analogs and the first and second insulin polypeptides are linked to one another via an amino acid side chain of an amino acid of the linking peptides of each of the first and second insulin polypeptide.

In one embodiment the A chains of the first and second insulin polypeptides comprises a sequence independently selected from GIVDECCX$_8$X$_9$SCDLRRLEX$_{18}$YCX$_{21}$-R$_{13}$ (SEQ ID NO: 81) and the B chains of said first and second insulin polypeptides comprises a sequence independently selected from X$_{25}$LCGAELVDALYLVCGDX$_{42}$GFY (SEQ ID NO: 82), wherein X$_8$ is histidine or phenylalanine; X$_9$ is arginine, ornithine or alanine; X$_{18}$ is methionine or asparagine; X$_{21}$ is alanine or asparagine; X$_{25}$ is histidine or threonine; X$_{42}$ is selected from the group consisting of alanine, ornithine and arginine; and R$_{13}$ is COOH. In one embodiment, the A chains are each GIVDECCFRSCDLR-RLENYCN (SEQ ID NO: 11), the B chain comprises the sequence FVNQHLCGSHLVEALYLVCGERGFFYTPKT (SEQ ID NO: 2) or GPEHLCGAELVDALYLVCGDRGFY (SEQ ID NO: 14) and the linking peptide joining the A and B chains consists of the sequence GYGSSSRKAPQT (SEQ ID NO: 21) or GYGSSSRX$_{68}$APQT (SEQ ID NO: 9). In one embodiment the partial insulin agonist/antagonist comprises a first single chain insulin polypeptide wherein the A and B chains are linked via the sequence GYGSSSRX$_{68}$APQT (SEQ ID NO: 9), wherein X$_{68}$ is an amino acid with a side chain of Structure I:

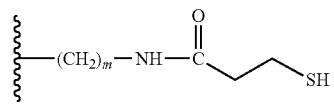

wherein m is an integer selected from 1 to 4 and the dimer is formed by a disulfide bond between the side chain of the amino acid at position 8 of the linking peptide of the first insulin polypeptide and the N-terminal amino group of the second insulin polypeptide. In one embodiment m is 4. In one embodiment the partial insulin agonist comprises a first and second single chain insulin polypeptide linked via a B1-C8 dimerizing linker or a C8-C8 dimerizing linker, wherein the A and B chains of both the first and second insulin polypeptide are single chain insulin analogs linked via a linking moiety having the sequence GYGSSSRX$_{68}$APQT (SEQ ID NO: 9), wherein X$_{68}$ is lysine or an amino acid with a side chain of Structure I:

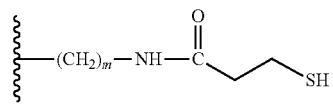

wherein m is an integer selected from 1 to 4 and the dimer is formed by a disulfide bond between the side chain of N terminal amino acid of the B chain with the side chain of an amino acid at position 8 of the linking moiety (B1-C8 linkage) or the two side chains of the amino acid at position 8 of the linking peptide of the respective first and second insulin polypeptides (C8-C8 linkage). In one embodiment the partial insulin agonist comprises a first and second single chain insulin polypeptide linked via a B1-C8 dimerizing linker, wherein the A and B chains of both the first and second insulin polypeptide are linked via a mini-PEG linker, including for example PEG8-K-PEG4. In one embodiment the insulin dimer is an insulin partial agonist comprising a dimer formed between a first and second insulin polypeptide, wherein the two insulin polypeptides are linked to one another via a linking moiety that joins the amino acid side chains of an N-terminal amino acid of the B chain of one of the first and second insulin polypeptides, including for example from positions B0, B1 and B2, to an amino acid side chain of the linking moiety of the other insulin polypeptide, including for example positions corresponding to C6, C7, C8, and C9 of the IGF1 C peptide. In one embodiment the linkage is selected form the group consisting of B0-C6, B0-C7, B0-C8, B0-C9, B1-C6, B1-C7, B1-C8, B1-C9, B2-C6, B2-C7, B2-C8, B2-C9.

In accordance with one embodiment an insulin analog dimer is provided that exhibits partial agonist and partial antagonist activity. In one embodiment the dimer comprises
i) a first insulin polypeptide and a second insulin polypeptide, wherein
said first insulin and second insulin polypeptide are both a single chain insulin analogs comprising an A chain, a B chain and a linking moiety, wherein a first end of said linking moiety is covalently bound to the carboxy terminus of the B chain and a second end of said linking moiety is covalently bound to the amino terminus of the A chain. The first and second insulin polypeptides are linked to one another via a PEG, or disulfide bearing, dimerization linker that covalently links the side chain of a lysine of the linking moiety of the respective first and second insulin polypeptides. In one embodiment the dimerization linker is selected from the group consisting of

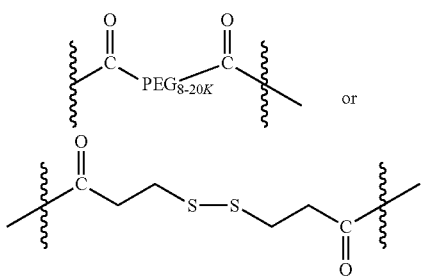

linked to a side chain aliphatic amine (e.g. lysine).

In this embodiment the A chain of the first and second insulin comprises a sequence independently selected from GIVEQCCTSICSLYQLENYCN (SEQ ID NO: 1), GIVDECCFRSCDLRRLENYCN (SEQ ID NO: 11), GIVDEC-CFRSCDLRRLEMYCA (SEQ ID NO: 5) and GIVEEC-CFRSCDLALLETYCA (SEQ ID NO: 7) and the B chain of the first and second insulin comprises a sequence independently selected from FVNQHLCGSHLVEALYL-VCGERGFF (SEQ ID NO: 23), GPETLCGAELVDALYL-VCGDRGFY (SEQ ID NO: 77), GPETLCGAELVDALQFVCGDRGFY (SEQ ID NO: 89), GPEHLCGAELVDALYLVCGDRGFY (SEQ ID NO: 14); AYRPSETLCGGELVDTLQFVCGDRGFY (SEQ ID NO: 90) and AYRPSETLCGGELVDTLYLVCGDRGFY (SEQ ID NO: 92)

said linking moiety of the first and second insulin polypeptide comprising a sequence independently selected from GYGSSSRX$_{68}$APQT (SEQ ID NO: 9), X$_{51}$X$_{52}$GSSSX$_{57}$X$_{58}$APQT (SEQ ID NO: 16) and PEG8-X$_{68}$-PEG4, wherein
X$_{51}$ is selected from the group consisting of glycine, alanine, valine, leucine, isoleucine and proline;
X$_{52}$ is alanine, tyrosine, valine, leucine, isoleucine or proline;
one of X$_{57}$ and X$_{58}$ is arginine and the other is an amino acid comprising a side chain of Structure I:

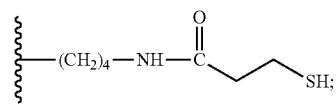

and
X$_{68}$ is an amino acid comprising a side chain of Structure I:

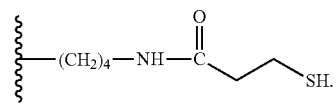

In accordance with one embodiment an insulin analog dimer is provided that exhibits partial agonist and partial antagonist activity. In one embodiment the dimer comprises a first insulin polypeptide and a second insulin polypeptide, wherein
said first insulin polypeptide is a two chain insulin analogs comprising a first A chain, and a first B chain, wherein said first A chain and first B chain are linked to one another through interchain disulfide bonds;
said second insulin polypeptide is a single chain insulin analog comprising a second A chain, a second B chain and a linking moiety, wherein a first end of said linking moiety is covalently bound to the carboxy terminus of the second B chain and a second end of said linking moiety is covalently bound to the amino terminus of the second A chain,
wherein the first and second insulin polypeptides are linked to one another via a disulfide bearing, dimerization linker, wherein a first end of the dimerization linker is covalently linked to the side chain of the N-terminal amino acid, or the N-terminal amine of the B chain of said first insulin polypeptide and a second end of the dimerization linker is covalently linked to the side chain of a lysine of the linking moiety of the second insulin polypeptide,
said A chain of the first and second insulin polypeptide comprising a sequence independently selected from GIVEQCCTSICSLYQLENYCN (SEQ ID NO: 1), GIV-DECCFRSCDLRRLENYCN (SEQ ID NO: 11), GIVDEC- CFRSCDLRRLEMYCA (SEQ ID NO: 5) and GIVEEC-CFRSCDLALLETYCA (SEQ ID NO: 7)

said B chain of the first insulin polypeptide comprising a sequence independently selected from CFVNQHLCGSHLVEALYLVCGERGFFYTPKT (SEQ ID NO: 94), CGPETLCGAELVDALYLVCGDRGFYFNKPT (SEQ ID NO: 95), CGPETLCGAELVDALQFVCGDRGFYFNKPT (SEQ ID NO: 96), CGPEHLCGAELVDALYLVCGDRGFYNKPT (SEQ ID NO: 9796); CAYRPSETLCGGELVDTLQFVCGDRGFY (SEQ ID NO: 91) and CAYRPSETLCGGELVDTLYLVCGDRGFY (SEQ ID NO: 93);

said B chain of the second insulin polypeptide comprising a sequence independently selected from FVNQHLCGSHLVEALYLVCGERGFF (SEQ ID NO: 23), GPETLCGAELVDALYLVCGDRGFY (SEQ ID NO: 77), GPETLCGAELVDALQFVCGDRGFY (SEQ ID NO: 89), GPEHLCGAELVDALYLVCGDRGFY (SEQ ID NO: 14); AYRPSETLCGGELVDTLQFVCGDRGFY (SEQ ID NO: 90) and AYRPSETLCGGELVDTLYLVCGDRGFY (SEQ ID NO: 92)

said linking moiety of the second insulin polypeptide comprising a sequence independently selected from GYGSSSRX$_{68}$APQT (SEQ ID NO: 9), X$_{51}$X$_{52}$GSSSX$_{57}$X$_{58}$APQT (SEQ ID NO: 16) and PEG8-X$_{68}$-PEG4, wherein X$_{51}$ is selected from the group consisting of glycine, alanine, valine, leucine, isoleucine and proline;

X$_{52}$ is alanine, tyrosine, valine, leucine, isoleucine or proline;

one of X$_{57}$ and X$_{58}$ is arginine and the other is an amino acid comprising a side chain of Structure I:

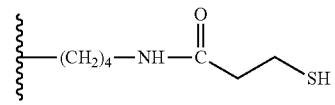

X$_{68}$ is an amino acid comprising a side chain of Structure I:

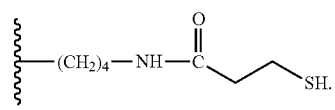

In accordance with one embodiment an insulin analog dimer is provided that exhibits partial agonist and partial antagonist activity. In one embodiment the dimer comprises a first insulin polypeptide and a second insulin polypeptide, wherein said first insulin and second insulin polypeptide are both single chain insulin analogs comprising an A chain, a B chain and a linking moiety, wherein a first end of said linking moiety is covalently bound to the carboxy terminus of the B chain and a second end of said linking moiety is covalently bound to the amino terminus of the A chain, further wherein the first and second insulin polypeptides are linked to one another via a PEG, or disulfide bearing, dimerization linker, wherein a first end of the dimerization linker is covalently linked to the side chain of a lysine of the linking moiety of one of the first or second insulin polypeptides and a second end of the dimerization linker is covalently linked to the N-terminal amine of the B chain of the other first or second insulin polypeptide. In one embodiment the dimerization linker is selected from the group consisting of

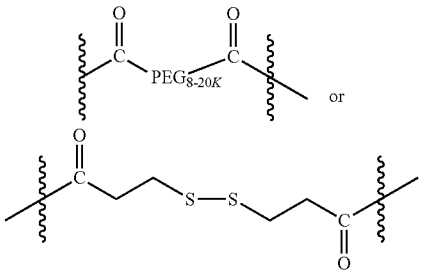

linked to a side chain aliphatic amine (e.g. lysine) or an N-terminal amine of the insulin B chain. In this embodiment, the A chain of the first insulin polypeptide comprises the sequence TPAKSEGIVEECCFRSCDLALLETYCA (SEQ ID NO: 103); the B chain of the first insulin polypeptide comprises the sequence AYRPSETLCGGELVDTLQFVCGDRGFY (SEQ ID NO: 90) or AYRPSETLCGGELVDTLYLVCGDRGFY (SEQ ID NO: 92); the A chain of the second insulin polypeptide comprises the sequence GIVEQCCTSICSLYQLENYCN (SEQ ID NO: 1); and the B chain of the second insulin polypeptide comprises a sequence independently selected from FVNQHLCGSHLVEALYLVCGERGFF (SEQ ID NO: 23), and GPEHLCGAELVDALYLVCGDRGFY (SEQ ID NO: 14). The linking moiety of the first and second insulin polypeptides comprises a sequence independently selected from GYGSSSRX$_{68}$APQT (SEQ ID NO: 9), SRVSRX$_{68}$SR (SEQ ID NO: 98) and PEG8-X$_{68}$-PEG4, wherein X$_{68}$ is arginine or an amino acid comprising a side chain of Structure I:

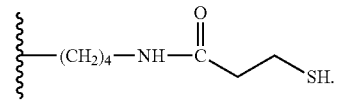

In accordance with one embodiment an insulin analog dimer is provided that exhibits partial agonist and partial antagonist activity. In one embodiment the dimer comprises a first insulin polypeptide and a second insulin polypeptide, wherein said first insulin and second insulin polypeptide are both a single chain insulin analogs comprising an A chain, a B chain and a linking moiety, wherein a first end of said linking moiety is covalently bound to the carboxy terminus of the B chain and a second end of said linking moiety is covalently bound to the amino terminus of the A chain further wherein the first and second insulin polypeptides are linked to one another via a PEG or disulfide bearing dimerization linker covalently linked to the side chain of a lysine of the linking moiety of the respective first and second insulin polypeptides, said A chain of the first and second insulin comprising a sequence independently selected from GIVEQCCTSICSLYQLENYCN (SEQ ID NO: 1) and GIVDECCFRSCDLRRLENYCN (SEQ ID NO: 11), said B chain of the first and second insulin comprising a sequence independently selected from FVNQHLCGSHLVEALYLVCGERGFF (SEQ ID NO: 23) and GPEHLCGAELVDALYLVCGDRGFY (SEQ ID NO: 14), said dimerization linker comprising a sequence independently selected from GYGSSSRX$_{68}$APQT (SEQ ID NO: 9) and PEG8-X$_{68}$-PEG4, wherein X$_{68}$ is an amino acid comprising a side chain of Structure I:

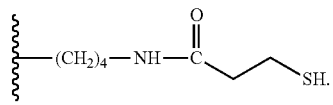

In accordance with one embodiment an insulin analog dimer is provided that exhibits partial agonist and partial antagonist activity. In one embodiment the dimer comprises a first insulin polypeptide and a second insulin polypeptide, wherein said first insulin polypeptide is a two chain insulin analogs comprising a first A chain, and a first B chain, wherein said first A chain and first B chain are linked to one another through interchain disulfide bonds;

said second insulin polypeptide is a single chain insulin analog comprising a second A chain, a second B chain and a linking moiety, wherein a first end of said linking moiety is covalently bound to the carboxy terminus of the second B chain and a second end of said linking moiety is covalently bound to the amino terminus of the second A chain, wherein the first and second insulin polypeptides are linked to one another via a disulfide bond between the N-terminal cysteine side chain of the B chain of the first insulin polypeptide and the side chain of a modified lysine of the linking moiety of the second insulin polypeptide, said A chain of the first and second insulin polypeptide comprising a sequence independently selected from GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7)

said B chain of the first insulin polypeptide comprising a sequence independently selected from CFVNQHLCGSHLVEALYLVCGERGFFYTPKT (SEQ ID NO: 94) and CGPEHLCGAELVDALYLVCGDRGFYNKPT (SEQ ID NO: 97);

said B chain of the second insulin polypeptide comprising a sequence independently selected from FVNQHLCGSHLVEALYLVCGERGFF (SEQ ID NO: 23) and GPEHLCGAELVDALYLVCGDRGFY (SEQ ID NO: 14);

said linking moiety of the second insulin polypeptide comprising the sequence GYGSSSRX$_{68}$APQT (SEQ ID NO: 9), wherein X$_{68}$ is an amino acid comprising a side chain of Structure I:

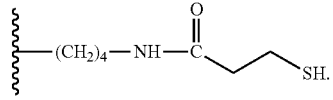

Receptor Subtype Selectivity

In a further embodiment insulin dimers are provided that are selective for the subtype B insulin receptor (IR-B). Applicants have discovered that a heterodimer formed between an insulin based polypeptide and a peptide (e.g., IGF I or IGF II) that exhibits a higher IR-A/IR-B ratio (i.e., higher affinity for IR-A relative to IR-B) showed a preference for IR-B activation as indicated by the higher level of maximal receptor response at IR-B relative to IR-A. In one embodiment insulin heterodimers are provided that showed a preference for IR-B activation relative to the subtype A insulin receptor.

In one embodiment the first insulin polypeptide comprises an A chain amino acid sequence of GIVX$_4$X$_5$CCX$_8$X$_9$X$_{10}$CX$_{12}$LX$_{14}$X$_{15}$LEX$_{18}$X$_{19}$CX$_{21}$-R$_{13}$ (SEQ ID NO: 70) and a B chain amino acid sequence of X$_{25}$LCGX$_{29}$X$_{30}$LVX$_{33}$X$_{34}$LYLVCGX$_{41}$X$_{42}$GFX$_{45}$ (SEQ ID NO: 44), and the second polypeptide comprises an A chain sequence of GIVEECCFRSCDLALLETYCA (SEQ ID NO: 7) TPAX$_{75}$SEGIVEECCFRSCDLALLETYCA (SEQ ID NO: 88) or GIVDECCFRSCDLRRLEMYCA (SEQ ID NO: 5), a B chain sequence of AYRPSETLCGGELVDTLQFVCGDRGFYFSRPA SEQ ID NO: 87) or GPETLCGAELVDALQFVCGDRGFYFNKPT (SEQ ID NO: 10); and a linking moiety comprising a sequence selected from the group consisting of PEG8-X$_{68}$-PEG4 and GYGSSSRX$_{68}$APQT (SEQ ID NO: 9), wherein X$_4$ is glutamic acid or aspartic acid; X$_5$ is glutamic acid or glutamine; X$_8$ is threonine, histidine or phenylalanine; X$_9$ is serine, arginine, ornithine or alanine; X$_{10}$ is serine or isoleucine; X$_{12}$ is serine or aspartic acid; X$_{14}$ is arginine, tyrosine, ornithine or alanine; X$_{15}$ is glutamine, arginine, alanine, ornithine or leucine; X$_{18}$ is methionine, asparagine or threonine; X$_{19}$ is tyrosine, 4-methoxy-phenylalanine or 4-amino phenylalanine; X$_{21}$ is alanine, glycine or asparagine; X$_{25}$ is histidine or threonine; X$_{29}$ is alanine, glycine or serine; X$_{30}$ is histidine, aspartic acid, glutamic acid, homocysteic acid or cysteic acid; X$_{33}$ is aspartic acid or glutamic acid; X$_{34}$ is alanine or threonine; X$_{41}$ is aspartic acid or glutamic acid; X$_{42}$ is alanine, ornithine or arginine; X$_{45}$ is tyrosine or phenylalanine; R$_{13}$ is COOH or CONH$_2$; X$_{68}$ is arginine, lysine or an amino acid comprising a side chain of Structure I:

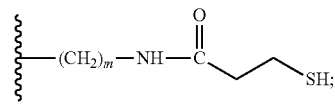

and X$_{75}$ is lysine or arginine. In one embodiment the insulin polypeptide of the heterodimer is a two chain insulin polypeptide. In an alternative embodiment both the first and second polypeptides of the heterodimer are single chain insulin polypeptides having a linking moiety independently selected from the group consisting of GYGSSSRX$_{68}$APQT (SEQ ID NO: 9),
X$_{51}$X$_{52}$GSSSX$_{57}$X$_{58}$APQT (SEQ ID NO: 16);
(SSSSX$_{59}$APPPSLPSPSRLPGPSDTPILPQX$_{60}$)$_n$ (SEQ ID NO: 18);
MGSSSX$_{59}$APPPSLPSPSRLPGPSDTPILPQEEEEEX$_{60}$ (SEQ ID NO: 19); and
W$_2$-Z$_2$-Y$_2$, wherein
W$_2$ is a PEG6, PEG7 or PEG8;
Y$_2$ is a PEG4, PEG5 or PEG6; and
Z$_2$ is lysine, cysteine or an amino acid comprising a side chain of Structure I:

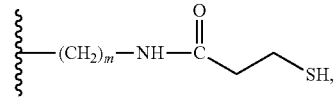

wherein n is an integer selected from the group consisting of 1, 2 or 3;

$X_{51}$ is selected from the group consisting of glycine, alanine, valine, leucine, isoleucine and proline;

$X_{52}$ is alanine, tyrosine, valine, leucine, isoleucine or proline;

$X_{57}$ and $X_{58}$ are independently arginine, lysine, cysteine, homocysteine, acetyl-phenylalanine or ornithine;

$X_{59}$ and $X_{60}$ are independently arginine or lysine; and and $X_{68}$ is arginine, lysine, cysteine or an amino acid comprising a side chain of Structure I:

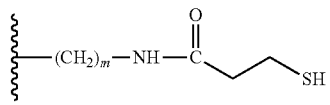

wherein m is an integer selected from 1 to 4.

In one embodiment the dimer comprises a first and second insulin like polypeptide, at least one of which is a single chain insulin like polypeptide, wherein the first insulin polypeptide comprises an A chain sequence of GIVEQCCTSICSLYQLENYCN (SEQ ID NO: 1);

a B chain sequence of FVNQHLCGSHLVEALYL-VCGERGFF (SEQ ID NO: 23); and optionally a first linking moiety comprising a sequence selected from the group consisting of PEG8-$X_{68}$-PEG4 and GYGSSSR$X_{68}$APQT (SEQ ID NO: 9), wherein $X_{68}$ is arginine, lysine or an amino acid comprising a side chain of Structure I:

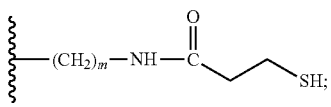

and
the second polypeptide comprises an A chain sequence of TPAX$_{75}$SEGIVEECCFRSCDLALLETYCA (SEQ ID NO: 88) or GIVDECCFRSCDLRRLEMYCA (SEQ ID NO: 5);

a B chain sequence of AYRPSETLCG-GELVDTLQFVCGDRGFYFSRPA SEQ ID NO: 87) or GPETLCGAELVDALQFVCGDRGFYFNKPT (SEQ ID NO: 10); and optionally a first linking moiety comprising a sequence selected from the group consisting of PEG8-$X_{68}$-PEG4 and GYGSSSR$X_{68}$APQT (SEQ ID NO: 9), wherein $X_{68}$ is arginine, lysine or an amino acid comprising a side chain of Structure I:

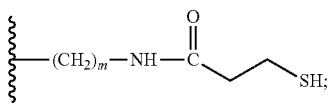

and $X_{75}$ is lysine or arginine; further wherein the first and second insulin polypeptides are linked to one another via the N terminal amine or side chain of the amino acid at the N-terminal amino acid of one of said first or second insulin polypeptide and the lysine side chain of the linking moiety of the other insulin polypeptide, optionally at position 8 of the linking moiety. In one embodiment both the first and second insulin polypeptides are single chain insulin polypeptides. In one embodiment one of the first or second polypeptides is a two chain heteroduplex comprising an A chain and a B chain linked via interchain disulfide bonds; and the other insulin polypeptide is a single chain insulin polypeptide comprising an A chain, a B chain and a linking moiety, wherein the linking moiety is PEG8-$X_{68}$-PEG4 or GYGSSSR$X_{68}$APQT (SEQ ID NO: 9), wherein $X_{68}$ is lysine or an amino acid comprising a side chain of Structure I:

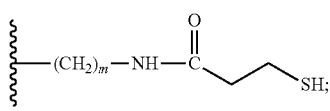

and m is 4 and said first and second insulin polypeptides are linked one another via the side chain of the amino acid at position B1 of the two chain insulin polypeptide and the side chain of the amino acid at position 8 of GYGSSSR$X_{68}$APQT (SEQ ID NO: 9), or the side chain of the lysine of PEG8-$X_{68}$-PEG4 of the single chain insulin polypeptide.

In one embodiment the first and second polypeptides of the heterodimer are each single chain insulin polypeptides, wherein the first insulin polypeptide comprises an A chain sequence of GIVEQCCTSICSLYQLENYCN (SEQ ID NO: 1);

a B chain sequence of FVNQHLCGSHLVEALYL-VCGERGFF (SEQ ID NO: 23); and a first linking moiety comprising a sequence selected from the group consisting of PEG8-$X_6$-PEG4 and GYGSSSR$X_{68}$APQT (SEQ ID NO: 9); and the second IGF polypeptide comprises an A chain sequence of TPAX$_{75}$SEGIVEECCFRSCDLALLETYCA (SEQ ID NO: 88) or GIVDECCFRSCDLRRLEMYCA (SEQ ID NO: 5);

a B chain sequence of AYRPSETLCG-GELVDTLQFVCGDRGFYFSRPA SEQ ID NO: 87) or GPETLCGAELVDALQFVCGDRGFYFNKPT (SEQ ID NO: 10); and a second linking moiety comprising a sequence selected from the group consisting of PEG8-K-PEG4 and GYGSSSR$X_{68}$APQT (SEQ ID NO: 9), wherein $X_{68}$ is lysine, arginine, or an amino acid comprising a side chain of Structure I:

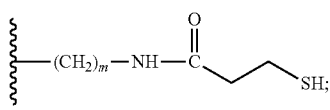

and $X_{75}$ is lysine or arginine; further wherein the first and second linking moieties join the carboxy terminus of the respective B chains to the A chains and the first and second insulin polypeptides are linked to one another via the N terminal amine or side chain of the amino acid at position B1 of one of said first or second polypeptides and the lysine side chain of the linking moiety of the other polypeptide.

In one embodiment the first and second polypeptides of the heterodimer are each single chain insulin polypeptides, wherein the first insulin polypeptide comprises an A chain sequence of GIVEQCCTSICSLYQLENYCN (SEQ ID NO: 1);

a B chain sequence of FVNQHLCGSHLVEALYL-VCGERGFF (SEQ ID NO: 23); and a first linking moiety comprising a sequence selected from the group consisting of PEG8-K-PEG4 and GYGSSSRX$_{68}$APQT (SEQ ID NO: 9); and the second IGF polypeptide comprises an A chain sequence of TPAX$_{75}$SEGIVEECCFRSCDLALLETYCA (SEQ ID NO: 88);

a B chain sequence of AYRPSETLCG-GELVDTLQFVCGDRGFYFSRPA SEQ ID NO: 87); and a second linking moiety comprising a sequence selected from the group consisting of PEG8-X$_{68}$-PEG4 and GYGSSSRX$_{68}$APQT (SEQ ID NO: 9), wherein X$_{68}$ is arginine, or an amino acid comprising a side chain of Structure I:

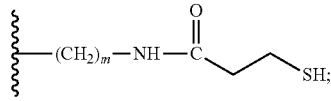

and

X$_{75}$ is lysine or arginine; further wherein the first and second linking moieties join the carboxy terminus of the respective B chains to the A chains and the first and second insulin polypeptides are linked to one another via the N terminal amine or side chain of the amino acid at position B1 of one of said first or second polypeptides and the lysine side chain of the linking moiety of the other polypeptide.

In accordance with one embodiment an insulin analog dimer is provided that exhibits partial agonist and partial antagonist activity and selectivity for the subtype B insulin receptor. In one embodiment the dimer comprises a first insulin polypeptide and a second insulin polypeptide, wherein said first insulin and second insulin polypeptide are both single chain insulin analogs comprising an A chain, a B chain and a linking moiety, wherein for each of said first and second insulin polypeptides a first end of their respective linking moieties is covalently bound to the carboxy terminus of the B chain and a second end of their respective linking moieties is covalently bound to the amino terminus of the A chain, further wherein the first and second insulin polypeptides are linked to one another via a disulfide bearing dimerization linker, wherein a first end of the dimerization linker is covalently linked to the side chain of a lysine of the linking moiety of one of the first or second insulin polypeptides and a second end of the dimerization linker is covalently linked to the N-terminal amine of the B chain of the other first or second insulin polypeptide. In one embodiment the first and second insulin polypeptides are linked to one another via a disulfide bearing dimerization linker, wherein a first end of the dimerization linker is covalently linked to the side chain of a lysine of the linking moiety of the first insulin polypeptides and a second end of the dimerization linker is covalently linked to the N-terminal amine of the B chain of the second insulin polypeptide. In one embodiment the first and second insulin polypeptides are linked to one another via a disulfide bearing dimerization linker, wherein a first end of the dimerization linker is covalently linked to the side chain of a lysine of the linking moiety of one of the second insulin polypeptides and a second end of the dimerization linker is covalently linked to the N-terminal amine of the B chain of the first insulin polypeptide. In this embodiment the A chain of the first insulin polypeptide comprises the sequence TPAKSEGIVEECCFRSCDLAL-LETYCA (SEQ ID NO: 103), the B chain of the first insulin polypeptide comprises the sequence AYRPSETLCG-GELVDTLQFVCGDRGFY (SEQ ID NO: 90), and the linking moiety for said first insulin polypeptide comprises the sequence SRVSRX$_{68}$SR (SEQ ID NO: 98). The A chain of the second insulin polypeptide comprises the sequence GIVEQCCTSICSLYQLENYCN (SEQ ID NO: 1), the B chain of the second insulin polypeptide comprises the sequence FVNQHLCGSHLVEALYLVCGERGFF (SEQ ID NO: 23) and the linking moiety for said second insulin polypeptide comprises the sequence GYGSSSRX$_{68}$APQT (SEQ ID NO: 9), wherein X$_{68}$ is arginine or an amino acid comprising a side chain of Structure I:

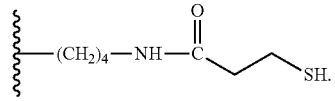

The Peptide Linkers of the Single Chain Insulin Analogs

In accordance with one embodiment the linking moiety of the single chain insulin analogs disclosed herein is the IGF 1 C chain sequence (GYGSSSRRAPQT; SEQ ID NO: 24) or a derivative thereof. In one embodiment the derivative is a peptide that differs from SEQ ID NO: 24 by a single amino acid substitution of a lysine, cysteine ornithine, homocysteine, or acetyl-phenylalanine residue, and in a further embodiment the lysine, cysteine ornithine, homocysteine, or acetyl-phenylalanine amino acid is pegylated or fatty acylated. In one further embodiment the linking moiety is a peptide that differs from SEQ ID NO: 24 by a single lysine substitution. In one specific embodiment the substitution is made at position 8 of SEQ ID NO: 24.

Applicants have discovered that use of the IGF 1 C chain sequence and analogs thereof as a linking moiety will generate a single chain insulin analog that has near wild type insulin activity. Furthermore, use of a IGF 1 C chain sequence analog as the linking moiety, wherein position 2 of the IGF 1 C chain sequence is modified, or the carboxy terminal four amino acids are deleted from the IGF 1 C chain sequence, produces a single chain insulin polypeptide that is selective for insulin (i.e., has a higher binding and/or activity at the insulin receptor compared to the IGF-1 receptor). In one embodiment the single chain insulin polypeptide has 5×, 10×, 20×, 30×, 40×, or 50× higher affinity or activity at the insulin receptor relative to the IGF-1 receptor.

In accordance with one embodiment the linking moiety is a derivative of the IGF 1 C chain sequence (GYGSSSRRA-PQT; SEQ ID NO: 24) and comprises a non-native sequence that differs from GYGSSSRR (SEQ ID NO: 25) or GAGSSSRRAPQT (SEQ ID NO: 26) by 1 to 3 amino acid substitutions, or 1 to 2 amino acid substitutions. In one embodiment at least one of the amino acid substitutions is a lysine or cysteine substitution, and in one embodiment the amino acid substitutions are conservative amino acid substitutions. In one embodiment the linking moiety is a peptide (or peptidomimetic) of 8 to 17 amino acids comprising a non-native amino acid sequence that differs from GYGSSSRR (SEQ ID NO: 25) or GAGSSSRRAPQT (SEQ ID NO: 26) by 1 amino acid substitution, including for example substitution with a lysine or cysteine. In one embodiment the linking moiety comprises the sequence GYGSSSRR (SEQ ID NO: 25) or GAGSSSRRAPQT (SEQ ID NO: 26). In one embodiment the linking moiety comprises the sequence GAGSSSRX$_{68}$APQT (SEQ ID NO: 15), GYGSSSX$_{57}$X$_{68}$APQT (SEQ ID NO: 37), or an amino acid that differs from SEQ ID NO: 15 by a single amino acid substitution, wherein X$_{57}$ is arginine and X$_{68}$ is an amino acid with a side chain of Structure I:

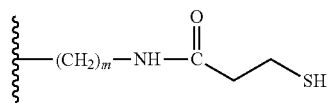

wherein m is an integer selected from 1 to 4.

In a further embodiment a polyethylene glycol chain is linked to the side chain of the amino acid at position 8 of said linking moiety. In another embodiment the linking moiety comprises the sequence GX$_{52}$GSSSRX$_{58}$APQT (SEQ ID NO: 38), wherein X$_{52}$ is any non-aromatic amino acid, including for example, alanine, valine, leucine, isoleucine or proline, and X$_{58}$ represents an amino acid that has a polyethylene chain covalently linked to its side chain. In one embodiment X$_{58}$ is a pegylated lysine. In one embodiment the linking moiety comprises the sequence GYGSSSRX$_{58}$ (SEQ ID NO: 100) or GAGSSSRX$_{58}$APQT (SEQ ID NO: 15), wherein X$_{58}$ represents an amino acid that has a polyethylene chain covalently linked to its side chain.

In one embodiment the linking moiety is an 8 to 17 amino acid sequence consisting of the sequence X$_{51}$X$_{52}$GSSSRR (SEQ ID NO: 27), a peptidomimetic of SEQ ID NO: 27, or an amino acid sequence that differs from SEQ ID NO: 27 by 1, 2, or 3 amino acid substitutions at one of positions 3-8 of SEQ ID NO: 27, wherein X$_{51}$ is selected from the group consisting of glycine, alanine, valine, leucine, isoleucine, proline and methionine, and X$_{52}$ is any amino acid. In one embodiment the linking moiety is a peptide of eight amino acids in length and comprises the sequence GYGSSSRR (SEQ ID NO: 25), or an amino acid sequence that differs from SEQ ID NO: 18 by a single amino acid substitution, or a derivative thereof.

In another embodiment, the linking moiety is an 8 to 17 amino acid sequence comprising the sequence GX$_{52}$GSSSRR (SEQ ID NO: 31), wherein X$_{52}$ is any amino acid, a peptidomimetic of SEQ ID NO: 31, or an analog thereof that differs from SEQ ID NO: 31 by a single amino acid substitution at any of positions 1, 3, 4, 5, 6, 7 or 8 of SEQ ID NO: 31, with the proviso that when the linking peptide is longer than 8 amino acids X$_{52}$ is other than tyrosine. In accordance with one embodiment the linking moiety comprises an 8-17 amino acid sequence selected from the group consisting of GYGSSSRR (SEQ ID NO: 25), GAGSSSRR (SEQ ID NO: 27), GAGSSSRRA (SEQ ID NO: 28), GAGSSSRRAP (SEQ ID NO: 29), GAGSSSRRAPQ (SEQ ID NO: 30), GAGSSSRRAPQT (SEQ ID NO: 26), PYGSSSRR (SEQ ID NO: 31), PAGSSSRR (SEQ ID NO: 32), PAGSSSRRA (SEQ ID NO: 33), PAGSSSRRAP (SEQ ID NO: 34), PAGSSSRRAPQ (SEQ ID NO: 35), PAGSSSRRAPQT (SEQ ID NO: 36).

Non-Peptide Linking Moieties

In one embodiment the linking moiety of a single chain insulin polypeptide disclosed herein is a relatively short bifunctional non-peptide polymer linker that approximates the length of an 8-16 amino acid sequence. In accordance with one embodiment the non-peptide linking moiety is a polyethylene glycol linker of approximately 4 to 20, 8 to 18, 8 to 16, 8 to 14, 10 to 14, 10 to 12 or 11 to 13 monomers. In one embodiment a single chain insulin agonist is provided wherein the last five carboxy amino acids of the native B chain are deleted, and amino acid B25 is directly linked to the linking moiety by a covalent bond. The second end of the linking moiety is covalently bound to amino acid A1 of the A chain thus linking the B and A chain via the linking moiety. In one embodiment the linking moiety is a linear polyethylene glycol linking moiety comprising at least 10 but no more than 16 monomer units and in another embodiment the polyethylene glycol linking moiety comprises at least 12 but no more than 16 monomer units, and in a further embodiment the polyethylene glycol linking moiety comprises at least 10 but no more than 14 monomer units.

In accordance with one embodiment the polyethylene glycol linking moiety comprises the structure:

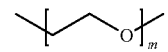

wherein m is an integer ranging from 6 to 18, 8 to 16, 10 to 14 or 11 to 13. In one embodiment m is an integer selected from 10, 11, 12, 13 or 14. In one embodiment m is 12.

In one embodiment a single chain insulin agonist is provided wherein the last five carboxy amino acids of the native B chain are deleted, and amino acid B25 is linked to amino acid A1 of the A chain via a linking moiety comprising polyethylene glycol of at least 8 but no more than 16 monomer units and an amino acid sequence of one to four amino acids. In accordance with one embodiment the linking moiety comprises a 1-4 amino acid sequence and a linear polyethylene glycol of at least 8 but less than 14 monomer units in length covalently bound to said 1-4 amino acid sequence, with the proviso that the amino acid sequence is not YTPK (SEQ ID NO: 37) or FNKP (SEQ ID NO: 38). In another embodiment a single chain insulin agonist is provided wherein the last five carboxy amino acids of the native B chain are deleted, and amino acid B25 is linked to amino acid A1 of the A chain via a linking moiety comprising a polyethylene glycol of at least 8 but less than 14 monomer units in length and a 2-5 amino acid sequence. The 2-5 amino acid sequence can be located between the B chain and the polyethylene glycol chain or between the A chain and the polyethylene glycol chain. However, when the 2-5 amino acid sequence is located between the B chain and the polyethylene glycol chain, the amino acid sequence is not YTPKT (SEQ ID NO: 39) or FNKPT (SEQ ID NO: 40).

In one embodiment the linking moiety comprises two polyethylene chains separated by 1, 2, 3 or 4 amino acids. In this embodiment the linking moiety comprises the general structure: W$_2$-Z$_2$-Y$_2$ wherein W$_2$ and Y$_2$ are independently a polyethylene glycol of the general structure

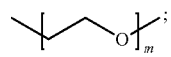

and $Z_2$ is a1-3 amino acid sequence, wherein m is an integer ranging from 3-7. In one embodiment $W_2$ is a PEG6, PEG7 or PEG8, $Y_2$ is a PEG4, PEG5 or PEG6, and $Z_2$ is a single amino acid. In one embodiment $Z_2$ is Lys or Cys. In one embodiment $Z_2$ comprises a pegylated Lys or Cys amino acid. In one embodiment the linking moiety comprises a two polyethylene chains representing a total of 8-12 or 10-14 or 12 monomeric units of ethylene glycol separated by a single amino acid. In one embodiment the single amino acid is lysine or cysteine. In one embodiment $W_2$ is PEG8, $Y_2$ is a PEG4 and $Z_2$ is lysine.

Insulin A and B Chains

The insulin polypeptides of the present invention may comprise the native B and A chain sequences of human insulin (SEQ ID NOs: 1 and 2, respectively) or any of the known analogs or derivatives thereof that exhibit insulin agonist activity when linked to one another in a heteroduplex. Such analogs include, for example, proteins that having an A-chain and a B-chain that differ from the A-chain and B-chain of human insulin by having one or more amino acid deletions, one or more amino acid substitutions, and/or one or more amino acid insertions that do not destroy the insulin activity of the insulin analog.

One type of insulin analog, "monomeric insulin analog," is well known in the art. These are fast-acting analogs of human insulin, including, for example, insulin analogs wherein:

(a) the amino acyl residue at position B28 is substituted with Asp, Lys, Leu, Val, or Ala, and the amino acyl residue at position B29 is Lys or Pro;

(b) the amino acyl residues at any of positions B27, B28, B29, and B30 are deleted or substituted with a nonnative amino acid. In one embodiment an insulin analog is provided comprising an Asp substituted at position B28 or a Lys substituted at position 28 and a proline substituted at position B29. Additional monomeric insulin analogs are disclosed in Chance, et al., U.S. Pat. No. 5,514,646; Chance, et al., U.S. patent application Ser. No. 08/255,297; Brems, et al., Protein Engineering, 5:527-533 (1992); Brange, et al., EPO Publication No. 214,826 (published Mar. 18, 1987); and Brange, et al., Current Opinion in Structural Biology, 1:934-940 (1991). These disclosures are expressly incorporated herein by reference for describing monomeric insulin analogs.

Insulin analogs may also have replacements of the amidated amino acids with acidic forms. For example, Asn may be replaced with Asp or Glu. Likewise, Gln may be replaced with Asp or Glu. In particular, Asn(A18), Asn(A21), or Asp(B3), or any combination of those residues, may be replaced by Asp or Glu. Also, Gln(A15) or Gln(B4), or both, may be replaced by either Asp or Glu.

As disclosed herein insulin single chain analogs are provided comprising a B chain and A chain of human insulin, or analogs or derivative thereof, wherein the carboxy terminus of the B chain is linked to the amino terminus of the A chain via a linking moiety. In one embodiment the A chain is an amino acid sequence selected from the group consisting of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises a sequence selected from FVNQHLCGSHLVEALYLVCGERGFFYTPKT (SEQ ID NO: 2), GPEHLCGAELVDALYLVCGDRGFY (SEQ ID NO: 14) and GPETLCGX$_{26}$ELVDX$_{27}$LYLVCGDX$_{42}$GFYFNKPT-R$_{14}$ (SEQ ID NO: 41), wherein X$_{26}$ and X$_{27}$ are each alanine and X$_{42}$ is arginine, or a carboxy shortened sequence thereof having one to five amino acids corresponding to B26, B27, B28, B29 and B30 deleted, and analogs of those sequences wherein each sequence is modified to comprise one to five amino acid substitutions at positions corresponding to native insulin positions (see peptide alignment shown in FIG. 4) selected from A5, A8, A9, A10, A14, A15, A17, A18, A21, B1, B2, B3, B4, B5, B9, B10, B13, B14, B20, B22, B23, B26, B27, B28, B29 and B30. In one embodiment the amino acid substitutions are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

In accordance with one embodiment the insulin analog peptides may comprise an insulin A chain and an insulin B chain or analogs thereof, wherein the A chain comprises an amino acid sequence that shares at least 70% sequence identity (e.g., 70%, 75%, 80%, 85%, 90%, 95%) over the length of the native peptide, with at least one of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises an amino acid sequence that shares at least 60% sequence identity (e.g., 60%, 65%, 70%, 75%, 80%, 85%, 90%, 95%) over the length of the native peptide, with at least one of the sequence FVNQHLCGSHLVEALYLVCGERGFFYTPKT (SEQ ID NO: 2), GPETLCGX$_{26}$ELVDX$_{27}$LYLVCGDX$_{42}$GFYFNKPT-R$_{14}$ (SEQ ID NO: 41), wherein X$_{26}$ and X$_{27}$ are each alanine and X$_{42}$ is arginine, or a carboxy shortened sequence thereof having one to four amino acids corresponding to B27, B28, B29 and B30 deleted.

Additional amino acid sequences can be added to the amino terminus of the B chain or to the carboxy terminus of the A chain of the insulin polypeptides of the present invention. For example, a series of negatively charged amino acids can be added to the amino terminus of the B chain, including for example a peptide of 1 to 12, 1 to 10, 1 to 8 or 1 to 6 amino acids in length and comprising one or more negatively charged amino acids including for example glutamic acid and aspartic acid. In one embodiment the B chain amino terminal extension comprises 1 to 6 charged amino acids. In one embodiment the B chain comprises the sequence GEEEEEWFVNQHLCGSHLVEALYLVCGERGFFYTPR (SEQ ID NO: 42) or GEEEEEKGPEHLCGAHLVDALYLVCGDX$_{42}$GFY (SEQ ID NO: 43), wherein X$_{42}$ is selected from the group consisting of alanine lysine, ornithine and arginine. In accordance with one embodiment the insulin polypeptides disclosed comprise a C-terminal amide or ester in place of a C-terminal carboxylate on the A chain.

High potency insulin polypeptides can also be prepared based on modified IGF I and IGF II sequences, as described in International application PCT/2009/068713, the disclosure of which is expressly incorporated herein by reference. More particularly, analogs of IGF I and IGF II that comprise a substitution of a tyrosine leucine dipeptide for the native IGF amino acids at positions corresponding to B16 and B17 of native insulin have a tenfold increase in potency at the insulin receptor. Accordingly, the insulin polypeptides disclosed herein may include an A chain of IGF I (SEQ ID NO: 5) or IGF II (SEQ ID NO: 7) and a B chain of IGF I YL (SEQ ID NO: 6) or IGF II YL (SEQ ID NO: 8) or the B chain of native insulin (SEQ ID NO: 2). In addition, the insulin polypeptides disclosed herein may include a native insulin A chain, or analog thereof, and a B chain of IGF I YL (SEQ ID NO: 6) or IGF II YL (SEQ ID NO: 8), as well as analogs of said B chains. In one embodiment the insulin polypeptide comprises an IGF I (SEQ ID NO: 5) A chain, or analog or derivative thereof and a B chain of IGF I YL (SEQ ID NO: 6), IGF II YL (SEQ ID NO: 8) or native insulin (SEQ ID NO: 2), or analogs or derivatives thereof.

Additional modifications to the single chain IGF or insulin A and B chains include, for example, modification of the amino acids at one or more of positions A19, B16 or B25 (relative to the native insulin A and B chains) to a 4-amino phenylalanine or one or more amino acid substitutions at positions selected from A5, A8, A9, A10, A14, A15, A17, A18, A21, B1, B2, B3, B4, B5, B9, B10, B13, B14, B20, B21, B22, B23, B26, B27, B28, B29 and B30 (relative to the native A and B chains of insulin) or deletions of any or all of positions B1-4 and B26-30. In one embodiment the substitutions at positions selected from A5, A8, A9, A10, A14, A15, A17, A18, A21, B1, B2, B3, B4, B5, B9, B10, B13, B14, B20, B21, B22, B23, B26, B27, B28, B29 and B30 are conservative amino acid substitutions relative to the native insulin sequence.

In accordance with one embodiment the B chain comprises the sequence $R_{22}$-$X_{25}LCGX_{29}X_{30}LVX_{33}X_{34}LYLVCGX_{41}X_{42}GFX_{45}$ (SEQ ID NO: 44), and the A chain comprises the sequence $GIVX_4X_5CCX_8X_9X_{10}CX_{12}LX_{14}X_{15}LX_{17}X_{18}X_{19}CX_{21}$-$R_{13}$ (SEQ ID NO: 45), wherein $X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid, aspartic acid, asparagine, lysine, ornithine or glutamine;

$X_{18}$ is methionine, asparagine, glutamine, aspartic acid, glutamic acid or threonine;

$X_{19}$ is tyrosine, 4-methoxy-phenylalanine or 4-amino phenylalanine;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is tyrosine or phenylalanine;

$R_{22}$ is selected from the group consisting of AYRPSE (SEQ ID NO: 46), FVNQ (SEQ ID NO: 47), PGPE (SEQ ID NO: 48), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal alpha amine; and $R_{13}$ is COOH or $CONH_2$. In one embodiment $X_8$, $X_{25}$ and $X_{30}$ are each histidine. In a further embodiment the insulin polypeptide comprises an analog of the A chain peptide sequence of SEQ ID NO: 68 and/or a B chain peptide sequence of SEQ ID NO: 69 wherein the analog of the A chain and B chain each comprise 1-3 further amino acid substitutions.

In accordance with one embodiment an insulin analog is provided wherein the A chain of the insulin peptide comprises the sequence $GIVEQCCX_8SICSLYQLX_{17}NX_{19}CX_{23}$ (SEQ ID NO: 49) and the B chain comprising the sequence $X_{25}LCGX_{29}X_{30}LVEALYLVCGERGFF$ (SEQ ID NO: 65) wherein $X_8$ is selected from the group consisting of threonine and histidine;

$X_{17}$ is glutamic acid or glutamine;

$X_{19}$ is tyrosine, 4-methoxy-phenylalanine or 4-amino phenylalanine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid. In a further embodiment the B chain comprises the sequence $X_{22}VNQX_{25}LCGX_{29}X_{30}LVEALYLVCGERGFFYT$-$Z_1$-$B_1$ (SEQ ID NO: 66) wherein $X_{22}$ is selected from the group consisting of phenylalanine and desamino-phenylalanine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with some embodiments the insulin polypeptide comprises a B chain having the sequence $R_{23}$-$R_{24}$-$X_{25}LCGX_{29}X_{30}LVX_{33}X_{34}LYLVCGX_{41}X_{42}GFX_{45}$ (SEQ ID NO: 44) or $R_{23}$-$R_{22}$-$HLCGSX_{30}LVEALYLVCGERGFF$ (SEQ ID NO: 67) and an A chain having the sequence $GIVX_4ECCX_8X_9SCDLX_{14}X_{15}LX_{17}X_{18}X_{19}CX_{21}$-$R_{13}$ (SEQ ID NO: 68)

wherein $X_4$ is glutamic acid or aspartic acid;

$X_8$ is histidine, threonine or phenylalanine;

$X_9$ is arginine, lysine, ornithine or alanine;

$X_{14}$ is arginine, lysine, ornithine or alanine;

$X_{15}$ is glutamine, glutamic acid, arginine, alanine, lysine, ornithine or leucine;

$X_{17}$ is glutamine or glutamic acid;

$X_{18}$ is methionine, asparagine, glutamine, aspartic acid, glutamic acid or threonine;

$X_{19}$ is tyrosine, 4-methoxy-phenylalanine or 4-amino phenylalanine;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{22}$ is selected from the group consisting of phenylalanine and desamino-phenylalanine;

$X_{25}$ is histidine or threonine;

$X_{29}$ is selected from the group consisting of alanine and glycine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is tyrosine or phenylalanine;

$R_{22}$ is selected from the group consisting of $X_{22}$VNQ (SEQ ID NO: 101), a tripeptide valine-asparagine-glutamine, a dipeptide asparagine-glutamine, glutamine, and a bond;

$R_{23}$ is an N-terminal alpha amine or $X_{60}(X_{61}X_{62})_dX_{63}K$ (SEQ ID NO: 102)

wherein $X_{60}$ is selected from the group consisting of glycine, glutamic acid and aspartic acid;

$X_{61}$ and $X_{62}$ are independently selected from the group consisting of glutamic acid and aspartic acid;

$X_{63}$ is selected from the group consisting of arginine, aspartic acid and glutamic acid;

d is an integer selected from 1-3;

$R_{24}$ is selected from the group consisting of AYRPSE (SEQ ID NO: 46), PGPE (SEQ ID NO: 48), a tripeptide glycine-proline-glutamic acid, a dipeptide proline-glutamic acid, glutamine, glutamic acid and a bond; and $R_{13}$ is COOH or $CONH_2$.

In accordance with some embodiments the A chain comprises the sequence GIVEQCCX$SICSLYQLX_{17}NX_{19}CX_{23}$ (SEQ ID NO: 49) or GIVDECCX$_8X_9SCDLX_{14}X_{15}LX_{17}X_{18}X_{19}CX_{21}$-$R_{13}$ (SEQ ID NO: 50), and the B chain comprises the sequence $X_{25}LCGX_{29}X_{30}LVX_{33}X_{34}LYLVCGDX_{42}GFX_{45}$ (SEQ ID NO: 51) wherein $X_8$ is histidine or phenylalanine;

$X_9$ and $X_{14}$ are independently selected from arginine, lysine, ornithine or alanine;

$X_{15}$ is arginine, lysine, ornithine or leucine;

$X_{17}$ is glutamic acid or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine, ornithine and arginine;

$X_{45}$ is tyrosine; and $R_{13}$ is COOH or $CONH_2$. In one embodiment at least one of n and k is 1.

In a further embodiment the A chain comprises the sequence GIVDECCHX$_9SCDLX_{14}X_{15}LX_{17}X_{18}X_{19}CX_{21}$-$R_{13}$ (SEQ ID NO: 50), and the B chain comprises the sequence $X_{25}LCGX_{29}X_{30}LVX_{33}X_{34}LYLVCGDX_{42}GFX_{45}$ (SEQ ID NO: 51) wherein $X_9$ and $X_{14}$ are independently selected from arginine, lysine, ornithine or alanine;

$X_{15}$ is arginine, lysine, ornithine or leucine;

$X_{17}$ is glutamic acid, aspartic acid, asparagine, lysine, ornithine or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine, ornithine and arginine;

$X_{45}$ is tyrosine or phenylalanine and $R_{13}$ is COOH or $CONH_2$. In a further embodiment the A chain comprises the sequence GIVDECCHX$_9SCDLX_{14}X_{15}LX_{17}MX_{19}CX_{21}$-$R_{13}$ (SEQ ID NO: 52), and the B chain comprises the sequence $X_{25}LCGAX_{30}LVDALYLVCGDX_{42}GFX_{45}$ (SEQ ID NO: 53) wherein $X_9$, $X_{14}$ and $X_{15}$ are independently ornithine, lysine or arginine;

$X_{17}$ is glutamic acid or glutamine;

$X_{19}$ is tyrosine, 4-methoxy-phenylalanine or 4-amino phenylalanine;

$X_{21}$ is alanine, glycine or asparagine;

$X_{25}$ is selected from the group consisting of histidine and threonine;

$X_{30}$ is selected from the group consisting of histidine, aspartic acid and glutamic acid;

$X_{42}$ is selected from the group consisting of alanine, lysine, ornithine and arginine;

$X_{45}$ is tyrosine or phenylalanine and $R_{13}$ is COOH or $CONH_2$. In one embodiment the B chain is selected from the group consisting of HLCGAELVDALYLVCGDX$_{42}$GFY (SEQ ID NO: 54), GPEHLCGAELVDALYLVCGDX$_{42}$GFY (SEQ ID NO: 55), GPEHLCGAELVDALYLVCGDX$_{42}$GFYFNPKT (SEQ ID NO: 56) and GPEHLCGAELVDALYLVCGDX$_{42}$GFYFNKPT (SEQ ID NO: 57), wherein $X_{42}$ is selected from the group consisting of ornithine, lysine and arginine. In a further embodiment the A chain comprises the sequence GIVDECCHX$_9SCDLX_{14}X_{15}LQMYCN$-$R_{13}$ (SEQ ID NO: 18), wherein $X_9$, $X_{14}$ and $X_{15}$ are independently ornithine, lysine or arginine.

In one embodiment an insulin single chain analog is provided comprising the general formula IB-LM-IA wherein IB is an amino acid sequence selected from the group consisting of HLCGAELVDALYLVCGDX$_{42}$GFY (SEQ ID NO: 54), GPEHLCGAELVDALYLVCGDX$_{42}$GFY (SEQ ID NO: 55), GPEHLCGAELVDALYLVCGDX$_{42}$GFYFNPKT (SEQ ID NO: 56) and GPEHLCGAELVDALYLVCGDX$_{42}$GFYFNPKT (SEQ ID NO: 57), LM is a linking moiety selected from the group consisting of GAGSSSX$_{57}$RAPQT SEQ ID NO: 18), GYGSSSX$_{57}$R (SEQ ID NO: 58) and IA is the amino acid sequence GIVDECCHX$_9$SCDLX$_{14}$X$_{15}$LQMYCN-R$_{13}$ (SEQ ID NO: 18), wherein X$_9$, X$_{14}$, X$_{15}$X$_{42}$ and X$_{57}$ are independently ornithine, lysine or arginine. In one further embodiment the linking moiety is GYGSSSOR (SEQ ID NO: 59).

In one embodiment the B chain is selected from the group consisting of HLCGAELVDALYLVCGDOGFY (SEQ ID NO: 60), GPEHLCGAELVDALYLVCGDOGFY (SEQ ID NO: 61), GPEHLCGAELVDALYLVCGDOGFYFNPKT (SEQ ID NO: 62) and GPEHLCGAELVDALYLVCGDOGFYFNPKT (SEQ ID NO: 63) and the A chain is GIVDECCHOSCDLOOLQMX$_{19}$CN-R$_{13}$ (SEQ ID NO: 64), wherein X$_{19}$ is tyrosine, 4-methoxy-phenylalanine or 4-amino phenylalanine.

Pegylation of Insulin Polypeptides

Applicants have surprisingly discovered that covalently linkage of a hydrophilic moiety to the insulin single chain analogs disclosed herein provide analogs having slower onset, extended duration and exhibit a basal profile of activity. In one embodiment, the insulin polypeptides disclosed herein are further modified to comprise a hydrophilic moiety covalently linked to the side chain of an amino acid at a position selected from the group consisting of A9, A14 and A15 of the A chain or at the N-terminal alpha amine of the B chain (e.g. at position B1 for insulin based B chain or position B2 for IGF-1 based B chain) or at the side chain of an amino acid at position B1, B2, B10, B22, B28 or B29 of the B chain or at any position of the linking moiety that links the A chain and B chain in single chain insulin analogs. In exemplary embodiments, this hydrophilic moiety is covalently linked to a Lys, Cys, Orn, homocysteine, or acetyl-phenylalanine residue at any of these positions. In one embodiment the hydrophilic moiety is covalently linked to the side chain of an amino acid of the linking moiety.

Exemplary hydrophilic moieties include polyethylene glycol (PEG), for example, of a molecular weight of about 1,000 Daltons to about 40,000 Daltons, or about 20,000 Daltons to about 40,000 Daltons. Additional suitable hydrophilic moieties include, polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly(beta-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with some embodiments has a molecular weight selected from the range of about 500 to about 40,000 Daltons. In one embodiment the hydrophilic moiety, e.g. PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiment the hydrophilic moiety, e.g., PEG, has a molecular weight of about 20,000 to about 40,000 Daltons. In one embodiment the hydrophilic moiety, e.g. PEG, has a molecular weight of about 20,000 Daltons. In one embodiment an insulin polypeptide is provided wherein one or more amino acids of the analog are pegylated, and the combined molecular weight of the covalently linked PEG chains is about 20,000 Daltons.

In one embodiment dextrans are used as the hydrophilic moiety. Dextrans are polysaccharide polymers of glucose subunits, predominantly linked by al-6 linkages. Dextran is available in many molecular weight ranges, e.g., about 1 kD to about 100 kD, or from about 5, 10, 15 or 20 kD to about 20, 30, 40, 50, 60, 70, 80 or 90 kD.

Linear or branched polymers are contemplated. Resulting preparations of conjugates may be essentially monodisperse or polydisperse, and may have about 0.5, 0.7, 1, 1.2, 1.5 or 2 polymer moieties per peptide.

In one embodiment the hydrophilic moiety is a polyethylene glycol (PEG) chain, optionally linked to the side chain of an amino acid at a position selected from the group consisting of A9, A14 and A15 of the A chain, positions B1, B2, B10, B22, B28 or B29 of the B chain, at the N-terminal alpha amine of the B chain, or at any position of the linking moiety that links the A chain and B chain, including for example at position C8 in an insulin single chain analog. In one embodiment the insulin single chain analog comprises a peptide linking moiety of 8 to 12 amino acids, wherein one of the amino acids of the linking moiety has a polyethylene chain covalently bound to its side chain. In one embodiment the insulin single chain analog comprises a peptide linking moiety of 8 to 12 amino acids, wherein an amino acid of the linking moiety is pegylated and one or more amino acid at a position selected from the group consisting of A9, A14 and A15 of the A chain, positions B1, B2, B10, B22, B28 or B29 of the B chain is also pegylated. In one embodiment the total molecular weight of the covalently linked PEG chain(s) is about 20,000 Daltons.

Hydrophilic moieties such as polyethylene glycol can be attached to the insulin polypeptide under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

In a specific aspect of the invention, an amino acid residue on the insulin polypeptide having a thiol is modified with a hydrophilic moiety such as PEG. In some embodiments, the thiol is modified with maleimide-activated PEG in a Michael addition reaction to result in a PEGylated peptide comprising the thioether linkage shown below:

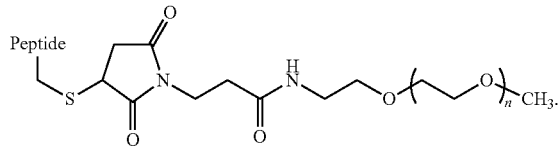

In some embodiments, the thiol is modified with a haloacetyl-activated PEG in a nucleophilic substitution reaction to result in a PEGylated peptide comprising the thioether linkage shown below:

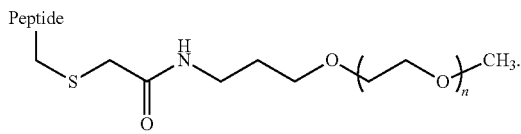

Acylation of Insulin Polypeptides

In some embodiments, the insulin polypeptide is modified to comprise an acyl group. The acyl group can be covalently linked directly to an amino acid of the insulin polypeptide, or indirectly to an amino acid of the insulin polypeptide via a spacer, wherein the spacer is positioned between the amino acid of the insulin polypeptide and the acyl group. The insulin polypeptide may be acylated at the same amino acid position where a hydrophilic moiety is linked, or at a different amino acid position. For example, acylation may occur at any position including any amino acid of the A or B chains as well as a position within the linking moiety, provided that the activity exhibited by the non-acylated insulin polypeptide is retained upon acylation. Nonlimiting examples include acylation at positions A14 and A15 of the A chain, positions position B1 for insulin based B chain or position B2 for IGF-1 based B chain or positions B10, B22, B28 or B29 of the B chain or at any position of the linking moiety of a single chain insulin analog.

In one specific aspect of the invention, the insulin polypeptide (or derivative or conjugate thereof) is modified to comprise an acyl group by direct acylation of an amine, hydroxyl, or thiol of a side chain of an amino acid of the insulin polypeptide. In some embodiments, the insulin polypeptide is directly acylated through the side chain amine, hydroxyl, or thiol of an amino acid. In some embodiments, acylation is at position B28 or B29 (according to the amino acid numbering of the native insulin A and B chain sequences). In this regard, an insulin polypeptide can be provided that has been modified by one or more amino acid substitutions in the A or B chain sequence, including for example at positions A14, A15, B1, B2, B10, B22, B28 or B29 (according to the amino acid numbering of the native insulin A and B chain sequences) or at any position of the linking moiety with an amino acid comprising a side chain amine, hydroxyl, or thiol. In some specific embodiments of the invention, the direct acylation of the insulin polypeptide occurs through the side chain amine, hydroxyl, or thiol of the amino acid at position B28 or B29 (according to the amino acid numbering of the native insulin A and B chain sequences).

In one embodiment, the insulin polypeptide comprises an amino acid of Formula I:

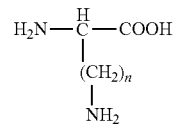

wherein n=1 to 4
[Formula I]

In some exemplary embodiments, the amino acid of Formula I, is the amino acid wherein n is 4 (Lys) or n is 3 (Orn).

In another embodiment, the insulin polypeptide comprises an amino acid of Formula II:

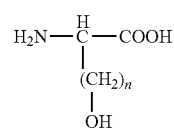

wherein n=1 to 4
[Formula II]

In some exemplary embodiments, the amino acid of Formula II is the amino acid wherein n is 1 (Ser).

In yet another embodiment, the insulin polypeptide comprises a side chain thiol is an amino acid of Formula III:

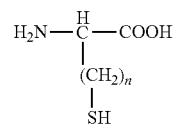

wherein n=1 to 4
[Formula III]

In some exemplary embodiments, the amino acid of Formula III is the amino acid wherein n is 1 (Cys).

In yet another embodiment, the insulin polypeptide comprises a disubstituted amino acid comprising the same structure of Formula I, Formula II, or Formula III, except that the hydrogen bonded to the alpha carbon of the amino acid of Formula I, Formula II, or Formula III is replaced with a second side chain.

In accordance with one embodiment, the acylated insulin polypeptides comprise a spacer between the peptide and the acyl group. In some embodiments, the insulin polypeptide is covalently bound to the spacer, which is covalently bound to the acyl group. In some exemplary embodiments, the insulin polypeptide is modified to comprise an acyl group by acylation of an amine, hydroxyl, or thiol of a spacer, which spacer is attached to a side chain of an amino acid at position B28 or B29 (according to the amino acid numbering of the A or B chain of native insulin), or at any position of the spacer moiety. The amino acid of the insulin polypeptide to which the spacer is attached can be any amino acid comprising a moiety which permits linkage to the spacer. For example, an amino acid comprising a side chain —NH$_2$, —OH, or —COOH (e.g., Lys, Orn, Ser, Asp, or Glu) is suitable.

In some embodiments, the spacer between the insulin polypeptide and the acyl group is an amino acid comprising a side chain amine, hydroxyl, or thiol (or a dipeptide or tripeptide comprising an amino acid comprising a side chain amine, hydroxyl, or thiol). In some embodiments, the spacer comprises a hydrophilic bifunctional spacer. In a specific embodiment, the spacer comprises an amino poly(alkyloxy) carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In one embodiment, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between peptide the insulin polypeptide and the acyl group is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In accordance with certain embodiments the bifunctional spacer can be a synthetic or naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer attached to the insulin polypeptide can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine (β-Ala), N-α-methyl-alanine (Me-Ala), aminobutyric acid (Abu), α-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(02)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO2)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), U-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), U-Benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), 1-amino-1-cyclohexane carboxylic acid (Acx), aminovaleric acid, beta-cyclopropyl-alanine (Cpa), propargylglycine (Prg), allylglycine (Alg), 2-amino-2-cyclohexyl-propanoic acid (2-Cha), tertbutylglycine (Tbg), vinylglycine (Vg), 1-amino-1-cyclopropane carboxylic acid (Acp), 1-amino-1-cyclopentane carboxylic acid (Acpe), alkylated 3-mercaptopropionic acid, 1-amino-1-cyclobutane carboxylic acid (Acb). In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

The insulin polypeptide can be modified to comprise an acyl group by acylation of a long chain alkane. In specific aspects, the long chain alkane comprises an amine, hydroxyl, or thiol group (e.g. octadecylamine, tetradecanol, and hexadecanethiol) which reacts with a carboxyl group, or activated form thereof, of the insulin polypeptide. The carboxyl group, or activated form thereof, of the insulin polypeptide can be part of a side chain of an amino acid (e.g., glutamic acid, aspartic acid) of the insulin polypeptide or can be part of the peptide backbone.

In certain embodiments, the insulin polypeptide is modified to comprise an acyl group by acylation of the long chain alkane by a spacer which is attached to the insulin polypeptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers. As used herein, the term "activated form of a carboxyl group" refers to a carboxyl group with the general formula $R(C=O)X$, wherein X is a leaving group and R is the insulin polypeptide or the spacer. For example, activated forms of a carboxyl groups may include, but are not limited to, acyl chlorides, anhydrides, and esters. In some embodiments, the activated carboxyl group is an ester with a N-hydroxysuccinimide (NHS) leaving group.

With regard to these aspects of the invention, in which a long chain alkane is acylated by the peptide the insulin polypeptide or the spacer, the long chain alkane may be of any size and can comprise any length of carbon chain. The long chain alkane can be linear or branched.

In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

In some embodiments, an amine, hydroxyl, or thiol group of the insulin polypeptide is acylated with a cholesterol acid. In a specific embodiment, the peptide is linked to the cholesterol acid through an alkylated des-amino Cys spacer, i.e., an alkylated 3-mercaptopropionic acid spacer. Suitable methods of peptide acylation via amines, hydroxyls, and thiols are known in the art. See, for example, Miller, Biochem Biophys Res Commun 218: 377-382 (1996); Shimohigashi and Stammer, Int J Pept Protein Res 19: 54-62 (1982); and Previero et al., Biochim Biophys Acta 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

The acyl group of the acylated peptide the insulin polypeptide can be of any size, e.g., any length carbon chain, and can be linear or branched. In some specific embodiments of the invention, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

The acylated insulin polypeptide described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the acylated single chain analog comprises an amino acid selected from the group consisting of a Cys, Lys, Orn, homo-Cys, or Ac-Phe, and the side chain of the amino acid is covalently bonded to a hydrophilic moiety (e.g., PEG). In one embodiment, the acyl group is attached to position A14, A15, B1 (for insulin based B chains), B2 (for IGF-1 based B chains), B10, B22, B28 or B29 (according to the amino acid numbering of the A and B chains of native insulin), optionally via a spacer comprising Cys, Lys, Orn, homo-Cys, or Ac-Phe.

Alternatively, the acylated insulin polypeptide comprises a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Alkylation of the Insulin Polypeptide

In some embodiments, the insulin polypeptide is modified to comprise an alkyl group. The alkyl group can be covalently linked directly to an amino acid of the insulin polypeptide, or indirectly to an amino acid of the insulin polypeptide via a spacer, wherein the spacer is positioned between the amino acid of the insulin polypeptide and the alkyl group. The alkyl group can be attached to the insulin polypeptide via an ether, thioether, or amino linkage. For example, the insulin polypeptide may be alkylated at the same amino acid position where a hydrophilic moiety is linked, or at a different amino acid position. Alkylation can be carried out at any position within the insulin polypeptide, including for example in the C-terminal region of the B chain or at a position in the linking moiety, provided that insulin activity is retained. In a specific aspect of the invention, the insulin polypeptide is modified to comprise an alkyl group by direct alkylation of an amine, hydroxyl, or thiol of a side chain of an amino acid of the insulin polypeptide. In some embodiments, the insulin polypeptide is directly alkylated through the side chain amine, hydroxyl, or thiol of an amino acid. In some specific embodiments of the invention, the direct alkylation of the insulin polypeptide occurs through the side chain amine, hydroxyl, or thiol of the amino acid at position A14, A15, B1 (for insulin based B chains), B2 (for IGF-1 based b chains), B10, B22, B28 or B29 (according to the amino acid numbering of the A and B chain of native insulin).

In some embodiments, the amino acid of the insulin polypeptide comprises an amino acid selected from of Formula I, Formula II, and Formula III, and the alkyl group is linked through the amino, hydroxyl or thiol group contained in Formula I, Formula II, and Formula III, respectively. In some exemplary embodiments, the amino acid of Formula I, is the amino acid wherein n is 4 (Lys) or n is 3 (Orn). In some exemplary embodiments, the amino acid of Formula II is the amino acid wherein n is 1 (Ser). In some exemplary embodiments, the amino acid of Formula II is the amino acid wherein n is 1 (Cys). In yet other embodiments, the amino acid of peptide the insulin polypeptide comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In some embodiments of the invention, the insulin polypeptide comprises a spacer between the peptide and the alkyl group. In some embodiments, the insulin polypeptide is covalently bound to the spacer, which is covalently bound to the alkyl group. In some exemplary embodiments, the insulin polypeptide is modified to comprise an alkyl group by alkylation of an amine, hydroxyl, or thiol of a spacer, wherein the spacer is attached to a side chain of an amino acid at position A14, A15, B1 (for insulin based b chains), B2 (for IGF-1 based B chains), B10, B22, B28 or B29 (according to the amino acid numbering of the A and B chains of native insulin). The amino acid of the insulin polypeptide to which the spacer is attached can be any amino acid (e.g., a singly α-substituted amino acid or an α,α-disubstituted amino acid) comprising a moiety which permits linkage to the spacer. An amino acid of the insulin polypeptide comprising a side chain —NH$_2$, —OH, or —COOH (e.g., Lys, Orn, Ser, Asp, or Glu) is suitable. In some embodiments, the spacer between the peptide the insulin polypeptide and the alkyl group is an amino acid comprising a side chain amine, hydroxyl, or thiol or a dipeptide or tripeptide comprising an amino acid comprising a side chain amine, hydroxyl, or thiol.

In the instance in which the alpha amine is alkylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In exemplary embodiments, the spacer amino acid can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, 8-aminooctanoic acid. Alternatively, the spacer amino acid can be an acidic residue, e.g., Asp and Glu, provided that the alkylation occurs on the alpha amine of the acidic residue. In the instance in which the side chain amine of the spacer amino acid is alkylated, the spacer amino acid is an amino acid comprising a side chain amine, e.g., an amino acid of Formula I (e.g., Lys or Orn). In this instance, it is possible for both the alpha amine and the side chain amine of the spacer amino acid to be alkylated, such that the peptide is dialkylated. Embodiments of the invention include such dialkylated molecules.

When alkylation occurs through a hydroxyl group of the amino acid of the spacer, the amino acid or one of the amino acids of the spacer can be an amino acid of Formula II. In a specific exemplary embodiment, the amino acid is Ser.

When alkylation occurs through a thiol group of the amino acid of the spacer, the amino acid or one of the amino acids of the spacer can be an amino acid of Formula III. In a specific exemplary embodiment, the amino acid is Cys.

In some embodiments, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In some embodiments, the spacer between peptide the insulin polypeptide and the alkyl group is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between peptide the insulin polypeptide and the alkyl group is a hydrophobic bifunctional spacer. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

The spacer (e.g., amino acid, dipeptide, tripeptide, hydrophilic bifunctional spacer, or hydrophobic bifunctional spacer) is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a $C_{12}$ to $C_{18}$ alkyl group, e.g., $C_{14}$ alkyl group, $C_{16}$ alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments the length of the spacer and alkyl is 17 to 28 (e.g., 19 to 26, 19 to 21) atoms.

In accordance with one embodiment the bifunctional spacer is a synthetic or non-naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer attached to the insulin polypeptide can be composed of naturally-occurring and/or non-naturally occurring amino acids, including, for example, any of the amino acids taught herein. In some embodiments the spacer comprises an overall negative charge, e.g., comprises one or two negatively charged amino acids. In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu. In one embodiment the dipeptide spacer is γ-Glu-γ-Glu.

Suitable methods of peptide alkylation via amines, hydroxyls, and thiols are known in the art. For example, a Williamson ether synthesis can be used to form an ether linkage between the insulin peptide and the alkyl group. Also, a nucleophilic substitution reaction of the peptide with an alkyl halide can result in any of an ether, thioether, or amino linkage. The alkyl group of the alkylated peptide the insulin polypeptide can be of any size, e.g., any length carbon chain, and can be linear or branched. In some embodiments of the invention, the alkyl group is a $C_4$ to $C_{30}$ alkyl. For example, the alkyl group can be any of a $C_4$ alkyl, $C_6$ alkyl, $C_8$ alkyl, $C_{10}$ alkyl, $C_{12}$ alkyl, $C_{14}$ alkyl, $C_{16}$ alkyl, $C_{18}$ alkyl, $C_{20}$ alkyl, $C_{22}$ alkyl, $C_{24}$ alkyl, $C_{26}$ alkyl, $C_{28}$ alkyl, or a $C_{30}$ alkyl. In some embodiments, the alkyl group is a $C_8$ to $C_{20}$ alkyl, e.g., a $C_{14}$ alkyl or a $C_{16}$ alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

In some embodiments the insulin polypeptide is modified to comprise an alkyl group by reacting a nucleophilic, long chain alkane with the insulin polypeptide, wherein the insulin polypeptide comprises a leaving group suitable for nucleophilic substitution. In specific aspects, the nucleophilic group of the long chain alkane comprises an amine, hydroxyl, or thiol group (e.g. octadecylamine, tetradecanol, and hexadecanethiol). The leaving group of the insulin polypeptide can be part of a side chain of an amino acid or can be part of the peptide backbone. Suitable leaving groups include, for example, N-hydroxysuccinimide, halogens, and sulfonate esters.

In certain embodiments, the insulin polypeptide is modified to comprise an alkyl group by reacting the nucleophilic, long chain alkane with a spacer, which is attached to the insulin polypeptide, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group.

When a long chain alkane is alkylated by the insulin polypeptide or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments the long chain alkane comprises a $C_8$ to $C_{20}$ alkane, e.g., a $C_{14}$ alkane, $C_{16}$ alkane, or a $C_{18}$ alkane.

Also, in some embodiments alkylation can occur between the insulin polypeptide and a cholesterol moiety. For example, the hydroxyl group of cholesterol can displace a leaving group on the long chain alkane to form a cholesterol-insulin peptide product. The alkylated insulin polypeptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the insulin polypeptide can comprise an amino acid selected from Cys, Lys, Orn, homo-Cys, or Ac-Phe, wherein the side chain of the amino acid is covalently bonded to a hydrophilic moiety (e.g., PEG). In some embodiments the alkyl group is attached to position A14, A15, B1 (for insulin based B chains), B2 (for IGF-1 based B chains), B10, B22, B28 or B29 (according to the amino acid numbering of the A or B chain of native insulin), optionally via a spacer comprising Cys, Lys, Orn, homo-Cys, or Ac-Phe, and optionally further comprising a hydrophilic moiety linked to the side chain of another amino acid. Alternatively, the alkylated insulin polypeptide can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Conjugates

In some embodiments, the insulin polypeptides described herein are glycosylated, amidated, carboxylated, phosphorylated, esterified, N-acylated, cyclized via, e.g., a disulfide bridge, or converted into a salt (e.g., an acid addition salt, a basic addition salt), and/or optionally conjugated. The present disclosure also encompasses conjugates in which the insulin polypeptide is linked to a heterologous moiety. The conjugation between the insulin polypeptide and the heterologous moiety can be through covalent bonding, non-covalent bonding (e.g. electrostatic interactions, hydrogen bonds, van der Waals interactions, salt bridges, hydrophobic interactions, and the like), or both types of bonding. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other. In some aspects, the covalent bonds are peptide bonds. The conjugation of the insulin polypeptide to the heterologous moiety may be indirect or direct conjugation, the former of which may involve a linker or spacer. Suitable linkers and spacers are known in the art and include, but not limited to, any of the linkers or spacers described.

As used herein, the term "heterologous moiety" is synonymous with the term "conjugate moiety" and refers to any molecule (chemical or biochemical, naturally-occurring or non-coded) which is different from the insulin polypeptide to which it is attached. Exemplary conjugate moieties that can be linked to the insulin polypeptide include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments a conjugate is provided comprising the insulin polypeptide and a plasma protein, wherein the plasma protein is selected from the group consisting of albumin, transferin, fibrinogen and globulins. In some embodiments the plasma protein moiety of the conjugate is albumin or transferin. In one embodiment the heterologous moiety is albumin, including for example, albumins such as human serum albumin (HSA) and recombinant human albumin (rHA). The conjugate in some embodiments comprises the insulin polypeptide and one or more of a polypeptide, a nucleic acid molecule, an antibody or fragment thereof, a polymer, a the insulin polypeptideuantum dot, a small molecule, a toxin, a diagnostic agent, a carbohydrate, an amino acid.

Polymer Heterologous Moiety

In some embodiments, the heterologous moiety conjugated to the insulin polypeptide is a polymer. In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly (phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly (vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate).

In some embodiments, the polymer is a water-soluble polymer or a hydrophilic polymer. Hydrophilic polymers are further described herein under "Hydrophilic Heterologous Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene glycol, and derivatives, salts, and combinations thereof.

In one embodiment, the polymer is a polyalkylene glycol, including, for example, polyethylene glycol (PEG). In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

Controlled Release Formulations

Alternatively, the insulin polypeptides described herein can be modified into a depot form, such that the manner in which the conjugate of the present disclosure is released into the body to which it is administered is controlled with respect to time and location within the body (see, for example, U.S. Pat. No. 4,450,150). Depot forms of the conjugates of the present disclosures can be, for example, an implantable composition comprising the conjugate of the present disclosure and a porous or non-porous material, such as a polymer, wherein the conjugate of the present disclosures is encapsulated by or diffused throughout the material and/or degradation of the non-porous material. The depot is then implanted into the desired location within the body and the conjugate of the present disclosures are released from the implant at a predetermined rate.

Alternatively, a large depot polymer can be linked to a self-cleaving dipeptide element that is covalently bound to the insulin polypeptide as described herein. In this embodiment, the depot polymer effectively sequesters the insulin polypeptide at its site of administration until it is subsequently cleaved from the single chain analog via a non-enzymatic reaction at a predetermined rate. Depot formulations of insulin analogs using a self-cleaving dipeptide have been described in PCT/US2009/068713, the disclosure of which is incorporated herein. In one embodiment an insulin polypeptide is provided comprising a dipeptide prodrug element wherein the dipeptide prodrug element is linked to a large polymer such as PEG or dextran or is acylated with a C18-C25 hydrocarbon. In one embodiment a self-cleaving dipeptide element comprising a large depot polymer (including for example, PEG) is linked to the side chain of an amino acid of the linking moiety of an insulin single chain analog, including for example, the amino acid at position C8 of the linking moiety.

Pharmaceutical compositions can be prepared that comprise the single chain analogs and are formulated to have a desired in vivo release profile. In some aspects, the pharmaceutical composition is an immediate release, controlled release, sustained release, extended release, delayed release, or bi-phasic release formulation. Methods of formulating peptides or conjugates for controlled release are known in the art. See, for example, J Pharm 374: 46-52 (2009) and International Patent Application Publication Nos. WO 2008/130158, WO2004/033036; WO2000/032218; and WO 1999/040942. The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

Prodrug Derivatives of Insulin Polypeptides

The present disclosure also encompasses prodrug analogs of the insulin polypeptide peptides disclosed herein. Advantageously, the prodrug formulations improve the therapeutic index of the underlying peptide and delay onset of action and enhance the half-life of the insulin polypeptide peptide. The disclosed prodrug chemistry can be chemically conjugated to active site amines to form amides that revert to the parent amine upon diketopiperazine formation and release of the prodrug element (see International patent application PCT/US2009/068713, the disclosure of which is expressly incorporated herein). This novel biologically friendly prodrug chemistry spontaneously degrades under physiological conditions (e.g. pH of about 7, at 37° C. in an aqueous environment) and is not reliant on enzymatic degradation. The duration of the prodrug analog is determined by the selection of the dipeptide prodrug sequence, and thus allows for flexibility in prodrug formulation.

In one embodiment a prodrug is provided having a non-enzymatic activation half time (t½) of between 1-100 hrs under physiological conditions. Physiological conditions as disclosed herein are intended to include a temperature of about 35 to 40° C. and a pH of about 7.0 to about 7.4 and more typically include a pH of 7.2 to 7.4 and a temperature of 36 to 38° C. in an aqueous environment. In one embodiment a dipeptide, capable of undergoing diketopiperazine formation under physiological conditions, is covalently linked through an amide or ester linkage to the insulin polypeptide (see International applications WO 2009/099763 and PCT/US2009/068713 the disclosures of which are incorporated herein).

Advantageously, the rate of cleavage, and thus activation of the prodrug, depends on the structure and stereochemistry of the dipeptide pro-moiety and also on the strength of the nucleophile. The prodrugs disclosed herein will ultimately be chemically converted to structures that can be recognized by the insulin/IGF receptor, wherein the speed of this chemical conversion will determine the time of onset and duration of in vivo biological action. The prodrug chemistry disclosed in this application relies upon an intramolecular chemical reaction that is not dependent upon additional chemical additives, or enzymes. The speed of conversion is controlled by the chemical nature of the dipeptide substituent and its cleavage under physiological conditions. Since physiological pH and temperature are tightly regulated within a highly defined range, the speed of conversion from prodrug to drug will exhibit high intra and interpatient reproducibility.

As disclosed herein prodrugs are provided wherein the insulin polypeptide peptides have extended half-lives of at least 1 hour, and more typically greater than 20 hours but less than 100 hours, and are converted to the active form at physiological conditions through a non-enzymatic reaction driven by inherent chemical instability. In one embodiment the a non-enzymatic activation t½ time of the prodrug is between 1-100 hrs, and more typically between 12 and 72 hours, and in one embodiment the t½ is between 24-48 hrs as measured by incubating the prodrug in a phosphate buffer solution (e.g., PBS) at 37° C. and pH of 7.2. In one embodiment the half-life of the prodrugs is about 1, 8, 12, 20, 24, 48 or 72 hours. In one embodiment the half-life of the prodrugs is about 100 hours or greater including half-lives of up to about 168, 336, 504, 672 or 720 hours, and are converted to the active form at physiological conditions through a non-enzymatic reaction driven by inherent chemical instability. The half-lives of the various prodrugs are calculated by using the formula $t_{1/2}=0.693/k$, where 'k' is the first order rate constant for the degradation of the prodrug. In one embodiment, activation of the prodrug occurs after cleavage of an amide bond linked dipeptide, and formation of a diketopiperazine or diketomorpholine, and the active insulin polypeptide peptide.

In another embodiment, the dipeptide prodrug element is covalently bound to the insulin polypeptide peptide via an amide linkage, and the dipeptide further comprises a depot polymer linked to dipeptide. In one embodiment two or more depot polymers are linked to a single dipeptide element. In one embodiment the depot polymer is linked to the side chain of one of the amino acids comprising the dipeptide prodrug element. The depot polymer is selected to be biocompatible and of sufficient size that the insulin polypeptide, modified by covalent attachment of the dipeptide, remains sequestered at an injection site and/or incapable of interacting with its corresponding receptor upon administration to a patient. Subsequent cleavage of the dipeptide releases the insulin polypeptide to interact with its intended target. The depot bearing dipeptide element can be linked to the insulin polypeptide via an amide bond through any convenient amine group of the insulin polypeptide, including an N-terminal alpha amine or an amine bearing side chain of an internal natural or synthetic amino acid of the insulin polypeptide. In one embodiment the depot bearing dipeptide element is linked to the N-terminal alpha amine or to the amino group of a 4-amino phenylalanine present at position A19 of the single chain analog.

In accordance with one embodiment the depot polymer is selected from biocompatible polymers known to those skilled in the art. The depot polymers typically have a size selected from a range of about 20,000 to 120,000 Daltons. In one embodiment the depot polymer has a size selected from a range of about 40,000 to 100,000 or about 40,000 to 80,000 Daltons. In one embodiment the depot polymer has a size of about 40,000, 50,000, 60,000, 70,000 or 80,000 Daltons. Suitable depot polymers include but are not limited to dextrans, polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof, and biodegradable polymers and their copolymers including caprolactone-based polymers, polycaprolactones and copolymers which include polybutylene terephthalate. In one embodiment the depot polymer is selected from the group consisting of polyethylene glycol, dextran, polylactic acid, polyglycolic acid and a copolymer of lactic acid and glycolic acid, and in one specific embodiment the depot polymer is polyethylene glycol. In one embodiment the depot polymer is polyethylene glycol and the combined molecular weight of depot polymer(s) linked to the dipeptide element is about 40,000 to 80,000 Daltons.

Specific dipeptides composed of natural or synthetic amino acids have been identified that facilitate intramolecular decomposition under physiological conditions to release the active insulin polypeptide. The dipeptide can be linked (via an amide bond) to an amino group present on the insulin polypeptide, or an amino group introduced into the insulin polypeptide by modification of the peptide sequence. In one embodiment the dipeptide structure is selected to resist cleavage by peptidases present in mammalian sera, including for example dipeptidyl peptidase IV (DPP-IV). Accordingly, in one embodiment the rate of cleavage of the dipeptide prodrug element from the bioactive peptide is not substantially enhanced (e.g., greater than 2X) when the reaction is conducted using physiological conditions in the presence of serum proteases relative to conducting the reaction in the absence of the proteases. Thus the cleavage half-life of the dipeptide prodrug element from the insulin polypeptide (in PBS under physiological conditions) is not more than two, three, four or five fold the cleavage half-life of the dipeptide prodrug element from the insulin polypeptide in a solution comprising a DPP-IV protease. In one embodiment the solution comprising a DPP-IV protease is serum, more particularly mammalian serum, including human serum.

In accordance with one embodiment the dipeptide prodrug element comprises the structure U-B, wherein U is an amino acid or a hydroxyl acid and B is an N-alkylated amino acid. The structure of U-B is selected, in one embodiment, wherein chemical cleavage of U-B from the insulin polypeptide is at least about 90% complete within about 1 to about 720 hours in PBS under physiological conditions. In one embodiment the chemical cleavage half-life ($t_{1/2}$) of U-B from the insulin polypeptide peptide is at least about 1 hour to about 1 week in PBS under physiological conditions. In one embodiment U, B, or the amino acid of the insulin polypeptide to which U-B is linked is a non-coded amino acid. In some embodiments U and/or B is an amino acid in the D stereoisomer configuration. In some exemplary embodiments, U is an amino acid in the D stereoisomer configuration and B is an amino acid in the L stereoisomer configuration. In some exemplary embodiments, U is an amino acid in the L stereoisomer configuration and B is an amino acid in the D stereoisomer configuration. In some exemplary embodiments, U is an amino acid in the D stereoisomer configuration and B is an amino acid in the D stereoisomer configuration. In one embodiment B is an N-alkylated amino acid but is not proline. In one embodiment the N-alkylated group of amino acid B is a $C_1$-$C_{18}$ alkyl, and in one embodiment the N-alkylated group is $C_1$-$C_6$ alkyl. In one embodiment U is an amino acid having a disubstitution at the alpha carbon.

In one embodiment one or more dipeptide elements are linked to insulin polypeptide through an amide bond formed through one or more amino groups selected from the N-terminal amino group of the B chain, or the side chain amino group of an amino acid present in the insulin polypeptide. In one embodiment the insulin polypeptide comprises two dipeptide elements, wherein the dipeptide elements are optionally pegylated, alkylated, acylated or linked to a depot polymer. In accordance with one embodiment the dipeptide extension is covalently linked to an insulin polypeptide through the side chain amine of a lysine residue that resides at or near the active site. In one embodiment the dipeptide extension is attached through a synthetic amino acid or a modified amino acid, wherein the synthetic amino acid or modified amino acid exhibits a functional group suitable for covalent attachment of the dipeptide extension (e.g., the aromatic amine of an amino-phenylalanine). In accordance with one embodiment one or more dipeptide elements are linked to the insulin polypeptide at an amino group selected from the N-terminal amino group of the B chain, or the side chain amino group of an aromatic amine of a 4-amino-phenylalanine residue present at a position corresponding to position A19, B16 or B25 of native insulin.

Figure 5A:
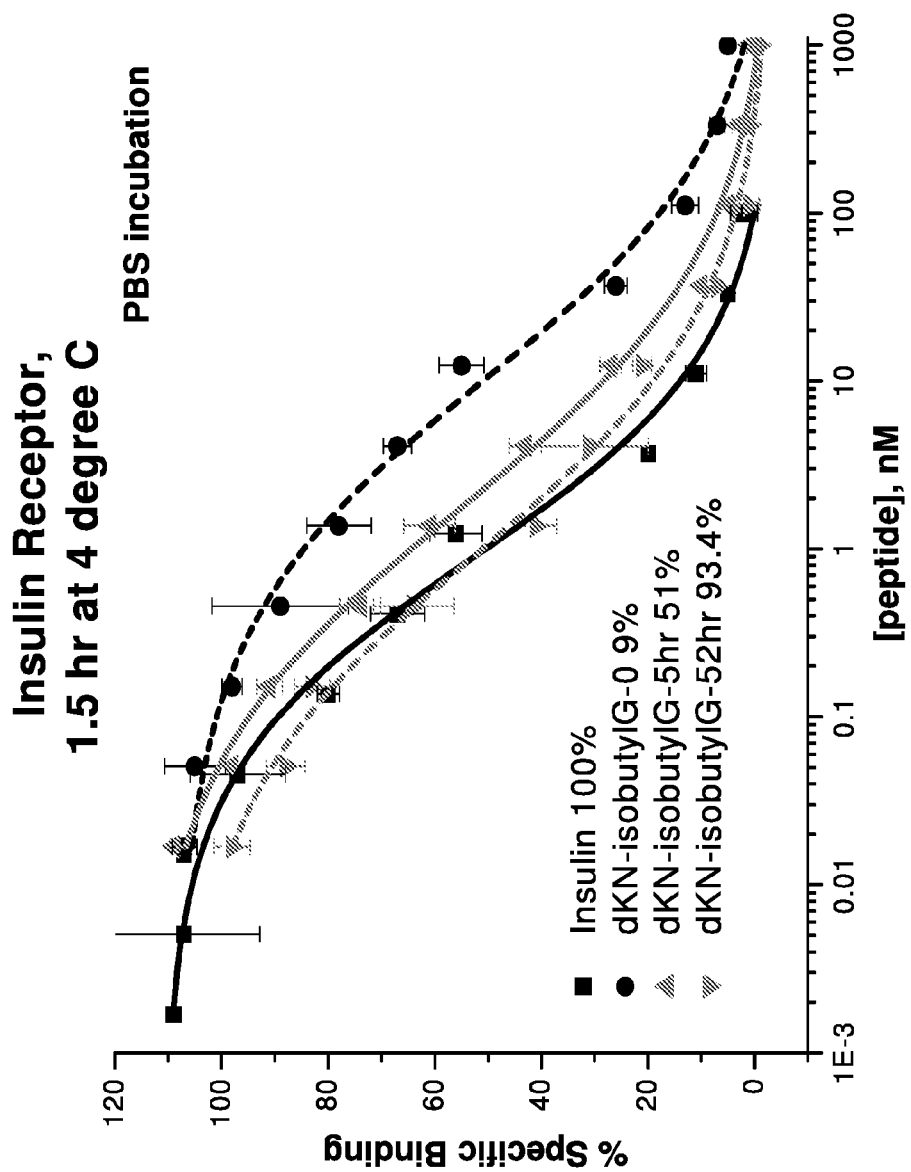
FIGS. 5A & 5B are graphs depicting the in vitro activity of the prodrug dK,(N-isobutylG)-IGF1YL (SEQ ID NO: 86, with dipeptide linked through the A19 4-aminoPhe).
Figure 5B:
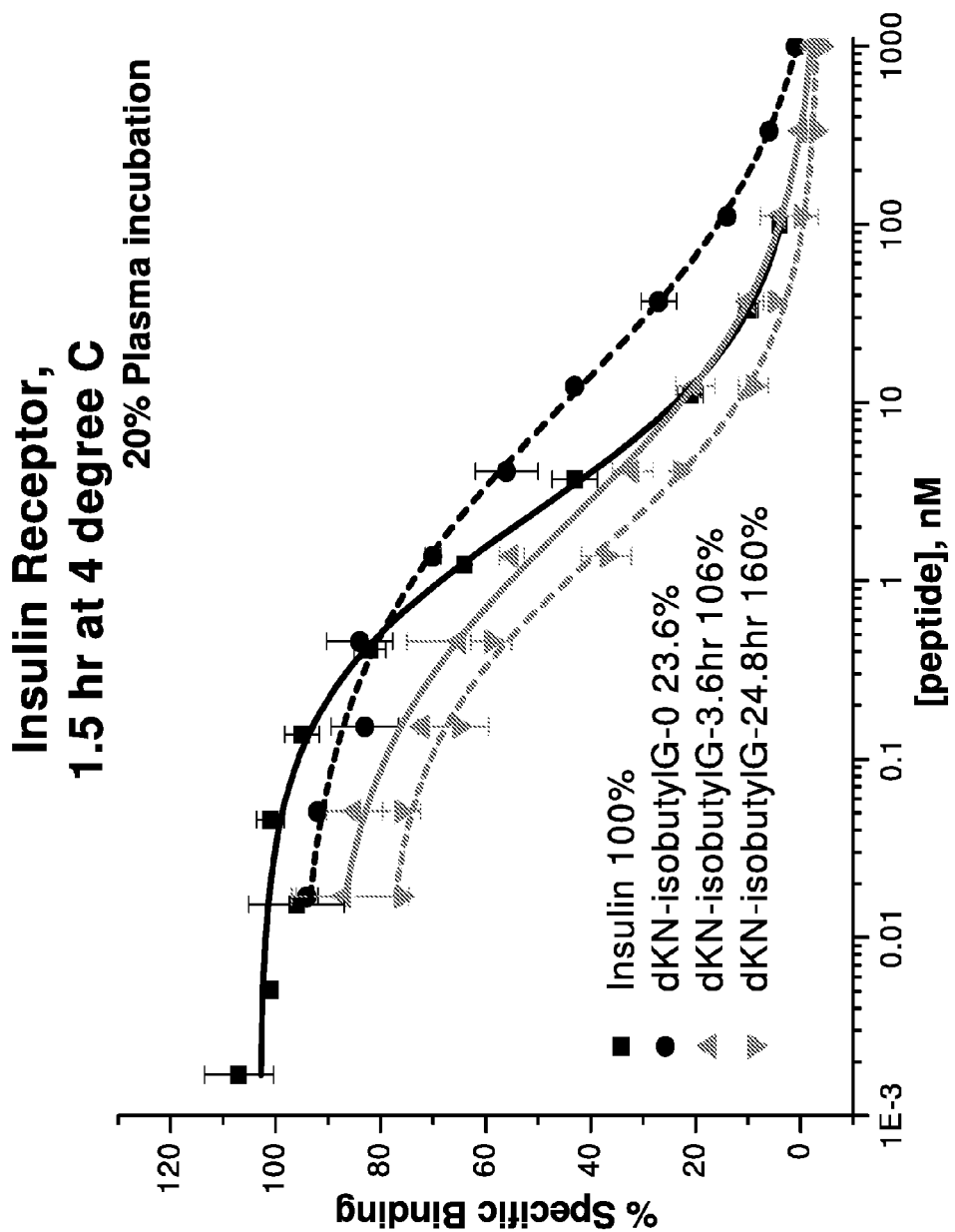

Applicants have discovered that the selective insertion of a 4-amino phenylalanine amino acid moiety for the native tyrosine at position 19 of the A chain can be accommodated without loss in potency of the insulin peptide. Subsequent chemical amidation of this active site amino group with the dipeptide prodrug element disclosed herein dramatically lessens insulin receptor binding activity and thus provides a suitable prodrug of insulin (see FIG. 5, data provided for the $IGF1Y^{16}17$ (p-$NH_2$—F)$^{A19}$ analog which has been demonstrated to have comparable activity as insulin (p-$NH_2$—F)$^{A19}$, see FIG. 3). Applicants have discovered that a similar modification can be made to the $IGF^{B16B17}$ analog peptides to provide a suitable attachment site for prodrug chemistry. Accordingly, in one embodiment the dipeptide prodrug element is linked to the aromatic ring of an A19 4-amino-phenylalanine of an insulin (p-$NH_2$—F)$^{A19}$ or $IGF^{B16B17}$ insulin polypeptide peptide via an amide bond, wherein the C-terminal amino acid of the dipeptide comprises an N-alkylated amino acid and the N-terminal amino acid of the dipeptide is any amino acid. In an alternative embodiment the prodrug comprises a dipeptide element linked to the N-terminal alpha amine via an amide bond wherein one of the side chains of the dipeptide element is acylated.

In accordance with one embodiment an insulin polypeptide prodrug derivative is provided comprising a B chain with a dipeptide prodrug element linked via an amide bond to the N-terminal alpha amine of the B chain, or the side chain amino group of an aromatic amine of a 4-amino-phenylalanine residue present at a position corresponding to A19, B16 or B25 of native insulin or present in the linking moiety, wherein one of the side chains of the dipeptide element is acylated with a C18 to C25 hydrocarbon group. The insulin polypeptide prodrug derivative may comprise a native insulin A chain or a native IGF-1 A chain or any analogs thereof disclosed herein. In one embodiment the dipeptide comprises an N-terminal C-alkylated amino acid followed by an N-alkylated amino acid.

In accordance with one embodiment the dipeptide prodrug element comprises the general structure of Formula X:

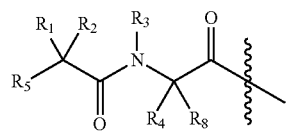

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl) ($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH. In one embodiment when the prodrug element is linked to the N-terminal alpha amine of the insulin polypeptide and $R_4$ and $R_3$ together with the atoms to which they are attached form a 4, 5 or 6 member heterocyclic ring, then at least one of $R_1$ and $R_2$ are other than H.

In one embodiment an insulin polypeptide is provided that comprises the structure: IB-LM-IA, wherein IB comprises the sequence J-$R_{23}R_{22}$-$X_{25}$LCG$X_{29}X_{30}$LVEALYLVCG ERGFF (SEQ ID NO: 65), LM is a linking moiety as disclosed herein and IA comprises the sequence GIVEQCC$X_8$SICSLYQL$X_{17}$N$X_{19}$C$X_{23}$ (SEQ ID NO: 49) wherein $X_8$ is selected from the group consisting of threonine and histidine;

$X_{17}$ is glutamic acid or glutamine;

$X_{19}$ is an amino acid of the general structure:

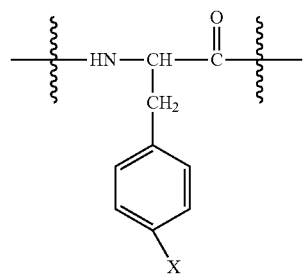

wherein X is selected from the group consisting of OH or NHR$_{10}$, wherein $R_{10}$ is H or a dipeptide element comprising the general structure U-B, wherein U is an amino acid or a hydroxyl acid and B is an N-alkylated amino acid;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$R_{22}$ is selected from the group consisting of FVNQ (SEQ ID NO: 47), a tripeptide valine-asparagine-glutamine, a dipeptide asparagine-glutamine, glutamine, glutamic acid and an N-terminal alpha amine; and $R_{23}$ is a bond or an amino sequence comprising 1 to 6 charged amino acids.

In a further embodiment the B chain comprises the sequence $X_{22}VNQX_{25}LCGX_{29}X_{30}LVEALYLVCGERGFFYT\text{-}Z_1\text{-}B_1$ (SEQ ID NO: 66) wherein $X_{22}$ is selected from the group consisting of phenylalanine and desamino-phenylalanine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with one embodiment an insulin polypeptide is provided that comprises the structure: IB-LM-IA, wherein IB comprises the sequence $X_{25}LCGX_{29}X_{30}LVEALYLVCG\ ERGFF$ (SEQ ID NO: 65), LM is a linking moiety as disclosed herein that covalently links IB to IA, and IA comprises the sequence $GIVEQCCX_8SICSLYQLENX_{19}CX_{21}$ (SEQ ID NO: 55), wherein the C-terminal phenylalanine residue of SEQ ID NO: 65 is directly covalently bound to the linking moiety, LM, in the absence of any intervening amino acids.

In one embodiment an insulin polypeptide is provided that comprises the structure: IB-LM-IA, wherein IB comprises the sequence J-R23-R22-$X_{25}LCGX_{29}X_{30}LVX_{33}X_{34}LYLVCGDX_{42}GFX_{45}$ (SEQ ID NO: 51), LM is a linking moiety as disclosed herein and IA comprises the sequence $GIVX_4ECCX_8X_9SCDLX_{14}X_{15}LX_{17}X_{18}X_{19}CX_{21}\text{-}R_{13}$ (SEQ ID NO: 68) wherein J is H or a dipeptide element comprising the general structure of U-B, wherein U is an amino acid or a hydroxyl acid and B is an N-alkylated amino acid linked through an amide bond;

$X_4$ is aspartic acid or glutamic acid;

$X_8$ is histidine or phenylalanine;

$X_9$ and $X_{14}$ are independently selected from arginine, ornithine, lysine or alanine;

$X_{15}$ is arginine, lysine, ornithine or leucine;

$X_{17}$ is glutamic acid or glutamine;

$X_{18}$ is methionine, asparagine or threonine;

$X_{19}$ is tyrosine;

$X_{21}$ is alanine, glycine or asparagine;

$R_{22}$ is selected from the group consisting of a covalent bond, AYRPSE (SEQ ID NO: 46), a glycine-proline-glutamic acid tripeptide, a proline-glutamic acid dipeptide and glutamic acid;

$R_{23}$ is a bond or an amino sequence comprising 1 to 6 charged amino acids;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine ornithine and arginine;

$X_{45}$ is tyrosine; and $R_{13}$ is COOH or $CONH_2$.

The Dipeptide Prodrug Element

The substituents of the dipeptide prodrug element, and its site of attachment to the insulin polypeptide, can be selected to provide the desired half-life of a prodrug analog of the insulin polypeptides disclosed herein. For example, when a dipeptide prodrug element comprising the structure:

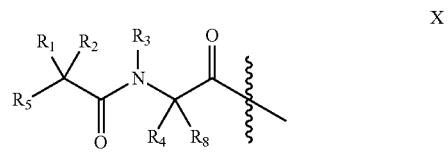

is linked to the alpha amino group of the N-terminal amino acid of the insulin polypeptide B chain, compounds having a $t_{1/2}$ of about 1 hour in PBS under physiological conditions are provided when $R_1$ and $R_2$ are independently $C_1\text{-}C_{18}$ alkyl or aryl; or $R_1$ and $R_2$ are linked through $-(CH_2)_p-$, wherein p is 2-9;

$R_3$ is $C_1\text{-}C_{18}$ alkyl;

$R_4$ and $R_8$ are each hydrogen; and $R_5$ is an amine.

In other embodiments, prodrugs linked at the N-terminus and having a $t_{1/2}$ of, e.g., about 1 hour comprise a dipeptide prodrug element with the structure:

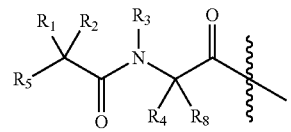

wherein $R_1$ and $R_2$ are independently $C_1\text{-}C_{18}$ alkyl or $(C_0\text{-}C_4$ alkyl)$(C_6\text{-}C_{10}$ aryl)$R_7$; or $R_1$ and $R_2$ are linked through $-(CH_2)_p-$, wherein p is 2-9;

$R_3$ is $C_1\text{-}C_{18}$ alkyl;

$R_4$ and $R_8$ are each hydrogen;

$R_5$ is $NH_2$;

$R_7$ is selected from the group consisting of hydrogen, $C_1\text{-}C_{18}$ alkyl, $C_2\text{-}C_{18}$ alkenyl, $(C_0\text{-}C_4$ alkyl)$CONH_2$, $(C_0\text{-}C_4$ alkyl)COOH, $(C_0\text{-}C_4$ alkyl)$NH_2$, $(C_0\text{-}C_4$ alkyl)OH, and halo; and $R_8$ is H.

Alternatively, in one embodiment an insulin polypeptide prodrug derivative is provided wherein the dipeptide prodrug is linked to the alpha amino group of the N-terminal amino acid of the insulin polypeptide B chain, and the prodrug has a $t_{1/2}$ between about 6 to about 24 hours in PBS under physiological conditions. In one embodiment an insulin polypeptide prodrug derivative having a $t_{1/2}$ between about 6 to about 24 hours in PBS under physiological conditions is provided wherein the prodrug element has the structure of Formula X and $R_1$ and $R_2$ are independently selected from the group consisting of hydrogen, $C_1$-$C_{18}$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and aryl; and $R_5$ is an amine, with the proviso that both $R_1$ and $R_2$ are not hydrogen and provided that one of $R_4$ or $R_8$ is hydrogen.

In a further embodiment an insulin polypeptide prodrug derivative is provided wherein the dipeptide prodrug is linked to the alpha amino group of the N-terminal amino acid of the insulin polypeptide B chain, and the prodrug has a $t_{1/2}$ between about 72 to about 168 hours in PBS under physiological conditions. In one embodiment an insulin polypeptide prodrug derivative having a $t_{1/2}$ between about 72 to about 168 hours in PBS under physiological conditions is provided wherein the prodrug element has the structure of Formula X and $R_1$ is selected from the group consisting of hydrogen, $C_1$-$C_8$ alkyl and aryl;

R2 is H;

$R_3$ is $C_1$-$C_{18}$ alkyl;

$R_4$ and $R_8$ are each hydrogen; and $R_5$ is an amine or N-substituted amine or a hydroxyl; with the proviso that, if $R_1$ is alkyl or aryl, then $R_1$ and $R_5$ together with the atoms to which they are attached form a 4-11 heterocyclic ring.

In some embodiments, prodrugs having the dipeptide prodrug element linked to the N-terminal alpha amino acid of the insulin polypeptide B chain peptide and having a $t_{1/2}$, e.g., between about 12 to about 72 hours, or in some embodiments between about 12 to about 48 hours, comprise a dipeptide prodrug element with the structure:

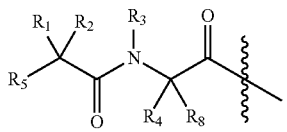

X wherein $R_1$ and $R_2$ are independently selected from the group consisting of hydrogen, $C_1$-$C_{18}$ alkyl, ($C_1$-$C_{18}$ alkyl)OH, ($C_1$-$C_4$ alkyl)NH$_2$, and ($C_0$-$C_4$ alkyl)($C_6$-$C_{10}$ aryl)R$_7$, or $R_1$ and $R_2$ are linked through $(CH_2)_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and ($C_0$-$C_4$ alkyl)($C_6$-$C_{10}$ aryl)R$_7$;

$R_5$ is NH$_2$; and $R_7$ is selected from the group consisting of H, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo;

with the proviso that both $R_1$ and $R_2$ are not hydrogen and provided that at least one of $R_4$ or $R_8$ is hydrogen.

In some embodiments, prodrugs having the dipeptide prodrug element linked to the N-terminal amino acid of the insulin polypeptide B chain peptide and having a $t_{1/2}$, e.g., between about 12 to about 72 hours, or in some embodiments between about 12 to about 48 hours, comprise a dipeptide prodrug element with the structure:

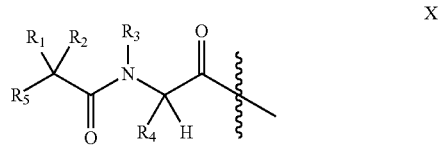

X wherein $R_1$ and $R_2$ are independently selected from the group consisting of hydrogen, $C_1$-$C_8$ alkyl and ($C_1$-$C_4$ alkyl)NH$_2$, or $R_1$ and $R_2$ are linked through $(CH_2)_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl; and $R_5$ is NH$_2$;

with the proviso that both $R_1$ and $R_2$ are not hydrogen.

In other embodiments, prodrugs having the dipeptide prodrug element linked to the N-terminal amino acid of the insulin polypeptide B chain peptide and having a $t_{1/2}$, e.g., between about 12 to about 72 hours, or in some embodiments between about 12 to about 48 hours, comprise a dipeptide prodrug element with the structure:

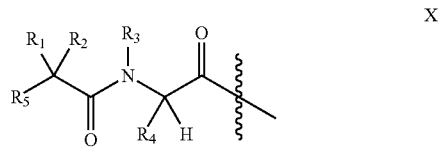

X wherein $R_1$ and $R_2$ are independently selected from the group consisting of hydrogen, $C_1$-$C_8$ alkyl and ($C_1$-$C_4$ alkyl)NH$_2$;

$R_3$ is $C_1$-$C_6$ alkyl;

$R_4$ is hydrogen; and $R_5$ is NH$_2$;

with the proviso that both $R_1$ and $R_2$ are not hydrogen.

In some embodiments, prodrugs having the dipeptide prodrug element linked to the N-terminal amino acid of the insulin polypeptide B chain peptide and having a $t_{1/2}$, e.g., between about 12 to about 72 hours, or in some embodiments between about 12 to about 48 hours, comprise a dipeptide prodrug element with the structure:

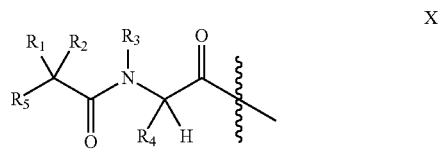

X wherein $R_1$ and $R_2$ are independently selected from the group consisting of hydrogen and $C_1$-$C_8$ alkyl, ($C_1$-$C_4$ alkyl)NH$_2$, or $R_1$ and $R_2$ are linked through $(CH_2)_p$, wherein p is 2-9;

$R_3$ is $C_1$-$C_8$ alkyl;

$R_4$ is ($C_0$-$C_4$ alkyl)($C_6$-$C_{10}$ aryl)R$_7$;

$R_5$ is NH$_2$; and $R_7$ is selected from the group consisting of hydrogen, $C_1$-$C_8$ alkyl and ($C_0$-$C_4$ alkyl)OH; with the proviso that both $R_1$ and $R_2$ are not hydrogen.

In addition a prodrug having the dipeptide prodrug element linked to the N-terminal alpha amino acid of the insulin polypeptide and having a $t_{1/2}$, e.g., of about 72 to about 168 hours is provided wherein the dipeptide prodrug element has the structure:

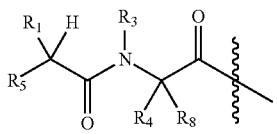

X wherein $R_1$ is selected from the group consisting of hydrogen, $C_1$-$C_8$ alkyl and ($C_0$-$C_4$ alkyl)($C_6$-$C_{10}$ aryl)$R_7$;

$R_3$ is $C_1$-$C_{18}$ alkyl;

$R_4$ and $R_8$ are each hydrogen;

$R_5$ is $NHR_6$ or OH;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo;

with the proviso that, if $R_1$ is alkyl or ($C_0$-$C_4$ alkyl)($C_6$-$C_{10}$ aryl)$R_7$, then $R_1$ and $R_5$ together with the atoms to which they are attached form a 4-11 heterocyclic ring.

In some embodiments the dipeptide prodrug element is linked to a side chain amine of an internal amino acid of the insulin polypeptide. In this embodiment prodrugs having a $t_{1/2}$, e.g., of about 1 hour have the structure:

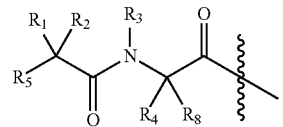

wherein $R_1$ and $R_2$ are independently $C_1$-$C_8$ alkyl or ($C_0$-$C_4$ alkyl)($C_6$-$C_{10}$ aryl)$R_7$; or $R_1$ and $R_2$ are linked through —(CH$_2$)$_p$—, wherein p is 2-9;

$R_3$ is $C_1$-$C_{18}$ alkyl;

$R_4$ and $R_8$ are each hydrogen;

$R_5$ is NH$_2$; and $R_7$ is selected from the group consisting of hydrogen, $C_1$-$C_{18}$ alkyl, $C_2$-$C_8$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

Furthermore, prodrugs having a $t_{1/2}$, e.g., between about 6 to about 24 hours and having the dipeptide prodrug element linked to an internal amino acid side chain are provided wherein the prodrug comprises a dipeptide prodrug element with the structure:

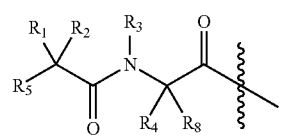

wherein $R_1$ and $R_2$ are independently selected from the group consisting of hydrogen, $C_1$-$C_8$ alkyl, and ($C_0$-$C_4$ alkyl)($C_6$-$C_{10}$ aryl)$R_7$, or $R_1$ and $R_2$ are linked through —(CH$_2$)$_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently hydrogen, $C_1$-$C_{18}$ alkyl or ($C_0$-$C_4$ alkyl)($C_6$-$C_{10}$ aryl)$R_7$;

$R_5$ is $NHR_6$;

$R_6$ is H or $C_1$-$C_8$ alkyl, or $R_6$ and $R_2$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo;

with the proviso that both $R_1$ and $R_2$ are not hydrogen and provided that at least one of $R_4$ or $R_8$ is hydrogen.

In addition a prodrug having a $t_{1/2}$, e.g., of about 72 to about 168 hours and having the dipeptide prodrug element linked to an internal amino acid side chain of the insulin polypeptide is provided wherein the dipeptide prodrug element has the structure:

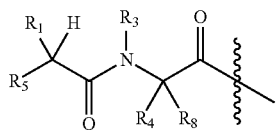

wherein $R_1$ is selected from the group consisting of hydrogen, $C_1$-$C_{18}$ alkyl and ($C_0$-$C_4$ alkyl)($C_6$-$C_{10}$ aryl)$R_7$;

$R_3$ is $C_1$-$C_{18}$ alkyl;

$R_4$ and $R_8$ are each hydrogen;

$R_5$ is $NHR_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo; with the proviso that, if $R_1$ and $R_2$ are both independently an alkyl or ($C_0$-$C_4$ alkyl)($C_6$-$C_{10}$ aryl)$R_7$, either $R_1$ or $R_2$ is linked through (CH$_2$)$_p$ to $R_5$, wherein p is 2-9.

In one embodiment, the dipeptide prodrug element is linked to the insulin polypeptide via an amine present on an aryl group of an aromatic amino acid of the insulin polypeptide, wherein the prodrug has a $t_{1/2}$, e.g., of about 1 hour has a dipeptide structure of:

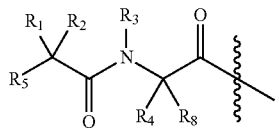

wherein $R_1$ and $R_2$ are independently $C_1$-$C_{18}$ alkyl or ($C_0$-$C_4$ alkyl)($C_6$-$C_{10}$ aryl)$R_7$;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and ($C_0$-$C_4$ alkyl)($C_6$-$C_{10}$ aryl)$R_7$;

$R_5$ is $NH_2$ or OH; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In another embodiment an insulin polypeptide prodrug derivative comprising the structure of Formula IV, wherein $m_1$ is an integer from 0 to 3 and having a t½ of about 6 to about 24 hours in PBS under physiological conditions, is provided. In one embodiment where the insulin polypeptide prodrug having a t½ of about 6 to about 24 hours in PBS under physiological conditions comprises the structure of formula IV wherein, $R_1$ is selected from the group consisting of hydrogen, $C_1$-$C_{18}$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and aryl; and $R_5$ is an amine or N-substituted amine. In one embodiment $m_1$ is 1.

In one embodiment, prodrugs having the dipeptide prodrug element linked via an aromatic amino acid and having a $t_{1/2}$, e.g., of about 6 to about 24 hours are provided wherein the dipeptide comprises a structure of:

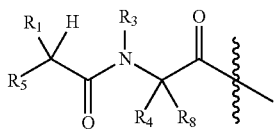

wherein $R_1$ is selected from the group consisting of hydrogen, $C_1$-$C_{18}$ alkyl, ($C_1$-$C_{18}$ alkyl)OH, ($C_1$-$C_4$ alkyl)$NH_2$, and ($C_0$-$C_4$ alkyl)($C_6$-$C_{10}$ aryl)$R_7$;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and ($C_0$-$C_4$ alkyl)($C_6$-$C_{10}$ aryl)$R_7$;

$R_5$ is $NHR_6$;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In another embodiment an insulin polypeptide prodrug derivative comprising the structure of Formula IV, wherein $m_1$ is an integer from 0 to 3 and having a t½ of about 72 to about 168 hours in PBS under physiological conditions, is provided. In one embodiment where the insulin polypeptide prodrug derivative having a t½ of about 72 to about 168 hours in PBS under physiological conditions comprises the structure of formula IV wherein, $R_1$ and $R_2$ are independently selected from the group consisting of hydrogen, $C_1$-$C_8$ alkyl and aryl;

$R_3$ is $C_1$-$C_{18}$ alkyl or $R_3$ and $R_4$ together with the atoms to which they are attached form a 4-6 heterocyclic ring;

$R_4$ and $R_8$ are each hydrogen; and $R_5$ is selected from the group consisting of amine, N-substituted amine and hydroxyl. In one embodiment $m_1$ is 1.

In one embodiment, prodrugs having the dipeptide prodrug element linked via an aromatic amino acid and having a $t_{1/2}$, e.g., of about 72 to about 168 hours are provided wherein the dipeptide comprises a structure of:

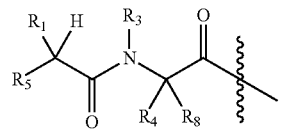

wherein $R_1$ and $R_2$ are independently selected from the group consisting of hydrogen, $C_1$-$C_8$ alkyl, ($C_1$-$C_4$ alkyl)COOH, and ($C_0$-$C_4$ alkyl)($C_6$-$C_{10}$ aryl)$R_7$, or $R_1$ and $R_5$ together with the atoms to which they are attached form a 4-11 heterocyclic ring;

$R_3$ is $C_1$-$C_{18}$ alkyl or $R_3$ and $R_4$ together with the atoms to which they are attached form a 4-6 heterocyclic ring;

$R_4$ is hydrogen or forms a 4-6 heterocyclic ring with $R_3$;

$R_8$ is hydrogen;

$R_5$ is $NHR_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In accordance with one embodiment the dipeptide of Formula X is further modified to comprise a large polymer that interferes with the insulin polypeptide's ability to interact with the insulin or IGF-1 receptor. Subsequent cleavage of the dipeptide releases the insulin polypeptide from the dipeptide complex wherein the released insulin polypeptide is fully active. In accordance with one embodiment the dipeptide of Formula X is further modified to comprises a large polymer that interferes with the bound insulin polypeptide's ability to interact with the insulin or IGF-1 receptor. In accordance with one embodiment the insulin polypeptide comprises a dipeptide of the general structure of Formula X:

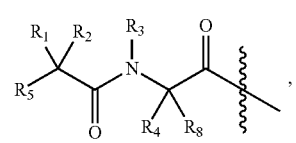

wherein one of the amino acid side chains of the dipeptide of Formula X is pegylated or acylated.

In one embodiment an insulin polypeptide is provided that comprises the structure IB-LM-IA, wherein IB comprises sequence J-$R_{23}$-$R_{22}$-$X_{25}$LCG$X_{29}X_{30}$LV$X_{33}X_{34}$L$X_{36}$LVCG$X_{41}X_{42}$GF$X_{45}$ (SEQ ID NO: 69);

LM comprises a linking moiety as described herein; and

IA comprises the sequence GIV$X_4X_5$CC$X_5X_9X_{10}$C$X_{12}$L$X_{14}X_{15}$LE$X_{18}X_{19}$C$X_{21}$-$R_{13}$ (SEQ ID NO: 70), wherein J is H or a dipeptide element of formula X;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{18}$ is methionine, asparagine, glutamine, aspartic acid, glutamic acid or threonine;

$X_{19}$ is an amino acid of the general structure:

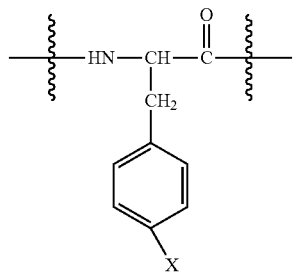

wherein X is selected from the group consisting of OH or $NHR_{10}$, wherein $R_{10}$ is H or a dipeptide element comprising the general structure of Formula X;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

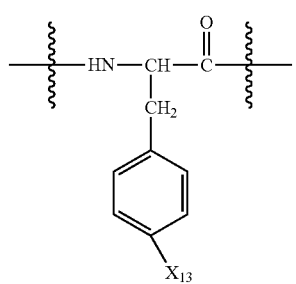

wherein $X_{13}$ is selected from the group consisting of H, OH and $NHR_{12}$, wherein $R_{12}$ is H or dipeptide element comprising the general structure of Formula X;

$R_{22}$ is selected from the group consisting of AYRPSE (SEQ ID NO: 46), FVNQ (SEQ ID NO: 47), PGPE (SEQ ID NO: 48), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal alpha amine;

$R_{23}$ is a bond or $G(X_{60})_d(X_{61})_gK$ (SEQ ID NO: 71) wherein $X_{60}$, $X_{61}$ are independently glutamic acid or aspartic acid; and d and g are integers independently ranging from 1-6; and $R_{13}$ is COOH or CONH, further wherein the dipeptide of Formula X is acylated or pegylated. In one embodiment J comprises an acylated or pegylated dipeptide of Formula X.

The insulin polypeptides and prodrug derivative thereof disclosed herein can be further modified to improve the peptide's solubility in aqueous solutions at physiological pH, while enhancing the effective duration of the peptide by preventing renal clearance of the peptide. Peptides are easily cleared because of their relatively small molecular size when compared to plasma proteins. Increasing the molecular weight of a peptide above 40 kDa exceeds the renal threshold and significantly extends duration in the plasma. Accordingly, in one embodiment the peptide prodrugs are further modified to comprise a covalently linked hydrophilic moiety.

In one embodiment the hydrophilic moiety is a plasma protein, polyethylene glycol chain or the Fc portion of an immunoglobin. Therefore, in one embodiment the presently disclosed insulin analogs are further modified to comprise one or more hydrophilic groups covalently linked to the side chains of amino acids.

In accordance with one embodiment the insulin prodrugs disclosed herein are further modified by linking a hydrophilic moiety to either the N-terminal amino acid of the B chain or to the side chain of a lysine amino acid (or other suitable amino acid) located at the carboxy terminus of the B chain, including for example, at position 29 of SEQ ID NO: 2. In one embodiment a single-chain insulin prodrug derivative is provided wherein one of the amino acids of the linking moiety is modified by linking a hydrophilic moiety to the side chain of the peptide linker. In one embodiment the modified amino acid is cysteine, lysine or acetyl phenylalanine.

In accordance with one embodiment a prodrug derivative of the insulin polypeptide is provided wherein the dipeptide element of Formula X further comprises an polyethylene glycol, alkyl or acyl group. In one embodiment one or more polyethylene glycol chains are linked to the dipeptide of Formula X wherein the combined molecular weight of the polyethylene glycol chains ranges from about 20,000 to about 80,000 Daltons, or 40,000 to 80,000 Daltons or 40,000 to 60,000 Daltons. In one embodiment at least one polyethylene glycol chain having a molecular weight of about 40,000 Daltons is linked to the dipeptide of Formula X. In another embodiment the dipeptide of Formula X is acylated with an acyl group of sufficient size to bind serum albumin and thus inactivate the $IGF^{B16B17}$ analog peptide upon administration. The acyl group can be linear or branched, and in one embodiment is a C16 to C30 fatty acid. For example, the acyl group can be any of a C16 fatty acid, C18 fatty acid, C20 fatty acid, C22 fatty acid, C24 fatty acid, C26 fatty acid, C28 fatty acid, or a C30 fatty acid. In some embodiments, the acyl group is a C16 to C20 fatty acid, e.g., a C18 fatty acid or a C20 fatty acid.

In another embodiment the insulin polypeptide peptides, and their prodrug analogs, disclosed herein are further modified by the addition of a modified amino acid to the carboxy or amino terminus of the A chain or the amino terminus of the B chain of the insulin polypeptide peptide, wherein the added amino acid is modified to comprise a hydrophilic moiety linked to the amino acid. In one embodiment the amino acid added to the C-terminus is a modified cysteine, lysine or acetyl phenylalanine. In one embodiment the hydrophilic moiety is selected from the group consisting of a plasma protein, polyethylene glycol chain and an Fc portion of an immunoglobin.

In accordance with one embodiment a pharmaceutical composition is provided comprising any of the novel insulin dimers disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an insulin dimer as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

The disclosed insulin dimers, and their corresponding prodrug derivatives, are believed to be suitable for any use that has previously been described for insulin peptides. Accordingly, the insulin dimers disclosed herein, and their corresponding prodrug derivatives, can be used to treat hyperglycemia, or treat other metabolic diseases that result from high blood glucose levels. Accordingly, the present invention encompasses pharmaceutical compositions comprising an insulin dimers as disclosed herein, or a prodrug derivative thereof, and a pharmaceutically acceptable carrier for use in treating a patient suffering from high blood glucose levels. In accordance with one embodiment the patient to be treated using an insulin dimer disclosed herein is a domesticated animal, and in another embodiment the patient to be treated is a human.

One method of treating hyperglycemia in accordance with the present disclosure comprises the steps of administering the presently disclosed insulin dimers, or depot or prodrug derivative thereof, to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the insulin polypeptide, or prodrug derivative thereof, is prepackaged in a syringe.

The insulin dimers disclosed herein, and depot or prodrug derivative thereof, may be administered alone or in combination with other anti-diabetic agents. Anti-diabetic agents known in the art or under investigation include native insulin, native glucagon and functional analogs thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the insulin dimers disclosed herein, or depot or prodrug derivatives thereof, can be formulated and administered to patients using standard pharmaceutically acceptable carriers and routes of administration known to those skilled in the art. Accordingly, the present disclosure also encompasses pharmaceutical compositions comprising one or more of the insulin dimers disclosed herein (or prodrug derivative thereof), or a pharmaceutically acceptable salt thereof, in combination with a pharmaceutically acceptable carrier. In one embodiment the pharmaceutical composition comprises a 1 mg/ml concentration of the insulin dimer at a pH of about 4.0 to about 7.0 in a phosphate buffer system. The pharmaceutical compositions may comprise the insulin dimer as the sole pharmaceutically active component, or the insulin dimer can be combined with one or more additional active agents.

All therapeutic methods, pharmaceutical compositions, kits and other similar embodiments described herein contemplate that insulin dimers, or prodrug derivatives thereof, include all pharmaceutically acceptable salts thereof.

In one embodiment the kit is provided with a device for administering the insulin dimers composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the insulin dimer composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

For all embodiments disclosed herein the first and second insulin polypeptides can be independently selected from any of the following pairings: A CHAIN 1 and B CHAIN 1, A CHAIN 1 and B CHAIN 2, A CHAIN 1 and B CHAIN 3, A CHAIN 1 and B CHAIN 4, A CHAIN 1 and B CHAIN 5, A CHAIN 1 and B CHAIN 6, A CHAIN 1 and B CHAIN 7, A CHAIN 1 and B CHAIN 8, A CHAIN 1 and B CHAIN 9, A CHAIN 1 and B CHAIN 10, A CHAIN 1 and B CHAIN 11, A CHAIN 1 and B CHAIN 12, A CHAIN 1 and B CHAIN 13, A CHAIN 1 and B CHAIN 14, A CHAIN 1 and B CHAIN 15, A CHAIN 1 and B CHAIN 16, A CHAIN 2 and B CHAIN 1, A CHAIN 2 and B CHAIN 2, A CHAIN 2 and B CHAIN 3, A CHAIN 2 and B CHAIN 4, A CHAIN 2 and B CHAIN 5, A CHAIN 2 and B CHAIN 6, A CHAIN 2 and B CHAIN 7, A CHAIN 2 and B CHAIN 8, A CHAIN 2 and B CHAIN 9, A CHAIN 2 and B CHAIN 10, A CHAIN 2 and B CHAIN 11, A CHAIN 2 and B CHAIN 12, A CHAIN 2 and B CHAIN 13, A CHAIN 2 and B CHAIN 14, A CHAIN 2 and B CHAIN 15, A CHAIN 2 and B CHAIN 16, A CHAIN 3 and B CHAIN 1, A CHAIN 3 and B CHAIN 2, A CHAIN 3 and B CHAIN 3, A CHAIN 3 and B CHAIN 4, A CHAIN 3 and B CHAIN 5, A CHAIN 3 and B CHAIN 6, A CHAIN 3 and B CHAIN 7, A CHAIN 3 and B CHAIN 8, A CHAIN 3 and B CHAIN 9, A CHAIN 3 and B CHAIN 10, A CHAIN 3 and B CHAIN 11, A CHAIN 3 and B CHAIN 12, A CHAIN 3 and B CHAIN 13, A CHAIN 3 and B CHAIN 14, A CHAIN 3 and B CHAIN 15, A CHAIN 3 and B CHAIN 16, A CHAIN 4 and B CHAIN 1, A CHAIN 4 and B CHAIN 2, A CHAIN 4 and B CHAIN 3, A CHAIN 4 and B CHAIN 4, A CHAIN 4 and B CHAIN 5, A CHAIN 4 and B CHAIN 6, A CHAIN 4 and B CHAIN 7, A CHAIN 4 and B CHAIN 8, A CHAIN 4 and B CHAIN 9, A CHAIN 4 and B CHAIN 10, A CHAIN 4 and B CHAIN 11, A CHAIN 4 and B CHAIN 12, A CHAIN 4 and B CHAIN 13, A CHAIN 4 and B CHAIN 14, A CHAIN 4 and B CHAIN 15, A CHAIN 4 and B CHAIN 16, A CHAIN 5 and B CHAIN 1, A CHAIN 5 and B CHAIN 2, A CHAIN 5 and B CHAIN 3, A CHAIN 5 and B CHAIN 4, A CHAIN 5 and B CHAIN 5, A CHAIN 5 and B CHAIN 6, A CHAIN 5 and B CHAIN 7, A CHAIN 5 and B CHAIN 8, A CHAIN 5 and B CHAIN 9, A CHAIN 5 and B CHAIN 10, A CHAIN 5 and B CHAIN 11, A CHAIN 5 and B CHAIN 12, A CHAIN 5 and B CHAIN 13, A CHAIN 5 and B CHAIN 14, A CHAIN 5 and B CHAIN 15, A CHAIN 5 and B CHAIN 16, A CHAIN 6 and B CHAIN 1, A CHAIN 6 and B CHAIN 2, A CHAIN 6 and B CHAIN 3, A CHAIN 6 and B CHAIN 4, A CHAIN 6 and B CHAIN 5, A CHAIN 6 and B CHAIN 6, A CHAIN 6 and B CHAIN 7, A CHAIN 6 and B CHAIN 8, A CHAIN 6 and B CHAIN 9, A CHAIN 6 and B CHAIN 10, A CHAIN 6 and B CHAIN 11, A CHAIN 6 and B CHAIN 12, A CHAIN 6 and B CHAIN 13, A CHAIN 6 and B CHAIN 14, A CHAIN 6 and B CHAIN 15, A CHAIN 6 and B CHAIN 16. In addition all single chain analogs of the above insulin polypeptides are also encompassed by the present dimer constructs disclosed herein wherein the linking moiety is SRVSRX$_{68}$SR (SEQ ID NO: 98) or GYGSSSRX$_{68}$APQT (SEQ ID NO: 9),

```
A chains:
A CHAIN 1.
                                          (SEQ ID NO: 1)
GIVEQCCTSICSLYQLENYCN, A CHAIN 2.
                                         (SEQ ID NO: 11)
GIVDECCFRSCDLRRLENYCN, A CHAIN 3.
                                          (SEQ ID NO: 5)
GIVDECCFRSCDLRRLEMYCA A CHAIN 4.
                                         (SEQ ID NO: 88)
TPAX75SEGIVEECCFRSCDLALLETYCA A CHAIN 5.
                                        (SEQ ID NO: 103)
TPAKSEGIVEECCFRSCDLALLETYCA,
and A CHAIN 6.
                                          (SEQ ID NO: 7)
GIVEECCFRSCDLALLETYCA B chains:
B CHAIN 1.
                                          (SEQ ID NO: 2)
FVNQHLCGSHLVEALYLVCGERGFFYTPKT, B CHAIN 2.
                                         (SEQ ID NO: 23)
FVNQHLCGSHLVEALYLVCGERGFF,
```

```
-continued
B CHAIN 3.
                                         (SEQ ID NO: 77)
GPETLCGAELVDALYLVCGDRGFY, B CHAIN 4.
                                         (SEQ ID NO: 78)
CGPEHLCGAELVDALYLVCGDRGFYFNPK, B CHAIN 5.
                                         (SEQ ID NO: 79)
GPETLCGAELVDALYLVCGDRGFYFNKPT, B CHAIN 6.
                                         SEQ ID NO: 87)
AYRPSETLCGGELVDTLQFVCGDRGFYFSRPA, B CHAIN 7.
                                         (SEQ ID NO: 10)
GPETLCGAELVDALQFVCGDRGFYFNKPT, B CHAIN 8.
                                        (SEQ ID NO: 103)
TPAKSEGIVEECCFRSCDLALLETYCA, B CHAIN 9.
                                         (SEQ ID NO: 90)
AYRPSETLCGGELVDTLQFVCGDRGFY, B CHAIN 10.
                                         (SEQ ID NO: 80)
AYRPSETLCGGELVDTLYLVCGDRGFYFSRPA, B CHAIN 11.
                                         (SEQ ID NO: 94)
CFVNQHLCGSHLVEALYLVCGERGFFYTPKT, B CHAIN 12.
                                         (SEQ ID NO: 95)
CGPETLCGAELVDALYLVCGDRGFYFNKPT, B CHAIN 13.
                                         (SEQ ID NO: 96)
CGPETLCGAELVDALQFVCGDRGFYFNKPT, B CHAIN 14.
                                         (SEQ ID NO: 97)
CGPEHLCGAELVDALYLVCGDRGFYNKPT;

B CHAIN 15.
                                         (SEQ ID NO: 91)
CAYRPSETLCGGELVDTLQFVCGDRGFY
and B CHAIN 16.
                                         (SEQ ID NO: 93)
CAYRPSETLCGGELVDTLYLVCGDRGFY.
```

Example 1

Synthesis of Insulin A & B Chains

Insulin A & B chains were synthesized on 4-methylbenzhyryl amine (MBHA) resin or 4-Hydroxymethyl-phenylacetamidomethyl (PAM) resin using Boc chemistry. The peptides were cleaved from the resin using HF/p-cresol 95:5 for 1 hour at 0° C. Following HF removal and ether precipitation, peptides were dissolved into 50% aqueous acetic acid and lyophilized. Alternatively, peptides were synthesized using Fmoc chemistry. The peptides were cleaved from the resin using Trifluoroacetic acid (TFA)/Triisopropylsilane (TIS)/H$_2$O (95:2.5:2.5), for 2 hour at room temperature. The peptide was precipitated through the addition of an excessive amount of diethyl ether and the pellet solubilized in aqueous acidic buffer. The quality of peptides were monitored by RP-HPLC and confirmed by Mass Spectrometry (ESI or MALDI).

Insulin A chains were synthesized with a single free cysteine at amino acid 7 and all other cysteines protected as acetamidomethyl A-(SH)$^7$(Acm)$^{6,11,20}$ Insulin B chains were synthesized with a single free cysteine at position 7 and the other cysteine protected as acetamidomethyl B—(SH)$^7$(Acm)$^{19}$. The crude peptides were purified by conventional RP-HPLC.

The synthesized A and B chains were linked to one another through their native disulfide bond linkage in accordance with the general procedure outlined in FIG. 1. The respective B chain was activated to the Cys$^7$-Npys analog through dissolution in DMF or DMSO and reacted with 2,2'-Dithiobis(5-nitropyridine) (Npys) at a 1:1 molar ratio, at room temperature. The activation was monitored by RP-HPLC and the product was confirmed by ESI-MS.

Figure 2:
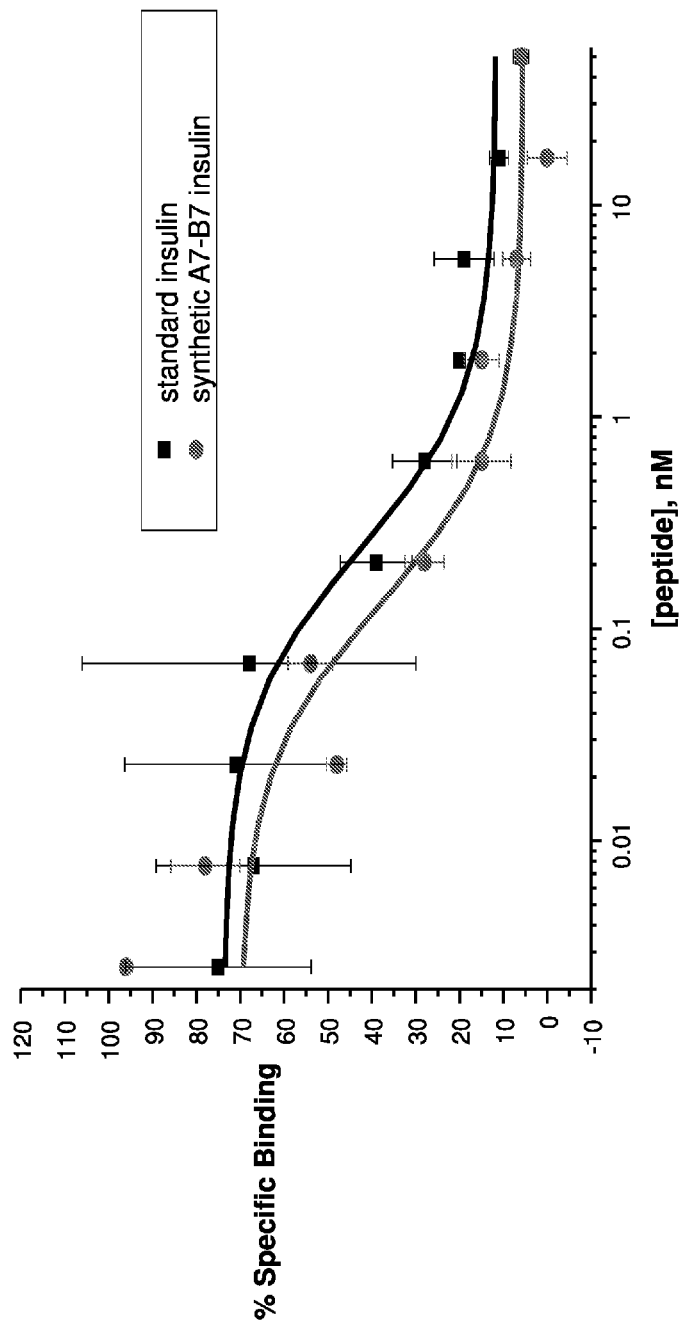
FIG. 2 is a graph comparing insulin receptor specific binding of synthetic human insulin relative to purified native insulin. The synthetic insulin was produced by the approach detailed in FIG. 1 where the $A^7$-$B^7$ bond is the first disulfide formed. As indicated by the data presented in the graph, the two molecules have similar binding activities.

The first B7-A7 disulfide bond was formed by dissolution of the respective A-(SH)$^7$(Acm)$^{6,11,20}$ and B-(Npys)$^7$(Acm)$^{19}$ at 1:1 molar ratio to a total peptide concentration of 10 mg/ml. When the chain combination reaction was complete the mixture was diluted to a concentration of 50% aqueous acetic acid. The last two disulfide bonds were formed simultaneously through the addition of iodine. A 40 fold molar excess of iodine was added to the solution and the mixture was stirred at room temperature for an additional hour. The reaction was terminated by the addition of an aqueous ascorbic acid solution. The mixture was purified by RP-HPLC and the final compound was confirmed by MALDI-MS. As shown in FIG. 2 and the data in Table 1, the synthetic insulin prepared in accordance with this procedure compares well with purified insulin for insulin receptor binding.

Insulin peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 1

Activity of synthesized insulin relative to native insulin

|  | Insulin Standard | | A7-B7 Insulin | |
| --- | --- | --- | --- | --- |
|  | AVER. | STDEV | AVER. | STDEV |
| IC$_{50}$(nM) | 0.24 | 0.07 | 0.13 | 0.08 |
| % of Insulin Activity | 100 | | 176.9 | |

Example 2

Pegylation of Amine Groups (N-Terminus and Lysine) by Reductive Alkylation a. Synthesis Insulin (or an insulin analog), mPEG20k-Aldyhyde, and NaBH$_3$CN, in a molar ratio of 1:2:30, were dissolved in acetic acid buffer at a pH of 4.1-4.4. The reaction solution was composed of 0.1 N NaCl, 0.2 N acetic acid and 0.1 N Na$_2$CO$_3$. The insulin peptide concentration was approximately 0.5 mg/ml. The reaction occurs over six hours at room temperature. The degree of reaction was monitored by RP-HPLC and the yield of the reaction was approximately 50%.

b. Purification

The reaction mixture was diluted 2-5 fold with 0.1% TFA and applied to a preparative RP-HPLC column. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was eluted at approximately 35% buffer B. The desired compounds were verified by MALDI-TOF, following chemical modification through sulftolysis or trypsin degradation.

Pegylation of Amine Groups (N-Terminus and Lysine) by N-Hydroxysuccinimide Acylation.

a. Synthesis

Insulin (or an insulin analog) along with mPEG20k-NHS were dissolved in 0.1 N Bicine buffer (pH 8.0) at a molar ratio of 1:1. The insulin peptide concentration was approximately 0.5 mg/ml. Reaction progress was monitored by HPLC. The yield of the reaction is approximately 90% after 2 hours at room temperature.

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was collected at approximately 35% B. The desired compounds were verified by MALDI-TOF, following chemical modification through sulftolysis or trypsin degradation.

Reductive Aminated Pegylation of Acetyl Group on the Aromatic Ring of The Phenylalanine a. Synthesis Insulin (or an insulin analogue), mPEG20k-Hydrazide, and NaBH$_3$CN in a molar ratio of 1:2:20 were dissolved in acetic acid buffer (pH of 4.1 to 4.4). The reaction solution was composed of 0.1 N NaCl, 0.2 N acetic acid and 0.1 N Na$_2$CO$_3$. Insulin or insulin analogue concentration was approximately 0.5 mg/ml. at room temperature for 24 h. The reaction process was monitored by HPLC. The conversion of the reaction was approximately 50%. (calculated by HPLC)

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin, or the PEG-insulin analogue was collected at approximately 35% B. The desired compounds were verified by MALDI-TOF, following chemical modification through sulftolysis or trypsin degradation.

Example 3

Insulin Receptor Binding Assay

The affinity of each peptide for the insulin or IGF-1 receptor was measured in a competition binding assay utilizing scintillation proximity technology. Serial 3-fold dilutions of the peptides were made in Tris-Cl buffer (0.05 M Tris-HCl, pH 7.5, 0.15 M NaCl, 0.1% w/v bovine serum albumin) and mixed in 96 well plates (Corning Inc., Acton, Mass.) with 0.05 nM (3-[125I]-iodotyrosyl) A TyrA14 insulin or (3-[125I]-iodotyrosyl) IGF-1 (Amersham Biosciences, Piscataway, N.J.). An aliquot of 1-6 micrograms of plasma membrane fragments prepared from cells over-expressing the human insulin or IGF-1 receptors were present in each well and 0.25 mg/well polyethylene imine-treated wheat germ agglutinin type A scintillation proximity assay beads (Amersham Biosciences, Piscataway, N.J.) were added. After five minutes of shaking at 800 rpm the plate was incubated for 12 h at room temperature and radioactivity was measured with MicroBeta1450 liquid scintillation counter (Perkin-Elmer, Wellesley, Mass.). Non-specifically bound (NSB) radioactivity was measured in the wells with a four-fold concentration excess of "cold" native ligand than the highest concentration in test samples. Total bound radioactivity was detected in the wells with no competitor. Percent specific binding was calculated as following: % Specific Binding=(Bound-NSB/Total bound-NSB)×100. IC50 values were determined by using Origin software (OriginLab, Northampton, Mass.).

Example 4

Insulin Receptor Phosphorylation Assay

To measure receptor phosphorylation of insulin or insulin analog, receptor transfected HEK293 cells were plated in 96 well tissue culture plates (Costar #3596, Cambridge, Mass.) and cultured in Dulbecco's modified Eagle medium (DMEM) supplemented with 100 IU/ml penicillin, 100 µg/ml streptomycin, 10 mM HEPES and 0.25% bovine growth serum (HyClone SH30541, Logan, Utah) for 16-20 hrs at 37° C., 5% $CO_2$ and 90% humidity. Serial dilutions of insulin or insulin analogs were prepared in DMEM supplemented with 0.5% bovine serum albumin (Roche Applied Science #100350, Indianapolis, Ind.) and added to the wells with adhered cells. After 15 min incubation at 37° C. in humidified atmosphere with 5% $CO_2$ the cells were fixed with 5% paraformaldehyde for 20 min at room temperature, washed twice with phosphate buffered saline pH 7.4 and blocked with 2% bovine serum albumin in PBS for 1 hr. The plate was then washed three times and filled with horseradish peroxidase-conjugated antibody against phosphotyrosine (Upstate biotechnology #16-105, Temecula, Calif.) reconstituted in PBS with 2% bovine serum albumin per manufacturer's recommendation. After 3 hrs incubation at room temperature the plate was washed 4 times and 0.1 ml of TMB single solution substrate (Invitrogen, #00-2023, Carlbad, Calif.) was added to each well. Color development was stopped 5 min later by adding 0.05 ml 1 N HCl. Absorbance at 450 nm was measured on Titertek Multiscan MCC340 (ThermoFisher, Pittsburgh, Pa.). Absorbance vs. peptide concentration dose response curves were plotted and $EC_{50}$ values were determined by using Origin software (OriginLab, Northampton, Mass.).

Example 5

Determination of Rate of Model Dipeptide Cleavage (in PBS)

A specific hexapeptide (HSRGTF-$NH_2$; SEQ ID NO: 72) was used as a model peptide upon which the rate of cleavage of dipeptide N-terminal extensions could be studied. The dipeptide-extended model peptides were prepared Boc-protected sarcosine and lysine were successively added to the model peptide-bound resin to produce peptide A (Lys-Sar-HSRGTF-$NH_2$; SEQ ID NO: 74). Peptide A was cleaved by HF and purified by preparative HPLC.

Preparative Purification Using HPLC:

Purification was performed using HPLC analysis on a silica based 1×25 cm Vydac C18 (5µ particle size, 300 A° pore size) column. The instruments used were: Waters Associates model 600 pump, Injector model 717, and UV detector model 486. A wavelength of 230 nm was used for all samples. Solvent A contained 10% $CH_3CN$/0.1% TFA in distilled water, and solvent B contained 0.1% TFA in $CH_3CN$. A linear gradient was employed (0 to 100% B in 2 hours). The flow rate was 10 ml/min and the fraction size was 4 ml. From ~150 mgs of crude peptide, 30 mgs of the pure peptide was obtained.

Peptide A was dissolved at a concentration of 1 mg/ml in PBS buffer. The solution was incubated at 37° C. Samples were collected for analysis at 5 h, 8 h, 24 h, 31 h, and 47 h. The dipeptide cleavage was quenched by lowering the pH with an equal volume of 0.1% TFA. The rate of cleavage was qualitatively monitored by LC-MS and quantitatively studied by HPLC. The retention time and relative peak area for the prodrug and the parent model peptide were quantified using Peak Simple Chromatography software.

Analysis Using Mass Spectrometry

The mass spectra were obtained using a Sciex API-III electrospray quadrapole mass spectrometer with a standard ESI ion source. Ionization conditions that were used are as follows: ESI in the positive-ion mode; ion spray voltage, 3.9 kV; orifice potential, 60 V. The nebulizing and curtain gas used was nitrogen flow rate of 0.9 L/min. Mass spectra were recorded from 600-1800 Thompsons at 0.5 Th per step and 2 msec dwell time. The sample (about 1 mg/mL) was dissolved in 50% aqueous acetonitrile with 1% acetic acid and introduced by an external syringe pump at the rate of 5 µL/min. Peptides solubilized in PBS were desalted using a ZipTip solid phase extraction tip containing 0.6 µL C4 resin, according to instructions provided by the manufacturer (Millipore Corporation, Billerica, Mass.) prior to analysis.

Analysis Using HPLC

The HPLC analyses were performed using a Beckman System Gold Chromatography system equipped with a UV detector at 214 nm and a 150 mm×4.6 mm C8 Vydac column. The flow rate was 1 ml/min. Solvent A contained 0.1% TFA in distilled water, and solvent B contained 0.1% TFA in 90% $CH_3CN$. A linear gradient was employed (0% to 30% B in 10 minutes). The data were collected and analyzed using Peak Simple Chromatography software.

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half-lives for cleavage of the various prodrugs were calculated by using the formula $t_{1/2}=0.693/k$. The half-life of the Lys-Sar extension to this model peptide HSRGTF-$NH_2$ (SEQ ID NO: 72) was determined to be 14.0 h.

Example 6

Rate of Dipeptide Cleavage Half Time in Plasma Using an all d-Isoform Model Peptide An additional model hexapeptide (dHdTdRGdTdF-$NH_2$ SEQ ID NO: 75) was used to determine the rate of dipeptide cleavage in plasma. The d-isomer of each amino acid was used to prevent enzymatic cleavage of the model peptide, with the exception of the prodrug extension. This model d-isomer hexapeptide was synthesized in an analogous fashion to the 1-isomer. The sarcosine and lysine were successively added to the N-terminus as reported previously for peptide A to prepare peptide B (dLys-dSar-dHdTdRGdTdF-$NH_2$ SEQ ID NO: 75)

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half-life of the Lys-Sar extension to this model peptide dHdT-dRGdTdF-NH$_2$ (SEQ ID NO: 74) was determined to be 18.6 h.

Example 7

The rate of cleavage for additional dipeptides linked to the model hexapeptide (HSRGTF-NH$_2$; SEQ ID NO: 72) were determined using the procedures described in Example 5. The results generated in these experiments are presented in Tables 2 and 3.

TABLE 2

Cleavage of the Dipeptide U-B that are linked to the side chain of an N-terminal para-amino-Phe from the Model Hexapeptide (HSRGTF-NH$_2$; SEQ ID NO: 72) in PBS

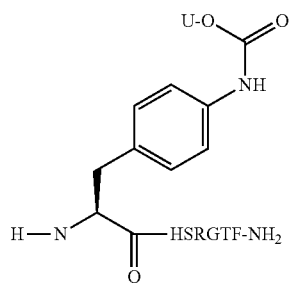

| Compounds | U (amino acid) | O (amino acid) | $t_{1/2}$ |
|---|---|---|---|
| 1 | F | P | 58 h |
| 2 | Hydroxyl-F | P | 327 h |
| 3 | d-F | P | 20 h |
| 4 | d-F | d-P | 39 h |
| 5 | G | P | 72 h |
| 6 | Hydroxyl-G | P | 603 h |
| 7 | L | P | 62 h |
| 8 | tert-L | P | 200 h |
| 9 | S | P | 34 h |
| 10 | P | P | 97 h |
| 11 | K | P | 33 h |
| 12 | dK | P | 11 h |
| 13 | E | P | 85 h |
| 14 | Sar | P | ≈1000 h |
| 15 | Aib | P | 69 min |
| 16 | Hydroxyl-Aib | P | 33 h |
| 17 | cyclohexane | P | 6 min |
| 18 | G | G | No cleavage |
| 19 | Hydroxyl-G | G | No cleavage |
| 20 | S | N-Methyl-Gly | 4.3 h |
| 21 | K | N-Methyl-Gly | 5.2 h |
| 22 | Aib | N-Methyl-Gly | 7.1 min |
| 23 | Hydroxyl-Aib | N-Methyl-Gly | 1.0 h |

TABLE 3

Cleavage of the Dipeptides U-B linked to histidine (or histidine analog) at position 1 (X) from the Model Hexapeptide (XSRGTF-NH$_2$; SEQ ID NO: 76) in PBS
NH$_2$-U-B-XSRGTF-NH$_2$ (SEQ ID NO: 76)

| Cmd. | U (amino acid) | O (amino acid) | X (amino acid) | $t_{1/2}$ |
|---|---|---|---|---|
| 1 | F | P | H | No cleavage |
| 2 | Hydroxyl-F | P | H | No cleavage |
| 3 | G | P | H | No cleavage |
| 4 | Hydroxyl-G | P | H | No cleavage |
| 5 | A | P | H | No cleavage |
| 6 | C | P | H | No cleavage |
| 7 | S | P | H | No cleavage |
| 8 | P | P | H | No cleavage |
| 9 | K | P | H | No cleavage |
| 10 | E | P | H | No cleavage |
| 11 | Dehydro V | P | H | No cleavage |
| 12 | P | d-P | H | No cleavage |
| 13 | d-P | P | H | No cleavage |
| 14 | Aib | P | H | 32 h |
| 15 | Aib | d-P | H | 20 h |
| 16 | Aib | P | d-H | 16 h |
| 17 | Cyclohexyl- | P | H | 5 h |
| 18 | Cyclopropyl- | P | H | 10 h |
| 19 | N—Me-Aib | P | H | >500 h |
| 20 | α,α-diethyl-Gly | P | H | 46 h |
| 21 | Hydroxyl-Aib | P | H | 61 |
| 22 | Aib | P | A | 58 |
| 23 | Aib | P | N-Methyl-His | 30 h |
| 24 | Aib | N-Methyl-Gly | H | 49 min |
| 25 | Aib | N-Hexyl-Gly | H | 10 min |
| 26 | Aib | Azetidine-2-carboxylic acid | H | >500 h |
| 27 | G | N-Methyl-Gly | H | 104 h |
| 28 | Hydroxyl-G | N-Methyl-Gly | H | 149 h |
| 29 | G | N-Hexyl-Gly | H | 70 h |
| 30 | dK | N-Methyl-Gly | H | 27 h |
| 31 | dK | N-Methyl-Ala | H | 14 h |
| 32 | dK | N-Methyl-Phe | H | 57 h |
| 33 | K | N-Methyl-Gly | H | 14 h |
| 34 | F | N-Methyl-Gly | H | 29 h |
| 35 | S | N-Methyl-Gly | H | 17 h |
| 36 | P | N-Methyl-Gly | H | 181 h |

Example 8

Identification of an Insulin Analog with Structure Suitable for Prodrug Construction Position 19 of the A chain is known to be an important site for insulin activity. Modification at this site to allow the attachment of a prodrug element is therefore desirable. Specific analogs of insulin at A19 have been synthesized and characterized for their activity at the insulin receptors. Two highly active structural analogs have been identified at A19, wherein comparable structural changes at a second active site aromatic residue (B24) were not successful in identification of similarly full activity insulin analogs.

Tables 4 and 5 illustrate the high structural conservation at position A19 for full activity at the insulin receptor (receptor binding determined using the assay described in Example 3). Table 4 demonstrates that only two insulin analogs with modifications at A19 have receptor binding activities similar to native insulin. For the 4-amino insulin analog, data from three separate experiments is provided. The column labeled "Activity (in test)" compares the percent binding of the insulin analog relative to native insulin for two separate experiments conducted simultaneously. The column labeled "Activity (0.60 nM)" is the relative percent binding of the insulin analog relative to the historical average value obtained for insulin binding using this assay. Under either analysis, two A19 insulin analogs (4-amino phenylalanine and 4-methoxy phenylalanine) demonstrate receptor binding approximately equivalent to native insulin. Table 5 presents data showing that the two A19 insulin analogs (4-amino and 4-methoxy) that demonstrate equivalent binding activities as native insulin also demonstrate equivalent activity at the insulin receptor (receptor activity determined using the assay described in Example 4).

TABLE 4

Insulin Receptor Binding Activity of A19 Insulin Analogs

| | Insulin Receptor | | | |
|---|---|---|---|---|
| Analogue | $IC_{50}$ | STDev | % native ligand Activity (in test) | % native ligand Activity (0.60 nM) |
| 4-OH (native insulin) | 0.64 | 0.15 | 100.0 | 100.0 |
| 4-COCH$_3$ | 31.9 | 9.47 | 0.6 | 1.9 |
| 4-NH$_2$ | 0.31 | 0.12 | 203.0 | 193.5 |
|  | 0.83 | 0.15 | 103.0 | 72.3 |
|  | 0.8 | 0.1 | 94.0 | 75.0 |
| 4-NO$_2$ | 215.7 | 108.01 | 0.3 | 1.3 |
| 3,4,5-3F | 123.29 | 31.10 | 0.5 | 0.5 |
| 4-OCH$_3$ | 0.5 | 0.50 | 173.0 | 120.0 |
| 3-OCH$_3$ | 4.74 | 1.09 | 28.0 | 12.7 |
|  | 5.16 | 3.88 | 18.0 | 11.6 |
| 4-OH, 3,5-2Br | 1807.17 | 849.72 | 0.0 | 0.0 |
| 4-OH, 3,5-2 NO$_2$ | 2346.2 | 338.93 | 0.0 | 0.0 |

TABLE 5

Insulin Receptor Phosphorylation Activity of A19 Insulin Analogs

| | Insulin Receptor | | |
|---|---|---|---|
| Analogue | $EC_{50}$ | STDev | % native ligand Activity (in test) |
| 4-OH (native insulin) | 1.22 | 0.4 | 100.0 |
| 4-NH$_2$ | 0.31 | 0.14 | 393.5 |
| 4-OCH$_3$ | 0.94 | 0.34 | 129.8 |

Example 9

Insulin Like Growth Factor (IGF) Analog IGF1 ($Y^{B16}L^{B17}$)

Figure 3:
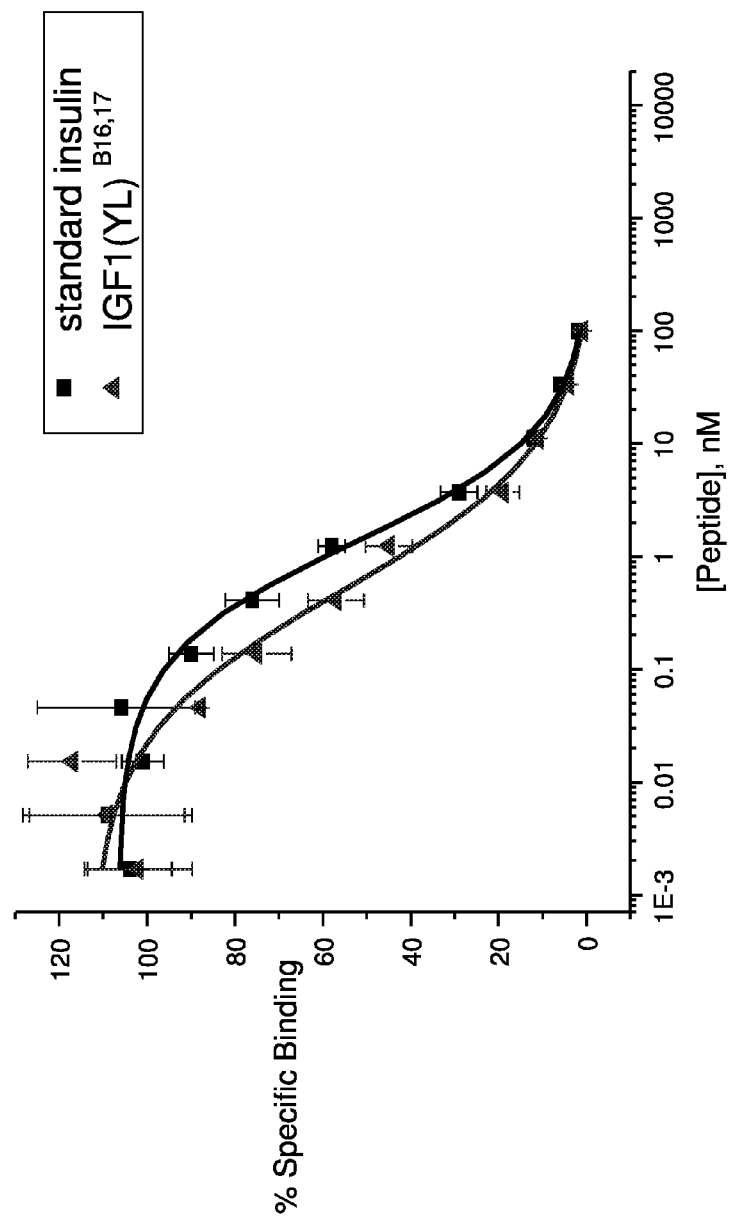
FIG. 3 is a graph comparing relative insulin receptor binding of native insulin and the IGF1($Y^{B16}L^{B17}$) analog. As indicated by the data presented in the graph, the two molecules have similar binding activities.

Applicants have discovered an IGF analog that demonstrates similar activity at the insulin receptor as native insulin. More particularly, the IGF analog (IGF1 ($Y^{B16}L^{B17}$) comprises the native IGFI A chain (SEQ ID NO: 5) and the modified IGFI B chain (SEQ ID NO: 6), wherein the native glutamine and phenylalanine at positions 15 and 16 of the native IGF B-chain (SEQ ID NO: 3) have been replaced with tyrosine and leucine residues, respectively. As shown in FIG. 3 and Table 6 below the binding activities of IGF1 ($Y^{B16}L^{B17}$) and native insulin demonstrate that each are highly potent agonists of the insulin receptor.

TABLE 6

| | Insulin Standard | | IGF1 ($Y^{B16}L^{B17}$) | |
|---|---|---|---|---|
| | AVER. | STDEV | AVER. | STDEV |
| $IC_{50}$ (nM) | 1.32 | 0.19 | 0.51 | 0.18 |
| % of Insulin Activity | 100 | | 262 | |

Example 10

IGF Prodrug Analogs

Based on the activity of the A19 insulin analog (see Example 8), a similar modification was made to the IGF1 A:B($Y^{B16}L^{B17}$) analog and its ability to bind and stimulate insulin receptor activity was investigated. As shown in Table 7, the IGF analog, IGF1 ($Y^{B16}L^{B17}$) A(p-NH$_2$—F)$^{19}$ specifically binds to the insulin receptor wherein the dipeptide extended analog of that analog fails to specifically bind the insulin receptor. Note the dipeptide extension lacks the proper structure to allow for spontaneous cleavage of the dipeptide (absence of an N-alkylated amino acid at the second position of the dipeptide) and therefore there is no restoration of insulin receptor binding.

IGF A:B($Y^{B16}L^{B17}$) insulin analog peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 7

| | Insulin Standard | | IGF1 ($Y^{B16}L^{B17}$) (p-NH$_2$—F)$^{A19}$ amide | | IGF1 ($Y^{B16}L^{B17}$) (AibAla)$^{A19}$ amide | |
|---|---|---|---|---|---|---|
| | AVER. | STDEV. | AVER. | STDEV. | AVER. | STDEV |
| $IC_{50}$ (nM) | 0.24 | 0.07 | 1.08 | .075 | No Activity | |
| % of Insulin Activity | 100 | | 22 | | | |

A further prodrug analog of an IGF$^{B16B17}$ analog peptide was prepared wherein the dipeptide prodrug element (alanine-proline) was linked via an amide bond to the amino terminus of the A chain (IGF1($Y^{B16}L^{B17}$) (AlaPro)$^{A-1,0}$). As shown in Table 8, the IGF1($Y^{B16}L^{B17}$)(AlaPro)$^{A-1,0}$ has reduced affinity for the insulin receptor. Note, based on the data of Table 3, the dipeptide prodrug element lacks the proper structure to allow for spontaneous cleavage of the dipeptide prodrug element, and therefore the detected insulin receptor binding is not the result of cleavage of the prodrug element.

TABLE 8

| | Insulin Standard | | IGF1 ($Y^{B16}L^{B17}$) (AlaPro)$^{A-1,0}$ | |
|---|---|---|---|---|
| | AVER. | STDEV | AVER. | STDEV. |
| $IC_{50}$ (nM) | 0.72 | 0.09 | 1.93 | .96 |
| % of Insulin Activity | 100 | | 37.12 | |

Example 11

Additional IGF Insulin Analogs

Further modifications of the IGF1 ($Y^{B16}L^{B17}$) peptide sequence reveal additional IGF insulin analogs that vary in their potency at the insulin and IGF-1 receptor. Binding data is presented in Table 9 for each of these analogs (using the assay of Example 3), wherein the position of the modification is designated based on the corresponding position in the native insulin peptide (DPI=des B26-30). For example, a reference herein to "position B28" absent any further elaboration would mean the corresponding position B27 of the B chain of an insulin analog in which the first amino acid of SEQ ID NO: 2 has been deleted. Thus a generic reference to "B(Y16)" refers to a substitution of a tyrosine residue at position 15 of the B chain of the native IGF-1 sequence (SEQ ID NO: 3). Data regarding the relative receptor binding of insulin and IGF analogs is provided in Table 9, and data regarding IGF analog stimulated phosphorylation (using the assay of Example 4) is provided in Table 10.

TABLE 9

Receptor Binding Affinity of Insulin and IGF Analogues

| | Insulin Receptor | | | | | IGF-1 Receptor | | | | | |
|---|---|---|---|---|---|---|---|---|---|---|---|
| Analogue | nM IC$_{50}$: | STDev | Date | % insulin (in test) | % native insulin activity (0.6 nM) | IC$_{80}$: | STDev | Date | % IGF-1 (in test) | % native IGF-1 activity (0.55 nM) | Ratio |
| IGF-1 A:B | 10.41 | 1.65 | Sep. 4, 2007 | 5.8 | 5.8 | | | | | | |
| IGF-1 A:B(E10Y16L17) | 0.66 | 0.36 | May 22, 2007 | 58.7 | 90.9 | 7.85 | 1.98 | Jun. 4, 2007 | 6.8 | 7.0 | 11.9 |
| | 0.51 | 0.18 | May 29, 2007 | 98.8 | 117.6 | 12.19 | 2.17 | Sep. 18, 2007 | 5.0 | 4.5 | |
| IGF-1 A:B(E10 Y16L17)-E31E3 2B-COOH | 1.22 | 0.30 | Mar. 20, 2008 | 36.5 | 50.0 | 17.50 | 2.25 | Apr. 4, 2007 | 3.0 | 3.1 | 14.3 |
| IGF-1 A:B(D10Y16L17) DPI A-COOH | 0.26 | 0.02 | Nov. 9, 2007 | 301.0 | 231.0 | 6.79 | 1.50 | Apr. 4, 2008 | 7.7 | 8.1 | |
| | 0.2 | 0.02 | Dec. 4, 2007 | 380.1 | 300.0 | | | | | | |
| | 0.42 | 0.06 | Jun. 5, 2008 | 174.1 | 144.1 | | | | | | |
| IGF-1 A:B (E10Y16L17) DPI | 0.38 | 0.08 | Aug. 10, 2007 | 51.1 | 157.9 | 22.89 | 5.26 | Sep. 18, 2007 | 3.3 | 2.4 | 60.2 |
| IGF-1 A:B (H5D10Y16L17) DPI | 0.16 | 0.07 | Nov. 9, 2007 | 479.0 | | 4.66 | 0.77 | Apr. 4, 2008 | 11.2 | 11.8 | 29.1 |
| IGF-1 A:B(H5D10Y16L17) (S=O) DPI | 0.25 | 0.04 | Nov. 9, 2007 | 316.0 | | | | | | | |
| IGF-1 A (H8 A9 N21): B(H5D10Y16L17) DPI A-COOH | 0.05 | 0.01 | Dec. 4, 2007 | 1576.7 | | 4.03 | 0.50 | Apr. 4, 2008 | 12.9 | 13.6 | 80.6 |
| | 0.09 | 0.02 | Dec. 14, 2007 | 1667.0 | | | | | | | |
| IGF-1 A (H8 A9 N21): B(H5D10Y16L17 A22) DPI A-COOH | 0.12 | 0.02 | Dec. 14, 2007 | 1171.4 | | 22.83 | 3.53 | Apr. 4, 2008 | 2.3 | 2.4 | 190.3 |
| IGF-1 A (H8 A9 N21): B(H5D10Y16L17A22) (S=O) DPI A-COOH | 0.36 | 0.10 | Dec. 14, 2007 | 400.7 | | | | | | | |
| IGF-1 A:IGF-1 B(1-8)-In (9-17)-IGF-1 B(18-30) | 1.59 | 0.62 | May 22, 2007 | 19.1 | 37.7 | 131.30 | 58.05 | Jun. 4, 2007 | 0.3 | 0.4 | 82.6 |
| IGF-1 A:In (1-17)-IGF-1 B(18-30) | 2.77 | 1.19 | May 22, 2007 | 14.0 | 21.7 | 62.50 | 30.28 | Jun. 4, 2007 | 0.9 | 0.9 | 22.6 |
| | 2.67 | 0.67 | May 18, 2007 | 11.3 | 22.5 | | | | | | |
| | 2.48 | 1.35 | May 29, 2007 | 20.1 | 24.2 | | | | | | |
| IGF-1 A:In B(1-5)-IGF-1 B(YL) (6-30) | 0.31 | 0.19 | Aug. 10, 2007 | 62.4 | 193.5 | 27.54 | 6.57 | Sep. 25, 2007 | 3.6 | 2 | 88.8 |
| IGF-2 native | | | | | | 13.33 | 1.85 | Sep. 25, 2007 | 7.5 | 4.5 | |
| IGF-2 AB | | | | | | | | | | | |
| IGF-2 AB(YL) | 6.81 | 3.81 | Oct. 10, 2007 | 8.4 | 8.8 | | | | | | |
| In A:IGF-1 B(YL) | 82.62 | 31.75 | Sep. 4, 2007 | 0.9 | 0.7 | | | | | | |
| | 107.24 | 65.38 | Sep. 4, 2007 | 0.7 | 0.6 | | | | | | |
| In A- IGF-2 D:In B-IGF-2 C | 0.53 | 0.11 | Sep. 4, 2007 | 141.0 | 113.0 | 1.59 | 0.34 | Sep. 18, 2007 | 47.6 | 34.6 | |
| | 0.37 | 0.05 | Oct. 13, 2007 | 179.1 | 162.2 | 14.69 | 3.02 | Sep. 25, 2007 | 6.8 | 3.7 | 39.7 |

**All C terminals are amides (DPI) unless specified otherwise

TABLE 10

Total Phosphorylation by IGF-1 & IGF-2 Analogues

| | Insulin Receptor | | | | IGF-1 Receptor | | | | |
|---|---|---|---|---|---|---|---|---|---|
| Analogue | EC50: | STDev | Date | % Insulin | EC50: | STDev | Date | % IGF | Selective Ratio |
| Insulin | 1.26 | 0.098 | Dec. 14, 2007 | | 114.88 | 46.66 | Jan. 23, 2008 | | 90.89 |
| | 1.43 | 0.72 | Apr. 1, 2008 | | 86.02 | 29.35 | May 20, 2008 | | |
| | 1.12 | 0.11 | Mar. 31, 2008 | | | | | | |
| | 1.53 | 0.13 | Apr. 11, 2008 | | | | | | |
| | 2.70 | 0.71 | Apr. 16, 2008 | | | | | | |
| | 1.22 | 0.40 | May 20, 2008 | | | | | | |
| IGF-1 | 54.39 | 21.102 | Dec. 14, 2007 | 2.3 | 0.87 | 0.16 | Jan. 23, 2008 | 100 | 0.02 |
| | | | | | 0.49 | 0.13 | May 20, 2008 | | |
| | | | | | 0.97 | 0.48 | Jul. 23, 2008 | | |
| IGF-1 AB | | | | | | | | | |
| IGF-1 A:B(E10Y16L17) | 2.57 | 0.59 | Mar. 31, 2008 | 49.2 | 7.42 | 5.59 | Jul. 23, 2008 | 13 | |
| IGF-1 A:B(E10Y16L17)-E31E32 B-COOH | 7.00 | 2.82 | Mar. 31, 2008 | 18.1 | | | | | |
| | 8.52 | 4.34 | Apr. 16, 2008 | 31.7 | | | | | |

TABLE 10-continued

Total Phosphorylation by IGF-1 & IGF-2 Analogues

| | Insulin Receptor | | | | IGF-1 Receptor | | | | |
|---|---|---|---|---|---|---|---|---|---|
| Analogue | EC50: | STDev | Date | % Insulin | EC50: | STDev | Date | % IGF | Selective Ratio |
| IGF-1 AB(D10Y16L17) DPI A-COOH | 0.08 | 0.006 | Dec. 14, 2007 | 1575 | 0.78 | 0.17 | Jan. 23, 2008 | 111.538 | 9.75 |
| | 4.38 | 2.98 | Apr. 16, 2008 | ?? | | | | | |
| IGF-1 AB(E10Y16L17) DPI | | | | | | | | | |
| IGF-1 AB(H5D10Y16L17) DPI | | | | | 12.22 | 5.46 | Jan. 23, 2008 | 7.1 | |
| IGF-1 AB (H5D10Y16L17) (S=O)DPI | | | | | | | | | |
| IGF-1 A (H8 A9 N21) B(H5D10Y16L17) DPI A-COOH | 0.15 | 0.054 | Dec. 14, 2007 | 840 | 0.43 | 0.44 | Jan. 23, 2008 | 181.395 | 2.81 |
| | 0.25 | 0.2 | Apr. 16, 2008 | 1080 | | | | | |
| IGF-1 A (H8 A9 N21) B(H5D10Y16L17A22) DPI A-COOH | 0.35 | 0.064 | Dec. 14, 2007 | 360 | 11.26 | 2.55 | Jan. 23, 2008 | 7.7 | 32.54 |
| | 0.44 | 0.17 | Apr. 16, 2008 | 614 | | | | | |
| IGF-1 A (H8 A9 N21) B(H5D10Y16L17A22) (S=O) DPI A-COOH | 0.72 | 0.098 | Dec. 14, 2007 | | | | | | |

*All C-terminals are amides unless specified otherwise.

Example 12

Biosynthesis and Purification of Insulin Polypeptides

An insulin-IGF-I minigene comprising a native insulin B and A chain linked via the IGF-I C chain ($B^0$-$C^1$-$A^0$) was cloned into expression vector pGAPZα A (purchased from Invitrogen) under GAP promoter (promoter of the glyceraldehyde-3-phosphate dehydrogenase (GAPDH)) for constitutive expression and purification of recombinant protein in yeast Pichia pastoris. The minigene was fused to an N-terminal peptide encoding Saccharomyces cerevisiae α-mating factor leader signal for secretion of the recombinant protein into the medium. A Kex2 cleavage site between the minigene and the leading α-mating factor sequence was used to cleave the leader sequence for secretion of the minigene with native amino termini. Single-site alanine mutations were introduced into C peptide at positions 1 (G1A), 2 (Y2A), 3 (G3A), 4 (S4A), 5 (S5A), 6 (S6A), 7 (R7A), 8 (R8A), 10 (P10A), 11 (Q11A), and 12 (T12A) of the $B^0C^1A^0$ minigene.

The minigenes including $B^0C^1A^0$, eleven alanine mutants, and other select derivatives were transformed into yeast Pichia pastoris by electroporation. Positive transformants were selected on minimal methanol plates and a genomic preparation of each Pichia isolate was performed and integration of the constructs into the yeast genome was confirmed by PCR. An 833 base pair PCR product was visualized on an agarose DNA gel. The insulin analogs were produced by fermentation of a corresponding yeast line. The yeast cells were pelleted by centrifugation at 5 K for 20 minutes in 500 ml Beckman centrifuge tubes and the media was kept for subsequent protein purification.

Growth media supernatants were filtered through 0.2 µm Millipore filter. Acetonitrile (ACN) was added to the supernatant to a final volume of 20%. The supernatant was purified over a Amberlite XAD7HP resin from Sigma, pre-equilibrated with 20% aqueous ACN. The resin was then rinsed twice with 30 ml of 20% aqueous ACN and contaminants were removed with 30% aqueous ACN containing 0.1% TFA. Partially purified insulin analogs were eluted from the column with 54% aqueous ACN containing 0.1% TFA and lyophilizied. Lyophilized samples were re-suspended in 0.025M $NH_3HCO_3$ pH 8 and purified on a Luna C18 column (10 µm particle size, 300 A° pore size). Protein was eluted from the column using a linear gradient of 20-60% aqueous ACN. MALDI-MS positive fractions were pooled and transferred to a disposable scintillation vial for subsequent lyophilization. Lyophilized samples were then resuspended in 20% aqueous ACN containing 0.1% TFA, and purified on a Luna C18 column (10 µm particle size, 300 A° pore size). The protein was eluted from the column using a linear gradient of 18-54% aqueous ACN with 0.1% TFA. Protein elution was monitored at an absorbance 280 nm. MALDI-TOF MS positive fractions were analyzed via a C8 analytical column to insure purity.

The $B^0$-$C^1$-$A^0$ analog demonstrated potency that was equally effective at both insulin receptor isoforms and the IGF-1 receptor. Mutation of the tyrosine at position 2 to alanine or the shortening of the C-peptide to eight amino acids through deletion of C9-12 provided a selective enhancement in the specificity of insulin action by significant reduction in the IGF-1 receptor activity. See the data provided in Tables 11A and 11B:

TABLE 11A

Insulin Binding & Phosphorylation Analysis ($B^0C^1A^0$)

| | Insulin Binding | | Insulin Phosphorylation | |
|---|---|---|---|---|
| Peptide | $IC_{50}$, nM | n | $EC_{50}$, nM | n |
| Insulin | 0.54 ± 0.02 | 4 | 1.67 ± 0.13 | 1 |
| IGF-1 | 18.81 ± 1.77 | 3 | 29.20 ± 8.41 | 1 |
| 010 ($B^0C^1A^0$) | 2.83 ± 0.52 | 2 | 1.93 ± 0.43 | 1 |
| G1A | 1.21 ± 0.15 | 1 | 2.4 ± 0.24 | 1 |
| Y2A | 1.95 ± 0.28 | 3 | 1.86 ± 0.42 | 1 |
| G3A | 1.41 ± 0.05 | 2 | 2.13 ± 0.02 | 1 |
| S4A | 0.84 ± 0.47 | 2 | 0.76 ± 0.35 | 1 |
| S5A | 0.93 ± 0.44 | 1 | 2.23 ± 1.27 | 1 |
| S6A | 1.15 ± 0.24 | 1 | 2.33 ± 1.65 | 2 |
| R7A | 6.04 ± 0.82 | 1 | 5.21 ± 4.14 | 1 |
| R8A | 0.63 ± 0.09 | 1 | 2.03 ± 0.06 | 2 |
| P10A | 2.86 ± 0.93 | 1 | 2.59 ± 1.2 | 1 |
| Q11A | 1.79 ± 0.47 | 1 | 2.58 ± 0.83 | 1 |
| T12A | 1.2 ± 0.18 | 1 | 2.83 ± 1.31 | 1 |

TABLE 11B

IGF-1 Binding & Phosphorylation Analysis
($B^0C^1A^0$)

| Peptide | IGF-1 Binding | | IGF-1 Phosphorylation | |
|---|---|---|---|---|
| | $IC_{50}$, nM | n | $EC_{50}$, nM | n |
| Insulin | 60.63 ± 4.43 | 1 | 48.66 ± 1.59 | 1 |
| IGF-1 | 0.38 ± 0.07 | 1 | 0.88 ± 0.41 | 1 |
| 010 ($B^0C^1A^0$) | 4.49 ± 1.04 | 1 | 1.29 ± 2.28 | 1 |
| G1A | 42.36 ± 16.24 | 1 | 1.4 ± 0.62 | 1 |
| Y2A | 257.9 ± 29.59 | 1 | 35.6 ± 14.55 | 1 |
| G3A | 34.02 ± 16.09 | 1 | 7.85 ± 0.78 | 1 |
| S4A | 15.30 ± 3.10 | 1 | 1.64 ± 1.65 | 1 |
| S5A | 13.06 ± 3.01 | 1 | 2.63 ± 1.88 | 1 |
| S6A | 2.44 ± 0.79 | 1 | 1.54 ± 0.62 | 2 |
| R7 | 43.86 ± 8.72 | 1 | 1.26 ± 1.55 | 1 |
| R8 | 10.85 ± 1.47 | 1 | 0.50 ± 0.23 | 2 |
| P10A | 6.42 ± 0.47 | 1 | 2.79 ± 1.12 | 1 |
| Q11A | 4.23 ± 0.43 | 1 | 0.41 ± 0.69 | 1 |
| T12A | 9.15 ± 0.83 | 1 | 1.44 ± 1.36 | 1 |

Figure 6:
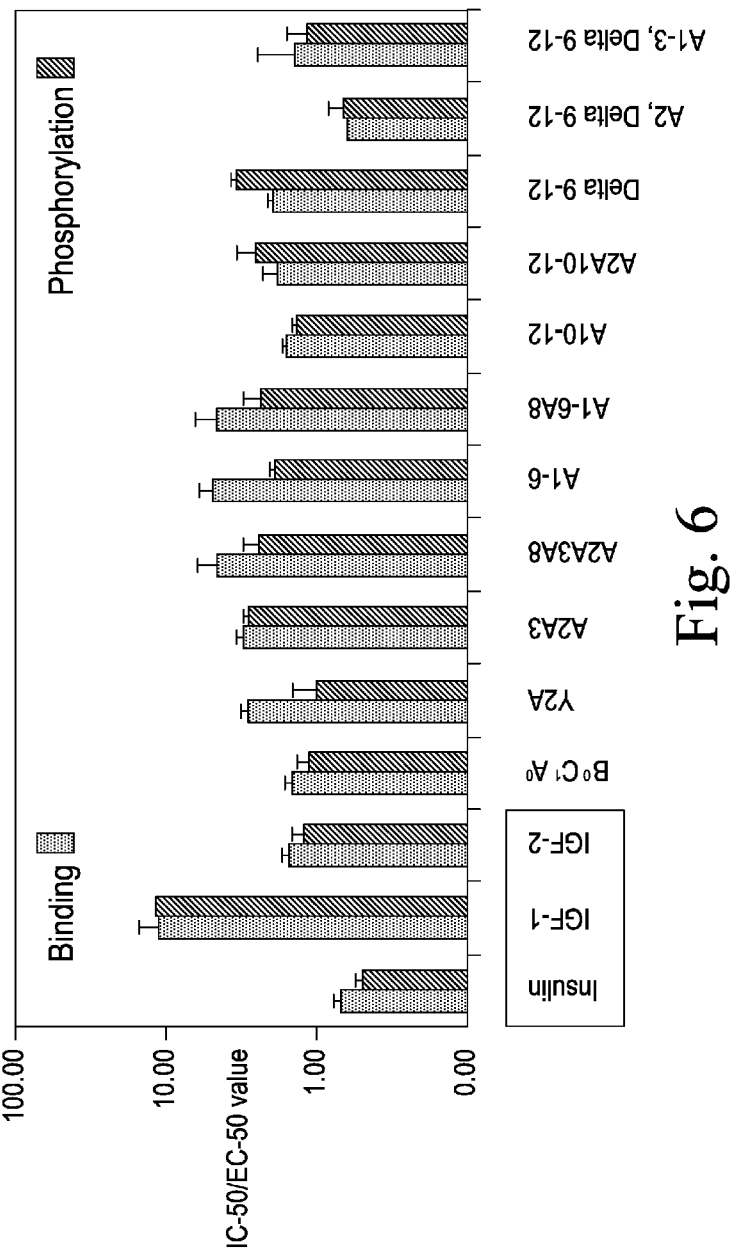
FIG. 6 is a bar graph depicting the relative in vitro binding activity and phosphorylation activity of single chain $B^0C^1A^0$ insulin analogs at the A subtype insulin. The activity of the native IGF-1 C peptide (010) relative to various amino acid substitutions or deletions in the C peptide linking moiety was compared. In the $B^0C^1A^0$ insulin analog nomenclature, the $B^0$ and $A^0$ designations refer to the native insulin sequences of the A and B chain, while $C^1$ designates the IGF-1 C peptide.
Figure 7:
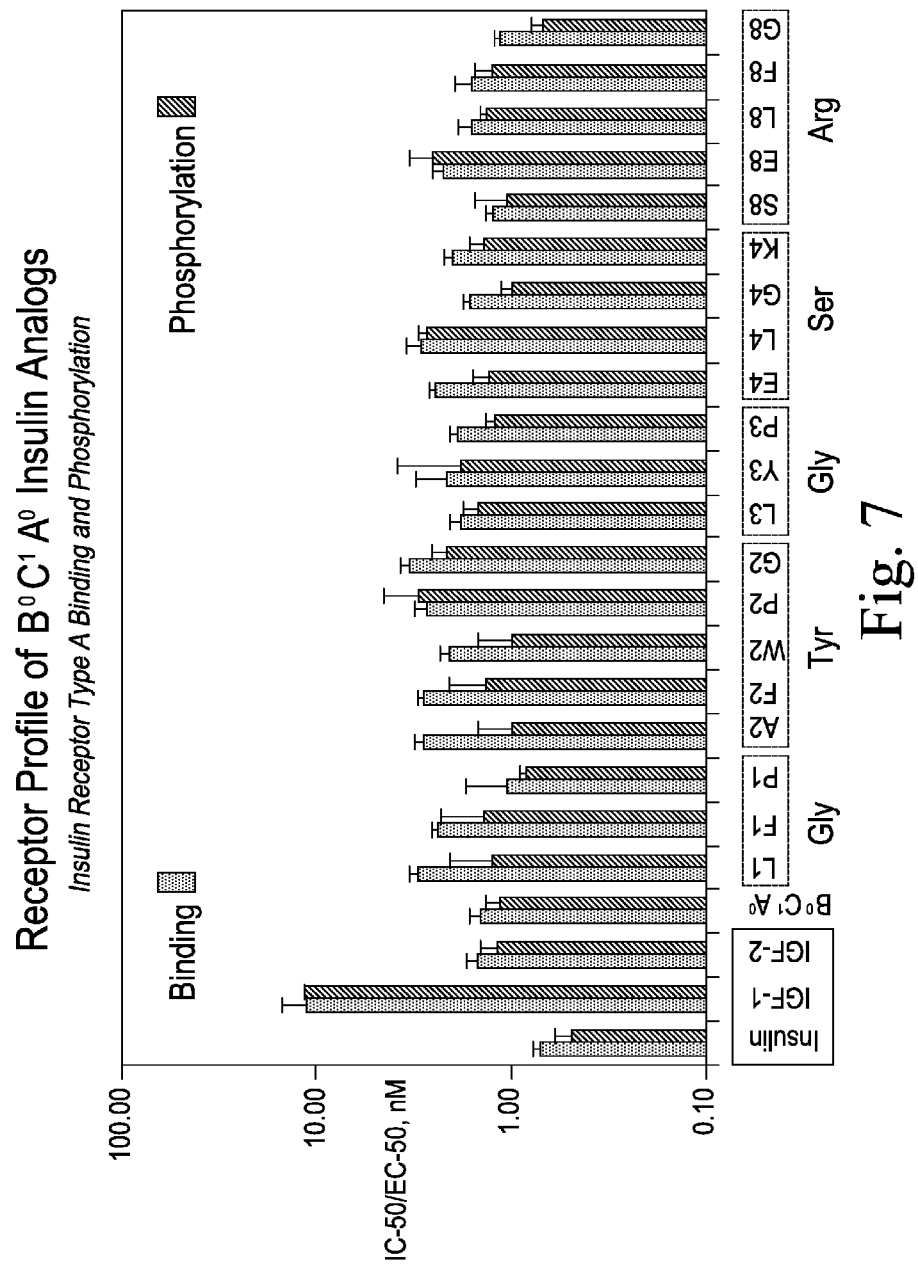
FIG. 7 is a bar graph depicting the relative in vitro binding activity and phosphorylation activity of single chain $B^0C^1A^0$ insulin analogs at the A subtype insulin wherein the native sequence of the linking IGF-1 C peptide has been modified by the indicated amino acid substitutions at position 1, 2, 3, 4 or 8. This data in conjunction with the data provided in FIG. 8 demonstrate the consistency between the binding and phosphorylation activity of the insulin analogs.

FIGS. 6 and 7 present the in vitro analysis of the single-chain insulin mutants as a ratio of binding affinity (IC50) and biochemical signaling through tyrosine phosphorylation (EC50). The two independent measurements demonstrate great consistency thereby validating this in vitro approach to structure-function analysis. All of the analogs maintained single unit nanomolar activity with certain specific analogs proving to be slightly enhanced in potency (low single unit nanomolar). The most insulin selective analogs were those that we missing the last four residues of the C-peptide, had an alanine mutation at position two of the C-peptide, or a combination of the two changes.

Example 13

Synthesis and Characterization of Single Chain Insulin Analogs Linked by Mini-Peg A series of single chain insulin analogs were prepared by solid-phase synthesis using a two-step native chain ligation approach. The initial peptide was a linear construct where the N-terminus started at CysB19 and continued through to AsnA21 with a short linear polymer of ethylene glycol serving as a connection from the C-terminus of the last B-chain amino acid to the N-terminus of the first amino acid of the A-chain, typically glycine. The N-terminal end of the B-chain (which typically starts with the first N-terminal amino acid of the final insulin analog and ends with amino acid 18 of the B-chain, typically valine) was fragment-coupled to the single linear peptide. Once coupled by thiol-assisted native chain ligation, the peptide was purified chromatographically, converted to the correct disulfide isomer and purified once more by high performance chromatography. All insulin analogs were analyzed for purity by HPLC and MS analysis.

FIG. 8A provides a schematic overview of the synthetic design with a single example of using PEG8 as a linker. The same approach was employed to synthesize analogs of shorter and longer length as well as those of variable length obtained by the use of more than one mini-peg covalently linked in linear fashion as an amide.

Figure 8B:
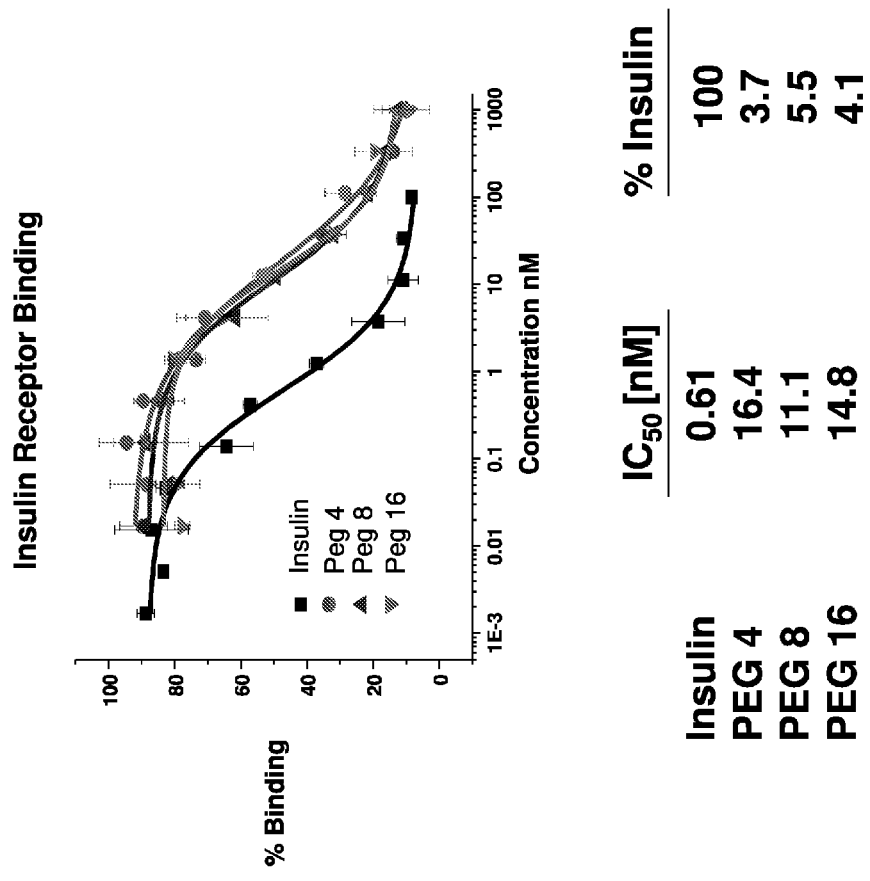
Figure 8C:
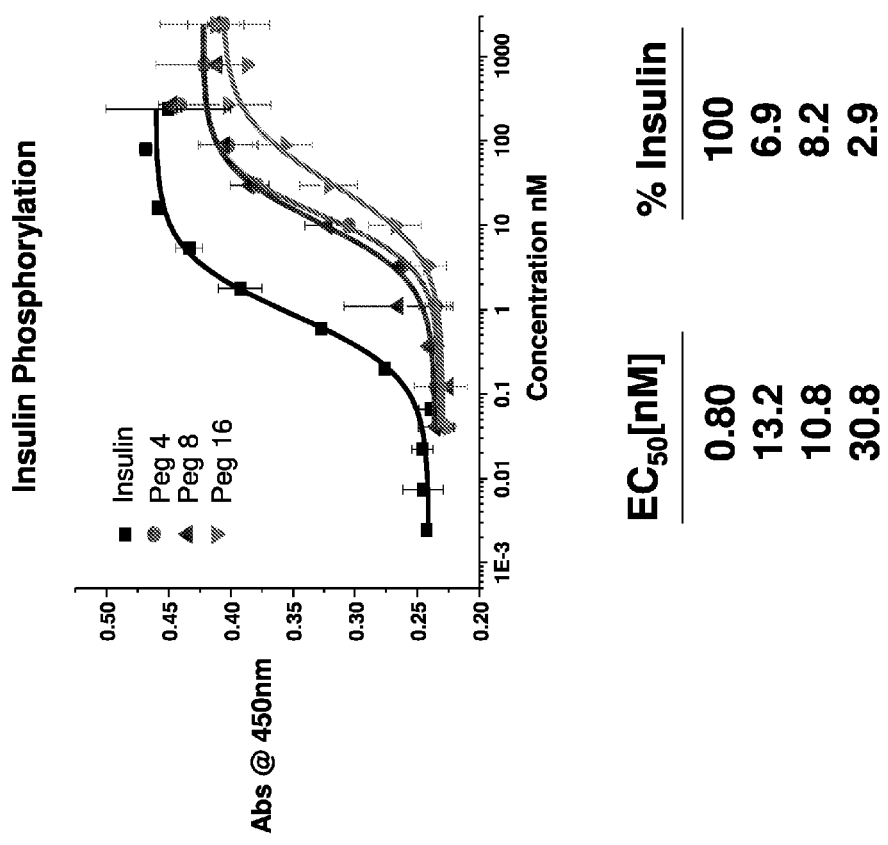
Figure 9A:
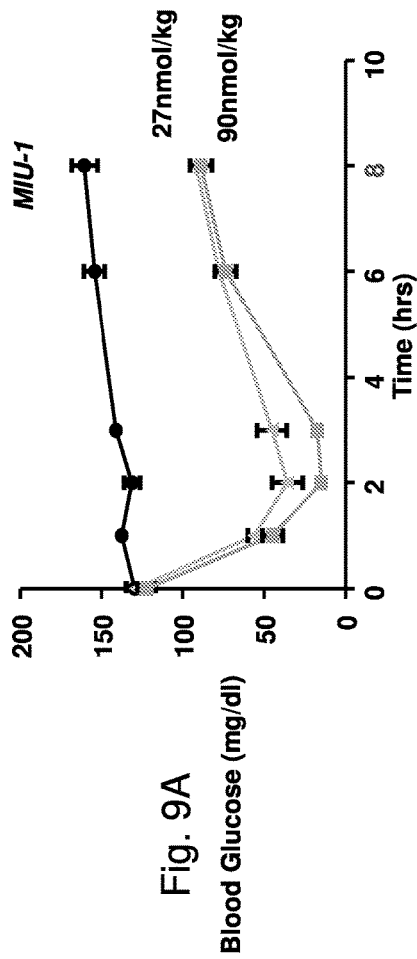
Figure 9B:
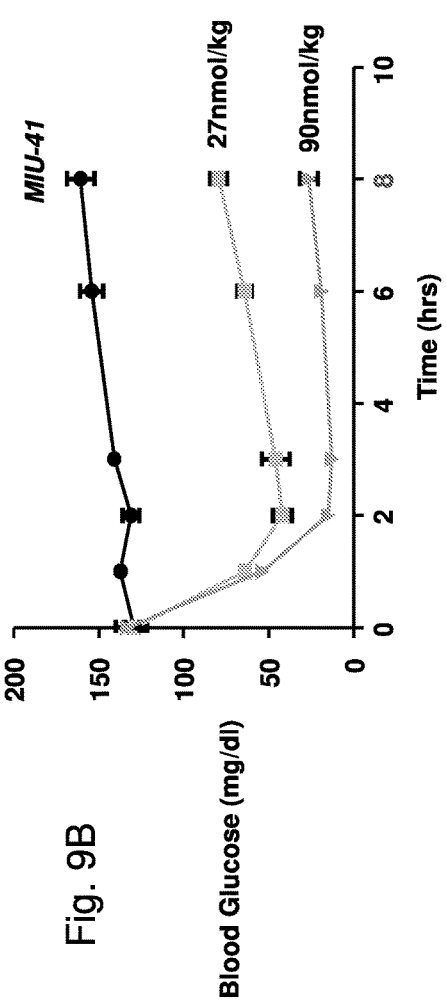
Figure 10A:
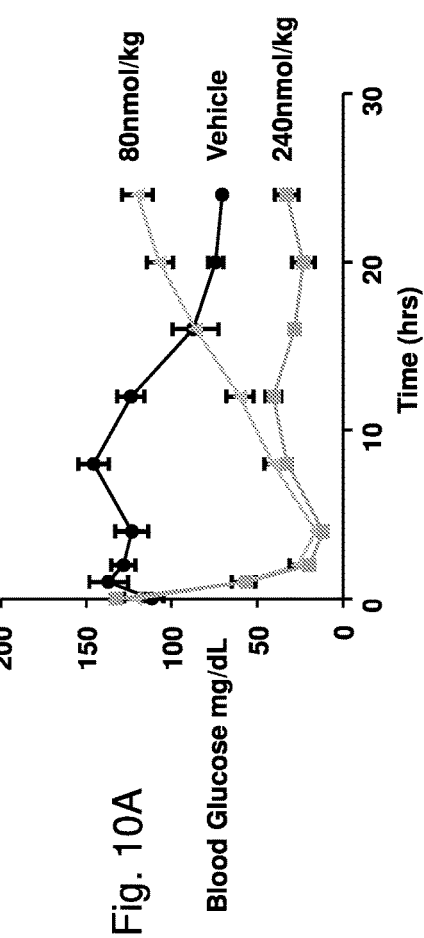
FIGS. 10A-10D represents the results obtained from a comparative insulin tolerance test for Detemir and MIU-56 using C57/Blk mice. MIU-56 is an insulin single chain analog $B^1$(H5,Y16,L17)26A-PEG8-K-PEG4-$A^1$(N18,21) comprising a 20 kDa PEG linked to the side chain of the single lysine residue in the linking moiety (PEG8-K-PEG4) that joins the A chain and the B chain.
Figure 10B:
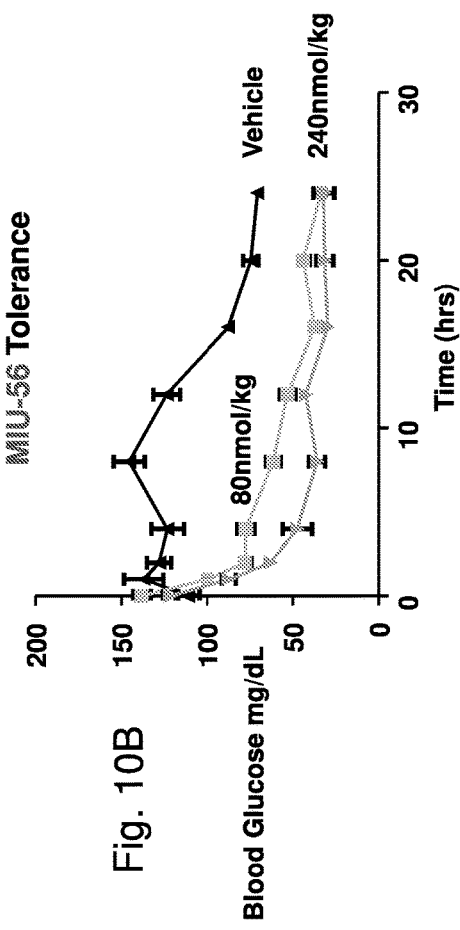
Figure 10C:
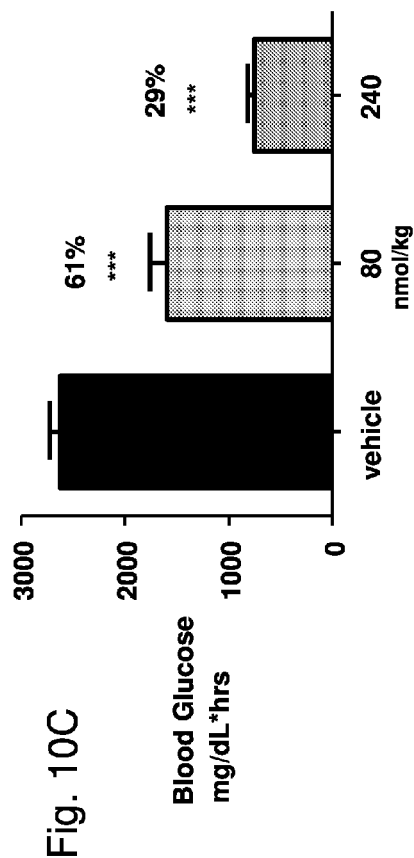
Figure 10D:
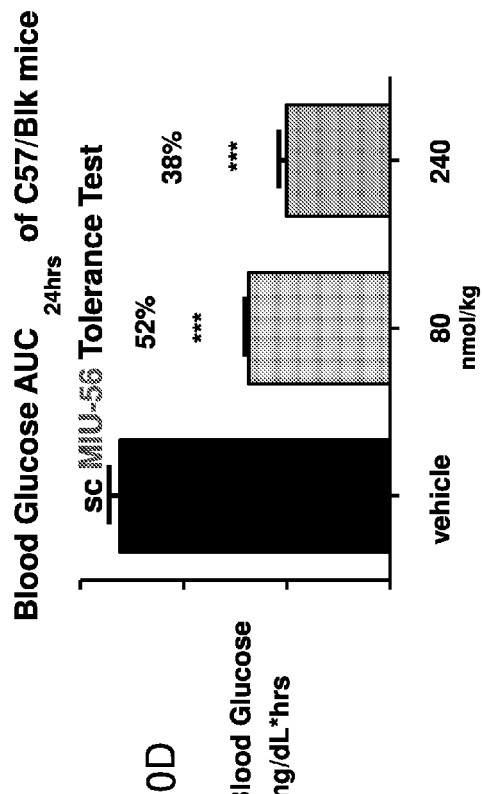

FIGS. 8B and 8C provide in vitro experimental results obtained through the study of the single chain insulin analogs linked by a mini-peg of defined length at a specific location. FIGS. 8b & 8C illustrates that the use of the minipeg of 4, 8, or 16 ethylene glycol units yielded poor potency insulin analogs of less than 5% activity relative to the native hormone as measured by binding or biochemical signaling.

The data presented in Table 11C demonstrate a dramatic increase in potency when the same size mini-peg linkers were used to couple the C-terminus of a shortened B-chain to the N-terminus of the A-chain. The des-V (missing amino acids B26-30) insulin analog once coupled with the mini-pegs were competitively potent with native hormone, more than a tenfold increase relative to the full length B-chain analogs.

TABLE 11C

Phosphorylation Activity of mini-PEG linked Single Chain
Insulin Analogs at Insulin and IGF-1 receptors

| | Insulin | | IGF-1 | |
|---|---|---|---|---|
| | % Insulin | n | % Insulin | n |
| PEG 4 | 5.69 | 3 | 0.44 | 2 |
| PEG 8 | 7.44 | 5 | 1.21 | 4 |
| PEG 16 | 5.17 | 3 | 0.16 | 2 |
| No PEG DesV | 0.04 | 1 | 0 | 1 |
| k-PEG 4 DesV | 2.37 | 2 | 0.16 | 2 |
| PEG 8 DesV | 91.2 | 5 | 2.43 | 5 |
| PEG 12 DesV | 179 | 3 | 4.51 | 3 |
| PEG 16 DesV | 83.3 | 3 | 1.39 | 3 |

A comparative analysis was conducted on single chain analogs using PEG chain linkers to measure how different sized PEG linking moieties impact in vitro activities at the at the insulin and IGF-1 receptors as measured by receptor signaling through phosphorylation. The data revealed that a $PEG_{12}DesV$ construct (wherein the 5 carboxy terminal amino acid of the B chain have been deleted) provides the most potent compounds.

A single chain analog was constructed comprising a $PEG_{12}$ and a single amino acid (glycine or lysine) as the linking moiety, linking a DesV B chain to the native insulin A chain. Comparative analysis of single chain peg/amino acid-linked analogs in vitro activities at the insulin and IGF-1 receptors as measured by receptor binding and receptor signaling through phosphorylation revealed the peg/amino acid-linked analogs were potent insulin receptor agonists. Similarly the addition of two lysine residues to the linking moiety (single chain peg/(lysine)$_2$-linked analog) produced a potent single chain peg/amino acid-linked insulin receptor agonist) as measured by receptor binding and receptor signaling through phosphorylation.

Example 14

Acylated Insulin Analogs

Comparative insulin tolerance tests were conducted on mice comparing the ability of human insulin relative to three different acylated insulin analogs to reduce and sustain low blood glucose concentration. The compounds were tested at two different concentrations (27 nmol/kg and 90 nmol/kg). The acylated insulins included MIU-41 (a two chain insulin analog having a C16 acylation via a gamma glutamic acid linker attached to a lysine residue located at position A14), MIU-36 (a two chain insulin analog having a C16 acylation linked to the N-terminus of the B chain) and MIU-37 (a two chain insulin analog having a C16 acylation via a gamma glutamic acid linker attached to a lysine residue located at position B22). All three acylated insulin analogs provided a more basal and sustained lowered glucose levels relative to native insulin, even after 8 hours (See FIGS. 9A-9D).

Example 15

Pegylated Insulin Analogs

Various pegylated insulin analogs were prepared and tested in vitro. Table 12 shows the percent activity of each analog relative to native insulin.

TABLE 12

Pegylated IGF-1 and Insulin Analogs

| MIU # | Name | | % Insulin Activity | | |
|---|---|---|---|---|---|
| | | | IR-B | IR-A | IGF-1 R |
| MIU-35 | $B^1$(H5,H10,Y16,L17)25-$C^1$-$A^1$(8,N18,N21) | | 17.4 | 61.4 | 3.2 |
| MIU-56 | C8-PEG20K $B^1$(H5,Y16,L17)25-PEG8-K-PEG4-$A^1$(N18,N21) | | | 14.8 | |
| MIU-57 | B1-PEG20K | MIU-35 | 1.1 | 3.1 | 1.2 |
| MIU-58 | B2-PEG20K-B2-Dimer | MIU-35 | 5.8 | 19.7 | 2.6 |
| MIU-59 | B1-PEG20K | insulin | 11.7 | 17.3 | 0.3 |
| MIU-60 | B29-PEG20K, B1,A1-$NH_2$CO | insulin | 2.7 | 2.4 | <<0.3 |
| MIU-61 | B1,B29,A1-tri-PEG5K | insulin | <0.1 | 0.2 | <<<0.3 |
| MIU-66 | B1-PEG20K, A1-$NH_2$CO | insulin | 2.9 | 3.0 | <0.3 |
| MIU-67 | B2, C8-PEG10K di-PEGylated | MIU-35 | 0.1 | 0.2 | <0.1 |
| MIU-68 | B2, B22-PEG10K di-PEGylated | MIU-35 | 0.1 | 0.4 | <0.1 |
| MIU-69 | B2, A14-PEG10K di-PEGylated | MIU-35 | 0.5 | 1.0 | <0.1 |
| MIU-1 | Insulin Standard | | 100 | 100 | 1.77 |

Comparative insulin tolerance tests were conducted on mice comparing the ability of the acylated insulin analog Detemir relative to the pegylated single chain insulin analog MIU-56: $B^1$(H5,Y16,L17)25-PEG8-K-PEG4-$A^1$(N18,21). This single chain analog comprises a 20 kDa PEG linked to the side chain of the single lysine residue in the linking moiety (PEG8-K-PEG4) that joins the A chain and the B chain. The pegylated analog has a sustained duration of action for 24 hours and its onset is gradual enough to avoid sedation of animals at the dosage required for sustained action through 24 hours.

A dimer (MIU 58) was prepared comprising two insulin single chain analogs ($B^1$(H5,Y16,L17)25-$C^1$-$A^1$(N18,21) linked head to head via a 20 kDa PEG chain. The dimer was found to be less potent than the parent compound, but is still active.

In summary, pegylation of insulin analogs, whether using an insulin based or IGF based peptide backbone, in vivo, provides for a more extended duration of action and a basal profile in the absence of hypoglycemia.

Example 16

Comparative Insulin Tolerance for Insulin Prodrug Analogs

Normal mice were administered either an insulin heterodimer analog [$B^1$(Y16,L17,Y25)29a: $A^1$(aF19-$NH_2$)], or a prodrug derivative thereof. The prodrug derivative [$B^1$(Y16,L17,Y25)29a: $A^1$(aF19-dLys(Ac),NLeu)] comprises a 4-amino-phenylalnine substitution at position A19 wherein a dipeptide dLys(Ac),NLeu have been covalently linked at the 4-amino position of the A19 residue. This dipeptide will autocleave under physiological conditions with a half-life of approximately 5 hours. After incubating the prodrug derivative [$B^1$(Y16,L17,Y25)29a: A (aF19-dLys(Ac),NLeu)] for 24 hours ex vivo, the resultant compound was administered to mice and its ability to lower blood glucose was compared to parent compound. The two compounds were found to performed almost identically.

Example 17

Pegylated Low Potency Alanine Analogs

The duration of action of the various insulin analogs disclosed herein can be increased by decreasing their activity at the insulin receptor. Accordingly, in one embodiment the insulin analogs disclosed herein can be modified to decrease their potency at the insulin receptor, including modification by 1 to 8, 1 to 5, 1 to 3, 1 to 2 or 1 amino acid substitution. In one embodiment the amino acid substitution is an alanine substitution at a position selected from the group consisting of B5, B10, B24, A1 or A8. Alanine substitutions at one or more of these positions substantially reduces potency, thus extending the duration of action at the insulin receptors. In one embodiment an insulin analog as disclosed herein is further modified by a single alanine amino acid substitution at position B5, B24, A1 or A8. These compounds can be further modified by pegylation as indicated in Table 13 ($GE_5$W=GEEEEEW, a peptide added to the N-terminus of the insulin analog to increase solubility).

TABLE 13

| Name | Sequence | | IR-B | IR-A | IGF-1 R |
|---|---|---|---|---|---|
| MIU-35 | $B^1$(H5,10Y16L17)25-$C^1$-$A^1$(H8N18,21) | | 17.4% | 61.4% | 3.2% |
| $GE_5$W-Ala,B5 | $GE_5$W-$B^1$(A5H10Y16L17)25-$C^1$-$A^1$(H8N18N21) | | 2.3% | 8.6% | 0.3% |
| Ala,B5 | $B^1$(A5H10Y16L17)25-$C^1$-$A^1$(H8N18N21) | | 5.7% | | 2.5% |
| Ala,B24 | $B^1$(H5,10Y16L17A24)25-$C^1$-$A^1$(H8N18,N21) | | 0.4% | 0.1% | 0.3% |
| $GE_5$W-Ala,A1 | $GE_5$W-$B^1$(H5,10Y16L17)25-$C^1$-$A^1$(A1H8N18,21) | | 0.7% | 2.1% | 0.5% |
| Thr,A8 | $B^1$(H5,10Y16L17)25-$C^1$-$A^1$(T8N18,21) | | 8.4% | 20.4% | 3.7% |
| PEGylated Analogs | | | | | |
| MIU-57 | B1-PEG20K | MIU-35 | 1.1% | 4.5% | 1.2% |
| | B1-PEG20K ($GE_5$W)-Ala,A1 | MIU-35 | 0.1% | 0.3% | |

As shown in Table 14, single chain and two chain insulin analogs have been prepared and tested in vitro for activity at the insulin and IGF-1 receptors and compared to their pegylated derivatives. Non-pegylated forms have higher activity relative to the pegylated derivatives. Furthermore, dipegylating two chain insulin analogs using two 10 kDa PEG chains produces compounds of approximately similar activity relative to the same analog comprising a single 20 kDa PEG chain (see the relative activities of $B^1$(H5,10Y16L17K29)29: $A^1$(H8,N18,21) relative to B1,A14-10K $B^1$(H5,10Y16L17R29)29: $A^1$(H8K14N18,21) and $B^1$(H5,10Y16L17K29)29: $A^1$(H8N18,21). For the single chain analog $B^1$(H5,10Y16L17K29)29-$A^1$(H8,N18,21) the addition of a 20 kDa produces a compound ($B^1$(H5,10Y16L17K29) 29-$A^1$(H8N18,21) having almost 100 fold activity at the insulin type-A receptor. Accordingly, by preparing insulin analogs as two chain or single chain analogs and by selecting the size, number and site of attachment of a PEG chain, the in vivo potency of the insulin analog can be modified, and presumably the in vivo duration of action.

TABLE 14

PEGylation of Two-chain IGF-1 Analogs

| | Analog Name | Sequence | IR-A | IR-B | IGF-1R |
|---|---|---|---|---|---|
| | Parent Peptide Backbones | | | | |
| MIU-43 | DP8Mut3 | B$^1$(H5,10Y16L17R29)30-C$^1$des9-12-A$^1$(H8,N18,21) | 97.5% | 16.7% | 14.2% |
| | DP8Mut3KA14 | B$^1$(H5,10Y16L17R29)30-C$^1$des9-12-A$^1$(H8,K14,N18,21) | 132.2% | 12.6% | |
| | DP3(SC) | B$^1$(H5,10Y16L17K29)29-A$^1$(H8,N18,21) | 0.03% | | |
| | DP3(TC) | B$^1$(H5,10Y16L17K29)29:A$^1$(H8,N18,21) | 159.8% | 33.1% | |
| | PEGylated Analogs | | | | |
| MIU-79 | di-10K-SC | B1,A14-10K B$^1$(H5,10Y16L17R29)30-C$^1$des9-12-A$^1$(H8,K14,N18,21) | 1.7% | 0.2% | |
| | di-10K-TC | B1,A14-10K B$^1$(H5,10Y16L17R29)29:A$^1$(H8K14N18,21) | 6.4% | 2.1% | |
| MIU-77 | mono-20K-SC | B1-20K B$^1$(H5,10Y16L17K29)29-A$^1$(H8N18,21) | 0.1% | | |
| MIU-78 | mono-20K-TC | B1-20K B$^1$(H5,10Y16L17K29)29:A$^1$(H8N18,21) | 8.2% | 3.2% | |

Example 18

Preparation of Insulin Dimers

The sequences of monomeric peptides used to synthesize dimeric derivatives are listed in Table 16

TABLE 15

Sequences of insulin dimers.

| No. | Insulin Dimer | MIU# | | Sequence |
|---|---|---|---|---|
| 48 | Cys$^{B1}$-Cys$^{B1}$ dimer | #2* | | B$^1$[C1H5Y16L17O22R29]29:A$^1$[O9,14,15N18,21] |
| 49 | Phe$^{B1}$-Phe$^{B1}$ dimer | #28 | | B$^0$[R29]29:A$^0$ |
| 50 | Phe$^{B1}$-(GE$_5$W)$_2$-Phe$^{B1}$ dimer | #30 | MIU-96 | GE$_5$W-B$^0$[H22R29]29:A$^0$ |
| 51 | Lys$^{B29}$-Lys$^{B29}$ dimer | insulin | MIU-90 | B$^0$:A$^0$ |
| 52 | Lys$^{B29}$-Lys$^{B29}$ dimer | MIU-3* | | B$^0$-C$^1$-A$^0$ |
| 53 | Lys$^{C8}$-Lys$^{C8}$ dimer | #3 | | B$^1$[H5Y16L17]25-PEG$_8$KPEG$_4$-A$^1$[N18,21] |
| 54 | Lys$^{C8}$-Lys$^{C8}$ dimer | #11* | | B$^1$[H5,10Y16L17]25-C$^1$[K8]-A$^1$[H8N18,21] |
| 55 | Lys$^{B1}$-PEG$_9$-Lys$^{B1}$ dimer | #20* | | GE$_5$K-B$^1$[[H5,10Y16L17]25-C$^1$-A$^1$[H8N18,21] |
| 56 | Gly$^{B2}$-PEG10K-Gly$^{B2}$ dimer | #11 | | B$^1$[H5,10Y16L17]25-C$^1$-A$^1$[H8N18,21] |
| 57 | Gly$^{B2}$-PEG20K-Gly$^{B2}$ dimer | #11 | MIU-58 | B$^1$[H5,10Y16L17]25-C$^1$-A$^1$[H8N18,21] |
| 58 | Lys$^{C8}$-PEG20K-Lys$^{C8}$ dimer | #3 | | B$^1$[H5Y16L17]25-PEG$_8$KPEG$_4$-A$^1$[N18,21] |

TABLE 16

Sequences of starting insulin monomers.

| No. | Insulin Monomer | MIU# | Sequence |
|---|---|---|---|
| 2* | Thz-B$^1$-A$^1$ | | Thz-B$^1$[H5Y16L17O22R29]29:A$^1$[O9,14,15N18,21] |
| 3 | PEG8KPEG4 | | B$^1$[H5Y16L17]25-PEG$_8$KPEG$_4$-A$^1$[N18,21] |
| 11 | DP8 | MIU-35 | B$^1$[H5,10Y16L17]25-C$^1$-A$^1$[H8N18,21] |
| 11* | DP8KC8 | | B$^1$[H5,10Y16L17]25-C$^1$[K8]-A$^1$[H8N18,21] |
| 20* | GE5K-DP8 | | GE$_5$K-B$^1$[H5,10Y16L17]25-C$^1$-A$^1$[H8N18,21] |
| 28 | DP55 | | B$^0$[R29]29:A$^0$ |
| 30 | GE5W DP55H22 | | GE$_5$W-B$^0$[R29H22]29:A$^0$ |
| | MIU-3* | | B$^0$-C$^1$-A$^0$ |

48: Cys$^{B1}$-Cys$^{B1}$ #2* Dimer Total Chemical Synthesis

Dimer #48 was prepared by crosslinking two molecules of insulin analog #2* at their N terminal cysteines with a disulfide bond. Analog #2* was prepared through native chemical ligation of two peptide segments. An unnatural amino acid thiazolidine-4-carboxylic acid (Thz), which is a protected form of cysteine, was introduced to the B chain's N terminus. After the insulin analog folded to correct conformation with the three disulfide bonds formed, Thz was converted to cysteine through treatment with methoxylamine at pH 4.0 in aqueous solution. Introduction of Thz provides an additional cysteine on B chain's N terminus, without disrupting the disulfide pairing of the other six cysteines in the native insulin sequence. To facilitate the formation of a crosslinking disulfide at the B chain N termini, DTNP (2,2'-dithiobis(5-nitropyridine)) was added to half of the $Cys^{B1}$ peptides to activate the N-terminal cysteine. The activated peptide was then reacted with the other half of the $Cys^{B1}$ peptides to produce disulfide-linked homodimers. After the completion of synthesis, the dimeric analog was treated with trypsin to convert both peptide subunits into a two-chain structure (See FIG. 22A: Synthetic Scheme of #48 ($Cys^{B1}$-CysB1 #2 dimer).

49: $Phe^{B1}$-$Phe^{B1}$ #28 Dimer and #50: $Phe^{B1}$-$(GE_5W)_2$-$Phe^{B1}$ #30 Dimer Semi-Synthesis Analogs #49 and #50 were prepared by dimerizing two insulin analog (#28 or #30) monomers. Peptide #28 was composed of insulin B chain (desB30) and A chain, with a single $K^{B29}R$ mutation to enable enzyme cleavage. Peptide #28 contained another arginine at the B22 position, which is less accessible to protease digestion. By controlling reaction time, reaction temperature and enzyme/peptide ratio, we were able to selectively cleave at the C terminus of $Arg^{B29}$ and produce a two-chain insulin. The conversion to two-chain structure could be confirmed by addition of 18 Da in molecular weight measured by mass spectrometry. Peptide #30 was structurally similar to #28, except $R^{B22}H$ mutation and the presence of pre-sequence GEEEEEW at the N terminus. $Arg^{B22}$ was replaced by $His^{B22}$ to allow a more precise and efficient trypsin cleavage.

Figure 22B:
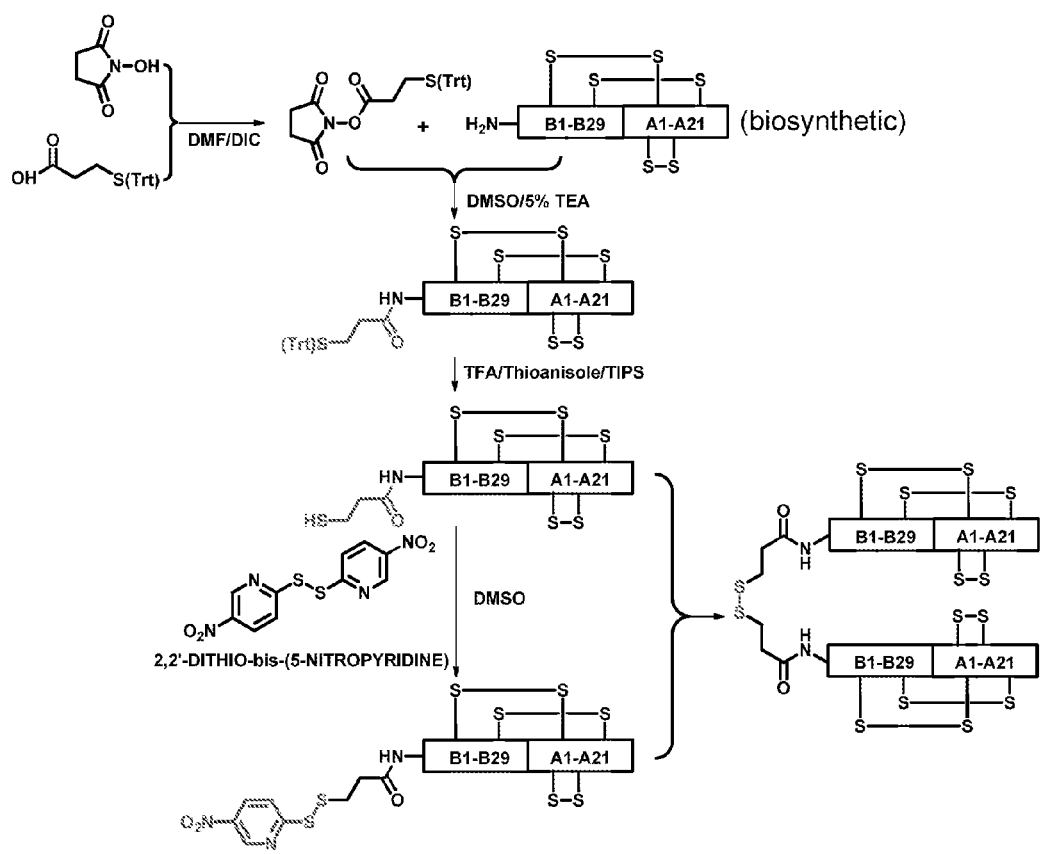
FIG. 22B: Synthetic Scheme for the preparation of compound #49 (PheB1-PheB1 #28 dimer; see Tables 15-17).

Both #49 and #50 were synthesized with a similar strategy by crosslinking two insulin peptides at N terminal amino groups. Synthesis of dimer #49 is illustrated in FIG. 22B. S-trityl-mecaptopropionic acid was activated with hydroxylsuccinimide in the presence of DIC and DIEA to form an amine reactive succinimidyl ester (NHS ester). The NHS ester was reacted with the N terminal amino groups to form amide bonds, with s-trityl-mercaptopropionic acid at the N termini of each peptide. The trityl protection groups were subsequently removed through treatment with anhydrous TFA. By this method an additional thiol group was introduced to the N terminus of each biosynthetic insulin peptide. Half of the N-terminal thiol-modified peptides were activated with DTNP (2,2'-dithiobis(5-nitropyridine)) and then mixed with the other half to produce N terminal crosslinked insulin dimers (#49 and #50). After the completion of the synthesis, the dimers were treated with trypsin to convert both peptide subunits to a two-chain structure.

51: $Lys^{B29}$-$Lys^{B29}$ Insulin Dimer Synthesis

Dimer #51 was synthesized by dimerizing two native human insulin peptides at their $Lys^{B29}$ residues. Amino groups on B chain and A chain N termini were selectively protected by carbamylation at pH 7.0. Subsequently, the ε-amine of $lysine^{B29}$'s side chain was reacted with the activated s-trityl-mercaptopropionic acid to produce $Lys^{B29}$ thiol-modified insulin. The trityl protection group was removed by TFA treatment, followed by disulfide bond formation between two thiol groups catalyzed by DTNP (2,2'-dithiobis(5-nitropyridine)) (see FIG. 22C).

52: $Lys^{B29}$-$Lys^{B29}$ MIU-3* Dimer and #54: $Lys^{C8}$-$Lys^{C8}$ #11* Dimer Synthesis Dimers #52 and #54 are both dimers of biosynthetic single-chain insulin analogs, which by design contained single lysines in sequence. Dimer #52 was composed of two molecules of MIU-3* symmetrically crosslinked at $Lys^{B29}$ residues. MIU-3 was a previously identified single-chain insulin analog, which exhibited co-agonisms on three receptors, including type A and type B insulin receptors and the IGF-1 receptor. MIU-3* shared the same peptide sequence with MIU-3, except for a pre-sequence GEEEEEW on the N terminus. Dimer #54 was constructed with single-chain insulin analog #11*, which contained a single lysine replacement at C8 position of analog #11. Both #52 and #54 were constructed by crosslinking lysine residues using a similar strategy as synthesis of #51. The N-terminal α-amine was selectively blocked with carbamylation and then thiol modification was introduced to the lysine side chain ε-amine, as described in the synthesis of #51 (Scheme 4).

53: $Lys^{C8}$-$Lys^{C8}$ #3 Dimer Synthesis

Figure 22C:
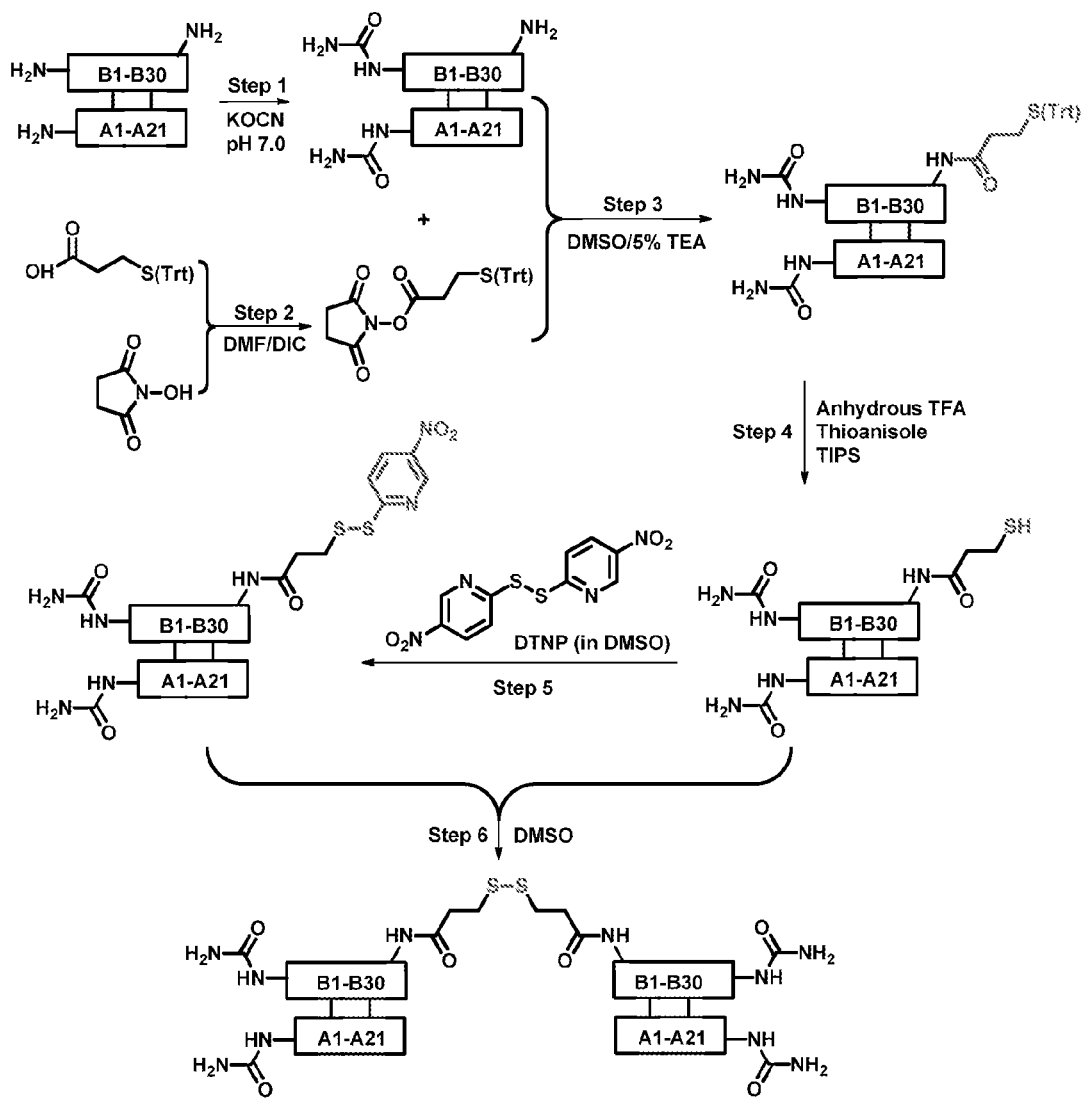
FIG. 22C: Synthetic Scheme for the preparation of compound #51 (LysB29-LysB29 insulin dimer; see Tables 15-17).
Figure 22D:
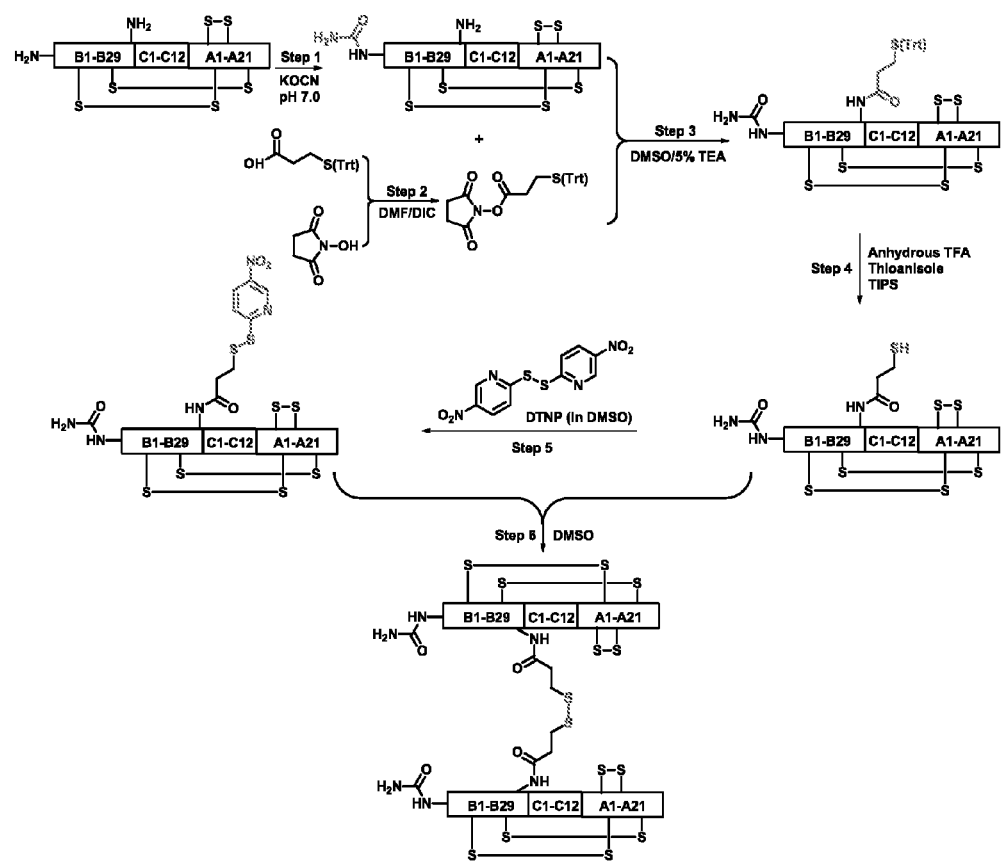
FIG. 22D: Synthetic Scheme for the preparation of compound #52 (LysB29-LysB29 MIU-3* dimer; see Tables 15-17).
Figure 22E:
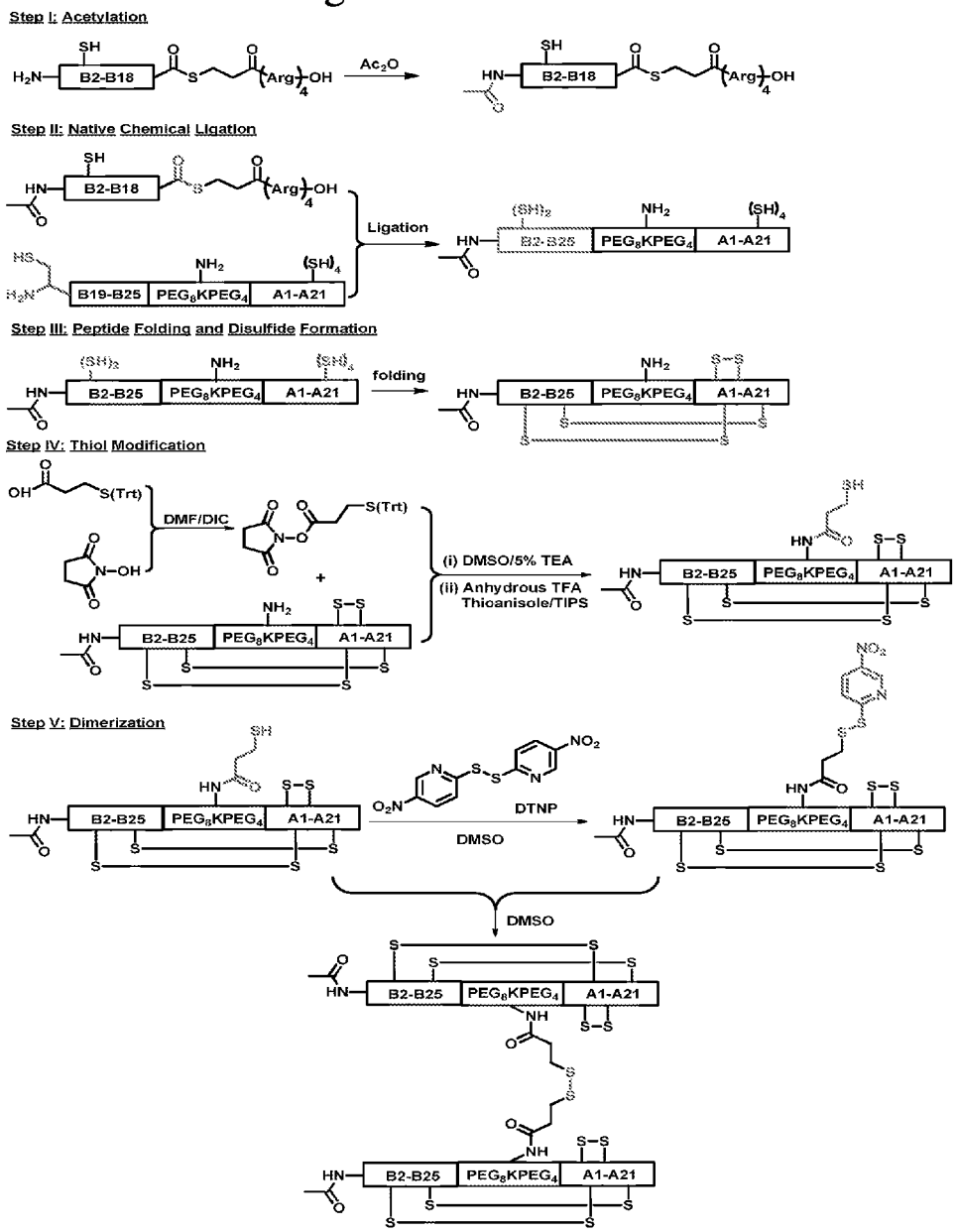
FIG. 22E: Synthetic Scheme for the preparation of compound #53 (LysC8-LysC8 #3 dimer; see Tables 15-17).

Dimer #53 was prepared from a single-chain insulin analog #3, which has a non-peptide linker as C domain. Peptide #3 was composed of desV B chain, PEG linker and A chain. A lysine residue was inserted between an 8-unit PEG and a 4-unit PEG to serve as a dimerization site. Peptide #3 was prepared through native chemical ligation between two peptide segments. Briefly, segment 1 contained the first 17 amino acids of the B chain and an activated thioester at its C terminus. The N terminus of segment 1 was acetylated while still on resin after completion of peptide assembly. Segment 1 was ligated to segment 2 which represented the C terminus of the B chain, a PEG linker and the A chain to produce a full length single-chain insulin peptide. The full-length product was desalted into folding buffer to allow peptide folding and disulfide formation. The correctly folded peptide was purified by reverse phase chromatography and used subsequently in thiol modification. Peptide #3 contained only one amino group on the lysine side chain in the middle of the C domain, which allowed site-specific thiol introduction. Thiol-modified insulin peptide (#3) was dimerized by forming a disulfide bond between two thiol groups under catalysis with DTNP (FIG. 22E).

55: $Lys^{B1}$-$PEG_9$-$Lys^{B1}$ #20* Dimer Synthesis

Figure 22F:
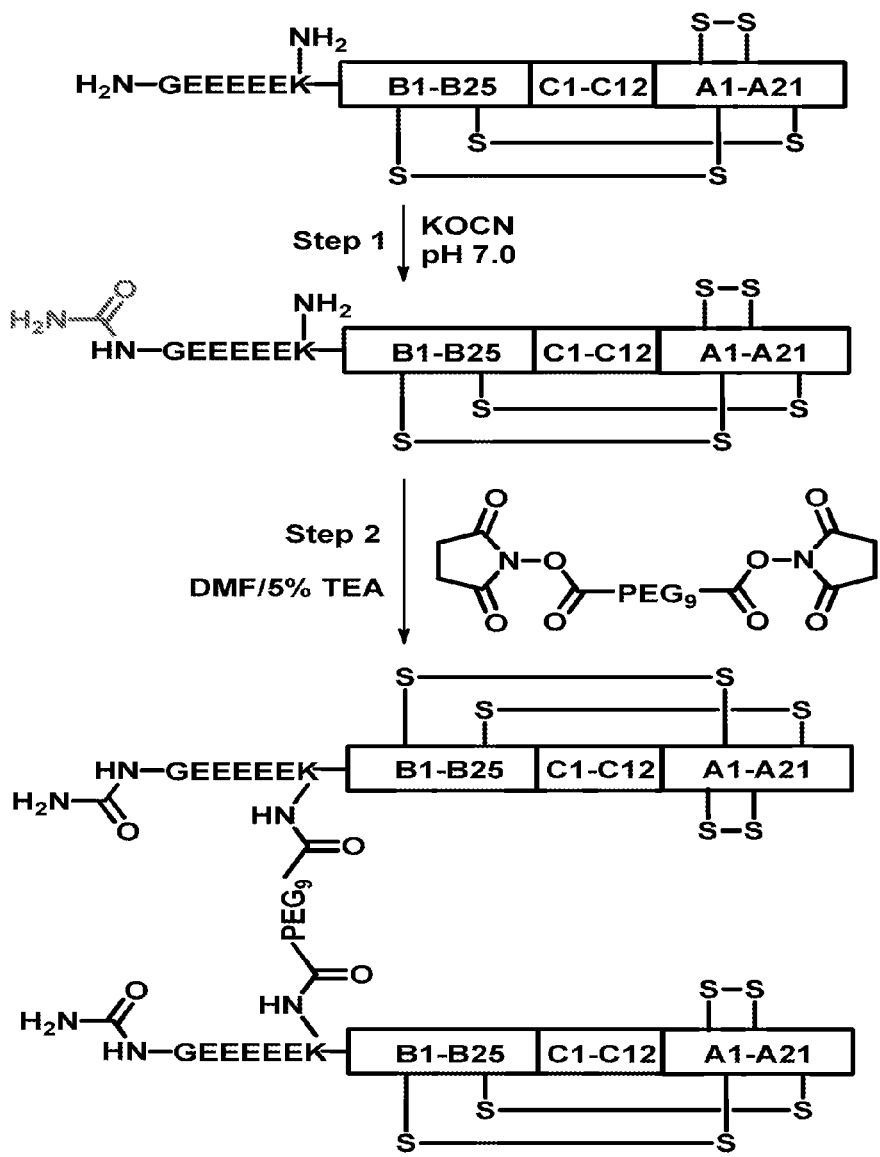
FIG. 22F Synthetic Scheme for the preparation of compound #55 (LysB1-LysB1 #20* dimer; see Tables 15-17).

Dimer #55 contained two single-chain insulin peptides #20* crosslinked with a short 9-unit PEG spacer at their $lysine^{B1}$ side chain amines. Peptide #20* shared the same sequence with #20, except for a mutation from Trp to Lys at B1 position. Peptide #20* contained a pre-sequence GEEEEE at the N terminus of insulin peptide with a lysine at B1 position as a LysC cleavage site for removal of the pre-sequence. The N terminal amine was selectively blocked by carbamylation, leaving the ε-amine of $Lys^{B1}$ for crosslinking reactions with amine-reactive reagents. Then ε-amine of $Lys^{B1}$ reacted with the homo-bifunctional 9-unit PEG with succinimidyl esters on both ends, which produced $PEG_9$-linked insulin dimer (see FIG. 22F). PEG peptide dimers were separated from mono-PEGylated peptide and unreacted reagents by reverse phase chromatography.

Figure 22G:
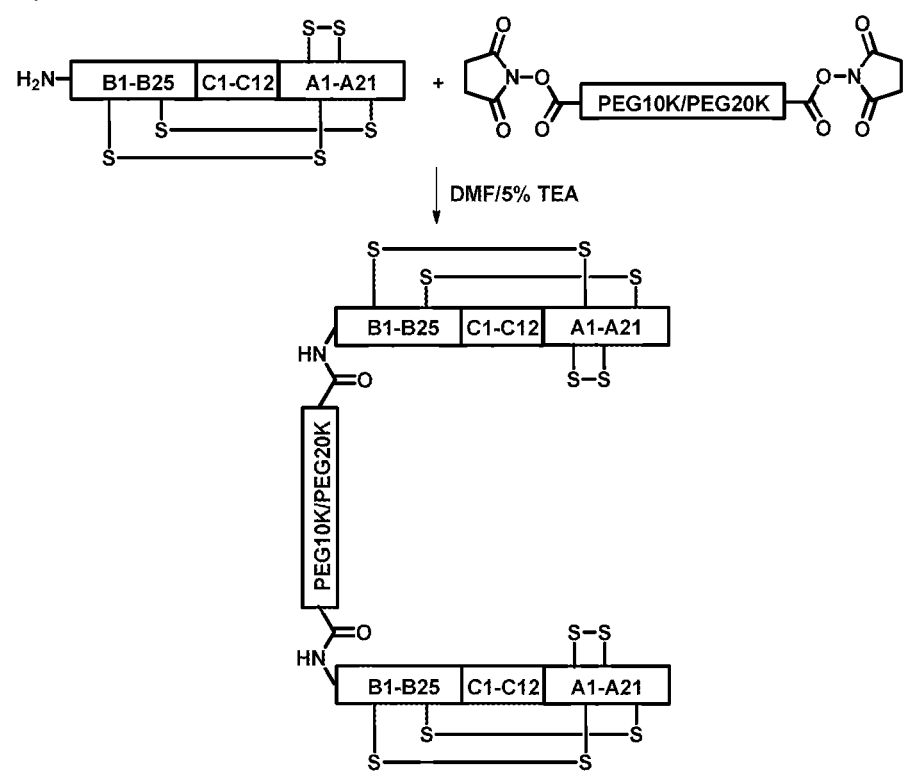
FIG. 22G: Synthetic Scheme for the preparation of compound #56 (LysB1-LysB1 #11 dimer; see Table 15-17).
Figure 22H:
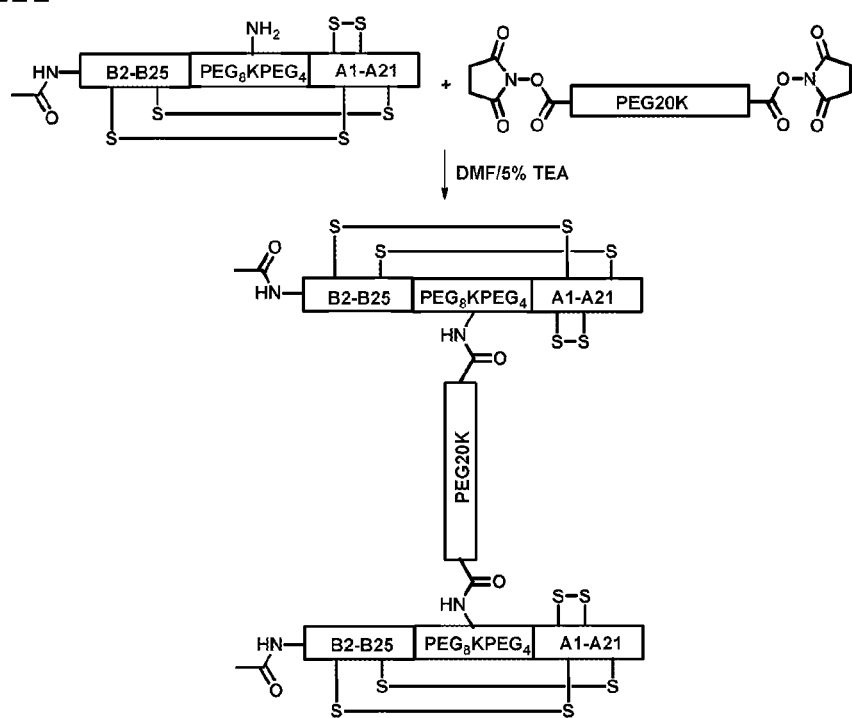
FIG. 22H: Synthetic Scheme for the preparation of compound #58 (LysC8-PEG20K-LysC8 #3 dimer; see Table 15-17).

56: $Gly^{B2}$-PEG10K-$Gly^{B2}$ #11 Dimer and #57: $Gly^{B2}$-PEG20K-$Gly^{B2}$ #11 Dimer Synthesis Dimers #56 and #57 were prepared by crosslinking the N terminal amino groups of two single-chain insulin peptides with bi-functional PEG linkers of different lengths. The PEG linker was functionalized with succinimidyl esters (NHS esters) on both ends, which reacted with N terminal amines and conjugated two insulin molecules to both ends of the PEG linker (see FIG. 22G). PEG peptide dimers were separated from mono-PEGylated peptide and unreacted reagents by reverse phase chromatography.

58: $Lys^{C8}$-PEG20K-$Lys^{C8}$ #3 Dimer Synthesis

Figure 21:
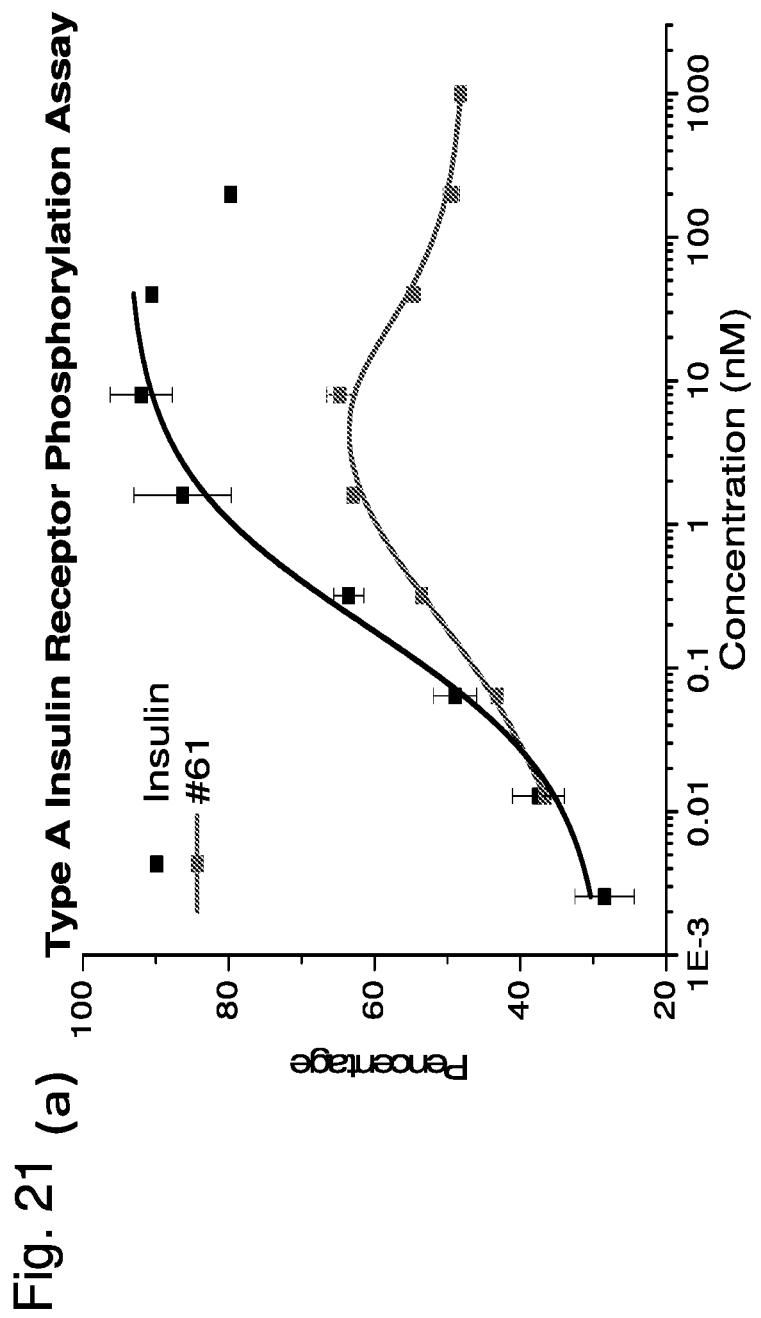
FIG. 21A-21E demonstrate the activities of an insulin heterodimer comprising an insulin polypeptide dimerized with an IGF2 polypeptide. Receptor activities of polypeptide #61 (B⁰25-C¹-A⁰ linked to B²-C²[K8]-A²-D²[R4]) and polypeptide #62 (B⁰25-C¹[K8]-A⁰ linked to B²-C²-A²-D²) were tested at the subtype A insulin receptor (see FIGS. 21A and 21C); the subtype B insulin receptor (see FIGS. 21B and 21D) and the IGF-1 receptor (see FIG. 21E) by phosphorylation assay in vitro. The graphs represents: subtype A or subtype B receptor phosphorylation stimulated by indicated concentrations of native insulin (■) #53 or #60 (●).
Figure 21:
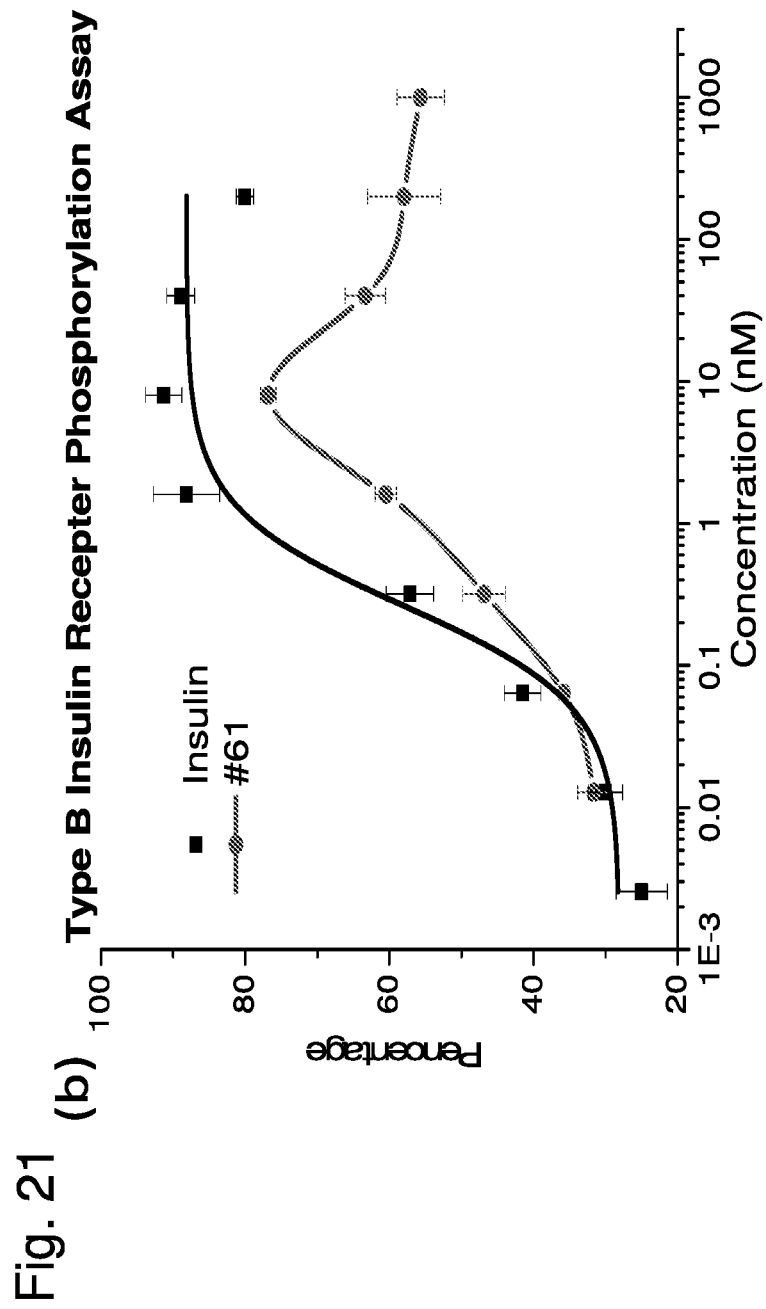
Figure 21:
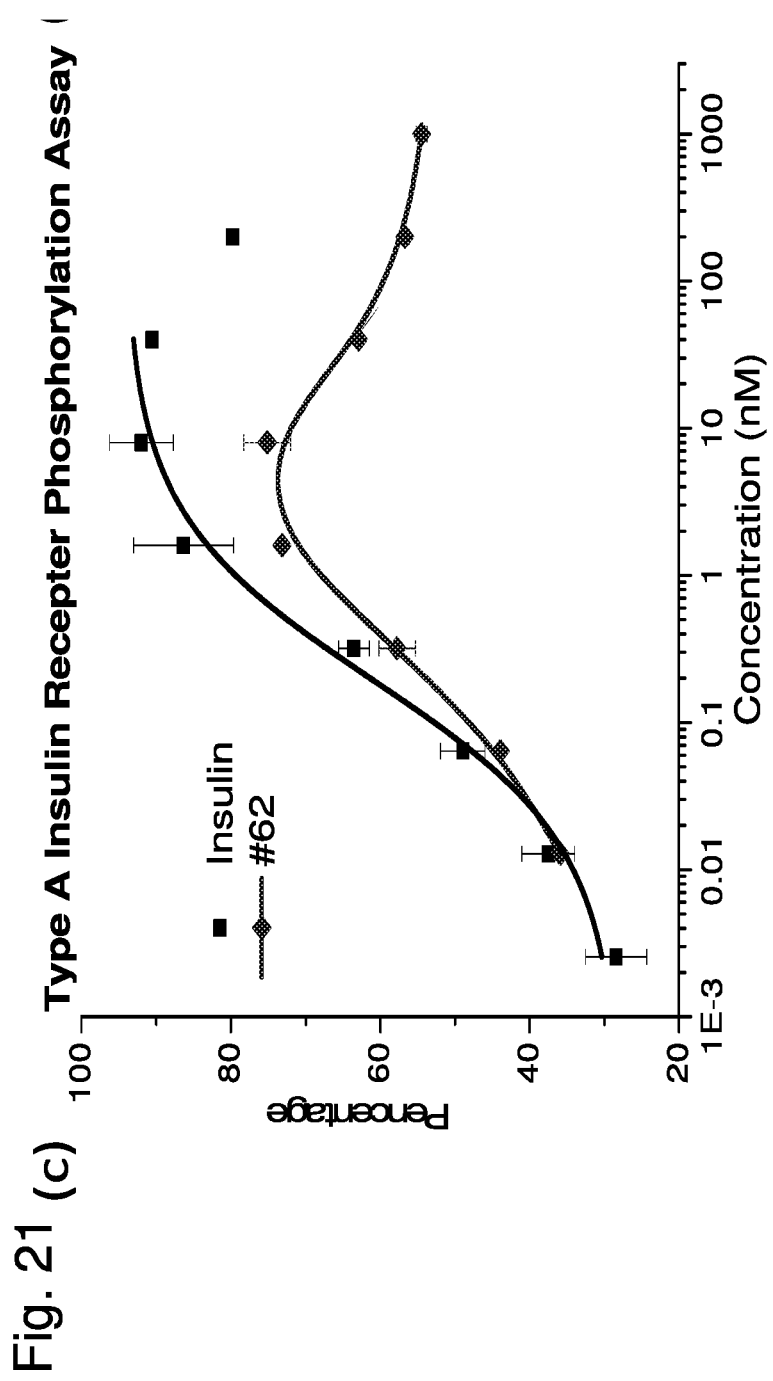
Figure 21:
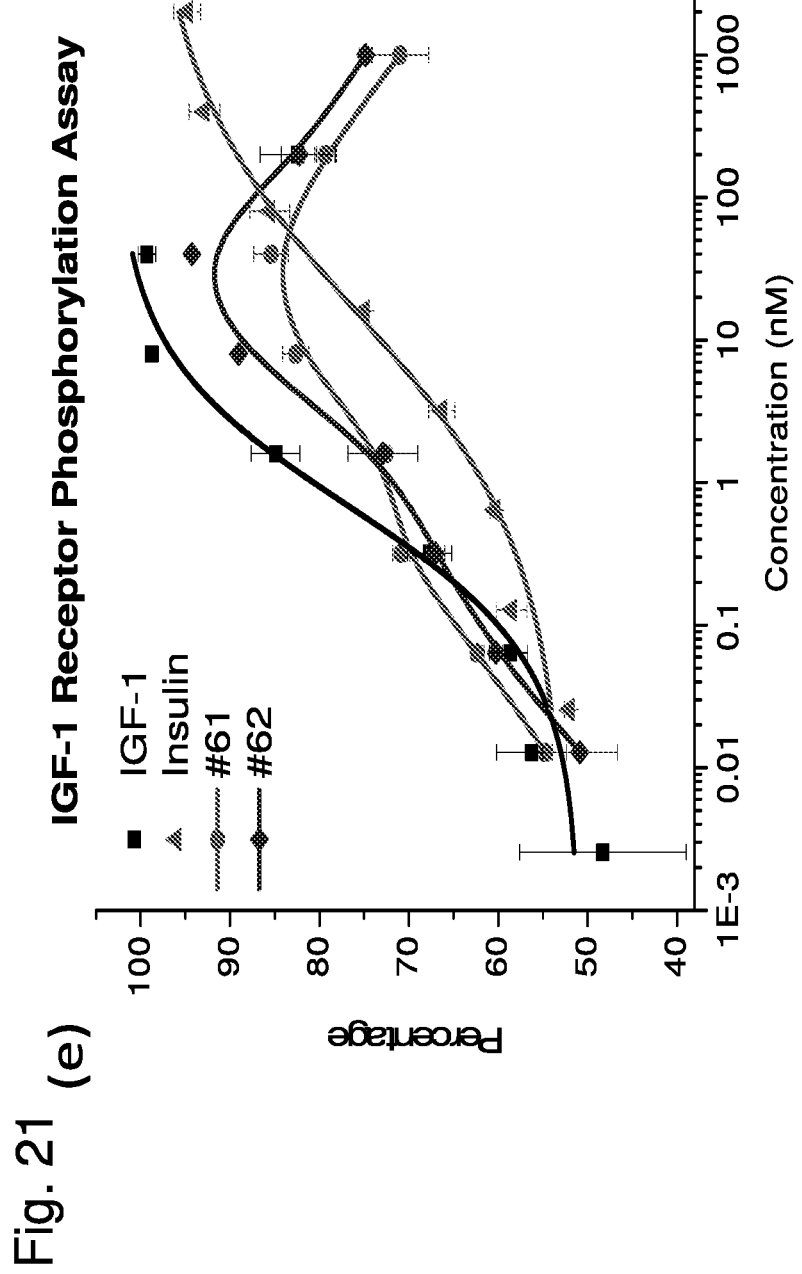

Dimer #58 was prepared by crosslinking the lysine ε-amines of two single-chain insulin analog #3 with a bi-functional 20K PEG linker with NHS esters on both ends. With the reaction between ε-amine and NHS ester, two peptides were conjugated to both ends of the PEG linker (see FIG. 21H). PEG peptide dimers were separated from mono-PEGylated peptide and unreacted reagents by reverse phase chromatography.

Example 19

In Vitro Biological Activities
B1-B1 Insulin Dimers
48: $Cys^{B1}$-$Cys^{B1}$ #2* Dimer (Full Agonist)
Insulin analog $B^1$[H5Y16L17022R29]29:$A^1$[O9,14,15N18,21] was derived from IGF-1 with all arginines replaced with ornithine except $Arg^{B29}$. The side chain of ornithine is one methylene group shorter than that of lysine. Ornithine peptides are not recognized by trypsin, because the shortened side chain does not fit the enzyme's active site. Therefore, trypsin cleavage was directed to $Arg^{B29}$ at the C terminus of the B chain, which produced two-chain insulin after cleavage. This analog showed 55% activity at the type A insulin receptor according to previous binding assay results. Analog #2* included an additional non-native amino acid Thz on B chain's N terminus, which could be converted to cysteine through treatment with methoxylamine. After the completion of the folding process, $Thz^{B1}$ was converted to $Cys^{B1}$ in folding buffer in the presence of free cysteine. Analog 2* was maintained in monomeric state by forming a disulfide bond between $Cys^{B1}$ and the added free amino acid cysteine present in solution. At type A insulin receptor, Cys-$Cys^{B1}$ peptide showed 23.1% activity in the phosphorylation assay and 55.4% activity in a binding assay. This indicated that adding a single cysteine to B chain's N terminus did not affect in vitro binding or signaling.

Analog #48, the dimeric form of analog #2* showed 101.7% receptor activity in the phosphorylation assay and 146.7% in the binding assay. Dimerization led to a 3-4 fold increase in receptor activity, which might be a function of.

Example 20

Preparation of Disulfide-Linked Dimer by Total Chemical Synthesis
Synthesis of B1-B1 Disulfide-Linked Dimer (#48)
Peptide segments $B^1$[Thz1H5Y16L17](1-18)-α-thioester-RRRR-$NH_2$, $B^1$(19-29)[O22]-$A^1$[O9,14,15N18,21]-$NH_2$ and N-acetyl-$B^1$[H5Y16L17](1-18)-α-thioester-RRRR-$NH_2$ were synthesized by stepwise solid phase peptide synthesis. Full-length insulin peptide was produced by ligating two peptide segments together through native chemical ligation. N terminal Thz amino acid was converted to cysteine by treating with 2 mM methoxylamine at pH 4.0. Reaction was stirred at room temperature for 3 h and the completion of conversion was confirmed by MALDI-TOF. Then the peptide solution was adjusted to pH 8.0 and 10% DMSO was added to induce disulfide formation. The dimer formation was monitored by analytical HPLC. The dimerized product was separated from the unreacted monomers on reverse phase column and the identity was confirmed by MALDI.

Synthesis of C8-C8 Disulfide-Linked Dimer (#53)
One mmol each of s-trityl-mercaptopropionic acid (Trt-$SCH_2CH_2COOH$) (National Biochemical Corp., Ohio), N-hydroxysuccinimide (NHS) (Sigma) and diisopropylcarbodiimide (DIC) was mixed in 2 mL DMF for 30 min at room temperature with stirring to prepare Trt-$SCH_2CH_2CO$—NHS ester. Insulin peptide was dissolved in anhydrous DMF with 5% TEA at a concentration of 10 mM. 2 eq of activated Trt-$SCH_2CH_2CO$—NHS ester was added to the solution. The reaction was stirred for 2 hours at room temperature before terminated with 2% ethanolamine. The reaction was then diluted by 5 fold with anhydrous TFA with 4% thioanisole (Sigma) and 8% triisopropylsilane (TIPS) (Sigma) to remove trityl protection group. The deprotection reaction was stirred at room temperature for 30 min and then diluted with ether by 20 fold to extract peptide into precipitates. The diluted reaction was centrifuged and the precipitated peptides were dissolved in 1% acetic acid/20% acetonitrile aqueous solution and lyophilized. Lyophilized products were re-dissolved in DMSO. Half of the peptide solution was mixed with 1 eq 2,2'-Dithiobis(5-nitropyridine) (DTNP) (Sigma) to activate the thiol group. The activation reaction can be monitored by analytical HPLC and the process of reaction was also indicated by the appearance of yellow color. The activated peptide was then mixed with the other half unreacted peptide to produce disulfide-linked dimer. The dimerized product was separated from the unreacted monomer by reverse phase HPLC and the desired fractions were pooled and lyophilized. The identity was confirmed by MALDI or LC-MS.

Preparation of Disulfide-Linked Dimer by Semi-Synthesis
Insulin analogs were prepared by biological synthesis from E. coli cells. To carbamylate N terminal amines, insulin peptide was dissolved at a concentration of 0.5 mg/ml in PBS buffer (pH 7.0) with 50 mM potassium cyanate (Sigma). The reaction was stirred at room temperature overnight and completion of carbamylation reaction was confirmed by MALDI. The carbamylated peptides were desalted on reverse phase column and fractions containing peptides were pooled and lyophilized. HS—$CH_2CH_2CO$ was conjugated to peptide on either α-amine on N terminus or ε-amine on Lysine's side chain and insulin dimer was produced by forming a disulfide bond between two insulin molecules, as described in synthesis of dimer #53.

Preparation of PEG-Linked Dimer by Semi-Synthesis
Insulin peptides prepared by either chemical synthesis or biosynthesis were dissolved in anhydrous DMF with 5% DIEA at a concentration of 10 mg/ml. 0.5 equivalent of bi-functional NHS-$PEG_n$-NHS (n=9, 10K, 20K) (Creative PEGWorks) was added to peptide solution. Reaction was stirred at room temperature for 1 hour. Reaction process was monitored by analytical HPLC. After completion, the reaction was diluted to at least 20 fold the reaction volume with 0.1% TFA/10% acetonitrile aqueous solution. The diluted reaction was then loaded on reverse phase column and the dimerized derivative was purified and lyophilized.

In Vitro Biological Activity Assays
Competitive Binding Assay
Receptor binding affinity of insulin analogs were tested in a competitive binding assay using scintillation proximity technology. Recombinant human insulin (Eli Lilly & Co., Indianapolis, Ind.) was included in the test as standard ("cold" native insulin). In a 96-well plate (Corning Inc., Acton, Mass.), serial 5-fold dilutions were performed toward insulin analogs and insulin standards with scintillation proximity assay buffer containing 50 mM Tris-HCl, 150 mM NaCl, 0.1% w/v bovine serum albumin (Sigma Aldrich, St Louis, Mo.), pH 7.5. Diluted peptides were mixed with 0.05 nM recombinant human $[^{125}I]$-Insulin (3-$[^{125}I]$iodotyrosyl $Tyr^{A14}$) Insulin (Perkin Elmer, Waltham, Mass.). An aliquot of 1-6 mg plasma membrane fragments prepared from cells over-expressing human insulin receptors were added to each well, along with protease inhibitors and 0.25 mg polyethyleneimine-treated (PVT) wheat germ agglutinin (WGA) scintillation proximity beads (Aersham Biosciences, Piscataway, N.J.). The plate was shaken at 800 rpm for 5 minutes and then incubated for 12 hours at room temperature. Radioactivity was measured with a MicroBeta1450 liquid scintillation counter (Perkin Elmer, Waltham, Mass.). Non-specific binding (NSB) radioactivity was measured in the wells with "cold" native insulin four times more concentrated than the highest concentration of testing samples. Total binding radioactivity (TB) was detected in wells without "cold" native insulin as competitor. Percentage of specific binding was calculated as [(Binding-NSB)/TB]× 100%. A plot of % specific binding vs. testing sample concentration gives IC50 values, which was determined by Origin software (Origin Lab, Northampton, Mass.). The affinities of the analogs were shown as values relative to the affinities of native human insulin, [$IC_{50}$ (insulin)/$IC_{50}$ (analog)×100%].

Receptor Kinase Activity Assay

Transfected HEK 293 cells with overexpression of type A insulin receptor, type B insulin receptor or IGF-1 receptor were maintained in Dulbecco's modified eagle medium (DMEM) (Hycone, Logan, Utah) supplemented with 10% bovine growth serum containing antibiotics, 10 mM HEPES and 125 µg/ml Zeocine. Cells were plated in 80 µl serum deprived medium at a density of 4.0×104 cells/well on poly-lysine coated 96 well plates (Corning). Cells were cultured for 16 hours in serum free DMEM supplemented with 0.25% bovine growth serum, antibiotics and 10 mM HEPES. Serial 5-fold dilutions were performed toward insulin analogs and insulin standards with DMEM with 0.5% BSA. 20 µl of analogs solution was added to each well containing the transfected cells and incubated at 37° C. for 15 min. After incubation cells were fixed by formalin for 20 minutes and then washed twice with PBS buffer containing 0.1% Triton X-100. Then blocking solution containing PBS, 0.1% Triton X-100 and 2% BSA was added to block the nonspecific antibody binding site. After three times washing, 50 µl of antibody 4G10 anti-phosphotyrosine-HRP conjugate (Millipore) was diluted by 10,000 fold and added to the plates. Cells were incubated with antibodies for 3 hour at room temperature and then washed 4 times with PBS containing 0.1% Triton X-100. 100 µl fluorogenic substrate 3,3',5,5'-tetramethylbezidine (TMB) (Invitrogen, Carlsbad, Calif.) was added and incubated for 5-10 minute for fluorescence development. Fluorescence developing reaction was stopped by adding 1N HCl. The fluorescence signals were recorded by scanning the plate at 450 nm in Titerteck multi-scan MCC340 reader. $EC_{50}$ values were calculated by plotting OD450 nm versus testing sample concentration with Origin software (Origin Lab, Northampton, Mass.).

In all assays, the activity relative to human insulin standard or human IGF standard will be determined within each experiment and then average over the number of experiments. Therefore the $EC_{50}$ or $IC_{50}$ for an analog will indicate the receptor binding activity.

Antagonism Assay

Serial 5-fold dilutions were performed toward insulin analogs and insulin standards with DMEM with 0.5% BSA. 10 µl of analogs solution was mix with 10 µl 12 nM insulin solution to prepare a mixture containing 6 nM insulin and desired concentration of insulin analogs. 20 µl of mixed solution was added to each well containing the transfected cells and incubated at 37° C. for 15 min. The following procedures were the same as receptor kinase activity assays described above.

Insulin Tolerance Tests in Rodents

Acute insulin tolerance tests were conducted in C57BL/6 mice or db/db mice fasted throughout the period of examination. Test compounds were administered subcutaneously. Blood glucose levels were measured just before injection and 1, 2, 3, 6 and 8 hour in 8-hr test or 1, 2, 3, 6, 8, 12 and 24 hour in 24-hr test.

B1-B1 PEG-linked Insulin Dimers (Full Agonists)

A series of PEG-linked B1-B1 dimers were prepared to identify the effects of the linker lengths on receptor activities. The molecular size of PEG linkers varied from 500 Da to 20 KDa. All the PEG-linked B1-B1 dimers were full agonists at insulin receptors and their receptor activities are summarized in Table 17. Dimer #55 included a 9-unit short PEG as a linker between two insulin analogs, and the activity of #55 was similar to its monomeric peptide backbone #20*. Dimers #56 and #57 contained relatively large PEG linkers. This decreased the receptor activity to a large degree, presumably because of steric hindrance. Increasing the molecular size of PEG linker clearly induced more negative effects on receptor activities. However, at both type A and type B insulin receptors, PEG20K crosslinked dimer (#57) was nearly 4 fold more potent than the 20K PEGylated monomer (#39), indicating that the dimeric structure appears to induce synergistic binding to insulin receptors leading to increased receptor activities.

TABLE 17

Receptor activities of PEG-linked insulin dimers

| No. | Name | MIU# | Sequence | Phosphorylation ($EC_{50}$) | | |
|---|---|---|---|---|---|---|
| | | | | % IR-B | % IR-A | % IGF-1 R |
| | Insulin | MIU-1 | $B^0$:$A^0$ | 100.0 | 100.0 | 1.8 |
| | IGF-1 | | $B^1C^1A^1D^1$ | 0.7 | 8.4 | 100.0 |
| 55 | $Lys^{B1}$-$PEG_9$-$Lys^{B1}$ #20* dimer | | $GE_5K$-$B^1$(H5,10Y16L17)25-$C^1$-$A^1$(H8N18,21) | — | 44.0 | — |
| 56 | $Gly^{B2}$-PEG10K-$Gly^{B2}$ #11 dimer | | $B^1$(H5,10Y16L17)25-$C^1$-$A^1$(H8N18,21) | 9.7 | 38.2 | — |
| 57 | $Gly^{B2}$-PEG20K-$Gly^{B2}$ #11 dimer | MIU-58 | $B^1$(H5,10Y16L17)25-$C^1$-$A^1$(H8N18,21) | 5.8 | 19.7 | 2.6% |
| 58 | $Lys^{C8}$-PEG20K-$Lys^{C8}$ #3 dimer | | $B^1$(H5Y16L17)25-$PEG_8$-K-$PEG_4$-$A^1$(N18,21) | — | 18.6 | — |
| 38 | C8-PEG20K #3 Monomer | MIU-56 | $B^1$(H5Y16L17)25-$PEG_8$-K-$PEG_4$-$A^1$(N18,21) | 2.0 | 14.8 | — |
| 39 | B1-PEG20K #11 Monomer | MIU-57 | $B^1$(H5,10Y16L17)25-$C^1$-$A^1$(H8N18,21) | 1.1 | 4.5 | 1.2 |

Example 21

B29-B29 Insulin Dimers

51: $Lys^{B29}$-$Lys^{B29}$ Insulin Dimer (Partial Agonist)

Dimer #51 is a B29-B29 crosslinked dimer built upon the native insulin sequences. Dimer #51 is structurally similar to the previously reported B29-B29' PEG linked dimer, except #51 is crosslinked by forming a disulfide bond. The linker length in #51 while not identical is approximately the same as the B29-B29' dimer, as $Lys^{B29}$'s ε-amines were separated by an 8-atom linker. Additionally, #51 contained carbamylations at the N termini of B chain and A chain, which decreased receptor potency to ~30% but maintained full agonism at the insulin receptor.

Figure 11:
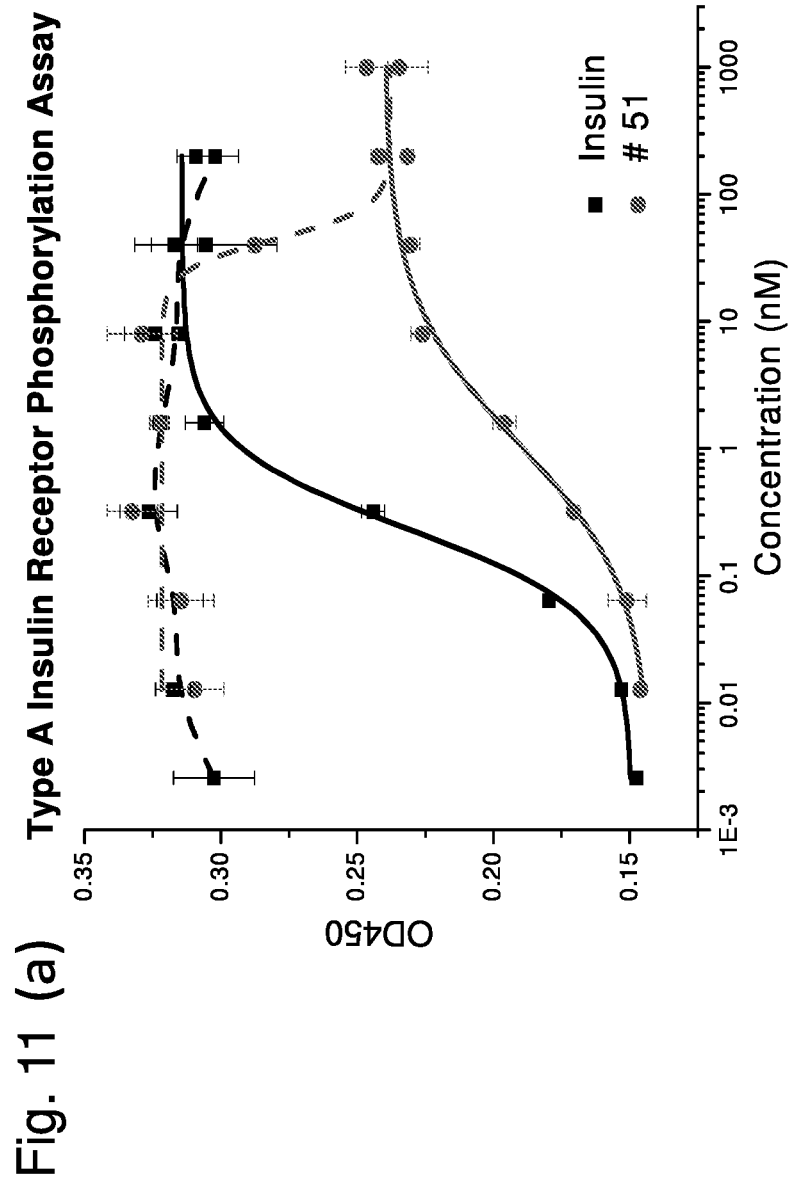
FIGS. 11A-11E. Receptor activities of the B29-B29' insulin dimer (polypeptide #51, a dimer formed between two native insulin polypeptides linked together by a disulfide bond between the side chains of the B29 lysine of the B chains) were tested at the type A insulin receptor (see FIG. 11A); the type B insulin receptor (see FIG. 11B) and the IGF-1 receptor (see FIG. 11C) by phosphorylation assay and mitogenicity tested by HMEC proliferation assay (see FIG. 11D) in vitro. The solid line on the graphs represents: Type A or Type B receptor phosphorylation (on FIGS. 11A-11B, respectively) stimulated by indicated concentrations of native insulin (■) or #51 (◆); the dashed line represents: Type A; or Type B receptor phosphorylation (on FIGS. 11A-11B, respectively) stimulated by co-incubating 6 nM insulin and indicated concentrations of insulin (■) or #51 (◆). The B29-B29' insulin dimer has an appreciably reduced (approximately 60%) maximal dose response at the insulin and IGF receptors relative to native insulin.
Figure 11:
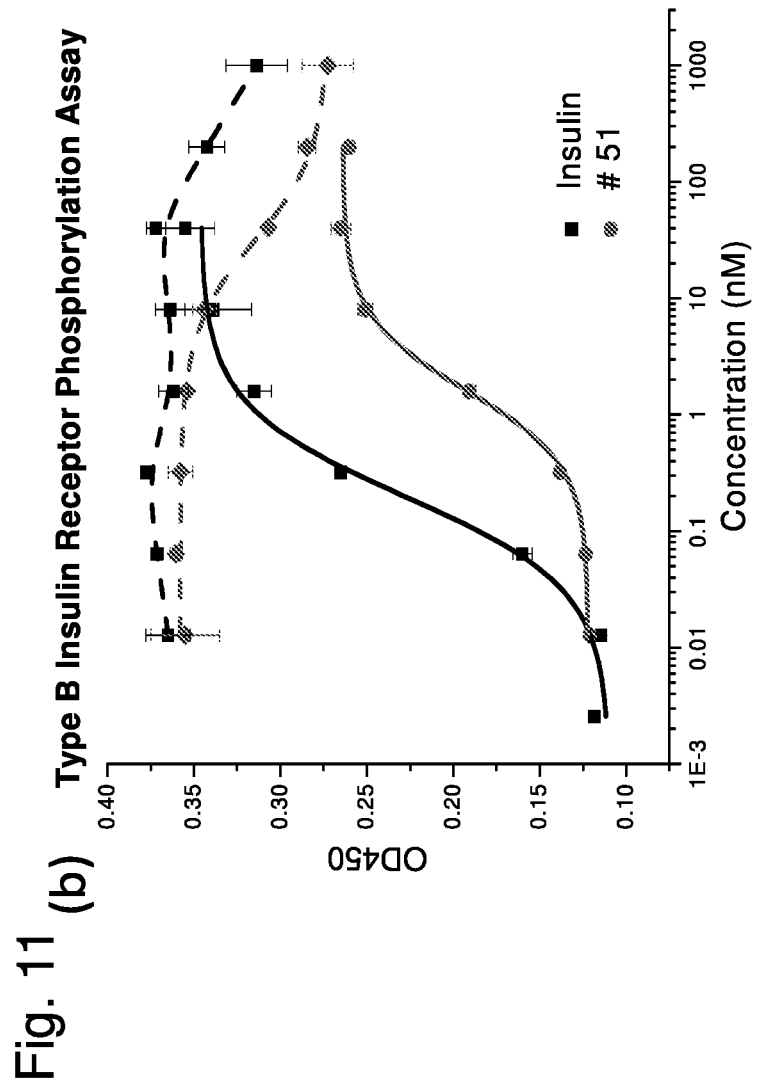
Figure 11:
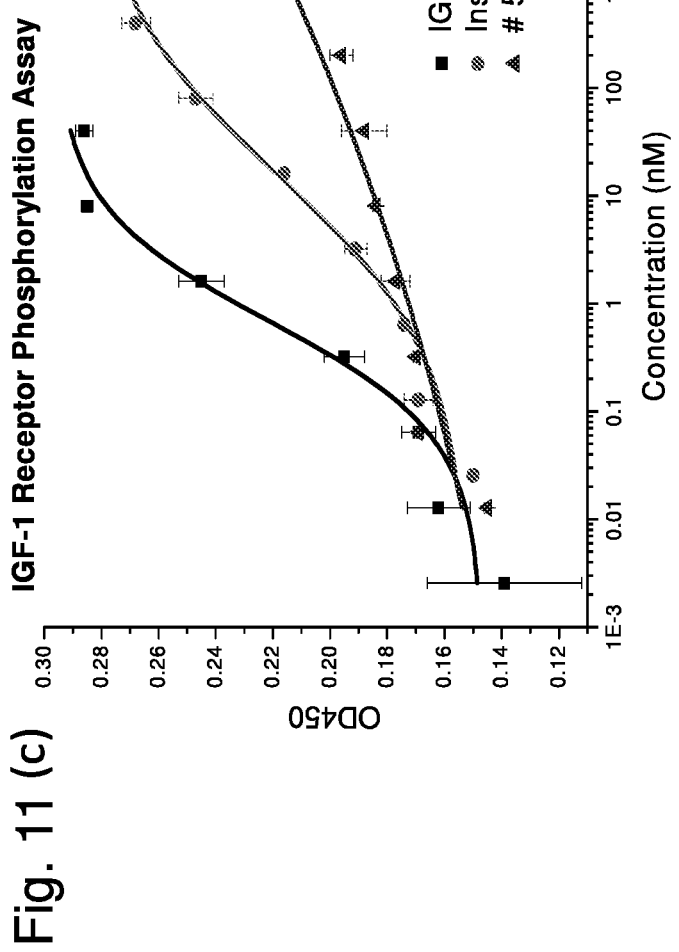
Figure 11:
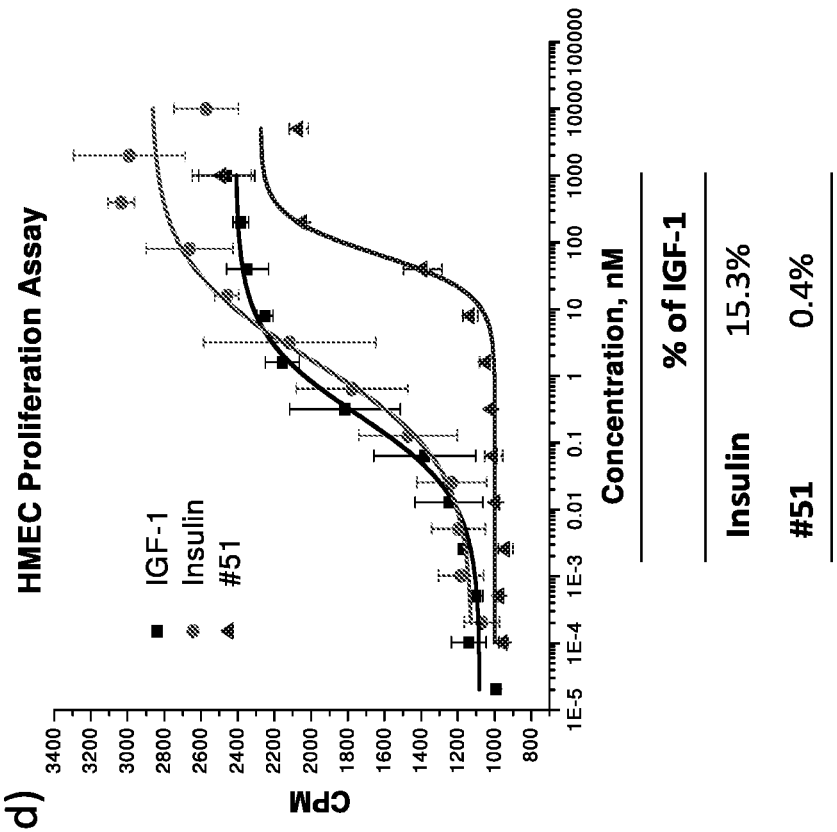
Figure 12A:
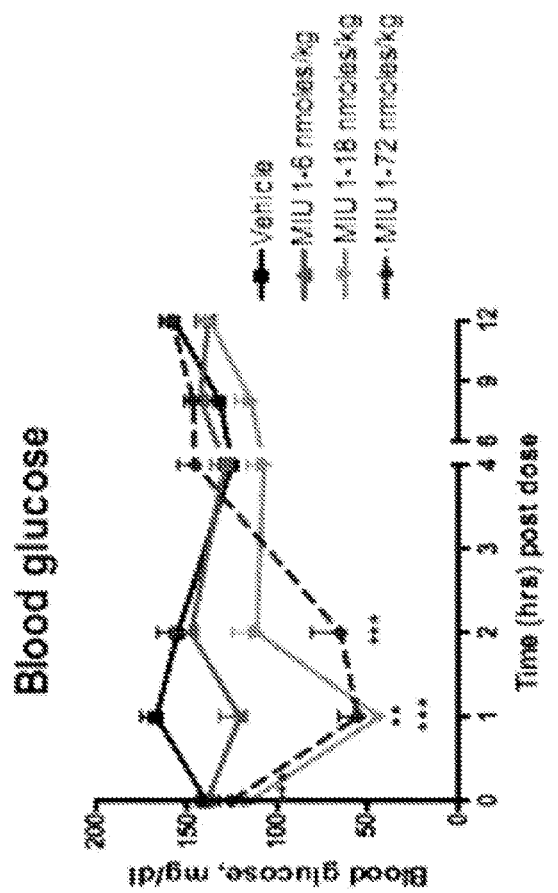
FIGS. 12A & 12B provide data from a comparative insulin dose titration of the B29-B29' insulin dimer (FIG. 12B) relative to native insulin (FIG. 12A). Native insulin was administered at three dosages (6 nmoles/kg, 18 nmoles/kg and 72 nmoles/kg) and the B29-B29' insulin dimer was administered at three higher dosages (18 nmoles/kg, 72 nmoles/kg and 144 nmoles/kg). Similar to native insulin, the B29-B29' insulin dimer lowers blood glucose levers, but the B29-B29' insulin dimer has a less steep initial lowering of glucose and holds the blood glucose levels at a more even plateau than is seen with native glucose.
Figure 12B:
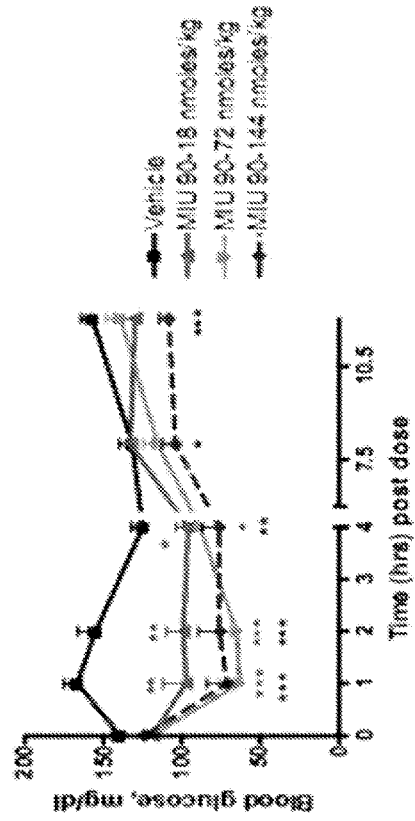
Figure 13C:
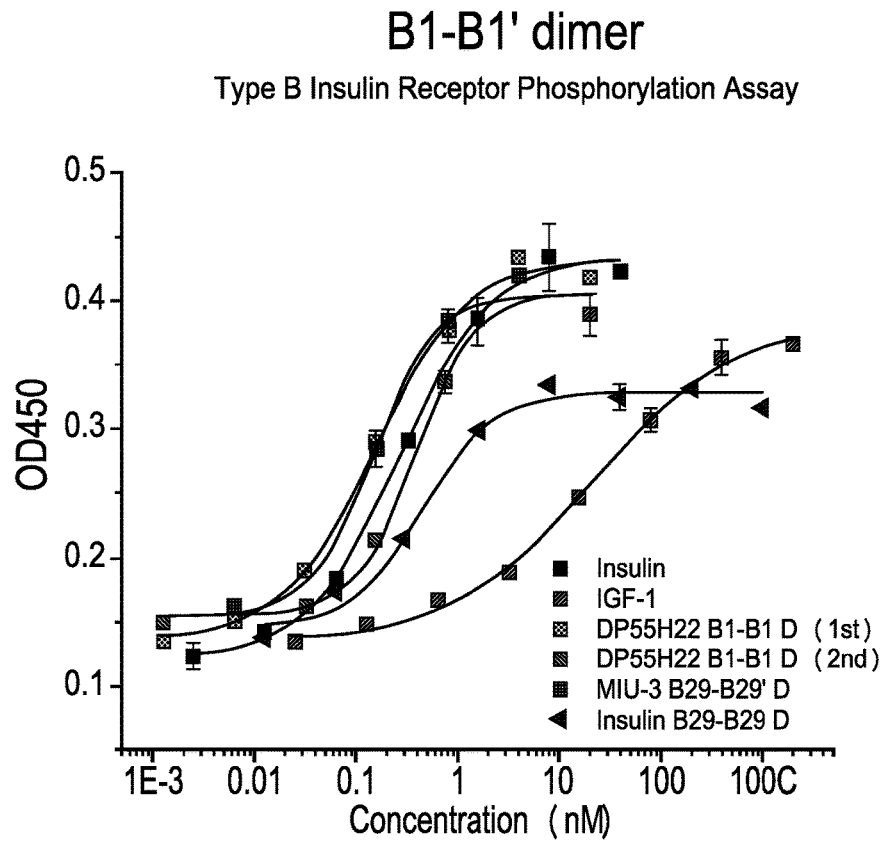

Same as the previously reported B29-B29' dimer, #51 also showed partial agonism at the insulin receptor. Dimer #51 was able to induce a sigmoidal dose response curve at the insulin receptor, with the maximal response induced by dimer #51 at the insulin receptor being just half of that induced by native insulin (FIG. 11A and FIG. 11B). Unlike other weak full agonists at the insulin receptor, maximal response could not be achieved by simply raising the ligand's concentration. The $EC_{50}$ of the partial agonists were not listed in FIG. 11, as the value was not comparable to that of full agonist due to different levels of maximal responses.

Partial agonist #51 also showed antagonistic effects against insulin's action at the insulin receptor. To test the antagonistic effects, engineered HEK293 cells overexpressing the insulin receptors were treated with a combination of #51 at indicated concentration and 6 nM insulin. Based on previous results of receptor kinase activity assay, 6 nM insulin was able to induce 95% maximal response. In the control experiment, the procedure was repeated with the dimer #51 replaced with insulin. The antagonism assay showed #51 was able to antagonize insulin's action and decrease the receptor response to half of the maximal response induced by native insulin.

Dimer #51 also showed reduced potency at the IGF-1 receptor when compared to native insulin (FIG. 11C). Since the response curve was incomplete due to low potency, it is not clear whether #51 was a partial agonist or a weak full agonist at the IGF-1 receptor. Dimer #51 also showed weak potency in stimulating HMEC cell growth in HMEC proliferation assay (FIG. 11D).

C8-C8 Insulin Dimers

53: $Lys^{C8}$-$Lys^{C8}$ #3 Dimer (Partial Agonist)

Dimer #53 was prepared by dimerizing two molecules of analog #3. Peptide #3 is an IGF-1 derived single-chain analog containing IGF-1 B chain and A chain connected with an 8-unit mini-PEG, a lysine and a 4-unit mini-PEG. Select mutations were introduced to B chain and A chain in order to restore insulin receptor activity and decrease IGF-1 receptor activity. Peptide #3 was fully potent at the insulin receptor. An additional thiol group was introduced to $Lys^{C8}$ side chain through the reaction with mercaptopropionic acid. A disulfide bond was formed between two thiol groups at the respective C8 positions to crosslink two peptides and produce the dimer #53.

Figure 17:
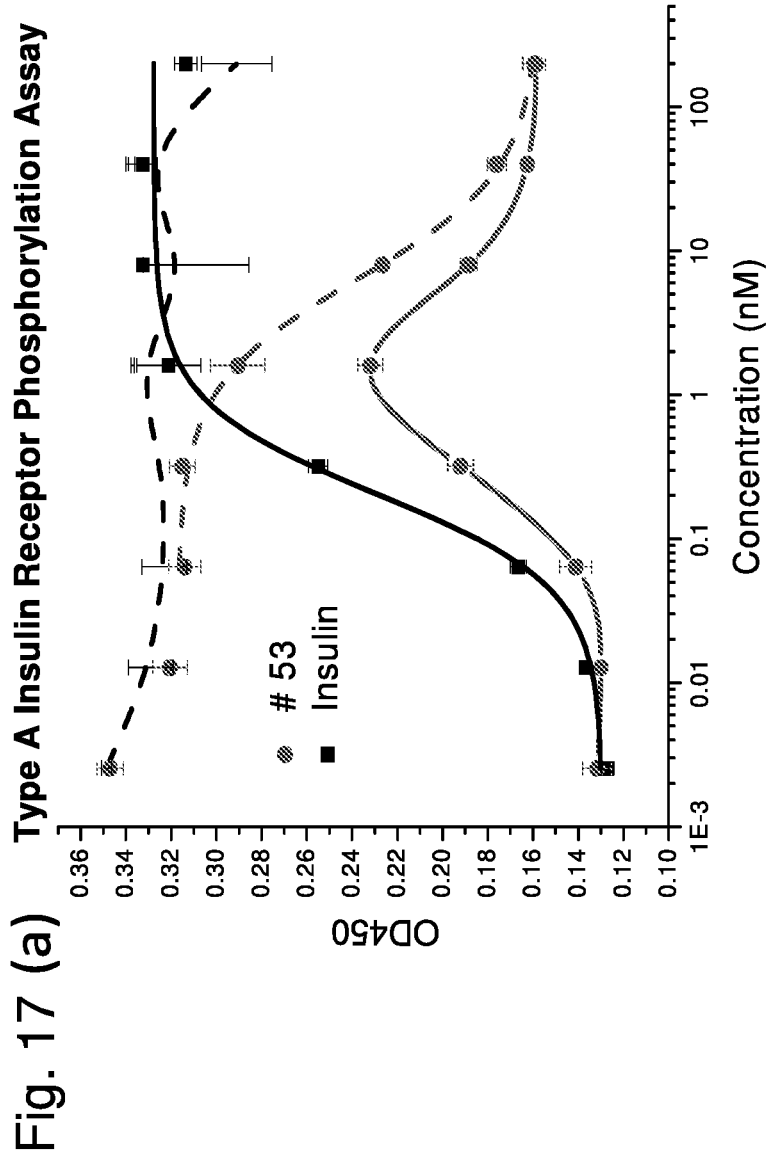
FIGS. 17A-17D demonstrate the activities of an insulin dimer comprising two single chain IGF-1 insulin agonist analogs wherein the A chain and the B chain are linked via a mini-peg linking moiety (PEG$_8$-K-PEG$_4$) and the two insulin polypeptides are joined via the lysine side chain of the respective linking moieties (LysC8-LysC8 dimer of B1[[H5Y16L17]25-PEG8KPEG4-A1[N18,21]; polypeptide #53). Activity was tested at the subtype A insulin receptor (see FIG. 17A); the subtype B insulin receptor (see FIG. 17B) and the IGF-1 receptor (see FIG. 17C) by phosphorylation assay, and receptor binding affinity tested by subtype A insulin receptor binding assay (see FIG. 17D) in vitro. The solid line on the graphs represents: subtype A or subtype B receptor phosphorylation (on FIGS. 17A-17B, respectively) stimulated by indicated concentrations of native insulin (■) or #53 (●); the dashed line represents: subtype A; or subtype B receptor phosphorylation (on FIGS. 17A-17B, respectively) stimulated by co-incubating 6 nM insulin and indicated concentrations of insulin (■) or #53 (●).
Figure 17:
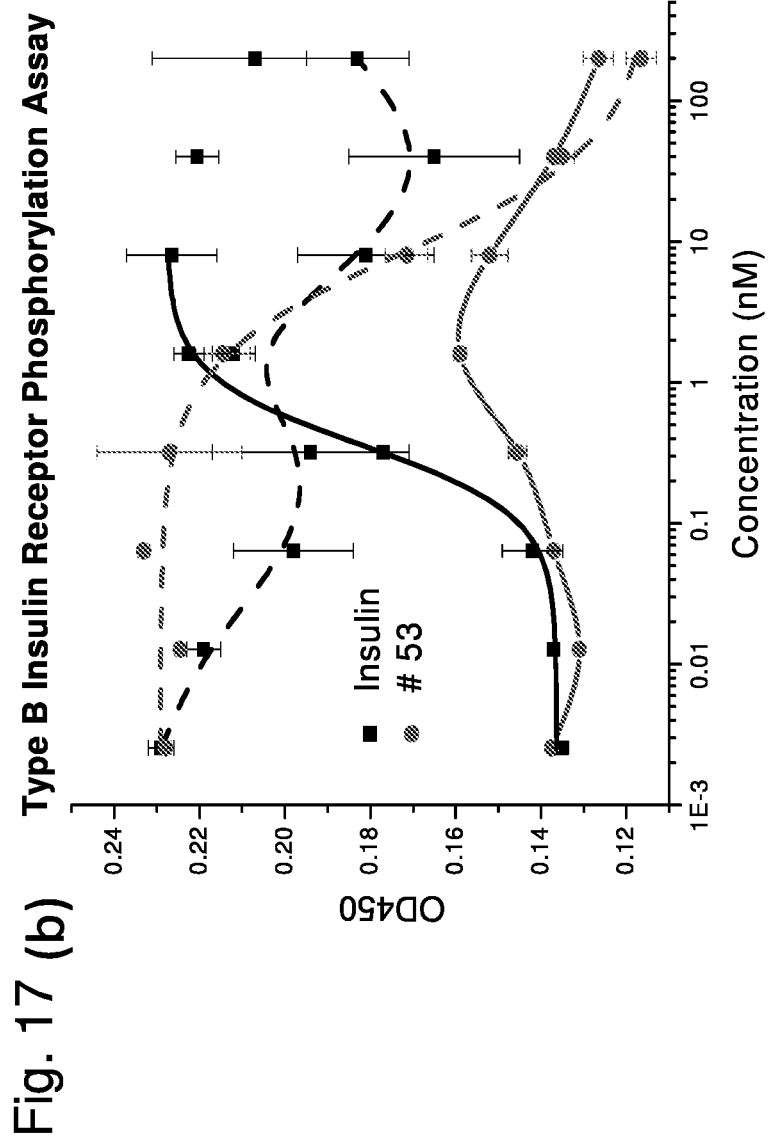
Figure 17:
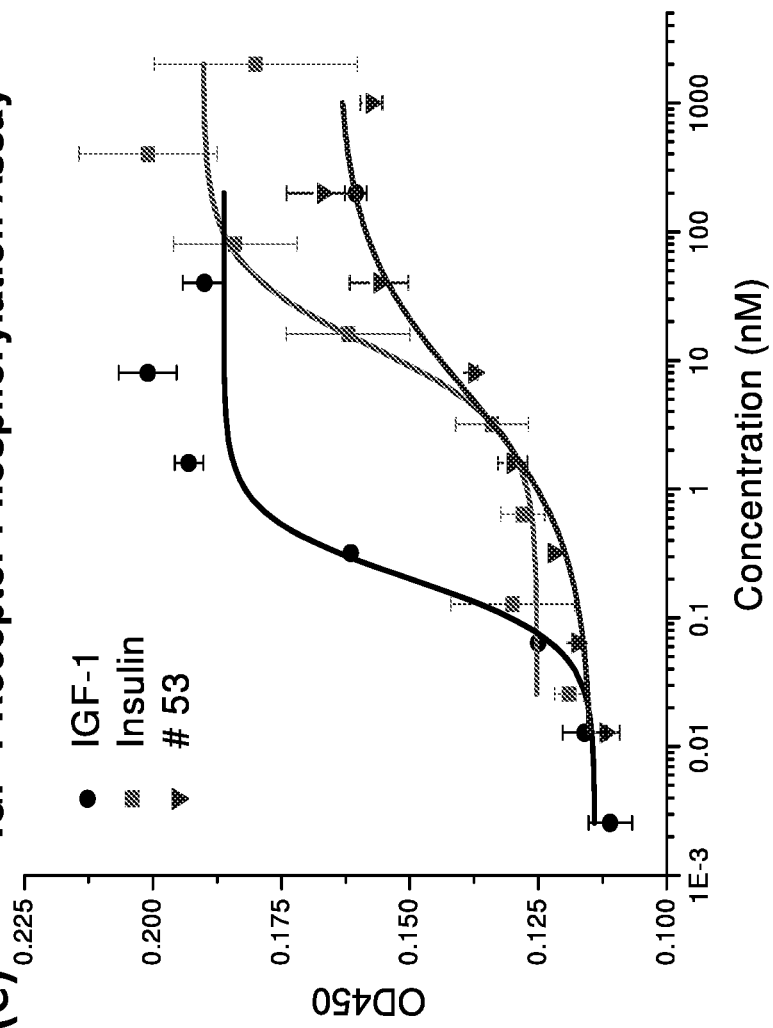
Figure 17:
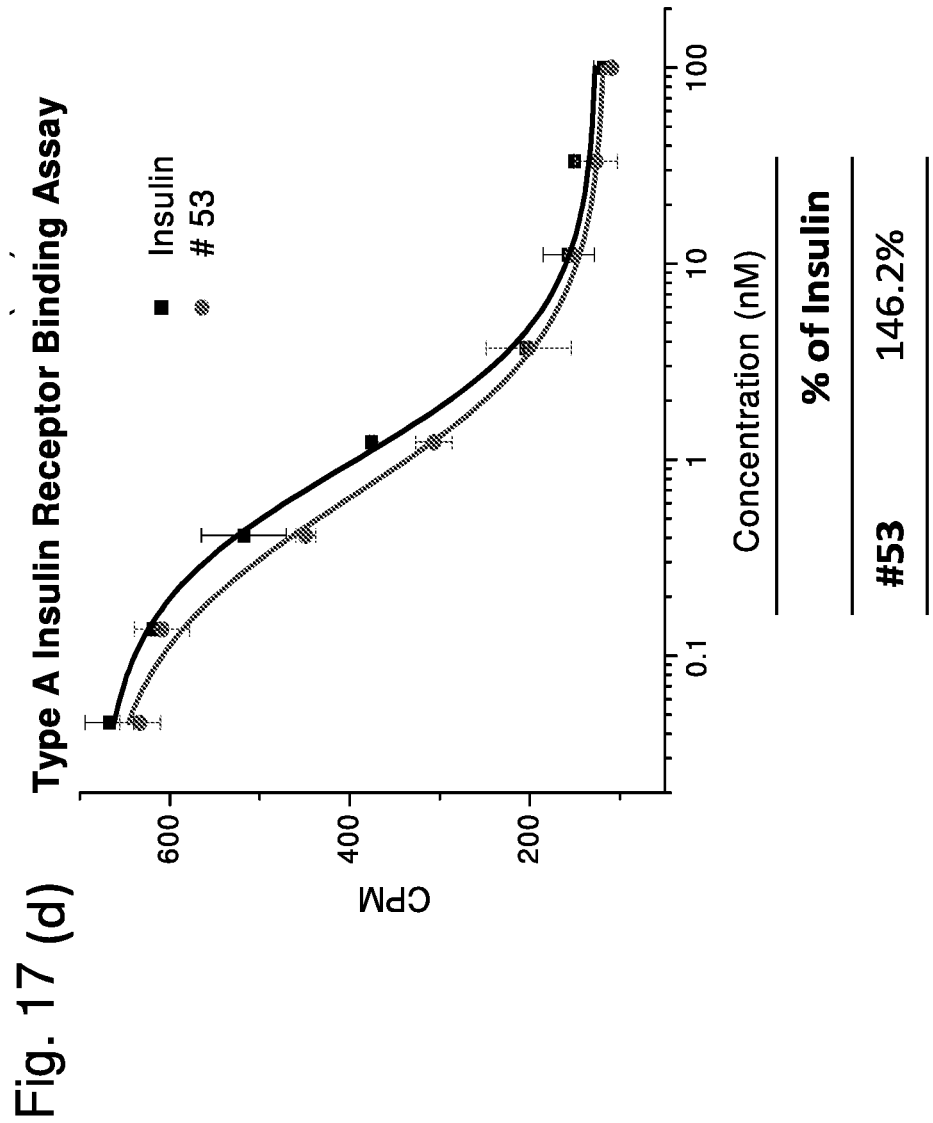

Dimer #53 was also a partial agonist at both type A and type B insulin receptor. The maximal response induced by #53 was also just half of that induced by insulin at both receptors. Unlike #51, the receptor response curve of #53 was bell-shaped. As concentration increased, the receptor response was decreased. At high concentration, #53 was able to completely inactivate the receptor. The antagonism assay showed #53 competitively inhibited insulin's action and at high concentration the insulin receptor was completely silenced. At the IGF-1 receptor, #53 also showed partial agonism. Although #53 showed a deficiency in stimulating the receptor response, it was fully potent in binding to the insulin receptor. In a binding assay, #53 was able to fully displace radiolabeled insulin from insulin receptor as concentration increased. The binding affinity of #53 was even ~1.5 fold stronger than native insulin (FIG. 17). The discrepancy between binding affinity and ability to induce a biological response should be the reason for the antagonistic effects on insulin's action. This phenomenon had been reported in the studies of B29-B29' dimer and was observed again in the present data of B29-B29' dimer and C8-C8' dimer, suggesting the discrepancy was a unique structural characteristic of partial agonist dimers. This partial agonism may be associated with novel therapeutic properties in vivo, as the ability to antagonize insulin's action might limit the propensity of overdosing.

58: $Lys^{C8}$-PEG-$Lys^{C8}$ #3 Dimer (Full Agonist)

Analog #38 with a 20k PEG conjugated at the C8 position of analog #3 is a full agonist. Therefore the partial agonism was not caused by the structural alteration induced by modification at C8 position. To study the effects of the distance between two insulin molecules within the dimer, a 20K PEG linker was introduced to crosslink two molecules of analog #3 at their C8 positions, which produced dimer #58. In #58, two insulin molecules were separated by a large PEG spacer and were expected to behave more independently. Dimer #58 showed full agonism at the insulin receptor with reduced potency, presumably due to the steric PEG linker. Separating two insulin molecules with the PEG linker abolished partial agonism at the insulin receptor, suggesting the distance between two active sites was critical for the partial agonism. The PEG-linked dimer #58 showed similar potency as the PEGylated monomer #38. An increase in potency observed for B1-B1 PEG-linked dimer did not appear in the C8-C8 PEG-linked dimer, suggesting the C8-C8' linkage might be less suitable than B1-B1' linkage for synergistic binding to insulin receptors.

54: $Lys^{C8}$-$Lys^{C8}$ #11* Dimer (Full Agonist)

Figure 18:
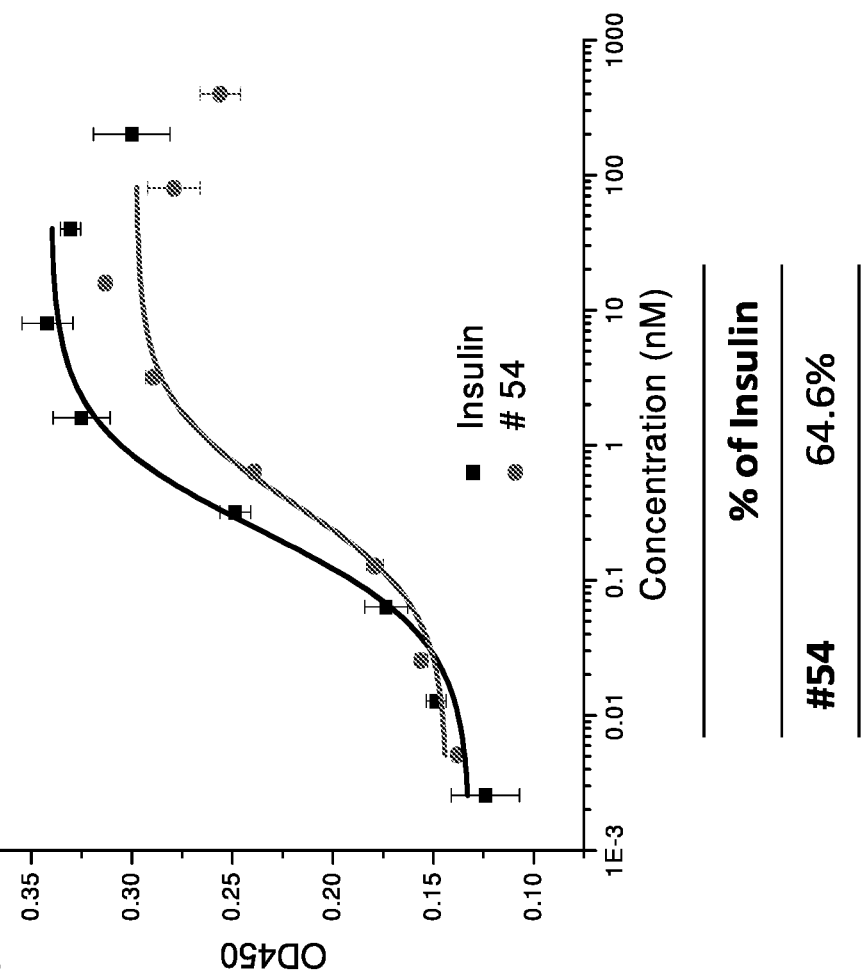
FIGS. 18A & 18B demonstrates the activities of an insulin dimer comprising two single chain IGF-1 insulin agonist analogs wherein the A chain and the B chain are linked via the $C^1$ peptide modified to contain a lysine at position 8 of the C peptide, wherein and the two insulin polypeptides are joined via the lysine side chain of the respective linking moieties (LysC8-LysC8 dimer of B1[[H5,10Y16L17]25-C1[K8]-A1[H8N18,21]; polypeptide #54). Activity was tested at the subtype A insulin receptor (see FIG. 18A); and the subtype B insulin receptor (see FIG. 18B) by phosphorylation assay in vitro. Subtype A or subtype B receptor phosphorylation (on FIGS. 18A-18B, respectively) stimulated by indicated concentrations of native insulin (■) or #53 (●) is shown.
Figure 18:
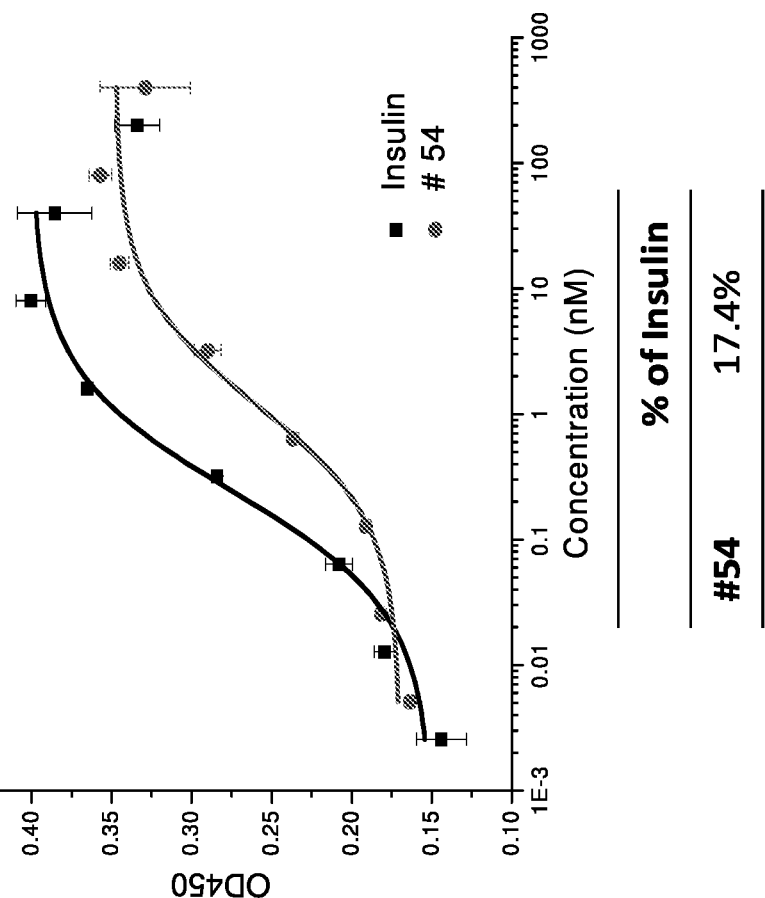

Dimer #54 was also made from an IGF-1 derived single-chain analog (#11*). Instead of a mini-PEG linker, the C domain of #11* contained the 12 amino acids derived from the IGF-1 C peptide. $Arg^{C8}$ of IGF-1 C peptide was replaced with $Lys^{C8}$, which was used as a dimerization site. Dimer #54 was almost a full agonist at the insulin receptor (FIGS. 18A & 18B). The level of the maximal receptor response induced by #54 was much higher than that induced by the other two partial agonists, #51 and #53. Dimer #53 and dimer #54 showed a pronounced difference in receptor behaviors, although they both had C8-C8' linkage. The difference should originate from the structure of peptide backbones. The most noticeable difference between #3 and #11* was the content of the C domain. Peptide #3 applied a non-peptidyl PEG linker as the C domain, while #11 contained a 12-amino-acid sequence. Although the lengths of both C domains were approximately the same, the PEG linker was believed to be more flexible than the amino acid sequence, and was less likely to be restricted by structural rigidity. Importance of structural flexibility was also observed in the studies of B29-B29 dimer. The dimer of two-chain insulin (#51) was a partial agonist, while connecting B Chain and A chain with a 12-amino-acid C peptide (#52) abolished the partial agonism. Peptide #11* also contained two additional His mutations at B10 and A8 positions, which were designed to increase receptor selectivity. These two mutations are believed to be less likely to be involved in the partial agonism determination.

Animal Studies: In Vivo Activities

B1-B1' dimer #50 (Full Agonist) and B29-B29' dimer #51 (Partial Agonist)

The full agonist #50 and partial agonist #51 were tested in normal mice fasted throughout the examination period. Test compounds were administered through subcutaneous injection and blood glucose levels were measured over 24 hours post injection.

Figure 14A:
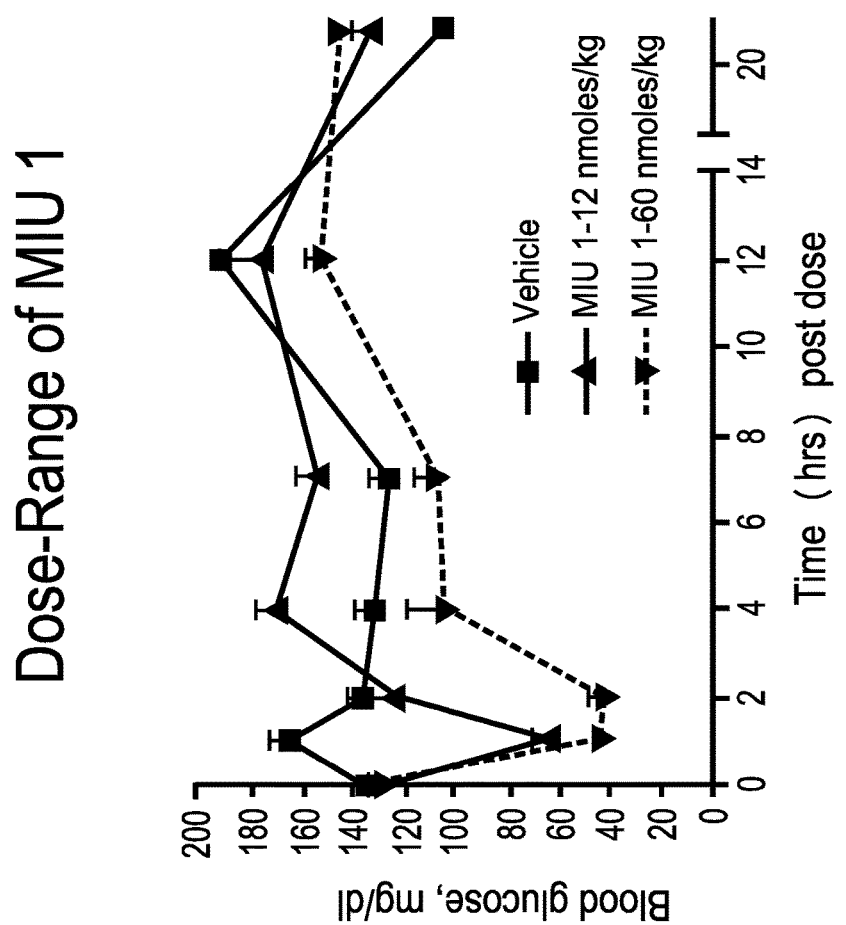
FIG. 14A-14C represents the results obtained from a comparative insulin tolerance test for the B1-B1' and B29-B29' insulin dimers using C57/Blk mice. Human insulin was administered at a dose of 12 or 60 nmoles/kg (FIG. 14A); and the B1-B1' insulin dimer and the B29-B29' insulin dimer was administered at a dose of 12, 60 or 300 nmoles/kg (FIGS. 14B and 14C, respectively). Results from the in vivo experiments show that the B1-B1' insulin dimer appears to be about 5 times more potent than native insulin (the glucose lowering profile of 12 nmole/kg B1-B1' insulin dimer compares similarly to 60 nmole/kg of native insulin). Alternatively the B29-B29' insulin dimer appears to be only about 20% as potent as native insulin (the glucose lowering profile of 60 nmole/kg of native insulin compares similarly to 300 nmole/kg of the B29-B29' insulin dimer).
Figure 14B:
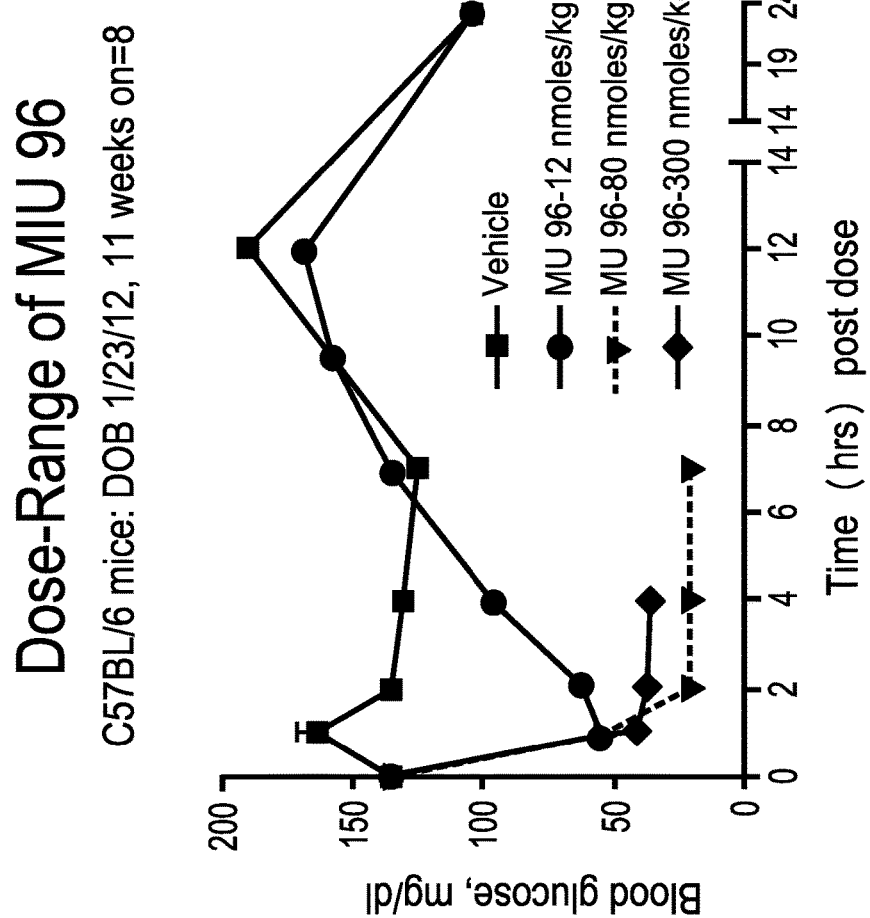

Insulin was administered to normal mice as a positive control. It induced a quick decrease in blood glucose level within 2 hours post injection. Blood glucose level started to rise 2 hours after injection and returned to baseline after 4 hours (FIG. 14A. The full agonist #50 showed significantly enhanced potency in vivo. A 12 nmol/kg dosage of #50 exhibited similar glycemic effects as a 60 nmol/kg dosage of native insulin. Only two mice survived in the group of 8 mice administered with #50 at 60 nmol/kg dose and none survived in the group dosed at 300 nmol/kg (FIG. 14B). Dimer #50 was ~2 fold more potent than native insulin in the in vitro assays, but in vivo #50 was approximately 5 fold more potent than insulin. The significantly increased in vivo activity might be a result of avidity, which was not captured in the in vitro cell-based assays.

Figure 14C:
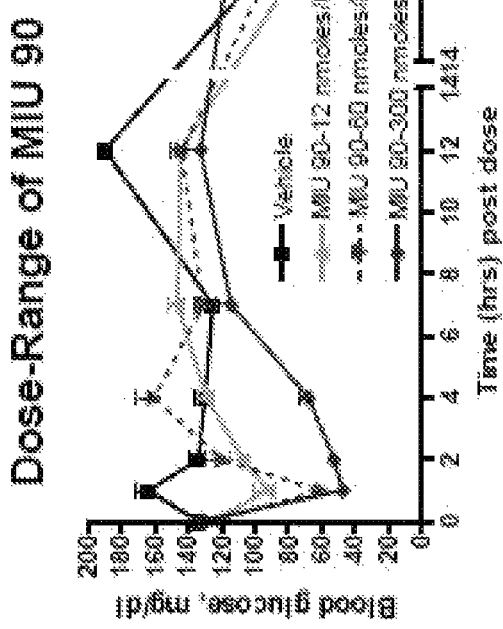

Partial agonist #51 showed reduced potency in vivo. The glycemic effects induced by a 60 nmol/kg dosage of #51 was similar to that induced by #20 nmol/kg dosage of insulin. Also, the blood glucose profile induced by 300 nmol/kg dosage of #51 was similar to that induced by a 60 nmol/kg dosage of insulin. Even at the highest dosage 300 nmol/kg, #51 did not induce hypoglycemia (FIG. 14C). The reduced potency is likely caused by the partial activation on the receptor, as observed in vitro.

PEG-Linked Dimer and PEGylated Monomer

Both PEGylated monomer and PEG-linked dimer were able to induce a decrease in blood glucose and the effects were prolonged compared to the non-PEGylated peptide. The glycemic effects of PEGylated monomers were extended over 24 hours, but after the administration of PEG-linked dimer, blood glucose level started to rise after 6 hours. This indicated PEG-linked dimer might be cleared faster from circulation than PEGylated monomers.

Figure 15A:
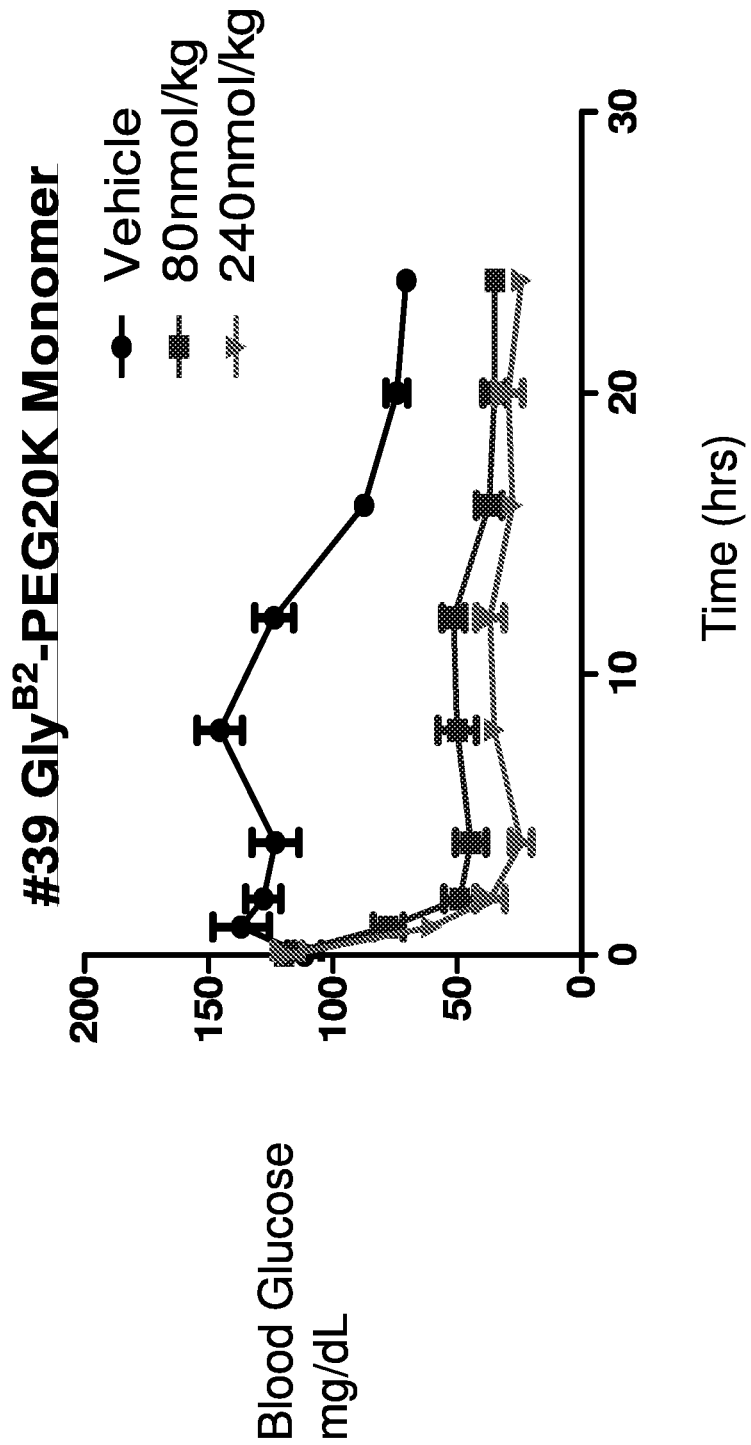
FIGS. 15A & 15B present data obtained from insulin tolerance tests of PEGylated monomer and PEGylated B1-B1' dimer of an IFG 1 single chain insulin analog. The dimer comprises two single chain insulin polypeptides each comprising an A chain and B chain linked via a $C^1$ peptide (the C peptide being modified to contain a lysine at position 8), wherein the two insulin polypeptides are joined via a PEG 20 dimerizing linker joining the N-terminal amino acid of the two respective insulin polypeptides. The 24 hour time profile of blood glucose levels after administration of polypeptide #39 (Gly$^{B2}$-PEG20K monomer; see FIG. 15A) and polypeptide #57 (Gly$^{B2}$-PEG20K-Gly$^{B2}$ dimer; see FIG. 15B) to normal mice was measured.
Figure 15B:
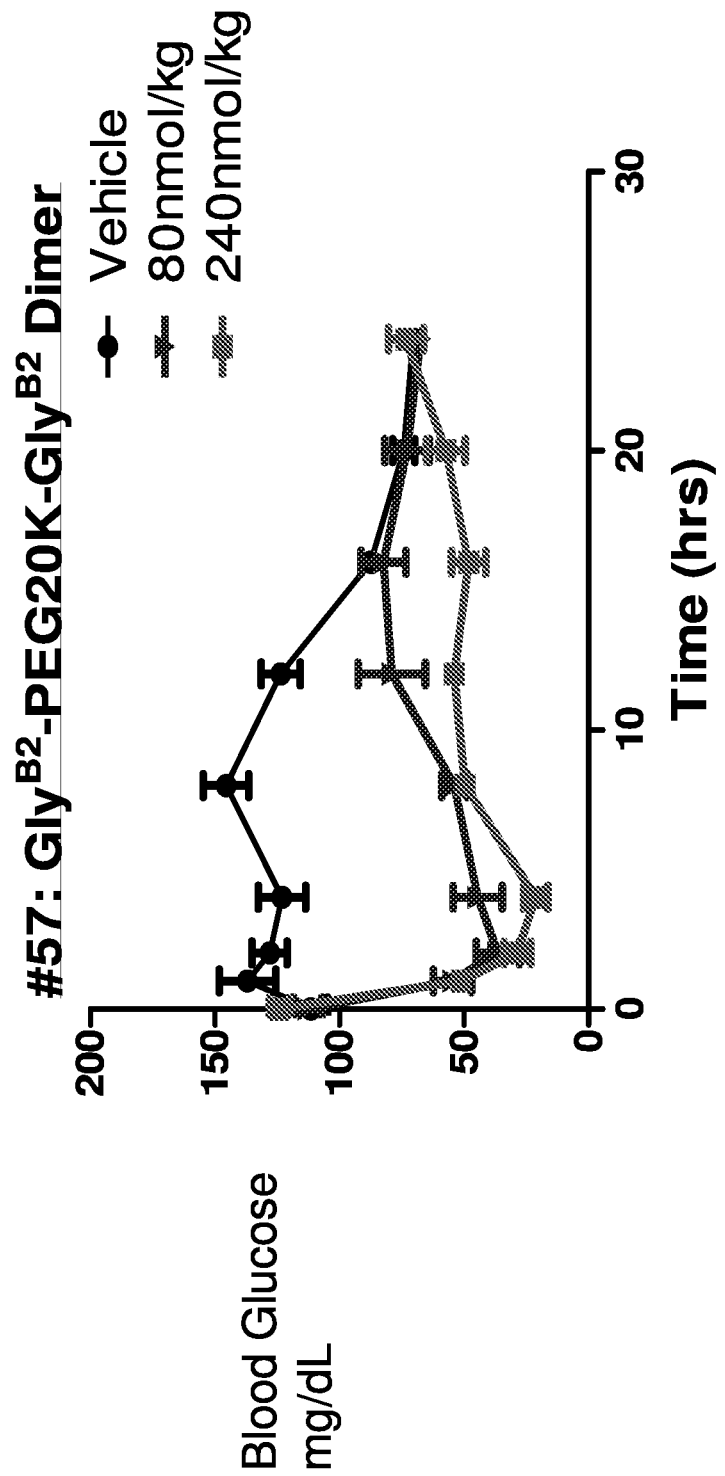
Figure 16C:
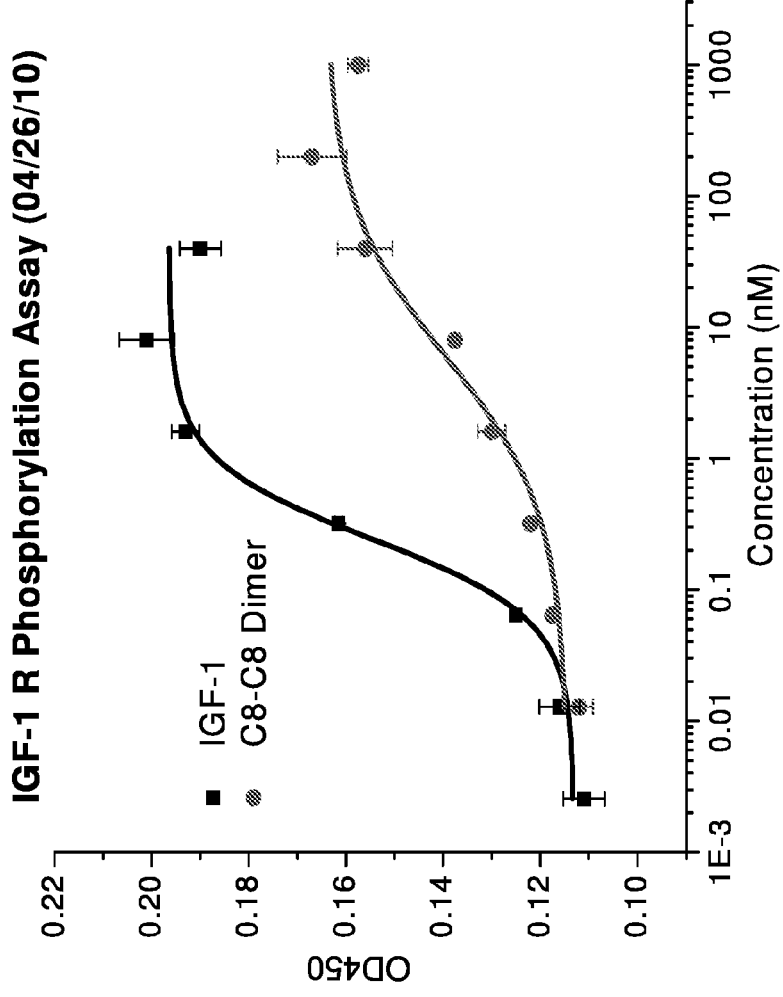

PEG-linked dimer was a full agonist at insulin receptor. $Gly^{B2}$-PEG20K-$Gly^{B2}$ dimer #57 was approximately 5 fold more potent than $Gly^{B2}$-PEG20K monomer #39 in vitro. However, the in vivo glycemic effects of dimer #57 was less extended than that of monomer #39 and the AUC at both dosages of dimer #57 were lower than that of monomer #39. The increased receptor potency caused by the dimeric structure might accelerate the receptor-mediated clearance, which would lead to a shortened pharmacokinetic profile (see FIGS. 15A & 15B).

Example 22

Preparation of Insulin Heterodimers

In the present studies, we prepared a covalently-linked insulin heterodimer composed of one active single-chain insulin and one inactive monomeric mini-proinsulin through a peptide bond connecting B29 and A1. The inactive monomeric unit could be enzymatically converted to active state, which allowed us to investigate the individual function of each monomeric unit. Additionally, we designed two insulin-IGF-2 heterodimers in order to selectively antagonize the IR-A activity through the IR-A preferred IGF-2 binding. The structural information of insulin-insulin heterodimers and insulin-IGF-2 heterodimers is summarized in Table 18 and the monomeric peptides used to construct these heterodimers is listed in Table 19.

TABLE 18

Sequences of insulin-insulin heterodimers and insulin-IGF-2 heterodimers.

| No. | Insulin Dimer | Sequence |
| --- | --- | --- |
| 59 | $Cys^{B1}$-$Lys^{C8}$ #2(sc)-#3 dimer | $B^1$[C1H5Y16L17K29]29-$A^1$[N18,21] + $B^1$[H5Y16L17]25-$PEG_8KPEG_4$-$A^1$[N18,21] |
| 60 | $Cys^{B1}$-$Lys^{C8}$ #2(tc)-#3 dimer | $B^1$[C1H5Y16L17K29]29:$A^1$[N18,21] + $B^1$[H5Y16L17]25-$PEG_8KPEG_4$-$A^1$[N18,21] |
| 61 | $Phe^{B1}$-$Lys^{C8}$ #27-#31 dimer | $B^025$-$C^1$-$A^0$ + $B^2$-$C^2$[K8]-$A^2$-$D^2$[R4] |
| 62 | $Lys^{C8}$-$Ala^{B1}$ #27*-IGF-2 dimer | $B^025$-$C^1$[K8]-$A^0$ + $B^2$-$C^2$-$A^2$-$D^2$[R4] |

TABLE 19

Sequences of insulin and IGF-2 monomers

| No. | Insulin Monomer | Sequence |
| --- | --- | --- |
| 2(sc) | Thz-$B^1$-$A^1$ (single-chain) | Thz-$B^1$[H5Y16L17K29]29-$A^1$[N18,21] |
| 2(tc) | Thz-$B^1$-$A^1$ (two-chain) | Thz-$B^1$[H5Y16L17K29]29:$A^1$[N18,21] |
| 3 | PEG8KPEG4(SC) | $B^1$[H5Y16L17K29]25-$PEG_8KPEG_4$-$A^1$[N18,21] |
| 27 | DP9 | $B^025$-$C^1$-$A^0$ |
| 31 | DP28 | $B^2$-$C^2$[K8]-$A^2$-$D^2$[R4] |
| 27* | DP9KC8 | $B^025$-$C^1$[K8]-$A^0$ |
|  | IGF-2 | $B^2$-$C^2$-$A^2$-$D^2$ |

Insulin heterodimers were synthesized by crosslinking two different insulin monomers. Site-specific crosslinking was achieved by forming a disulfide bond between a thiol-activated insulin peptide and a thiol-modified insulin derivative.

Dimer #59 was composed of two different insulin analogs #2(sc) and #3. It was crosslinked between B1 position of #2(sc) and C8 position of #3. Both #2 and #3 were derived from IGF-1 based sequences with select mutations to restore insulin receptor activity and reduce IGF-1 receptor activity. Peptide #2(sc) was composed of B chain and A chain with the $Lys^{B29}$ and $Gly^{A1}$ connected by a linear α-amide bond. Single-chain #2(sc) could be converted to two-chain analog #2(tc) through treatment with the LysC enzyme. Peptide #2(tc) was fully potent in binding to the insulin receptor and stimulating receptor activation. Analog #2 contained an unnatural amino acid Thz at the B chain's N-terminus, which could be converted to cysteine through treatment with methoxylamine at pH 4.0 in aqueous solution. The N-terminal cysteine was reacted with the activated thiol group on the other peptide to form a disulfide, crosslinking two insulin monomers to form dimer.

Figure 23A:
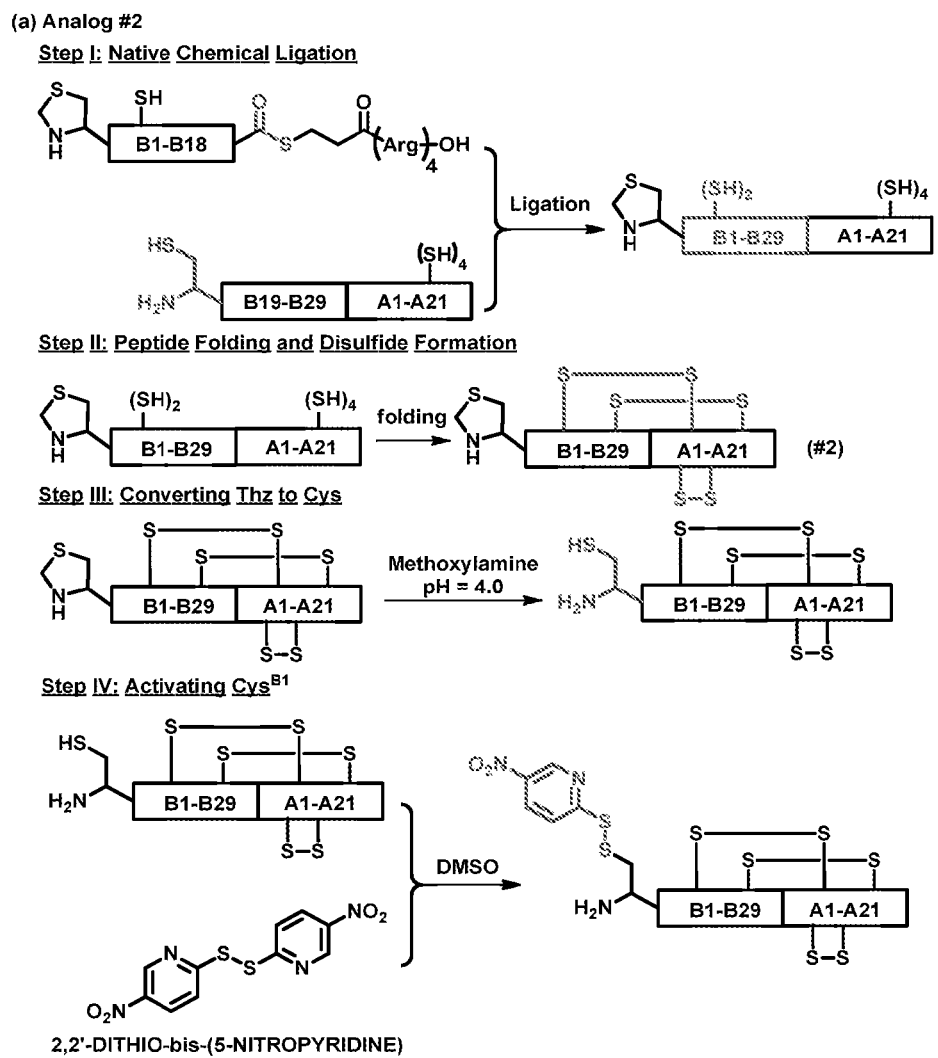
FIG. 23A: Synthetic scheme for the preparation of compound B1-thiol-activated insulin analog #2.

Total synthesis of #2 is illustrated in FIG. 23A. Two peptide segments were prepared individually by step-wise solid phase peptide synthesis. The first segment contained the N-terminal 18 amino acids of B chain as well as a thioester activation designed for native chemical ligation. Four arginines were added to the C terminus of the thioester to enhance the solubility of this segment. The second segment was composed of the remaining of the B chain and the full-length A chain. The two peptide segments were purified by reverse phase chromatography before being ligated together to produce the full-length single-chain insulin. The N-terminal cysteine of the second segment reacted with the C-terminal thioester of the first segment through a thiol-thioester exchange to produce a thioester linked intermediate. Rearrangement occurred within the five-membered ring to form a native peptide bond between the two peptide segments. Completion of the ligation reaction was confirmed by analytical HPLC and mass spectrometry. Once completed, the ligation reaction was loaded to a size exclusion column for desalting and buffer exchange. Peptide was separated from small molecule reagents and exchanged into folding buffer (20 mM glycine, 0.5 M GnHCl, pH 10.5). Fractions containing the desired peptide product were pooled and the peptide concentration was adjusted to 0.5 mg/ml. Cysteine was added to the folding reaction at a concentration of 8 mM to facilitate disulfide shuffling and the peptide refolding process. Nitrogen was pumped into the peptide solution to decrease the rate of air-mediated oxidation, which served to decrease formation of misfolded isomers. The folding reaction was kept without stirring at room temperature, or alternatively at 4° C. It generally took 24 hours at room temperature or 48 hours at 4° C. to complete the peptide folding process. Folding progress could be observed by analytical HPLC, since hydrophobicity of the peptide was decreased after folding to the correct conformation. Peptide folding could also be confirmed by mass spectrometry, indicated by a six-dalton decrease in molecular weight due to formation of three disulfide bonds. The correct folded peptide was separated from misfolded isomers and other reagents by reverse phase chromatography. The purified insulin analog #2 was then treated with methoxylamine at pH 4.0 to convert the N terminal Thz to cysteine. Thiol-activation reagent 2,2'-dithiobis(5-nitropyridine) (DTNP) was also added to the peptide solution to activate the thiol group of the N-terminal cysteine in situ. Thiol-activated insulin analog #2 was purified by reverse phase chromatography and used for heterodimer construction.

Figure 23B:
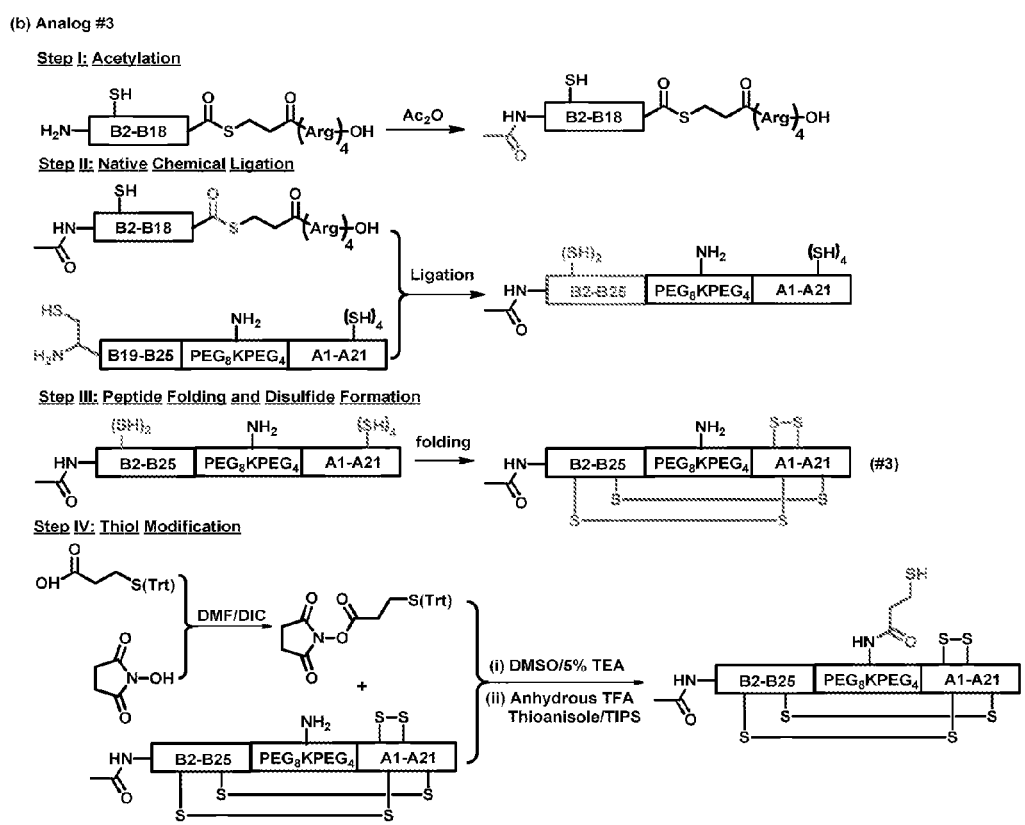
FIG. 23B: Synthetic scheme for the preparation of compound C8-thiol-modified insulin analog #3.

Preparation of thiol-modified insulin analog #3 is illustrated in FIG. 23B. Analog #3 was a single-chain insulin analog with a non-peptidyl linker as the C domain between B chain and A chain. Previous studies had identified connecting $Tyr^{B25}$ to $Gly^{A1}$ with a 12-unit PEG created a single-chain insulin analog that was fully potent at the insulin receptor (PCT/US2011/040699, the disclosure of which is incorporated herein). We included an additional lysine in the middle of PEG linker to serve as the site for modification. This change didn't affect receptor activity. Peptide #3 was acetylated on the B chain's N-terminus to block the α-amine, which allowed site-specific modification at the lysine side chain ε-amine. Peptide #3 was also synthesized divergently with a combination of solid phase peptide synthesis and native chemical ligation. The first segment contained the N-terminal 17 amino acids of the B chain and a thioester tail at the C terminus. This peptide segment was synthesized by t-Boc chemistry, as the C terminal thioester is base-labile. N-terminal amine was acetylated before the peptide was cleaved from the resin. The second segment contained the remaining seven amino acids of the B chain, an 8-unit mini-PEG, a lysine followed by a 4-unit mini-PEG and the full-length A chain. The second peptide segment could be prepared by both t-Boc chemistry and Fmoc chemistry and in this work it was synthesized by an Fmoc strategy. Full-length analog #3 was ligated and folded by the same method described above. To introduce a thiol group on lysine's side chain amine, we prepared an amine-reactive succinimidyl ester (NHS ester) by reacting s-trityl-mecaptopropionic acids with hydroxylsuccinimide in the presence of DIC and DIEA. The NHS esters were reacted with the N terminal amino groups to form amide bonds, which conjugated s-trityl-mercaptopropionic acids to the N termini of the peptides. The trityl protection groups were subsequently removed through treatment with anhydrous TFA. Therefore, an additional thiol group was introduced to the N-terminus of biosynthetic insulin peptide without disturbing the three pre-formed disulfide bonds.

Figure 24A:
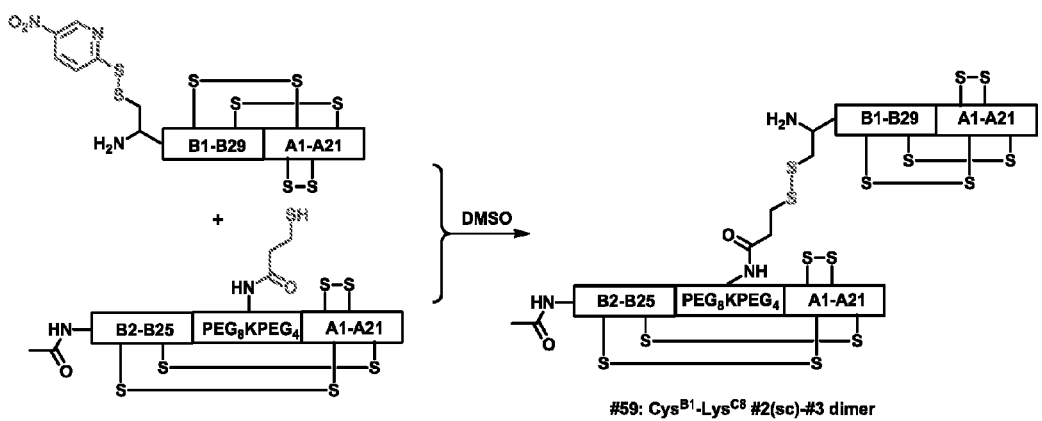
FIG. 24A: Synthetic scheme for the preparation of dimer #59 (see Table 18 for compound structure).
Figure 24B:
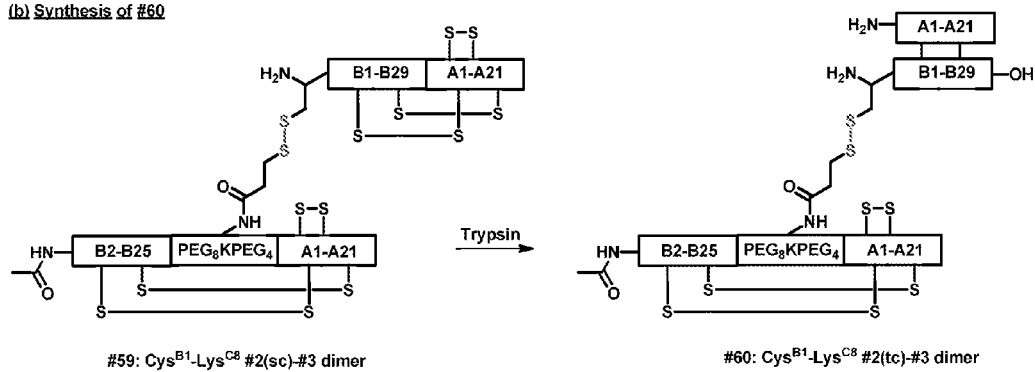
FIG. 24B: Synthetic scheme for the preparation of dimer #60 (see Table 18 for compound structure).

Thiol-activated insulin analog #2 and thiol-modified analog #3 were dissolved in DMSO at a ratio of 1:1. Disulfide bond formation between the two thiol groups generated a B1-C8 linkage between the two insulin molecules, which produced #59 ($Cys^{B1}$-$Lys^{C8}$ #2 (sc)-#3 insulin heterodimer) (FIG. 24A). Dimer #59 could be converted to #60 by LysC protease. LysC selectively cleaved at the C terminus of $Lys^{B29}$, which generated the two-chain structure (FIG. 24B).

Figure 25B:
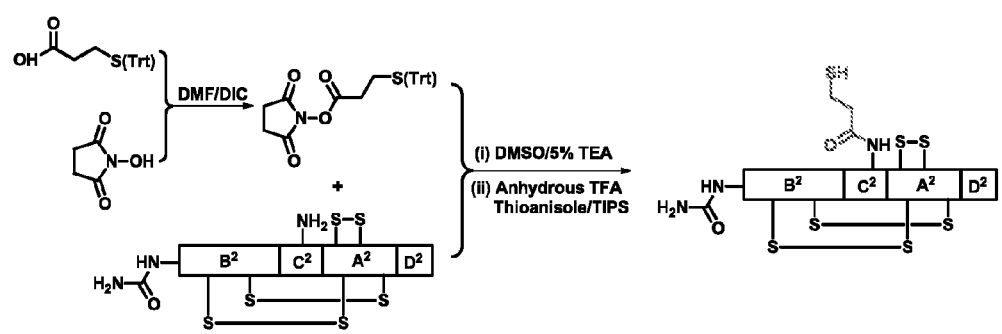
FIG. 25B: Synthetic scheme for the preparation of C8-thiol-modified IGF-2 analog #31.
Figure 25C:
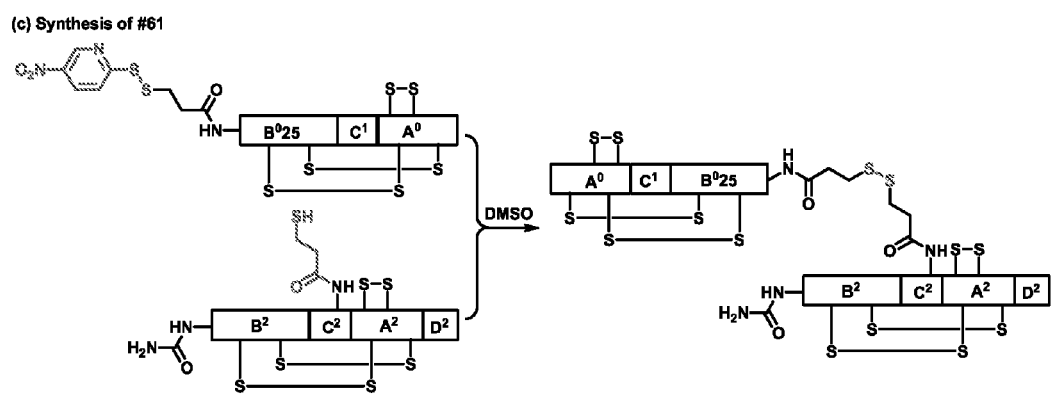
FIG. 25C: Synthetic scheme for the preparation of dimer #61 (see Table 18 for compound structure).

Analog #61 was a heterodimer composed of one single-chain insulin monomer and one IGF-2 monomer. Insulin analog #27's N-terminal amine was crosslinked via a disulfide bond to the $Lys^{C8}$ side-chain amine of IGF-2 analog #31. Peptide #27 was a single-chain insulin analog containing the insulin desV B chain, a 12 amino-acid IGF-1 C chain and the insulin A chain. Peptide #31 was an IGF-2 analog with two mutations of $Arg^{C8}Lys$ and $Lys^{D4}$ Arg, which allowed site-specific conjugation to the C8 position. Both #27 and #31 were prepared by biosynthesis in *E. coli* cells. Purified insulin analog #27 was modified on the N-terminal amine by reacting with an activated NHS ester of s-tritylmercaptopropionic acid. Trityl protection group was cleaved with TFA to generate the free thiol group, and the thiol group was subsequently activated with DTNP (2,2'-dithio-bis-(5-nitropyridine) (FIG. 25A). The thiol-activated insulin #27 was purified before crosslinking to IGF-2 analog #31. By design, #31 contained only one lysine amino acid in sequence at C8 position. The N-terminal amine of analog #31 was selectively blocked with carbamylation at pH 7.0 by reacting with potassium cyanate, which left $Lys^{C8}$ the only reactive site for coupling with this activated NHS ester. $Lys^{C8}$ was then modified with the mercapto-propionyl group using the same strategy described above (FIG. 25B). Thiol-modified #31 was then mixed with #27 in DMSO at a ratio of 1:1 to produce dimer #61 (#27-#31 heterodimer) (FIG. 25C). The 5-nitropyridine-2-thiol released in disulfide formation reaction showed yellow color in DMSO, which indicated the progression of the reaction.

Figure 26A:
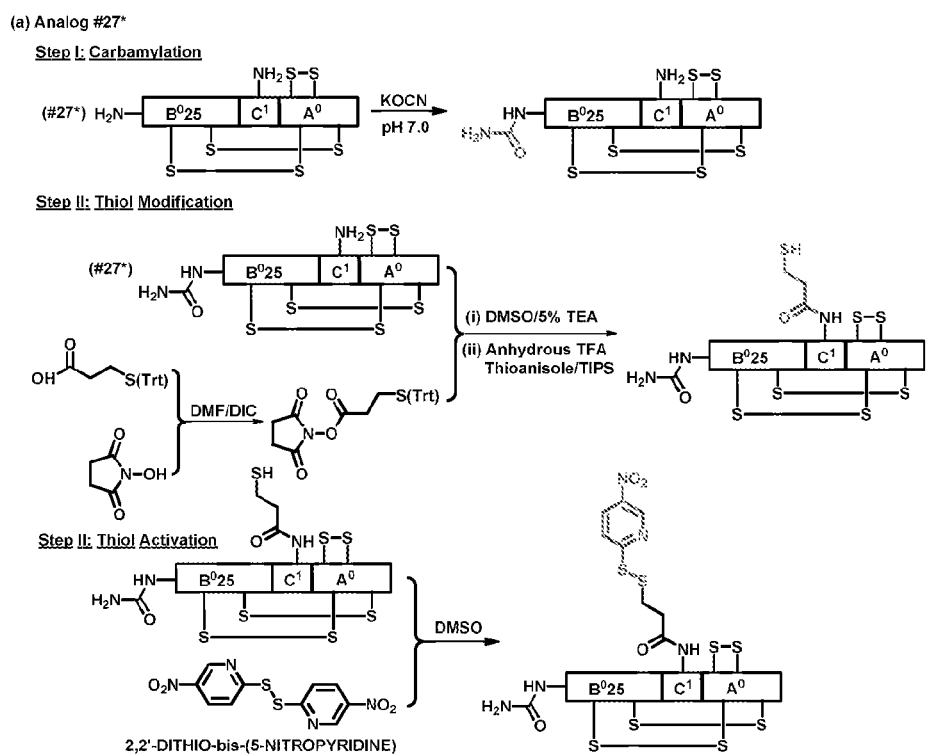
FIG. 26A: Synthetic scheme for the preparation of C8-thiol-activated insulin analog #27*.
Figure 26C:
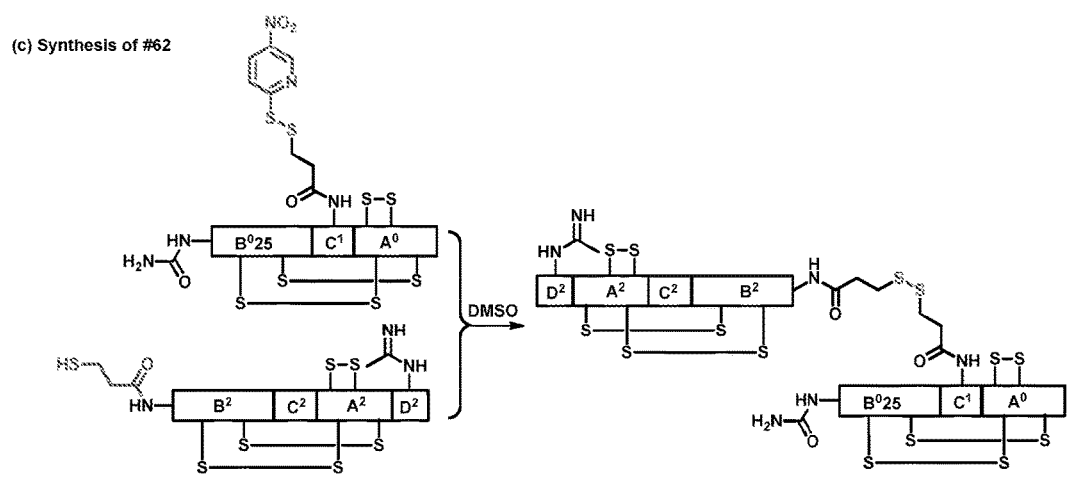
FIG. 26C: Synthetic scheme for the preparation of dimer #62 (see Table 18 for compound structure).

Dimer #62 contained a reversed linkage compared to #61. The N-terminus of IGF-2 was crosslinked to the $Lys^{C8}$ of single-chain insulin analog #27*. Peptide #27* shared the same sequence with #27 except for a lysine mutation at C8 position designed for crosslinking chemistry. Peptide #27* was selectively carbamylated at the N terminus and then the $Lys^{C8}$ was modified with a mercapto-propionyl group as described above (FIG. 26A). The other monomeric unit was prepared from native IGF-2 peptide. Native IGF-2 contained a lysine residue in D domain. The ε-amine of this lysine was selectively blocked by acetimidation at pH 10.5. The acetimidation reaction didn't occur at the N terminal α-amine, due to differentiated pKa of these two amino groups. The N terminal α-amine was then modified with the mercaptopropionyl group (FIG. 26B). Either thiol-modified #27* or thiol-modified IGF-2 could be activated by DTNP and subsequently reacted with the free thiol group of the other peptide. In this work we chose to activate thiol-modified #27*, as #27* was more hydrophobic than IGF-2, and the activated Cys(Npys)-27* had even increased hydrophobicity. This allowed clear separation of two monomer eluting peaks measured by retention time on reverse phase HPLC. The C8-thiol-activated #27* was mixed with B1-thiol-modified IGF-2 in DMSO at a ratio of 1:1 to produce dimer #62 (FIG. 26C). Dimer formation was indicated by appearance of a new eluting peak between the two monomer peaks.

In Vitro Receptor Activity of the Heterodimers

Figure 20:
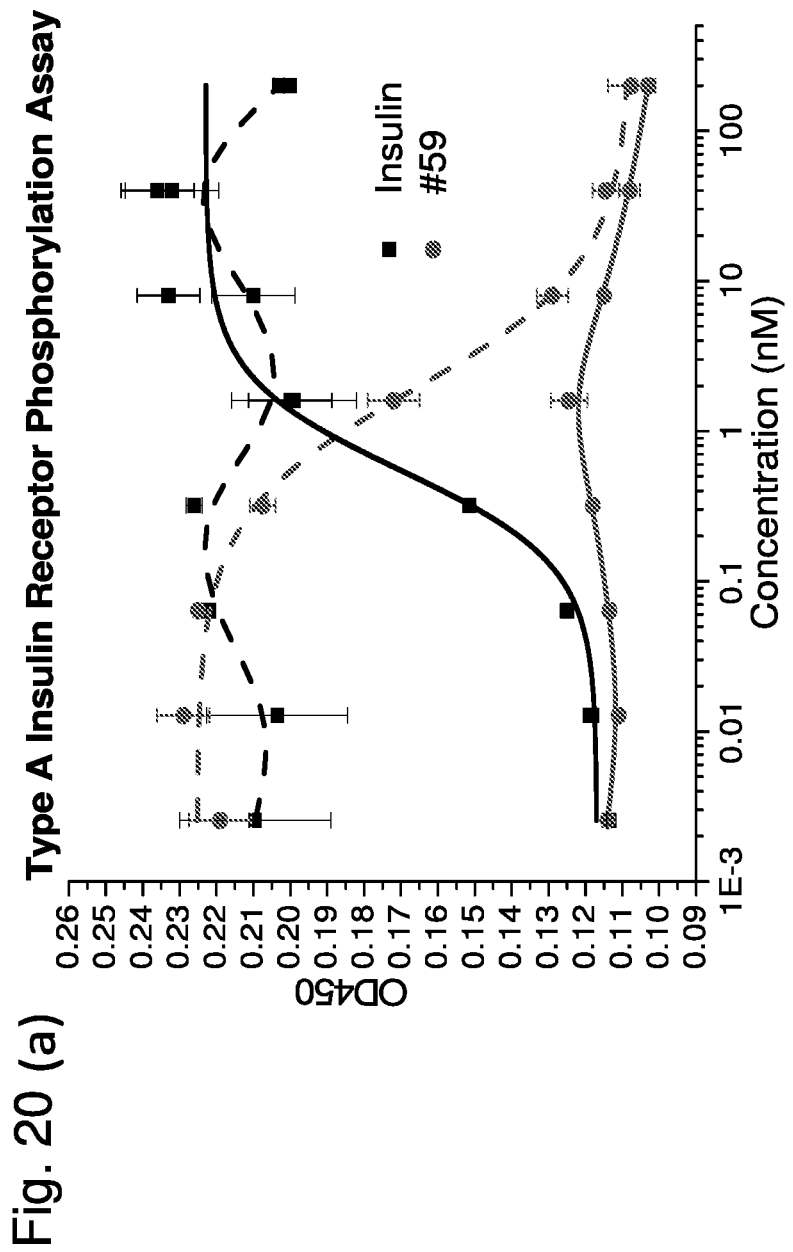
FIGS. 20A-20D demonstrate the activities of an insulin heterodimer comprising two different insulin polypeptides. Polypeptide #59 represents a dimer formed between a first insulin polypeptide comprising an inactive IGF 1 analog (B$^1$[[C1H5Y16L17K29]29-A$^1$[N18,21]; inactivity due to the direct connection of the A chain to the carboxy terminus of B chain) and a second active single chain IGF 1 analog (B¹[H5Y16L17]25-PEG$_8$KPEG$_4$-A¹[N18,21]) wherein the A chain and B chain are linked via a mini-peg linking moiety (PEG$_8$-K-PEG$_4$) and the two insulin polypeptides are joined via the lysine side chain of the linking moiety and the B1 amino acid side chain of the inactive insulin polypeptide. Polypeptide #60 is identical to polypeptide to polypeptide #59 except the inactive insulin peptide has been cleaved with trypsin to generate a two chain IGF 1 insulin analog with insulin activity being restored to the polypeptide. Activity was tested at the type A insulin receptor (see FIG. 20A); the type B insulin receptor (see FIG. 20B) and the IGF-1 receptor (see FIG. 20C) by phosphorylation assay, and receptor binding affinity tested by subtype A insulin receptor binding assay (see FIG. 20D) in vitro. The solid line on the graphs represents: subtype A or subtype B receptor phosphorylation (on FIGS. 20A-20B, respectively) stimulated by indicated concentrations of native insulin (■) #53 (●) or #60 (▲); the dashed line represents: subtype A; or subtype B receptor phosphorylation (on FIGS. 20A-20B, respectively) stimulated by co-incubating 6 nM insulin and indicated concentrations of insulin (■) or #53 (●).
Figure 20:
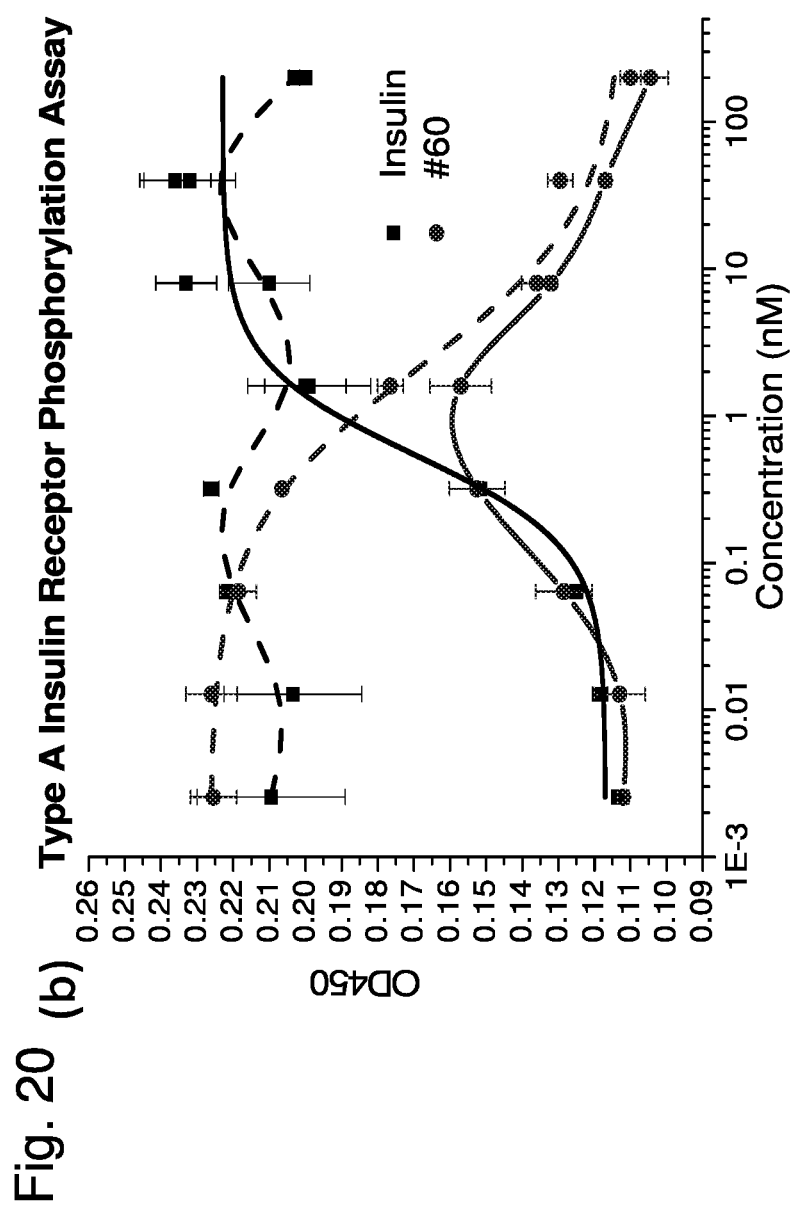
Figure 20:
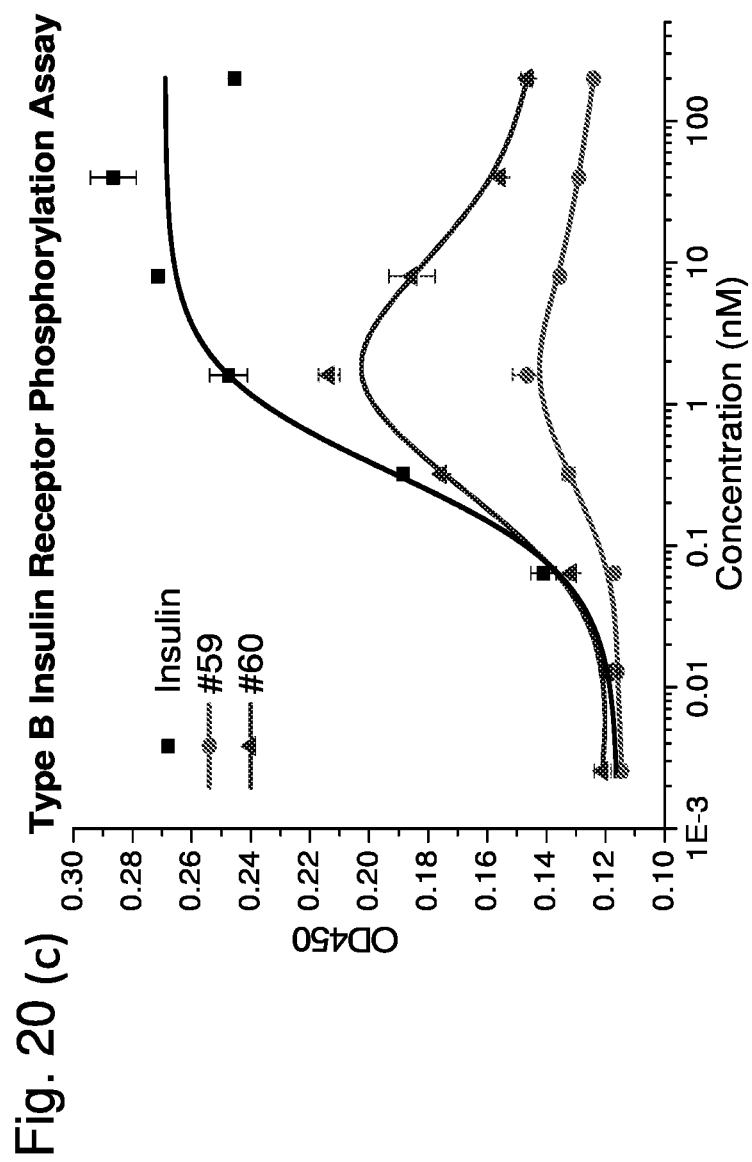

One monomeric unit of #59 was inactivated by connecting B29 to A1 with a linear α-amide bond. Previous studies showed a peptide bond between insulin's $Lys^{B29}$ and A chain's N terminus completely inactivate the molecule, but the crystal structure of B29-A1 insulin was essentially the same as native insulin. By inactivating one monomer, #59 was designed to study the function of the other active monomer. Dimer #59 showed very little agonism at the type A insulin receptors. Maximal receptor response induced by #59 did not differ significantly from baseline level. HEK293 cells overexpressing insulin receptors were treated with 6 nM insulin and a specific concentration of #59. Insulin concentration of 6 nM proved to be effective in inducing 95% of the maximal response at the insulin receptor. The receptor response was reduced by increasing concentration of #59 in the presence of 6 nM insulin, indicating that dimer #59 was able to inhibit the receptor response serving as an antagonist for the insulin receptor (FIG. 20A). Conjugating polyethylene glycol (PEG) to Lys$^{C8}$ of analog #3 did not change the level of this maximal response, as analog #38 is a full agonist with reduced potency (higher $EC_{50}$). Moieties conjugated to select residues of the insulin sequence, such as PEGs or fatty acids, have never been reported to affect maximal receptor activation. Biological consequence of conjugating an inactive insulin molecule to an active insulin peptide differed markedly from that of conjugating an inactive polymer such as PEG to insulin. Although analog #2(sc) was almost as inactive as PEG at the insulin receptor, it demonstrated significant inhibitory effects when present in dimeric structure.

Inactive monomeric unit #2(sc) was converted to active two-chain structure #2(tc) by treatment with LysC protease, which generated dimer #60. Both units in #60 were active entities that were crosslinked by a B1-C8 linkage. Enzyme treatment restored partial agonism at the insulin receptor, with maximal receptor response increased to 50%. Dimer #60 also showed antagonistic effects against insulin's action. When co-incubated with 6 nM insulin, increasing concentrations of #60 were able to reduce receptor response from near 100% back to 0% (baseline level) (FIG. 20B). Although #60 induced a higher maximal response at insulin receptor than #59, its ability to antagonize insulin's effects was almost the same as #59. Half maximal inhibition concentration ($IC_{50}$) of #60 was 1.89±0.29 nM, while $IC_{50}$ of #59 was 2.08±0.54 nM, as measured in the antagonism test. At the type B insulin receptor, the maximal response induced by #59 was only 10% of that induced by native insulin. Dimer #60 generated by enzyme treatment was still a partial agonist, but maximal response induced by #60 was increased to 50% (FIG. 20C). Dimer #59 showed partial agonism at the IGF-1 receptor. The level of maximal response induced by #59 was 50% that induced by native IGF-1. Dimer #60 was a full agonist with significantly increased potency at the IGF-1 receptor (FIG. 20D). The dimeric structure of #60 might enable the synergistic binding to the IGF-1 receptor, which converted the two monovalent weak IGF-1 receptor agonists to a potent bivalent dimer.

The receptor response curve of #60 was essentially the same as that of #53, a homodimer of insulin analog #3 with a C8-C8 linkage. This suggested crosslinking one insulin analog to the C8 position of another single-chain insulin was one factor for partial agonism at the insulin receptor, no matter whether it was a B1-C8 linkage or a C8-C8 linkage. Receptor activity of the monomeric insulin unit conjugated to C8 position affected the level of the maximal response induced by the dimerized derivatives at the insulin receptor. When this unit is inactive, the receptor activation was almost completely inhibited. Restoring receptor activity of this unit also increased the level of maximal receptor response.

Example 23

Insulin Dimers with Enhanced Receptor Isoform Selectivity

The inhibitory effects observed for the heterodimer containing one inactive monomeric unit provided a concept for designing a heterodimer of enhanced receptor isoform selectivity. Insulin receptors exist in two isoforms: type A insulin receptor (IR-A) and type B insulin receptor (IR-B). IR-B is predominantly expressed in insulin-response tissue, and is commonly believed to be associated with metabolic effects. Preference over IR-B has important implications in insulin drug design, as it might provide improved pharmacological benefits. Insulin binds and activates both receptor isoforms equally. A structurally similar peptide IGF-2 can bind to IR-A with an affinity close to that of insulin, but it has a 10 fold lower binding affinity for IR-B. As tethering two insulin molecules in dimeric structure produced antagonism at the insulin receptor, conjugating an IR-A preferred IGF-2 peptide to insulin might also provide more antagonism at IR-A than IR-B. Instead of modifying inherent potency in stimulating receptor activation, which is measured by $EC_{50}$, receptor selective heterodimers were designed to modulate levels of maximal receptor response.

Preparation of Insulin Heterodimers by Chemical Synthesis

Insulin analog #2(sc) B$^1$[Thz1H5Y16L17K29]29-A$^1$[N18,21] was synthesized by solid phase peptide synthesis and native chemical ligation. After completion of native chemical ligation reaction, ligated peptide #2(sc) were exchanged into folding buffer (0.5 M GnHCl, 20 mM Glycine, pH 10.5) by size-exclusion column. Peptide concentrations were adjusted to 0.5 mg/ml and 8 mM cysteine were added to peptide solution. Folding reaction was sit for 24 hours under room temperature without stirring. Completion of folding reaction could be monitored by analytical reverse phase HPLC and mass spectrometry. After folding completed, pH was adjusted to 4.0 and 2 mM methoxylamine was added to peptide solution. Thiol activation reagent 2,2'-Dithiobis(5-nitropyridine) (DTNP) was also added at 2 equivalent per 1 equivalent insulin peptide. Conversion from Thz to Cys generally took 4 hours to complete and Cys$^{B1}$ was activated in situ by DTNP. Cys$^{B1}$(Npys)-peptide #2(sc) was purified by reverse phase HPLC.

Single-chain insulin analog #3 was reacted with activated NHS ester to produce thiol-modified peptide. To prepare Trt-SCH$_2$CH$_2$CO—NHS ester, one mmol each of s-tritylmercaptopropionic acid (Trt-SCH$_2$CH$_2$COOH) (National Biochemical Corp., Ohio), N-hydroxysuccinimide (NHS) (Sigma) and diisopropylcarbodiimide (DIC) was mixed in 2 mL DMF for 30 min at room temperature with stirring. Insulin peptide was dissolved in anhydrous DMF with 5% TEA at a concentration of 10 mM. 2 eq of activated Trt-SCH$_2$CH$_2$CO—NHS ester was added to the solution. Reaction was stirred for 2 hours at room temperature before terminated with 2% ethanolamine. 5 fold volume of anhydrous TFA with 4% thioanisole (Sigma) and 8% triisopropylsilane (TIPS) (Sigma) was then added to the reaction to remove trityl protection group. The deprotection reaction was stirred at room temperature for 30 min and then diluted with ether by 20 fold to extract peptide into precipitates. The diluted reaction was centrifuged and the precipitated peptides were dissolved in 1% acetic acid/20% acetonitrile aqueous solution and lyophilized. Cys-activated #2(sc) and thiol-modified #3 were dissolved in DMSO at a ratio of 1:1 to allow disulfide formation between Cys$^{B1}$ of #2 and Lys$^{C8}$(SH—CH$_2$CH$_2$CO) of #3, which produced B1-C8 linked heterodimer #59. Dimer formation was indicated by appearance of yellow color, as Npys was released after disulfide formation. Process of reaction was monitored by analytical HPLC and dimer formation was confirmed by mass spectrometry. Dimer #59 was purified by reverse phase HPLC and lyophilized.

Dimer #61 was produced by cleaving monomeric #2 unit of dimer 59 into two-chain structure by LysC protease. Dimer #59 was dissolved in PBS at a concentration of 0.5 mg/ml. 0.5 unit of LysC was added to peptide solution per 1 mg peptide. Cleavage reaction was incubated in 37° C. water bath for 12 hours. Cleavage was confirmed by 18 dalton increase in molecular weight by mass spectrometry.

Preparation of Insulin Heterodimers by Semi-Synthesis

Insulin and IGF-2 analogs were prepared by biological synthesis from E. coli cells. Insulin analog #27* and IGF-2 analog #31 were carbamylated at N terminal amines. Peptides were dissolved at a concentration of 0.5 mg/ml in PBS buffer (pH 7.0) with 50 mM potassium cyanate (Sigma). The reaction was stirred at room temperature overnight and completion of carbamylation reaction was confirmed by MALDI. The carbamylated peptides were desalted on reverse phase column and fractions containing peptides were pooled and lyophilized. To block $Ly^{D4}$'s ϵ-amine of IGF-2, IGF-2 peptide was dissolved in 50 mM $NaHCO_3$ aqueous solution (pH 10.5). Methyl acetimidate (Sigma) was added in a 50 fold molar excess to peptide solution. Acetimidation reaction was stirred for 30 min under room temperature. Reaction was terminated by reducing pH to 3.0 with 1 N HCl.

$HS-CH_2CH_2CO$ was conjugated to N terminal α-amine of analog #27 or IGF-2 peptide or Lysine's side chain ϵ-amine of carbamylated #27* or #31. Thiol groups introduced to insulin analog #27 or #27* were activated with DTNP. Modified peptides were purified by reverse phase HPLC and lyophilized. #27 and #31 were dissolved in DMSO at a ratio of 1:1 to produce dimer #61. #27* and IGF-2 were dissolved in DMSO at a ratio of 1:1 to produce dimer #62.

Results

Two insulin-IGF-2 heterodimers with B1-C8 linkages were designed to investigate their activities at the two insulin receptor isoforms. Dimer #61 was composed of one single-chain insulin #27 and one IGF-2 analog #31. The N terminus of #27 was crosslinked to the $Lys^{C8}$ of #31 by a disulfide bond. Peptide #31 was derived from the IGF-2 sequence with two mutations of $Lys^{D4}$Arg and $Arg^{C8}$Lys. This design directed the crosslinking chemistry to the $Lys^{C8}$ position. These two sites were not essential for receptor activities and mutations at these two sites only slightly reduced potency by two fold at both IR-A and IR-B. Dimer #62 also contained one single-chain insulin analog #27*, whose $Lys^{C8}$ was crosslinked to the N-terminal amine of the native IGF-2 via a disulfide bond. Orientations of insulin and IGF-2 monomers were reversed in dimer #62 to study the effects of orientation in the two monomeric units.

Dimer #61 was a partial agonist at both receptors, but the maximal response was higher at IR-B. At IR-A, the maximal response induced by #61 was ~50% of that induced by native insulin, while at IR-B the maximal response was ~80% (FIGS. 22A and 22B). Dimer #62 containing the reversed orientation of insulin and IGF-2 units also showed higher maximal response at IR-B. Dimer #62 was almost a full agonist at IR-B, as the maximal response was nearly the same as that of insulin. In contrast, #62 was still a partial agonist at IR-A. It induced about 80% of the maximal response as insulin did at the type A insulin receptor (FIGS. 22C and 22D).

Both dimer #61 and #62 exhibited preference for the type B insulin receptor, indicated by higher maximal receptor response. Dimer #61 showed more inhibitory effects on receptor activation than #62, as maximal responses induced by #61 at both receptor isoforms were lower than those induced by #62. Orientation of the insulin and IGF-2 monomeric units did not change receptor selectivity, but still had effects on inhibition of receptor activation. Response curves of both #61 and #62 were bell-shaped, which was also observed for insulin homodimer #53 and insulin heterodimer #60. After achieving the maximal level, receptor responses were reduced by increasing concentrations of #61 or #62. However, receptor response could only be decreased to ~50% by #61 or #62, while #53 and #60 were able to completely inhibit receptor activation at high concentrations. Both #61 and #62 were partial agonists at the IGF-1 receptor, and #61 showed more inhibitory effects on maximal receptor activation than #62 (FIG. 22E).

The invention claimed is:

1. An insulin analog dimer, said dimer comprising
   i) a first insulin polypeptide and a second insulin polypeptide, wherein
   said first insulin and second insulin polypeptide are both single chain insulin analogs each comprising a first and second set of an A chain, a B chain and a linking moiety, wherein for each set of A chain, B chain and linking moiety a first end of said linking moiety is covalently bound to the carboxy terminus of the B chain and a second end of said linking moiety is covalently bound to the amino terminus of the A chain, further wherein the first and second insulin polypeptides are linked to one another via a PEG, or disulfide bearing, dimerization linker covalently linking the side chain of a lysine of the linking moiety of the respective first and second insulin polypeptides,
   said A chain of the first and second insulin polypeptide comprising a sequence independently selected from GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7)
   said B chain of the first and second insulin polypeptide comprising a sequence independently selected from FVNQHLCGSHLVEALYLVCGERGFF (SEQ ID NO: 23), GPETLCGAELVDALYLVCGDRGFY (SEQ ID NO: 77), GPETLCGAELVDALQFVCGDRGFY (SEQ ID NO: 89), GPEHLCGAELVDALYLVCGDRGFY (SEQ ID NO: 14); AYRPSETLCG-GELVDTLQFVCGDRGFY (SEQ ID NO: 90) and AYRPSETLCGGELVDTLYLVCGDRGFY (SEQ ID NO: 92)
   said linking moiety of the first and second insulin polypeptide comprising a sequence independently selected from GYGSSSRX$_{68}$APQT (SEQ ID NO: 9), X$_{51}$X$_{52}$GSSSX$_{57}$X$_{58}$APQT (SEQ ID NO: 16) and PEG8-X$_{68}$-PEG4, wherein
   X$_{51}$ is selected from the group consisting of glycine, alanine, valine, leucine, isoleucine and proline;
   X$_{52}$ is alanine, tyrosine, valine, leucine, isoleucine or proline;
   one of X$_{57}$ and X$_{58}$ is arginine and the other is an amino acid comprising a side chain of Structure I:

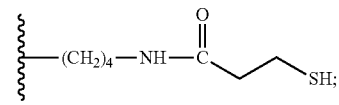

and

X$_{68}$ is an amino acid comprising a side chain of Structure I:

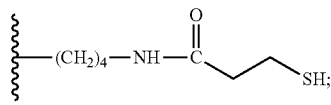

ii) a first insulin polypeptide and a second insulin polypeptide, wherein
said first insulin polypeptide is a two chain insulin analog comprising a first A chain, and a first B chain, wherein said first A chain and first B chain are linked to one another through interchain disulfide bonds;
said second insulin polypeptide is a single chain insulin analog comprising a second A chain, a second B chain and a linking moiety, wherein a first end of said linking moiety is covalently bound to the carboxy terminus of the second B chain and a second end of said linking moiety is covalently bound to the amino terminus of the second A chain,
wherein the first and second insulin polypeptides are linked to one another via a disulfide bearing, dimerization linker, wherein a first end of the dimerization linker is covalently linked to the side chain of the N-terminal amino acid of the B chain of said first insulin polypeptide and a second end of the dimerization linker is covalently linked to the side chain of a lysine of the linking moiety of the second insulin polypeptide,
said A chain of the first and second insulin polypeptide comprising a sequence independently selected from GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7)
said B chain of the first insulin polypeptide comprising a sequence independently selected from CFVNQHLCGSHLVEALYLVCGERGFFYTPKT (SEQ ID NO: 94), CGPETLCGAELVDALYLVCGDRGFYFNKPT (SEQ ID NO: 95), CGPETLCGAELVDALQFVCGDRGFYFNKPT (SEQ ID NO: 96), CGPEHLCGAELVDALYLVCGDRGFYNKPT (SEQ ID NO: 97); CAYRPSETLCGGELVDTLQFVCGDRGFY (SEQ ID NO: 91) and CAYRPSETLCGGELVDTLYLVCGDRGFY (SEQ ID NO: 93);
said B chain of the second insulin polypeptide comprising a sequence independently selected from FVNQHLCGSHLVEALYLVCGERGFF (SEQ ID NO: 23), GPETLCGAELVDALYLVCGDRGFY (SEQ ID NO: 77), GPETLCGAELVDALQFVCGDRGFY (SEQ ID NO: 89), GPEHLCGAELVDALYLVCGDRGFY (SEQ ID NO: 55 NO: 14); AYRPSETLCGGELVDTLQFVCGDRGFY (SEQ ID NO: 90) and AYRPSETLCGGELVDTLYLVCGDRGFY (SEQ ID NO: 92)
said linking moiety of the second insulin polypeptide comprising a sequence independently selected from GYGSSSRX$_{68}$APQT (SEQ ID NO: 9), X$_{51}$X$_{52}$GSSSX$_{57}$X$_{58}$APQT (SEQ ID NO: 16) and PEG8-X$_{68}$-PEG4, wherein
X$_{51}$ is selected from the group consisting of glycine, alanine, valine, leucine, isoleucine and proline;
X$_{52}$ is alanine, tyrosine, valine, leucine, isoleucine or proline;

one of X$_{57}$ and X$_{58}$ is arginine and the other is an amino acid comprising a side chain of Structure I:

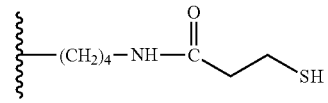

X$_{68}$ is an amino acid comprising a side chain of Structure I:

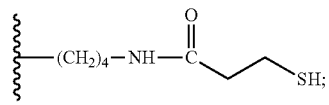

iii) a first insulin polypeptide and a second insulin polypeptide, wherein
said first insulin and second insulin polypeptide are both two chain insulin analogs comprising a first and second set of A chain and a B chain, respectively, wherein the A chain and B chain of each set are linked to one another through interchain disulfide bonds, further wherein the first and second insulin polypeptides are linked to one another via a dimerization linker joining the side chain of a carboxy terminal amino acid of the respective two B chains, wherein
said A chain of the first and second insulin polypeptide comprise a sequence independently selected from the group consisting of GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7)
said B chain of the first and second insulin comprise a sequence independently selected from the group consisting of FVNQHLCGSHLVEALYLVCGERGFFYTPX$_{68}$T (SEQ ID NO: 2) and GPETLCGAELVDALYLVCGDRGFYFNX$_{68}$PT (SEQ ID NO: 99), wherein
X$_{68}$ is an amino acid comprising a side chain of Structure I:

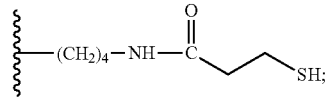

or
iv. a first insulin polypeptide and a second insulin polypeptide, wherein
said first insulin and second insulin polypeptide are both single chain insulin analogs each comprising a first and second set of an A chain, a B chain and a linking moiety, wherein for each set of A chain, B chain and linking moiety, a first end of said linking moiety is covalently bound to the carboxy terminus of the B chain and a second end of said linking moiety is covalently bound to the amino terminus of the A chain, further wherein the first and second insulin polypeptides are linked to one another via a PEG, or disulfide bearing, dimerization linker, wherein a first end of the dimerization linker is covalently linked to the side chain of a lysine of the linking moiety of one of the first or second insulin polypeptides and a second end of the dimerization linker is covalently linked to the N-terminal amine of the B chain of the other first or second insulin polypeptide, said A chain of the first insulin polypeptide comprising the sequence TPAKSEGIVEECCFRSCDLALLETYCA (SEQ ID NO: 103);

said B chain of the first insulin polypeptide comprising the sequence AYRPSETLCG-GELVDTLQFVCGDRGFY (SEQ ID NO: 90) or AYRPSETLCGGELVDTLYLVCGDRGFY (SEQ ID NO: 92);

said A chain of the second insulin polypeptide comprising the sequence GIVEQCCTSICSLYQLENYCN (SEQ ID NO: 1);

said B chain of the second insulin polypeptide comprising a sequence independently selected from FVNQHLCG-SHLVEALYLVCGERGFF (SEQ ID NO: 23), and GPEHLCGAELVDALYLVCGDRGFY (SEQ ID NO: 14), said linking moiety of the first and second insulin polypeptides comprising a sequence independently selected from GYGSSSRX$_{68}$APQT (SEQ ID NO: 9), SRVSR X$_{68}$SR (SEQ ID NO: 87) and PEG8-X$_{68}$-PEG4, wherein X$_{68}$ is arginine or an amino acid comprising a side chain of Structure I:

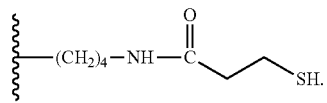

2. An insulin analog dimer of claim 1, wherein said dimer comprises a first insulin polypeptide and a second insulin polypeptide, wherein said first insulin and second insulin polypeptide are both single chain insulin analogs, said A chain of the first and second insulin comprising a sequence independently selected from GIVEQC-CTSICSLYQLENYCN (SEQ ID NO: 1) and GIVDEC-CFRSCDLRRLENYCN (SEQ ID NO: 11), said B chain of the first and second insulin comprising a sequence independently selected from FVNQHLCG-SHLVEALYLVCGERGFF (SEQ ID NO: 23) and GPEHLCGAELVDALYLVCGDRGFY (SEQ ID NO: 14), said dimerization linker comprising a sequence independently selected from GYGSSSRX$_{68}$APQT (SEQ ID NO: 9) and PEG8-X$_{68}$-PEG4, wherein X$_{68}$ is an amino acid comprising a side chain of Structure I:

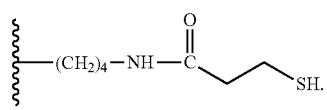

3. An insulin analog dimer of claim 1, wherein said dimer comprises a first insulin polypeptide and a second insulin polypeptide, wherein said first insulin polypeptide is a two chain insulin analogs comprising a first A chain, and a first B chain, wherein said first A chain and first B chain are linked to one another through interchain disulfide bonds;

said second insulin polypeptide is a single chain insulin analog comprising a second A chain, a second B chain and a linking moiety, wherein a first end of said linking moiety is covalently bound to the carboxy terminus of the second B chain and a second end of said linking moiety is covalently bound to the amino terminus of the second A chain, wherein the first and second insulin polypeptides are linked to one another via a disulfide bond between the N-terminal cysteine side chain of the B chain of the first insulin polypeptide and the side chain of a modified lysine of the linking moiety of the second insulin polypeptide, said A chain of the first and second insulin polypeptide comprising a sequence independently selected from GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7)

said B chain of the first insulin polypeptide comprising a sequence independently selected from CFVNQHLCG-SHLVEALYLVCGERGFFYTPKT (SEQ ID NO: 94) and CGPEHLCGAELVDALYLVCGDRGFYNKPT (SEQ ID NO: 97);

said B chain of the second insulin polypeptide comprising a sequence independently selected from FVNQHLCG-SHLVEALYLVCGERGFF (SEQ ID NO: 23) and GPEHLCGAELVDALYLVCGDRGFY (SEQ ID NO: 14);

said linking moiety of the second insulin polypeptide comprising the sequence GYGSSSRX$_{68}$APQT (SEQ ID NO: 9), wherein X$_{68}$ is an amino acid comprising a side chain of:

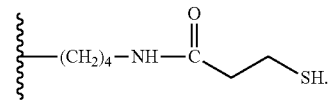

4. An insulin analog dimer of claim 1, wherein said dimer comprises a first insulin polypeptide and a second insulin polypeptide, wherein said first insulin and second insulin polypeptides are both single chain insulin analogs, said A chain of the first insulin polypeptide comprising the sequence TPAKSEGIVEECCFRSCDLALLETYCA (SEQ ID NO: 103);

said B chain of the first insulin polypeptide comprising the sequence AYRPSETLCG-GELVDTLQFVCGDRGFY (SEQ ID NO: 90); and the linking moiety for said first insulin polypeptide comprising the sequence SRVSRX$_{68}$SR (SEQ ID NO: 98)

said A chain of the second insulin polypeptide comprising the sequence GIVEQCCTSICSLYQLENYCN (SEQ ID NO: 1);

said B chain of the second insulin polypeptide comprising the sequence FVNQHLCGSHLVEALYLVCGERGFF (SEQ ID NO: 23) and the linking moiety for said second insulin polypeptide comprising the sequence GYGSSSRX$_{68}$APQT (SEQ ID NO: 9), wherein X$_{68}$ is arginine or an amino acid comprising a side chain of Structure I:

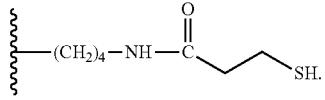

5. A method of reducing the risk of hypoglycemia associated with treating diabetes, said method comprising administering an effective amount of a pharmaceutical composition comprising an insulin analog dimer of claim 1.

6. The method of claim 5 wherein the second insulin polypeptide is a two chain heteroduplex comprising an A chain and a B chain linked via interchain disulfide bonds; and the first insulin polypeptide is a single chain insulin polypeptide comprising an A chain, a B chain and a linking moiety, wherein the linking moiety is PEG8-X$_{68}$PEG4 or GYGSSSRX$_{68}$APQT (SEQ ID NO: 9), wherein X$_{68}$ is an amino acid comprising a side chain of Structure II:

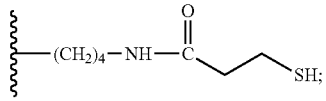

and and said first and second insulin polypeptides are linked to one another via the N-terminal amine or side chain of the amino acid at position B1 of the second insulin polypeptide and the amino acid comprising a side chain of Structure II present in the linking moiety of the first insulin polypeptide.

7. The method of claim 5 wherein the first and second insulin polypeptide comprise an A chain independently selected from the group consisting of GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7) and a B chain independently selected from the group consisting of FVNQHLCGSHLVEALYLVCGERGFFYT-PKT (SEQ ID NO: 2), FVNQHLCGSHLVEALYL-VCGERGFF (SEQ ID NO: 23), GPETLCGAELVDALYLVCGDRGFY (SEQ ID NO: 77), GPEHLCGAELVDALYLVCGDRGFY (SEQ ID NO: 14); GPETLCGAELVDALYLVCGDRGFYF-NKPT (SEQ ID NO: 79), and AYRPSETLCG-GELVDTLYLVCGDRGFYFSRPA (SEQ ID NO: 80).

8. An insulin analog dimer, said dimer comprising a first insulin polypeptide and a second insulin polypeptide, wherein said first insulin polypeptide is a single chain insulin, comprising
a first A chain sequence of GIVX$_4$X$_5$C-CX$_8$X$_9$X$_{10}$CX$_{12}$LX$_{14}$X$_{15}$LEX$_{18}$X$_{19}$CX$_{21}$-R$_{13}$ (SEQ ID NO: 70);
a first B chain sequence of X$_{25}$LCGX$_{29}$X$_{30}$LVX$_{33}$X$_{34}$LYLVCGX$_{41}$X$_{42}$GFX$_{45}$ (SEQ ID NO: 44); and a first linking moiety, wherein a first end of said first linking peptide is covalently bound to the carboxy terminus of the first B chain and a second end of said first linking moiety is covalently bound to the amino terminus of the first A chain;

said second insulin polypeptide is a single chain insulin or a two chain insulin comprising
a second A chain sequence of GIVX$_4$X$_5$CCX$_8$X$_9$X$_{10}$CX$_{12}$LX$_{14}$X$_{15}$LEX$_{18}$X$_{19}$-CX$_{21}$-R$_{13}$ (SEQ ID NO: 70); and
a second B chain sequence of X$_{25}$LCGX$_{29}$X$_{30}$LVX$_{33}$X$_{34}$LYLVCGX$_{41}$X$_{42}$GFX$_{45}$ (SEQ ID NO: 44), with the proviso that when said second insulin polypeptide is a single chain insulin, said second insulin polypeptide further comprises a second linking moiety, wherein a first end of said second linking moiety is covalently bound to the carboxy terminus of the B chain and a second end of said second linking moiety is covalently bound to the amino terminus of the A chain;

said first and second insulin polypeptides being linked to one another through a bond or a bifunctional linking moiety that covalently links the side chain of an amino acid at position 8 of said first linking moiety to
a) the amino terminus of the second insulin polypeptide; or
b) the side chain of an amino acid at position 8 of the second linking moiety, wherein X$_4$ is glutamic acid or aspartic acid;
X$_5$ is glutamic acid or glutamine;
X$_8$ is threonine, histidine or phenylalanine;
X$_9$ is serine, arginine, ornithine or alanine;
X$_{10}$ is serine or isoleucine;
X$_{12}$ is serine or aspartic acid;
X$_{14}$ is arginine, tyrosine, ornithine or alanine;
X$_{15}$ is glutamine, arginine, alanine, ornithine or leucine;
X$_{18}$ is methionine, asparagine or threonine;
X$_{19}$ is tyrosine, 4-methoxy-phenylalanine or 4-amino phenylalanine;
X$_{21}$ is alanine, glycine or asparagine;
X$_{25}$ is histidine or threonine;
X$_{29}$ is alanine, glycine or serine;
X$_{30}$ is histidine, aspartic acid, glutamic acid, homocysteic acid or cysteic acid;
X$_{33}$ is aspartic acid or glutamic acid;
X$_{34}$ is alanine or threonine;
X$_{41}$ is aspartic acid or glutamic acid;
X$_{42}$ is alanine, ornithine or arginine;
X$_{45}$ is tyrosine or phenylalanine; and
R$_{13}$ is COOH or CONH$_2$, further wherein said dimer exhibits a maximal dose response of 60% or less relative to native insulin.

9. The insulin analog dimer of claim 8 wherein said first and optional second linking moiety independently consist of the sequence GYGSSSRKAPQT (SEQ ID NO: 21), GYGSSSRX$_{68}$APQT (SEQ ID NO: 9), SRVSRX$_{68}$SR (SEQ ID NO: 98), or PEG8-X$_{68}$-PEG4, wherein m is 4.

10. The insulin analog dimer of claim 9 wherein the second insulin polypeptide is a two chain insulin and said first and second insulin polypeptides are covalently bound to one another through a bond or a bifunctional linking moiety that covalently links the amino acid side chain of the amino acid at position 8 of the first linking peptide to the N-terminal alpha amine of the B chain of the second insulin polypeptide.

11. The insulin analog dimer of claim 9 wherein the second insulin polypeptide is a single chain insulin and said first and second insulin polypeptides are covalently bound to one another through a bond or a bifunctional linking moiety that covalently links the amino acid side chain of the amino acid at position 8 of said first linking peptide to the side chain of the amino acid at position 8 of the second linking peptide.

12. The insulin analog dimer of claim 9 wherein the first linking moiety consists of PEG8-$X_{68}$-PEG4 or the sequence GYGSSSR$X_{68}$APQT (SEQ ID NO: 9), wherein $X_{68}$ is an amino acid with a side chain of Structure I:

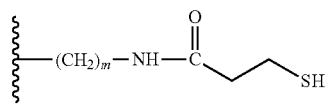

wherein m is an integer selected from 1 to 4, and the first and second insulin polypeptides are covalently bound to one another via a disulfide bond between the side chain of the first linking moiety amino acid having the side chain of Structure I:

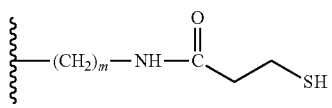

and the side chain of a cysteine added to the N-terminus of the second insulin polypeptide.

13. The insulin analog dimer of claim 9 wherein the first and second insulin polypeptide comprise an A chain independently selected from the group consisting of GIVEQCCTSICSLYQLENYCN (SEQ ID NO: 1), GIVDECCFRSCDLRRLEMYCA (SEQ ID NO: 5) and GIVEECCFRSCDLALLETYCA (SEQ ID NO: 7) and a B chain independently selected from the group consisting of FVNQHLCGSHLVEALYLVCGERGFFYTPKT (SEQ ID NO: 2), GPETLCGAELVDALYLVCGDRGFY (SEQ ID NO: 77), GPETLCGAELVDALYLVCGDRGFYFNKPT (SEQ ID NO: 79), and AYRPSETLCGGELVDTLYLVCGDRGFYFSRPA (SEQ ID NO: 80).

14. The insulin analog dimer of claim 1 wherein a hydrophilic moiety is covalently linked to an amino acid of the linking moiety or at an amino acid at a position selected from the group consisting of A9, A14 and A15 of the A chain or positions B1, B2, B10, B22, B28 or B29 of the B chain.

15. The insulin analog dimer of claim 14 wherein the hydrophilic moiety is a polyethylene glycol chain.

16. The insulin analog dimer of claim 1 further comprising a dipeptide element of the structure of Formula X:

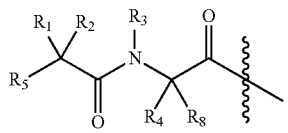

linked to said insulin analog dimer through an amide bond formed between said dipeptide element and an amine of the first or second insulin polypeptide, wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

17. The insulin analog dimer of claim 1, wherein an amino acid side chain of the first or second insulin polypeptide is covalently attached to an acyl group or an alkyl group via an alkyl amine, amide, ether, ester, thioether, or thioester linkage, wherein said acyl group or alkyl group is non-native to a naturally occurring amino acid.

18. A pharmaceutical composition comprising the insulin analog dimer of claim 1, and a pharmaceutically acceptable carrier.

19. The insulin analog dimer of claim 1 wherein said first insulin and second insulin polypeptide are both two chain insulin analogs comprising a first and second set of A chain and a B chain, respectively, wherein the A chain and B chain of each set are linked to one another through interchain disulfide bonds, further wherein the first and second insulin polypeptides are linked to one another via a disulfide bond formed between the side chains of amino acids at positions 27 and 27, 29 and 29 or at 27 and 29, of the respective two B chains, wherein said A chain of the first and second insulin polypeptide comprise a sequence independently selected from the group consisting of GIVEQCCTSICSLYQLENYCN (SEQ ID NO: 1), GIVDECCFRSCDLRRLENYCN (SEQ ID NO: 11), GIVDECCFRSCDLRRLEMYCA (SEQ ID NO: 5) and GIVEECCFRSCDLALLETYCA (SEQ ID NO: 7)

said B chain of the first and second insulin polypeptide comprises a sequence independently selected from the group consisting of FVNQHLCGSHLVEALYLVCGERGFFYTPX$_{68}$T (SEQ ID NO: 2) and GPETLCGAELVDALYLVCGDRGFYFNX$_{68}$PT (SEQ ID NO: 99), wherein $X_{68}$ is an amino acid comprising a side chain of Structure I:

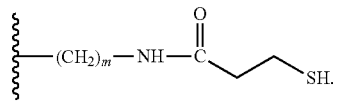

20. The insulin analog dimer of claim 19 wherein said first insulin and second insulin polypeptide are both two chain insulin analogs comprising a first and second set of A chain and a B chain, respectively, wherein the A chain and B chain of each set are linked to one another through interchain disulfide bonds, further wherein the first and second insulin polypeptides are linked to one another via a disulfide bond joining the side chains of the amino acids at positions 29 and 29 of the respective two B chains, wherein said A chain of the first and second insulin polypeptide comprise a sequence of GIVEQCCTSICSLYQLENYCN (SEQ ID NO: 1);

said B chain of the first and second insulin polypeptide comprise a sequence of FVNQHLCGSHLVEALYLVCGERGFFYTPX$_{68}$T (SEQ ID NO: 2), wherein $X_{68}$ is an amino acid comprising a side chain of Structure I:

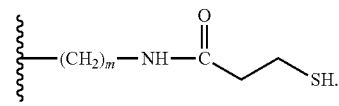

* * * * *

SEQUENCE LISTING

<160> NUMBER OF SEQ ID NOS: 103

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 4
<211> LENGTH: 67
<212> TYPE: PRT
<213> ORGANISM: Homo sapiens

<400> SEQUENCE: 4

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 5
<211> LENGTH: 21
<212> TYPE: PRT
<213> ORGANISM: Homo sapiens

<400> SEQUENCE: 5

Gly Ile Val Asp Glu Cys Cys Phe Arg Ser Cys Asp Leu Arg Arg Leu
1               5                   10                  15

Glu Met Tyr Cys Ala
            20

<210> SEQ ID NO 6
<211> LENGTH: 29
<212> TYPE: PRT
<213> ORGANISM: Homo sapiens

<400> SEQUENCE: 6

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Lys Pro Thr
            20                  25

<210> SEQ ID NO 7
<211> LENGTH: 21
<212> TYPE: PRT
<213> ORGANISM: Homo sapiens

```
<400> SEQUENCE: 7

Gly Ile Val Glu Glu Cys Cys Phe Arg Ser Cys Asp Leu Ala Leu Leu
1               5                   10                  15

Glu Thr Tyr Cys Ala
            20

<210> SEQ ID NO 8
<211> LENGTH: 32
<212> TYPE: PRT
<213> ORGANISM: Homo sapiens

<400> SEQUENCE: 8

Ala Tyr Arg Pro Ser Glu Thr Leu Cys Gly Gly Glu Leu Val Asp Thr
1               5                   10                  15

Leu Tyr Leu Val Cys Gly Asp Arg Gly Phe Tyr Phe Ser Arg Pro Ala
            20                  25                  30

<210> SEQ ID NO 9
<211> LENGTH: 12
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is ornithine, lysine,
      arginine or lysine analog

<400> SEQUENCE: 9

Gly Tyr Gly Ser Ser Ser Arg Xaa Ala Pro Gln Thr
1               5                   10

<210> SEQ ID NO 10
<211> LENGTH: 29
<212> TYPE: PRT
<213> ORGANISM: Homo sapiens

<400> SEQUENCE: 10

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr
            20                  25

<210> SEQ ID NO 11
<211> LENGTH: 21
<212> TYPE: PRT
<213> ORGANISM: Homo sapiens

<400> SEQUENCE: 11

Gly Ile Val Asp Glu Cys Cys Phe Arg Ser Cys Asp Leu Arg Arg Leu
1               5                   10                  15

Glu Asn Tyr Cys Asn
            20

<210> SEQ ID NO 12
<211> LENGTH: 21
<212> TYPE: PRT
<213> ORGANISM: Homo sapiens

<400> SEQUENCE: 12

Gly Ile Val Glu Glu Cys Cys Phe Arg Ser Cys Asp Leu Ala Leu Leu
1               5                   10                  15

Glu Asn Tyr Cys Asn
```

20

<210> SEQ ID NO 13
<211> LENGTH: 29
<212> TYPE: PRT
<213> ORGANISM: Homo sapiens

<400> SEQUENCE: 13

Phe Val Asn Gln His Leu Cys Gly Ser His Leu Val Glu Ala Leu Tyr
1               5                   10                  15

Leu Val Cys Gly Glu His Gly Phe Phe Tyr Thr Pro Arg
            20                  25

<210> SEQ ID NO 14
<211> LENGTH: 24
<212> TYPE: PRT
<213> ORGANISM: Homo sapiens

<400> SEQUENCE: 14

Gly Pro Glu His Leu Cys Gly Ala Glu Leu Val Asp Ala Leu Tyr Leu
1               5                   10                  15

Val Cys Gly Asp Arg Gly Phe Tyr
            20

<210> SEQ ID NO 15
<211> LENGTH: 12
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is ornithine, lysine,
      arginine or a lysine analog

<400> SEQUENCE: 15

Gly Ala Gly Ser Ser Ser Arg Xaa Ala Pro Gln Thr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position1 is glycine, alanine, valine,
      leucine, isoleucine, proline, phenylalanine and methionine
<220> FEATURE:
<221> NAME/KEY: MISC_FEATURE
<222> LOCATION: (2)..(2)
<223> OTHER INFORMATION: Xaa at position 2 is any non-aromatic amino
      acid
<220> FEATURE:
<221> NAME/KEY: MISC_FEATURE
<222> LOCATION: (7)..(8)
<223> OTHER INFORMATION: Xaas at positions 7 and 8 are independently
      arginine, lysine, cysteine, homocysteine, acetyl-phenylalanine or
      ornithine

<400> SEQUENCE: 16

Xaa Xaa Gly Ser Ser Ser Xaa Xaa Ala Pro Gln Thr
1               5                   10

<210> SEQ ID NO 17
<211> LENGTH: 12
<212> TYPE: PRT

```
<213> ORGANISM: Artificial Sequence
<220> FEATURE:
<223> OTHER INFORMATION: linker sequence
<220> FEATURE:
<221> NAME/KEY: MISC_FEATURE
<222> LOCATION: (1)..(1)
<223> OTHER INFORMATION: Xaa at position1 is glycine, alanine, valine,
      leucine, isoleucine, proline, phenylalanine and methionine
<220> FEATURE:
<221> NAME/KEY: MISC_FEATURE
<222> LOCATION: (2)..(2)
<223> OTHER INFORMATION: Xaa at position 2 is any non-aromatic amino
      acid
<220> FEATURE:
<221> NAME/KEY: MISC_FEATURE
<222> LOCATION: (7)..(8)
<223> OTHER INFORMATION: Xaas at positions 7 and 8 are independently
      arginine, lysine or ornithine or a lysine analog

<400> SEQUENCE: 17

Xaa Xaa Gly Ser Ser Ser Xaa Xaa Ala Pro Gln Thr
1               5                   10

<210> SEQ ID NO 18
<211> LENGTH: 29
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is arginine or lysine
<220> FEATURE:
<221> NAME/KEY: MISC_FEATURE
<222> LOCATION: (29)..(29)
<223> OTHER INFORMATION: Xaa at position 29 is arginine or lysine

<400> SEQUENCE: 18

Ser Ser Ser Ser Xaa Ala Pro Pro Ser Leu Pro Ser Pro Ser Arg
1               5                   10                  15

Leu Pro Gly Pro Ser Asp Thr Pro Ile Leu Pro Gln Xaa
                20                  25

<210> SEQ ID NO 19
<211> LENGTH: 36
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is arginine or lysine
<220> FEATURE:
<221> NAME/KEY: MISC_FEATURE
<222> LOCATION: (36)..(36)
<223> OTHER INFORMATION: Xaa at position 36 is arginine or lysine

<400> SEQUENCE: 19

Met Gly Ser Ser Ser Ser Xaa Ala Pro Pro Ser Leu Pro Ser Pro
1               5                   10                  15

Ser Arg Leu Pro Gly Pro Ser Asp Thr Pro Ile Leu Pro Gln Glu Glu
                20                  25                  30

Glu Glu Glu Xaa
        35

<210> SEQ ID NO 20
<211> LENGTH: 30
<212> TYPE: PRT
<213> ORGANISM: Homo sapiens

<400> SEQUENCE: 20
```

Phe Val Asn Gln His Leu Cys Gly Ser His Leu Val Glu Ala Leu Tyr
1               5                   10                  15

Leu Val Cys Gly Glu His Gly Phe Phe Tyr Thr Pro Lys Thr
            20                  25                  30

<210> SEQ ID NO 21
<211> LENGTH: 12
<212> TYPE: PRT
<213> ORGANISM: Homo sapiens

<400> SEQUENCE: 21

Gly Tyr Gly Ser Ser Ser Arg Lys Ala Pro Gln Thr
1               5                   10

<210> SEQ ID NO 22
<211> LENGTH: 29
<212> TYPE: PRT
<213> ORGANISM: Homo sapiens

<400> SEQUENCE: 22

Gly Pro Glu His Leu Cys Gly Ala Glu Leu Val Asp Ala Leu Tyr Leu
1               5                   10                  15

Val Cys Gly Asp Arg Gly Phe Tyr Phe Asn Lys Pro Thr
            20                  25

<210> SEQ ID NO 23
<211> LENGTH: 25
<212> TYPE: PRT
<213> ORGANISM: Homo sapiens

<400> SEQUENCE: 23

Phe Val Asn Gln His Leu Cys Gly Ser His Leu Val Glu Ala Leu Tyr
1               5                   10                  15

Leu Val Cys Gly Glu Arg Gly Phe Phe
            20                  25

<210> SEQ ID NO 24
<211> LENGTH: 12
<212> TYPE: PRT
<213> ORGANISM: Homo sapiens

<400> SEQUENCE: 24

Gly Tyr Gly Ser Ser Ser Arg Arg Ala Pro Gln Thr
1               5                   10

<210> SEQ ID NO 25
<211> LENGTH: 8
<212> TYPE: PRT
<213> ORGANISM: Homo sapiens

<400> SEQUENCE: 25

Gly Tyr Gly Ser Ser Ser Arg Arg
1               5

<210> SEQ ID NO 26
<211> LENGTH: 12
<212> TYPE: PRT
<213> ORGANISM: Homo sapiens

<400> SEQUENCE: 26

Gly Ala Gly Ser Ser Ser Arg Arg Ala Pro Gln Thr
1               5                   10

```
<210> SEQ ID NO 27
<211> LENGTH: 8
<212> TYPE: PRT
<213> ORGANISM: Artificial Sequence
<220> FEATURE:
<223> OTHER INFORMATION: peptide linker

<400> SEQUENCE: 27

Gly Ala Gly Ser Ser Ser Arg Arg
1               5

<210> SEQ ID NO 28
<211> LENGTH: 9
<212> TYPE: PRT
<213> ORGANISM: Artificial Sequence
<220> FEATURE:
<223> OTHER INFORMATION: linker sequence

<400> SEQUENCE: 28

Gly Ala Gly Ser Ser Ser Arg Arg Ala
1               5

<210> SEQ ID NO 29
<211> LENGTH: 10
<212> TYPE: PRT
<213> ORGANISM: Artificial Sequence
<220> FEATURE:
<223> OTHER INFORMATION: linker sequence

<400> SEQUENCE: 29

Gly Ala Gly Ser Ser Ser Arg Arg Ala Pro
1               5                   10

<210> SEQ ID NO 30
<211> LENGTH: 11
<212> TYPE: PRT
<213> ORGANISM: Artificial Sequence
<220> FEATURE:
<223> OTHER INFORMATION: peptide linker

<400> SEQUENCE: 30

Gly Ala Gly Ser Ser Ser Arg Arg Ala Pro Gln
1               5                   10

<210> SEQ ID NO 31
<211> LENGTH: 8
<212> TYPE: PRT
<213> ORGANISM: Artificial Sequence
<220> FEATURE:
<223> OTHER INFORMATION: linker sequence

<400> SEQUENCE: 31

Pro Tyr Gly Ser Ser Ser Arg Arg
1               5

<210> SEQ ID NO 32
<211> LENGTH: 8
<212> TYPE: PRT
<213> ORGANISM: Artificial Sequence
<220> FEATURE:
<223> OTHER INFORMATION: linker sequence

<400> SEQUENCE: 32

Pro Ala Gly Ser Ser Ser Arg Arg
1               5

<210> SEQ ID NO 33
```

```
<211> LENGTH: 9
<212> TYPE: PRT
<213> ORGANISM: Artificial Sequence
<220> FEATURE:
<223> OTHER INFORMATION: linker sequence

<400> SEQUENCE: 33

Pro Ala Gly Ser Ser Ser Arg Arg Ala
1               5

<210> SEQ ID NO 34
<211> LENGTH: 10
<212> TYPE: PRT
<213> ORGANISM: Artificial Sequence
<220> FEATURE:
<223> OTHER INFORMATION: linker sequence

<400> SEQUENCE: 34

Pro Ala Gly Ser Ser Ser Arg Arg Ala Pro
1               5                   10

<210> SEQ ID NO 35
<211> LENGTH: 11
<212> TYPE: PRT
<213> ORGANISM: Artificial Sequence
<220> FEATURE:
<223> OTHER INFORMATION: linker sequence

<400> SEQUENCE: 35

Pro Ala Gly Ser Ser Ser Arg Arg Ala Pro Gln
1               5                   10

<210> SEQ ID NO 36
<211> LENGTH: 12
<212> TYPE: PRT
<213> ORGANISM: Artificial Sequence
<220> FEATURE:
<223> OTHER INFORMATION: linker sequence

<400> SEQUENCE: 36

Pro Ala Gly Ser Ser Ser Arg Arg Ala Pro Gln Thr
1               5                   10

<210> SEQ ID NO 37
<211> LENGTH: 4
<212> TYPE: PRT
<213> ORGANISM: Homo sapiens

<400> SEQUENCE: 37

Tyr Thr Pro Lys
1

<210> SEQ ID NO 38
<211> LENGTH: 4
<212> TYPE: PRT
<213> ORGANISM: Homo sapiens

<400> SEQUENCE: 38

Phe Asn Lys Pro
1

<210> SEQ ID NO 39
<211> LENGTH: 5
<212> TYPE: PRT
<213> ORGANISM: Homo sapiens

<400> SEQUENCE: 39
```

```
Tyr Thr Pro Lys Thr
1               5

<210> SEQ ID NO 40
<211> LENGTH: 5
<212> TYPE: PRT
<213> ORGANISM: Homo sapiens

<400> SEQUENCE: 40

Phe Asn Lys Pro Thr
1               5

<210> SEQ ID NO 41
<211> LENGTH: 29
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (8)..(8)
<223> OTHER INFORMATION: Xaa at position 8 is serine or alanine
<220> FEATURE:
<221> NAME/KEY: MISC_FEATURE
<222> LOCATION: (13)..(13)
<223> OTHER INFORMATION: Xaa at position 13 is alanine
<220> FEATURE:
<221> NAME/KEY: MISC_FEATURE
<222> LOCATION: (21)..(21)
<223> OTHER INFORMATION: Xaa at position 21 is arginine or ornithine

<400> SEQUENCE: 41

Gly Pro Glu Thr Leu Cys Gly Xaa Glu Leu Val Asp Xaa Leu Tyr Leu
1               5                   10                  15

Val Cys Gly Asp Xaa Gly Phe Tyr Phe Asn Lys Pro Thr
            20                  25

<210> SEQ ID NO 42
<211> LENGTH: 36
<212> TYPE: PRT
<213> ORGANISM: Homo sapiens

<400> SEQUENCE: 42

Gly Glu Glu Glu Glu Glu Trp Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Tyr Thr Pro Arg
        35

<210> SEQ ID NO 43
<211> LENGTH: 31
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa at position 28 is alanine lysine,
      ornithine or arginine

<400> SEQUENCE: 43

Gly Glu Glu Glu Glu Glu Lys Gly Pro Glu His Leu Cys Gly Ala His
1               5                   10                  15

Leu Val Asp Ala Leu Tyr Leu Val Cys Gly Asp Xaa Gly Phe Tyr
            20                  25                  30
```

```
<210> SEQ ID NO 44
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or
      serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (17)..(17)
<223> OTHER INFORMATION: Xaa at position 17 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or 4-amino-
      phenylalanine

<400> SEQUENCE: 44

Xaa Leu Cys Gly Xaa Xaa Leu Val Xaa Xaa Leu Tyr Leu Val Cys Gly
1               5                   10                  15

Xaa Xaa Gly Phe Xaa
            20

<210> SEQ ID NO 45
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or
      glutamic acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
```

```
        ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
        ornithine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic
        acid, arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
        acid
<220> FEATURE:
<221> NAME/KEY: MISC_FEATURE
<222> LOCATION: (18)..(18)
<223> OTHER INFORMATION: Xaa at position 18 is methionine, asparagine,
        glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position19 is tyrosine, 4-methoxy
        phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine,
        serine, valine, threonine, isoleucine, leucine, glutamine,
        glutamic acid, asparagine, aspartic acid, histidine,
        tryptophan, tyrosine, or methionine

<400> SEQUENCE: 45

Gly Ile Val Xaa Xaa Cys Cys Xaa Xaa Xaa Cys Xaa Leu Xaa Xaa Leu
1               5                   10                  15

Xaa Xaa Xaa Cys Xaa
            20

<210> SEQ ID NO 46
<211> LENGTH: 6
<212> TYPE: PRT
<213> ORGANISM: Homo sapiens

<400> SEQUENCE: 46

Ala Tyr Arg Pro Ser Glu
1               5

<210> SEQ ID NO 47
<211> LENGTH: 4
<212> TYPE: PRT
<213> ORGANISM: Homo sapiens

<400> SEQUENCE: 47

Phe Val Asn Gln
1

<210> SEQ ID NO 48
<211> LENGTH: 4
<212> TYPE: PRT
<213> ORGANISM: Homo sapiens

<400> SEQUENCE: 48
```

Pro Gly Pro Glu
1

<210> SEQ ID NO 49
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or threonine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is asparagine or glycine

<400> SEQUENCE: 49

Gly Ile Val Glu Gln Cys Cys Xaa Ser Ile Cys Ser Leu Tyr Gln Leu
1               5                   10                  15

Xaa Asn Xaa Cys Xaa
            20

<210> SEQ ID NO 50
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalnine
<220> FEATURE:
<221> NAME/KEY: MISC_FEATURE
<222> LOCATION: (9)..(9)
<223> OTHER INFORMATION: Xaa at position 9 is arginine, lysine,
      ornithine or alanine
<220> FEATURE:
<221> NAME/KEY: MISC_FEATURE
<222> LOCATION: (14)..(14)
<223> OTHER INFORMATION: Xaa at position 14 is arginine, lysine,
      ornithine or alanine
<220> FEATURE:
<221> NAME/KEY: MISC_FEATURE
<222> LOCATION: (15)..(15)
<223> OTHER INFORMATION: Xaa at position 15 is arginine, lysine,
      ornithine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine
      or threonine
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine

```
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 50

Gly Ile Val Asp Glu Cys Cys Xaa Xaa Ser Cys Asp Leu Xaa Xaa Leu
1               5                   10                  15

Xaa Xaa Xaa Cys Xaa
            20

<210> SEQ ID NO 51
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or
      serine
<220> FEATURE:
<221> NAME/KEY: MISC_FEATURE
<222> LOCATION: (6)..(6)
<223> OTHER INFORMATION: Xaa at position 6 is histidine, aspartic
      acid, glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid or glutamic
      acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 51

Xaa Leu Cys Gly Xaa Xaa Leu Val Xaa Xaa Leu Tyr Leu Val Cys Gly
1               5                   10                  15

Asp Xaa Gly Phe Xaa
            20

<210> SEQ ID NO 52
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (9)..(9)
<223> OTHER INFORMATION: Xaa at position 9 is arginine, ornithine, or
      lysine
<220> FEATURE:
<221> NAME/KEY: MISC_FEATURE
<222> LOCATION: (14)..(14)
<223> OTHER INFORMATION: Xaa at position 14 is arginine, ornithine, or
      lysine
```

```
<220> FEATURE:
<221> NAME/KEY: MISC_FEATURE
<222> LOCATION: (15)..(15)
<223> OTHER INFORMATION: Xaa at position 15 is arginine, ornithine, or
      lysine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 52

Gly Ile Val Asp Glu Cys Cys His Xaa Ser Cys Asp Leu Xaa Xaa Leu
1               5                   10                  15

Xaa Met Xaa Cys Xaa
            20

<210> SEQ ID NO 53
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (6)..(6)
<223> OTHER INFORMATION: Xaa at position 6 is histidine, aspartic acid,
      or glutamic acid
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or
      phenylalanine

<400> SEQUENCE: 53

Xaa Leu Cys Gly Ala Xaa Leu Val Asp Ala Leu Tyr Leu Val Cys Gly
1               5                   10                  15

Asp Xaa Gly Phe Xaa
            20

<210> SEQ ID NO 54
<211> LENGTH: 21
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (18)..(18)
<223> OTHER INFORMATION: The Xaa at position 18 is ornithine,
      lysine or arginine

<400> SEQUENCE: 54
```

His Leu Cys Gly Ala Glu Leu Val Asp Ala Leu Tyr Leu Val Cys Gly
1               5                   10                  15

Asp Xaa Gly Phe Tyr
            20

<210> SEQ ID NO 55
<211> LENGTH: 24
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (21)..(21)
<223> OTHER INFORMATION: The Xaa at position 21 is ornithine,
      lysine or arginine

<400> SEQUENCE: 55

Gly Pro Glu His Leu Cys Gly Ala Glu Leu Val Asp Ala Leu Tyr Leu
1               5                   10                  15

Val Cys Gly Asp Xaa Gly Phe Tyr
            20

<210> SEQ ID NO 56
<211> LENGTH: 29
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (21)..(21)
<223> OTHER INFORMATION: The Xaa at position 21 is ornithine,
      lysine or arginine

<400> SEQUENCE: 56

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Pro Lys Thr
            20                  25

<210> SEQ ID NO 57
<211> LENGTH: 29
<212> TYPE: PRT
<213> ORGANISM: Artificial Sequence
<220> FEATURE:
<223> OTHER INFORMATION: analog of IGF B chain
<220> FEATURE:
<221> NAME/KEY: MISC_FEATURE
<222> LOCATION: (21)..(21)
<223> OTHER INFORMATION: The Xaa at position 21 is ornithine,
      lysine or arginine

<400> SEQUENCE: 57

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Lys Pro Thr
            20                  25

<210> SEQ ID NO 58
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (7)..(7)

```
<223> OTHER INFORMATION: The Xaa at position 7 is arginine,
      lysine or ornithine

<400> SEQUENCE: 58

Gly Tyr Gly Ser Ser Ser Xaa Arg
1               5

<210> SEQ ID NO 59
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is ornithine

<400> SEQUENCE: 59

Gly Tyr Gly Ser Ser Ser Xaa Arg
1               5

<210> SEQ ID NO 60
<211> LENGTH: 21
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The Xaa at position 18 is ornithine

<400> SEQUENCE: 60

His Leu Cys Gly Ala Glu Leu Val Asp Ala Leu Tyr Leu Val Cys Gly
1               5                   10                  15

Asp Xaa Gly Phe Tyr
            20

<210> SEQ ID NO 61
<211> LENGTH: 24
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The Xaa at position 21is ornithine

<400> SEQUENCE: 61

Gly Pro Glu His Leu Cys Gly Ala Glu Leu Val Asp Ala Leu Tyr Leu
1               5                   10                  15

Val Cys Gly Asp Xaa Gly Phe Tyr
            20

<210> SEQ ID NO 62
<211> LENGTH: 29
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The Xaa at position 21 is ornithine

<400> SEQUENCE: 62

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Pro Lys Thr
            20                  25

<210> SEQ ID NO 63
```

```
<211> LENGTH: 29
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: Xaa at position 21 is ornithine

<400> SEQUENCE: 63

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Lys Pro Thr
            20                  25

<210> SEQ ID NO 64
<211> LENGTH: 21
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The Xaa at position 9 is ornithine
<220> FEATURE:
<221> NAME/KEY: MISC_FEATURE
<222> LOCATION: (14)..(15)
<223> OTHER INFORMATION: The Xaas at positions 14 and 15 are both
      ornithine
<220> FEATURE:
<221> NAME/KEY: MISC_FEATURE
<222> LOCATION: (19)..(19)
<223> OTHER INFORMATION: The Xaa at position 19 is tyrosine, 4-methoxy-
      phenylalanine or 4-amino phenylalanine

<400> SEQUENCE: 64

Gly Ile Val Asp Glu Cys Cys His Xaa Ser Cys Asp Leu Xaa Xaa Leu
1               5                   10                  15

Gln Met Xaa Cys Asn
            20

<210> SEQ ID NO 65
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 65

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 66
<211> LENGTH: 27
<212> TYPE: PRT
<213> ORGANISM: Artificial Sequence
<220> FEATURE:
```

```
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine and
      desamino-phenylalanine
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 66

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr
            20                  25

<210> SEQ ID NO 67
<211> LENGTH: 21
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The Xaa at position 6 is histidine, aspartic
      acid, glutamic acid, homocysteic acid or cysteic acid

<400> SEQUENCE: 67

His Leu Cys Gly Ser Xaa Leu Val Glu Ala Leu Tyr Leu Val Cys Gly
1               5                   10                  15

Glu Arg Gly Phe Phe
            20

<210> SEQ ID NO 68
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (14)..(14)
<223> OTHER INFORMATION: Xaa at position 14 is tyrosine, arginine,
      ornithine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic
      acid, arginine, ornithine, alanine, lysine or leucine
```

```
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine,
      serine, valine, threonine, isoleucine, leucine, glutamine,
      glutamic acid, asparagine, aspartic acid, histidine, tryptophan,
      tyrosine, or methionine

<400> SEQUENCE: 68

Gly Ile Val Xaa Glu Cys Cys Xaa Xaa Ser Cys Asp Leu Xaa Xaa Leu
1               5                   10                  15

Xaa Xaa Xaa Cys Xaa
            20

<210> SEQ ID NO 69
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (12)..(12)
<223> OTHER INFORMATION: Xaa at position 12 is tyrosine or 4-amino-
      phenylalanine
<220> FEATURE:
<221> NAME/KEY: MISC_FEATURE
<222> LOCATION: (17)..(17)
<223> OTHER INFORMATION: Xaa at position 17 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine, phenylalanine
```

```
         or 4-amino-phenylalanine

<400> SEQUENCE: 69

Xaa Leu Cys Gly Xaa Xaa Leu Val Xaa Xaa Leu Xaa Leu Val Cys Gly
1               5                   10                  15

Xaa Xaa Gly Phe Xaa
            20

<210> SEQ ID NO 70
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornithine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 70

Gly Ile Val Xaa Xaa Cys Cys Xaa Xaa Xaa Cys Xaa Leu Xaa Xaa Leu
1               5                   10                  15

Glu Xaa Xaa Cys Xaa
            20
```

```
<210> SEQ ID NO 71
<211> LENGTH: 8
<212> TYPE: PRT
<213> ORGANISM: Artificial Sequence
<220> FEATURE:
<223> OTHER INFORMATION: N-terminal extension peptide
<220> FEATURE:
<221> NAME/KEY: MISC_FEATURE
<222> LOCATION: (2)..(7)
<223> OTHER INFORMATION: Xaa at positions 2-7 are independently glutamic
      acid or aspartic acid
<220> FEATURE:
<221> NAME/KEY: MISC_FEATURE
<222> LOCATION: (3)..(7)
<223> OTHER INFORMATION: any or all of amino acids at positions 3-7 are
      present or absent

<400> SEQUENCE: 71

Gly Xaa Xaa Xaa Xaa Xaa Xaa Lys
1               5

<210> SEQ ID NO 72
<211> LENGTH: 6
<212> TYPE: PRT
<213> ORGANISM: Artificial Sequence
<220> FEATURE:
<223> OTHER INFORMATION: synthetic peptide for testing cleavage of
      dipeptide prodrug element

<400> SEQUENCE: 72

His Ser Arg Gly Thr Phe
1               5

<210> SEQ ID NO 73
<211> LENGTH: 8
<212> TYPE: PRT
<213> ORGANISM: Artificial Sequence
<220> FEATURE:
<223> OTHER INFORMATION: synthetic peptide for testing cleavage of
      dipeptide prodrug element
<220> FEATURE:
<221> NAME/KEY: MISC_FEATURE
<222> LOCATION: (2)..(2)
<223> OTHER INFORMATION: Xaa at position 2 is Sarcosine

<400> SEQUENCE: 73

Lys Xaa His Ser Thr Gly Thr Phe
1               5

<210> SEQ ID NO 74
<211> LENGTH: 6
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-histidine
<220> FEATURE:
<221> NAME/KEY: MOD_RES
<222> LOCATION: (2)..(2)
<223> OTHER INFORMATION: Xaa at position 2 is d-threonine
<220> FEATURE:
<221> NAME/KEY: MOD_RES
<222> LOCATION: (3)..(3)
<223> OTHER INFORMATION: Xaa at position 3 is d-arginine
<220> FEATURE:
<221> NAME/KEY: MOD_RES
<222> LOCATION: (5)..(5)
<223> OTHER INFORMATION: Xaa at position 5 is d-threonine
```

```
<220> FEATURE:
<221> NAME/KEY: MOD_RES
<222> LOCATION: (6)..(6)
<223> OTHER INFORMATION: Xaa at position 6 is d-phenylalanine

<400> SEQUENCE: 74

Xaa Xaa Xaa Gly Xaa Xaa
1               5

<210> SEQ ID NO 75
<211> LENGTH: 8
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-lysine
<220> FEATURE:
<221> NAME/KEY: MOD_RES
<222> LOCATION: (2)..(2)
<223> OTHER INFORMATION: Xaa at position 2 is d-sarcosine
<220> FEATURE:
<221> NAME/KEY: MOD_RES
<222> LOCATION: (3)..(3)
<223> OTHER INFORMATION: Xaa at position 3 is d-histidine
<220> FEATURE:
<221> NAME/KEY: MOD_RES
<222> LOCATION: (4)..(4)
<223> OTHER INFORMATION: Xaa at position 4 is d-threonine
<220> FEATURE:
<221> NAME/KEY: MOD_RES
<222> LOCATION: (5)..(5)
<223> OTHER INFORMATION: Xaa at position 5 is d-arginine
<220> FEATURE:
<221> NAME/KEY: MOD_RES
<222> LOCATION: (7)..(7)
<223> OTHER INFORMATION: Xaa at position 7 is d-threonine
<220> FEATURE:
<221> NAME/KEY: MOD_RES
<222> LOCATION: (8)..(8)
<223> OTHER INFORMATION: Xaa at position 8 is d-phenylalanine

<400> SEQUENCE: 75

Xaa Xaa Xaa Xaa Xaa Gly Xaa Xaa
1               5

<210> SEQ ID NO 76
<211> LENGTH: 6
<212> TYPE: PRT
<213> ORGANISM: Artificial Sequence
<220> FEATURE:
<223> OTHER INFORMATION: synthetic peptide for testing cleavage of
      dipeptide prodrug element
<220> FEATURE:
<221> NAME/KEY: MISC_FEATURE
<222> LOCATION: (1)..(1)
<223> OTHER INFORMATION: The Xaa at position 1 is histidine, d-histidine
      or N-methyl-histdine

<400> SEQUENCE: 76

Xaa Ser Arg Gly Thr Phe
1               5

<210> SEQ ID NO 77
<211> LENGTH: 24
<212> TYPE: PRT
<213> ORGANISM: Homo sapiens

<400> SEQUENCE: 77

Gly Pro Glu Thr Leu Cys Gly Ala Glu Leu Val Asp Ala Leu Tyr Leu
```

```
                1               5                   10                  15
Val Cys Gly Asp Arg Gly Phe Tyr
            20

<210> SEQ ID NO 78
<211> LENGTH: 24
<212> TYPE: PRT
<213> ORGANISM: Homo sapiens

<400> SEQUENCE: 78

Gly Pro Glu Thr Leu Cys Gly Ala Glu Leu Val Asp Ala Leu Tyr Leu
1               5                   10                  15

Val Cys Gly Asp Arg Gly Phe Tyr
            20

<210> SEQ ID NO 79
<211> LENGTH: 29
<212> TYPE: PRT
<213> ORGANISM: Homo sapiens

<400> SEQUENCE: 79

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Lys Pro Thr
            20                  25

<210> SEQ ID NO 80
<211> LENGTH: 32
<212> TYPE: PRT
<213> ORGANISM: Homo sapiens

<400> SEQUENCE: 80

Ala Tyr Arg Pro Ser Glu Thr Leu Cys Gly Gly Glu Leu Val Asp Thr
1               5                   10                  15

Leu Tyr Leu Val Cys Gly Asp Arg Gly Phe Tyr Phe Ser Arg Pro Ala
            20                  25                  30

<210> SEQ ID NO 81
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalanine
<220> FEATURE:
<221> NAME/KEY: MISC_FEATURE
<222> LOCATION: (9)..(9)
<223> OTHER INFORMATION: Xaa at position 9 is arginine, ornithine,
      lysine or alanine
<220> FEATURE:
<221> NAME/KEY: MISC_FEATURE
<222> LOCATION: (18)..(18)
<223> OTHER INFORMATION: Xaa at position 18 is methionine or asparagine
<220> FEATURE:
<221> NAME/KEY: MISC_FEATURE
<222> LOCATION: (21)..(21)
<223> OTHER INFORMATION: Xaa at position 21 is alanine or asparagine

<400> SEQUENCE: 81

Gly Ile Val Asp Glu Cys Cys Xaa Xaa Ser Cys Asp Leu Arg Arg Leu
1               5                   10                  15

Glu Xaa Tyr Cys Xaa
            20
```

<210> SEQ ID NO 82
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (18)..(18)
<223> OTHER INFORMATION: Xaa at position 18 is alanine, ornithine or
      arginine

<400> SEQUENCE: 82

Xaa Leu Cys Gly Ala Glu Leu Val Asp Ala Leu Tyr Leu Val Cys Gly
1               5                   10                  15

Asp Xaa Gly Phe Tyr
            20

<210> SEQ ID NO 83
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is histidine or phenylalanine

<400> SEQUENCE: 83

Gly Ile Val Asp Glu Cys Cys Xaa Arg Ser Cys Asp Leu Arg Arg Leu
1               5                   10                  15

Glu Asn Tyr Cys Asn
            20

<210> SEQ ID NO 84
<211> LENGTH: 21
<212> TYPE: PRT
<213> ORGANISM: Homo sapiens

<400> SEQUENCE: 84

His Leu Cys Gly Ala Glu Leu Val Asp Ala Leu Tyr Leu Val Cys Gly
1               5                   10                  15

Asp Arg Gly Phe Tyr
            20

<210> SEQ ID NO 85
<211> LENGTH: 21
<212> TYPE: PRT
<213> ORGANISM: Homo sapiens

<400> SEQUENCE: 85

His Leu Cys Gly Ser His Leu Val Glu Ala Leu Tyr Leu Val Cys Gly
1               5                   10                  15

Glu Arg Gly Phe Phe
            20

<210> SEQ ID NO 86
<211> LENGTH: 70
<212> TYPE: PRT
<213> ORGANISM: Homo sapiens
<220> FEATURE:
<221> NAME/KEY: MISC_FEATURE

```
<222> LOCATION: (60)..(60)
<223> OTHER INFORMATION: Xaa at position 60 is 4-amino phenylalanine

<400> SEQUENCE: 86

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Xaa Cys Ala Pro Leu
    50                  55                  60

Lys Pro Ala Lys Ser Ala
65                  70

<210> SEQ ID NO 87
<211> LENGTH: 32
<212> TYPE: PRT
<213> ORGANISM: Homo sapiens

<400> SEQUENCE: 87

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

<210> SEQ ID NO 88
<211> LENGTH: 27
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa at position 4 is arginine or lysine

<400> SEQUENCE: 88

Thr Pro Ala Xaa Ser Glu Gly Ile Val Glu Glu Cys Cys Phe Arg Ser
1               5                   10                  15

Cys Asp Leu Ala Leu Leu Glu Thr Tyr Cys Ala
            20                  25

<210> SEQ ID NO 89
<211> LENGTH: 24
<212> TYPE: PRT
<213> ORGANISM: Homo sapiens

<400> SEQUENCE: 89

Gly Pro Glu Thr Leu Cys Gly Ala Glu Leu Val Asp Ala Leu Gln Phe
1               5                   10                  15

Val Cys Gly Asp Arg Gly Phe Tyr
            20

<210> SEQ ID NO 90
<211> LENGTH: 27
<212> TYPE: PRT
<213> ORGANISM: Homo sapiens

<400> SEQUENCE: 90

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr
            20                  25
```

```
<210> SEQ ID NO 91
<211> LENGTH: 28
<212> TYPE: PRT
<213> ORGANISM: Homo sapiens

<400> SEQUENCE: 91

Cys Ala Tyr Arg Pro Ser Glu Thr Leu Cys Gly Gly Glu Leu Val Asp
1               5                   10                  15

Thr Leu Gln Phe Val Cys Gly Asp Arg Gly Phe Tyr
            20                  25

<210> SEQ ID NO 92
<211> LENGTH: 27
<212> TYPE: PRT
<213> ORGANISM: Homo sapiens

<400> SEQUENCE: 92

Ala Tyr Arg Pro Ser Glu Thr Leu Cys Gly Gly Glu Leu Val Asp Thr
1               5                   10                  15

Leu Tyr Leu Val Cys Gly Asp Arg Gly Phe Tyr
            20                  25

<210> SEQ ID NO 93
<211> LENGTH: 28
<212> TYPE: PRT
<213> ORGANISM: Homo sapiens

<400> SEQUENCE: 93

Cys Ala Tyr Arg Pro Ser Glu Thr Leu Cys Gly Gly Glu Leu Val Asp
1               5                   10                  15

Thr Leu Tyr Leu Val Cys Gly Asp Arg Gly Phe Tyr
            20                  25

<210> SEQ ID NO 94
<211> LENGTH: 31
<212> TYPE: PRT
<213> ORGANISM: Homo sapiens

<400> SEQUENCE: 94

Cys Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr
            20                  25                  30

<210> SEQ ID NO 95
<211> LENGTH: 30
<212> TYPE: PRT
<213> ORGANISM: Homo sapiens

<400> SEQUENCE: 95

Cys Gly Pro Glu Thr Leu Cys Gly Ala Glu Leu Val Asp Ala Leu Tyr
1               5                   10                  15

Leu Val Cys Gly Asp Arg Gly Phe Tyr Phe Asn Lys Pro Thr
            20                  25                  30

<210> SEQ ID NO 96
<211> LENGTH: 30
<212> TYPE: PRT
<213> ORGANISM: Homo sapiens

<400> SEQUENCE: 96
```

```
Cys Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr
            20                  25                  30
```

<210> SEQ ID NO 97
<211> LENGTH: 29
<212> TYPE: PRT
<213> ORGANISM: Homo sapiens

<400> SEQUENCE: 97

```
Cys Gly Pro Glu His Leu Cys Gly Ala Glu Leu Val Asp Ala Leu Tyr
1               5                   10                  15

Leu Val Cys Gly Asp Arg Gly Phe Tyr Asn Lys Pro Thr
            20                  25
```

<210> SEQ ID NO 98
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa at position 6 is ornithine, lysine,
      arginine or a lysine analog

<400> SEQUENCE: 98

```
Ser Arg Val Ser Arg Xaa Ser Arg
1               5
```

<210> SEQ ID NO 99
<211> LENGTH: 29
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa at position 27 is a lysine analog

<400> SEQUENCE: 99

```
Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Xaa Pro Thr
            20                  25
```

<210> SEQ ID NO 100
<211> LENGTH: 8
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 is ornithine, lysine,
      arginine or a lysine analog

<400> SEQUENCE: 100

```
Gly Tyr Gly Ser Ser Ser Arg Xaa
1               5
```

<210> SEQ ID NO 101
<211> LENGTH: 4
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE

```
<222> LOCATION: (1)..(1)
<223> OTHER INFORMATION: Xaa at position 1 is phenylanine or desamino-
      phenylaalanine

<400> SEQUENCE: 101

Xaa Val Asn Gln
1

<210> SEQ ID NO 102
<211> LENGTH: 5
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(3)
<223> OTHER INFORMATION: Xaa at positions 1, 2,  and 3 are independently
      glutamic acid or
      aspartic acid
<220> FEATURE:
<221> NAME/KEY: MISC_FEATURE
<222> LOCATION: (4)..(4)
<223> OTHER INFORMATION: Xaa at position 4 is arginine, glutamic acid or
      aspartic acid

<400> SEQUENCE: 102

Xaa Xaa Xaa Xaa Lys
1               5

<210> SEQ ID NO 103
<211> LENGTH: 27
<212> TYPE: PRT
<213> ORGANISM: Homo sapiens

<400> SEQUENCE: 103

Thr Pro Ala Lys Ser Glu Gly Ile Val Glu Glu Cys Cys Phe Arg Ser
1               5                   10                  15

Cys Asp Leu Ala Leu Leu Glu Thr Tyr Cys Ala
            20                  25
```

UNITED STATES PATENT AND TRADEMARK OFFICE
CERTIFICATE OF CORRECTION

PATENT NO.       : 9,593,156 B2
APPLICATION NO.  : 14/431040
DATED            : March 14, 2017
INVENTOR(S)      : Richard D. DiMarchi and Yan Zhao It is certified that error appears in the above-identified patent and that said Letters Patent is hereby corrected as shown below:

In the Claims

In Claim 3, Column 168, Line 3, please delete "analogs" and insert -- analog -- therefor.

In Claim 6, Column 169, Line 33, appearing immediately below the structure, please delete "and.".

In Claim 11, Column 171, Line 7, please delete "8of" and insert -- 8 of -- therefor.

In Claim 19, Column 173, and Claim 20, Column 174, at each instance, please delete the structure:

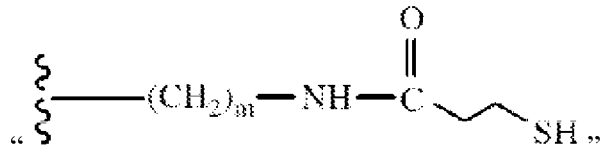

and insert the following structure therefor:

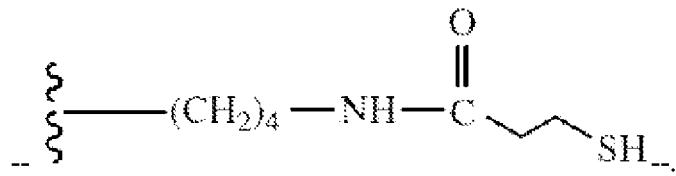

Signed and Sealed this
Sixth Day of June, 2017

Michelle K. Lee
*Director of the United States Patent and Trademark Office*